(12) United States Patent
Drndic et al.

(10) Patent No.: US 9,121,823 B2
(45) Date of Patent: Sep. 1, 2015

(54) HIGH-RESOLUTION ANALYSIS DEVICES AND RELATED METHODS

(75) Inventors: Marija Drndic, Philadelphia, PA (US); Meni Wanunu, Chestnut Hill, MA (US); Tali Dadosh, Elkins Park, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/587,141

(22) Filed: Aug. 16, 2012

(65) Prior Publication Data

US 2013/0092541 A1 Apr. 18, 2013

Related U.S. Application Data

(63) Continuation-in-part of application No. PCT/US2011/025434, filed on Feb. 18, 2011.

(60) Provisional application No. 61/306,114, filed on Feb. 19, 2010, provisional application No. 61/570,359, filed on Dec. 14, 2011.

(51) Int. Cl.
  *G01N 27/447* (2006.01)
  *G01N 33/68* (2006.01)
  (Continued)

(52) U.S. Cl.
  CPC ........ *G01N 27/44791* (2013.01); *C12Q 1/6813* (2013.01); *G01N 33/48721* (2013.01); *G01N 33/68* (2013.01)

(58) Field of Classification Search
  CPC .................. G01N 27/44791; G01N 27/4473; G01N 33/48721; G01N 33/68; C12Q 1/6813; C12Q 1/6876; C12Q 1/6825; C12Q 1/6869; Y10S 977/852; Y10S 977/733; Y10S 977/72; Y10S 977/721
  USPC ......... 435/6.1, 287.1–287.2; 422/68.1, 82.01; 204/516–543
  See application file for complete search history.

(56) References Cited

U.S. PATENT DOCUMENTS

| | | | |
|---|---|---|---|
| 2002/0117659 A1* | 8/2002 | Lieber et al. | 257/14 |
| 2005/0196876 A1 | 9/2005 | Chan et al. | |
| 2006/0105523 A1* | 5/2006 | Afzali-Ardakani et al. | 438/257 |

(Continued)

FOREIGN PATENT DOCUMENTS

| | | |
|---|---|---|
| WO | WO 00/28312 A1 | 5/2000 |
| WO | WO 2006/102292 A2 | 9/2006 |

(Continued)

OTHER PUBLICATIONS

Meller et al. (Adv. Mater. 2006, 18, 3149-3153).*

(Continued)

*Primary Examiner* — Jennifer Dieterle
(74) *Attorney, Agent, or Firm* — Baker & Hostetler LLP

(57) ABSTRACT

Disclosed are solid-state nanopore devices having pores of nanometer-scale thickness, which ultrathin (e.g., less than 10 nm thick) pores enable devices having improved resolution. Also provided are methods of fabricating such devices and of using such devices. The invention also provides nanometer-thick membranes and related methods of fabricating such membranes, which membranes are useful in high resolution microscopy applications. Further disclosed are devices for detection of analytes—including miRNA—that may be small in size and may also be present in only small quantities.

17 Claims, 116 Drawing Sheets

(51) Int. Cl.
*C12Q 1/68* (2006.01)
*G01N 33/487* (2006.01)

(56) References Cited

U.S. PATENT DOCUMENTS

| 2007/0161004 | A1* | 7/2007 | Brown et al. | 435/6 |
| 2009/0136948 | A1 | 5/2009 | Han et al. | |
| 2009/0142825 | A1 | 6/2009 | Murray et al. | |
| 2010/0035260 | A1* | 2/2010 | Olasagasti et al. | 435/6 |
| 2011/0227558 | A1* | 9/2011 | Mannion et al. | 324/71.1 |

FOREIGN PATENT DOCUMENTS

| WO | WO 2009/020682 | * | 2/2009 |
| WO | WO 2009/035647 | * | 3/2009 |
| WO | WO 2010/066851 | * | 6/2010 |

OTHER PUBLICATIONS

Choi et al., "Nanotechnology for Early Cancer Detection", Sensors, Jan. 2010, 10(1), 428-455.

Neely et al., "A Single-Molecule Method for the Quantitation of MicroRNA Gene Expression", Nature Methods, Jan. 2006, 3(1), 41-46.

Wanunu et al., "Rapid Electronic Detection of Probe-Specific MicroRNAS using Thin Nanopore Sensors", Nature Nanotechnology, Nov. 2010, 5(11), 807-814.

* cited by examiner

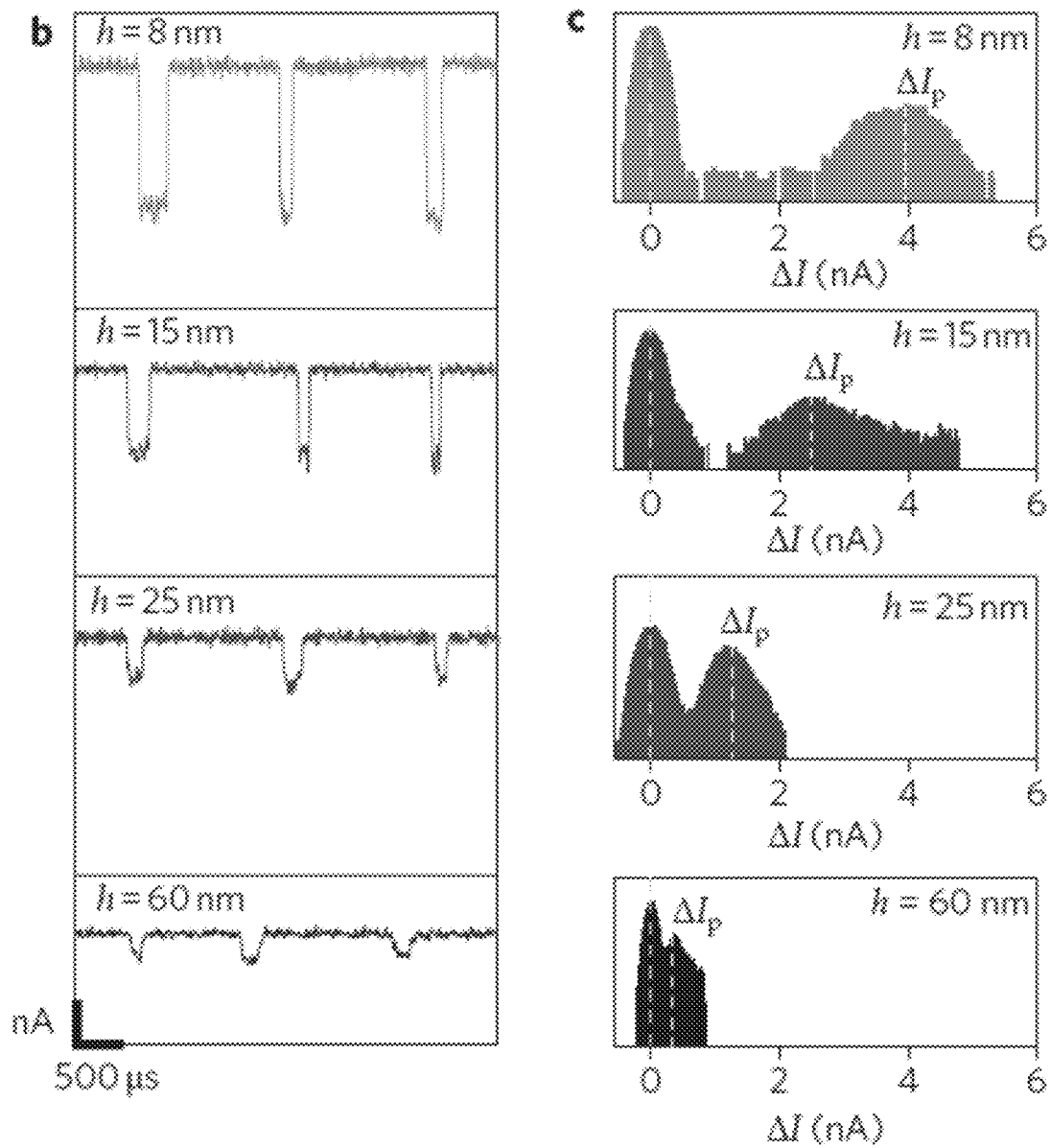
Figure 12b-c

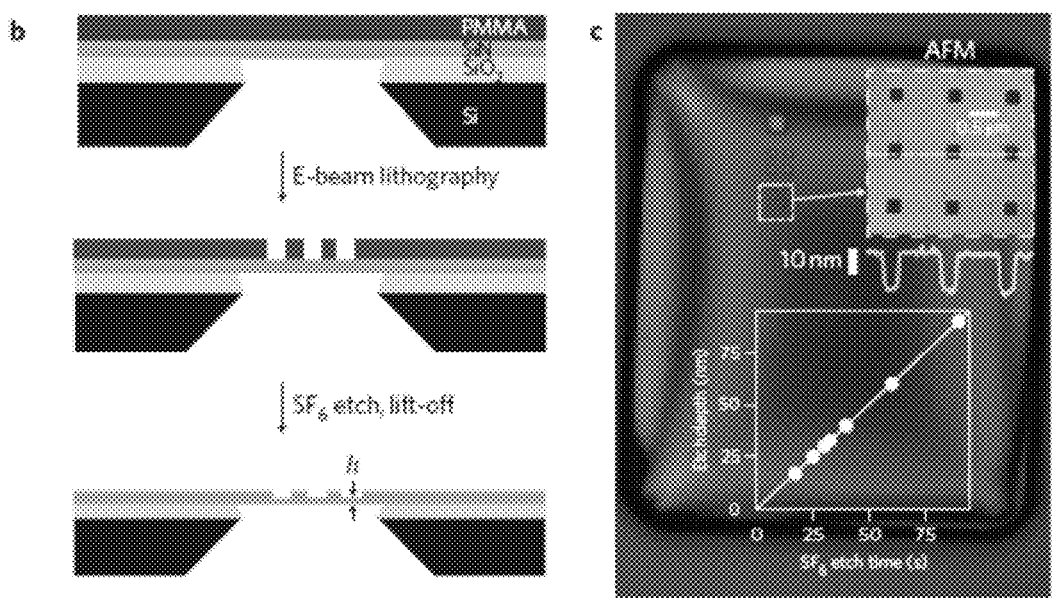
Figure 18b-c

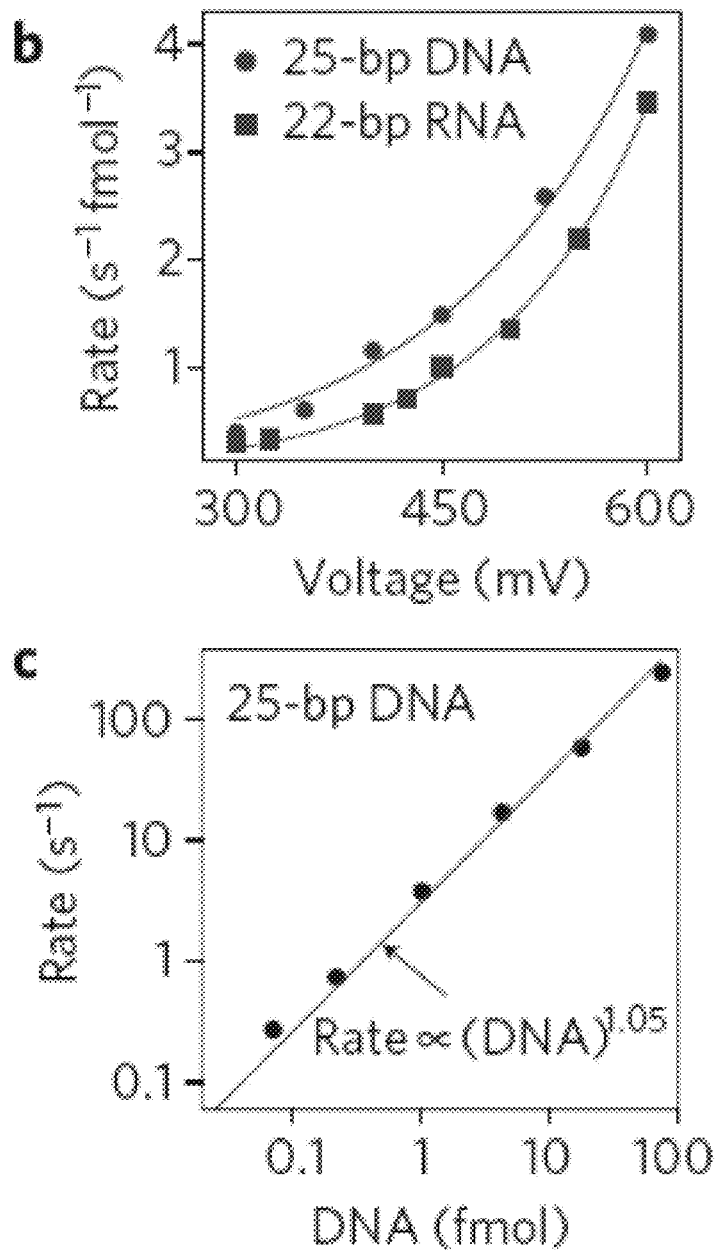
Figure 20b-c

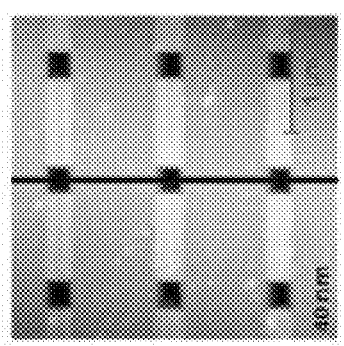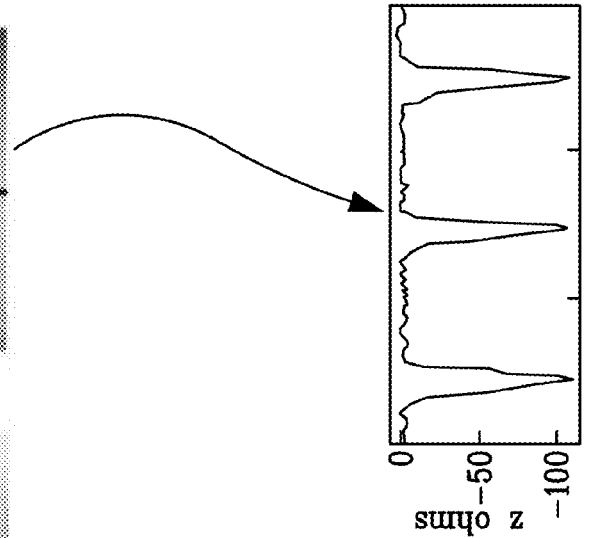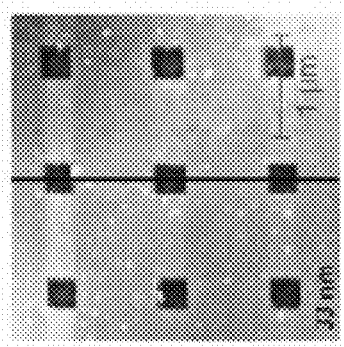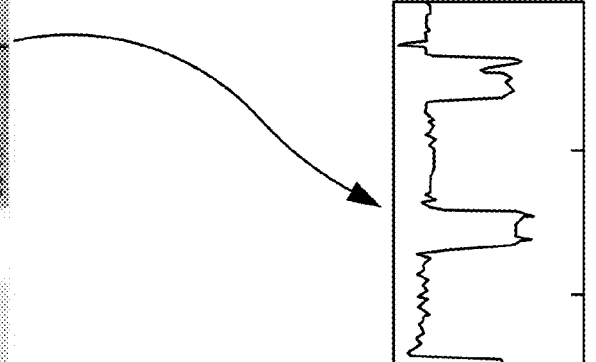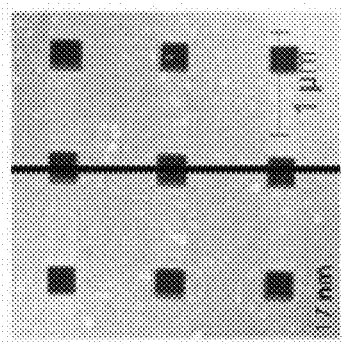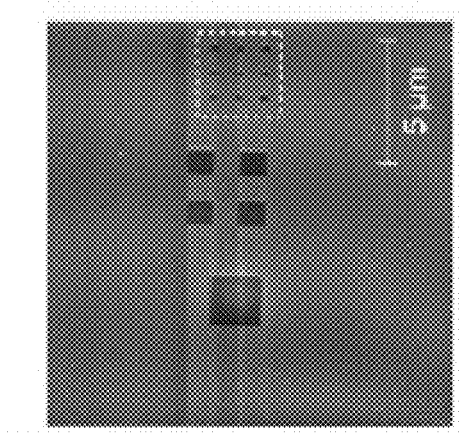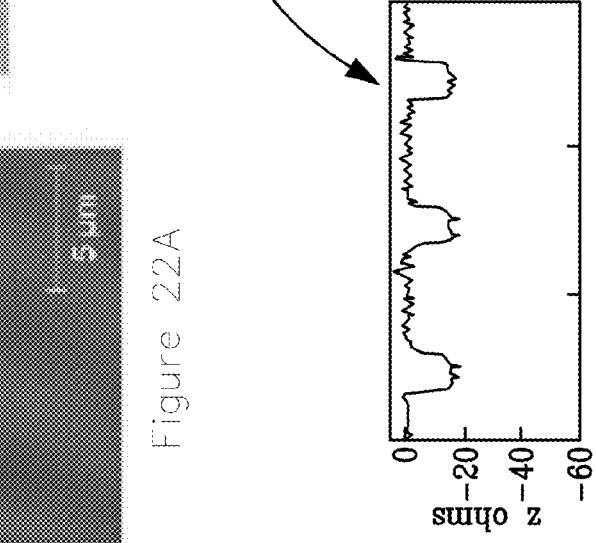
Figure 22B  AFM of trenches on SiN membrane
Figure 22A (thinned silicon nitride):

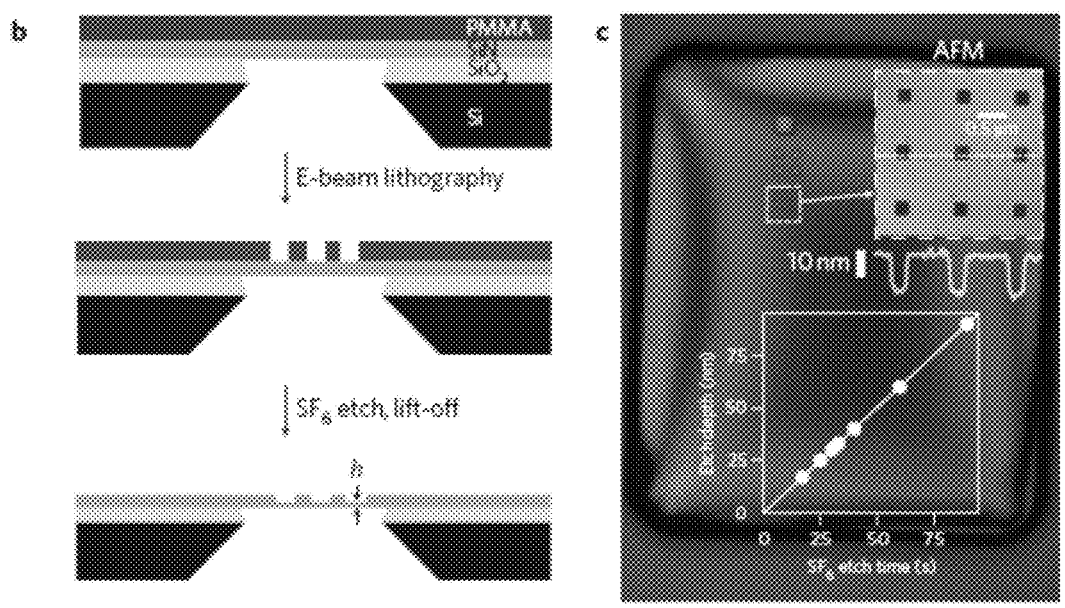
Figures 58b-c

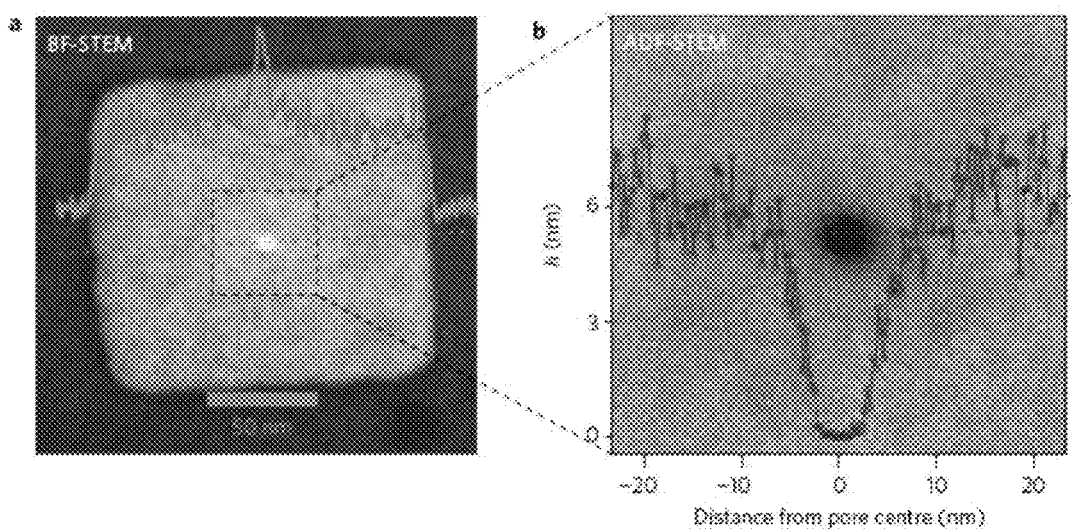
Figure 59a-b

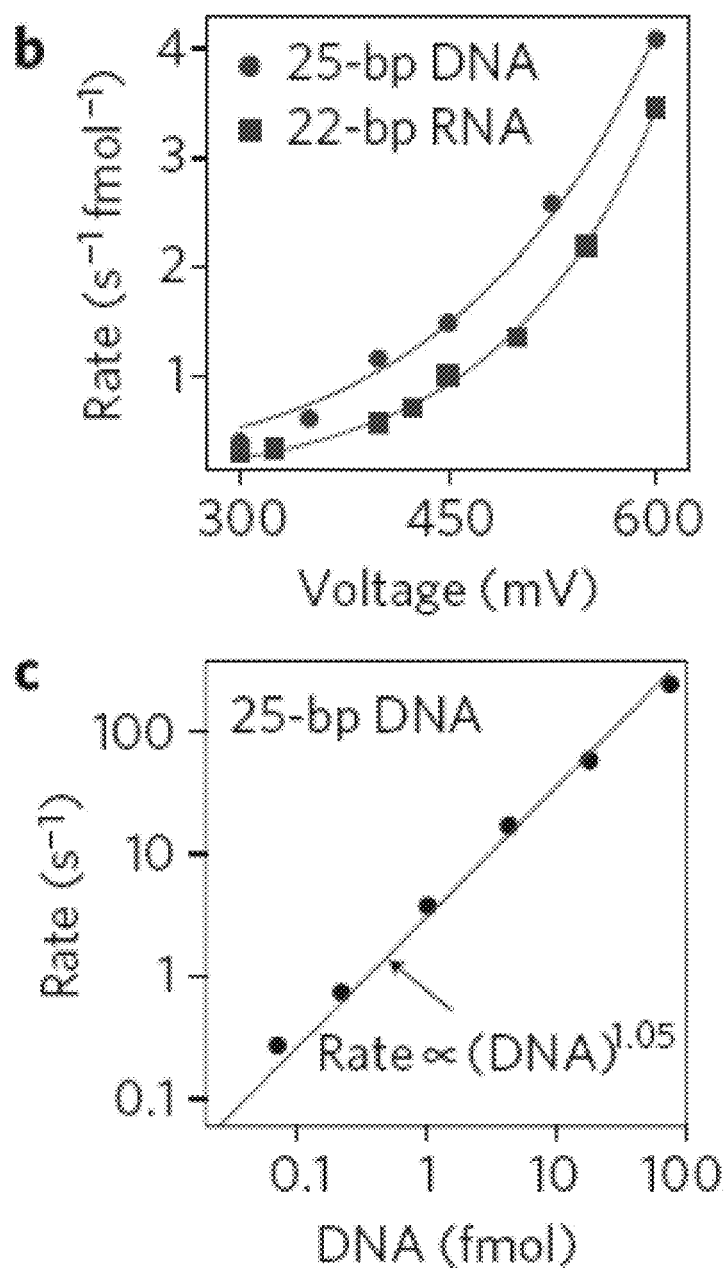
Figure 60b-c

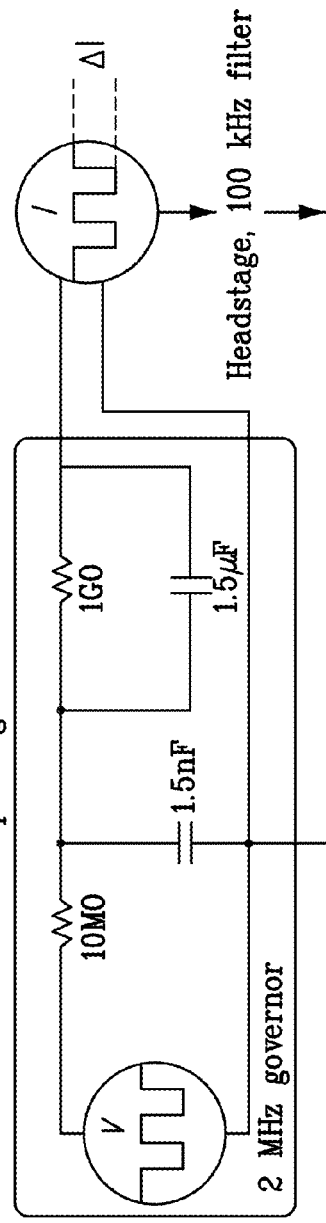
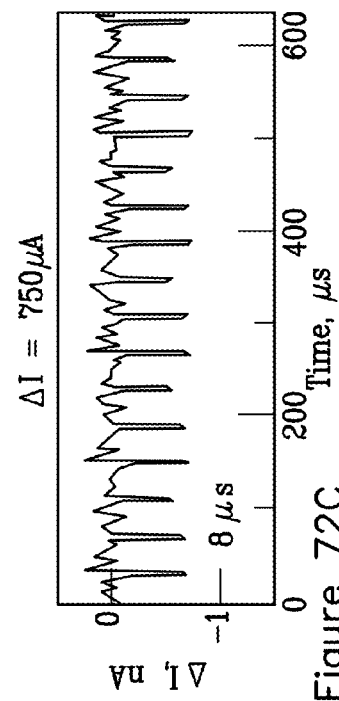
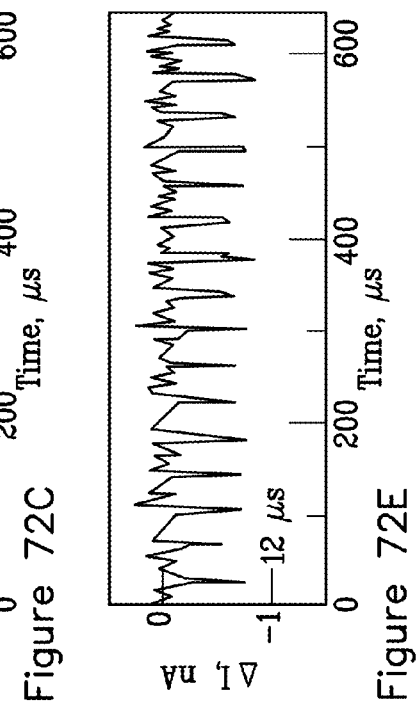
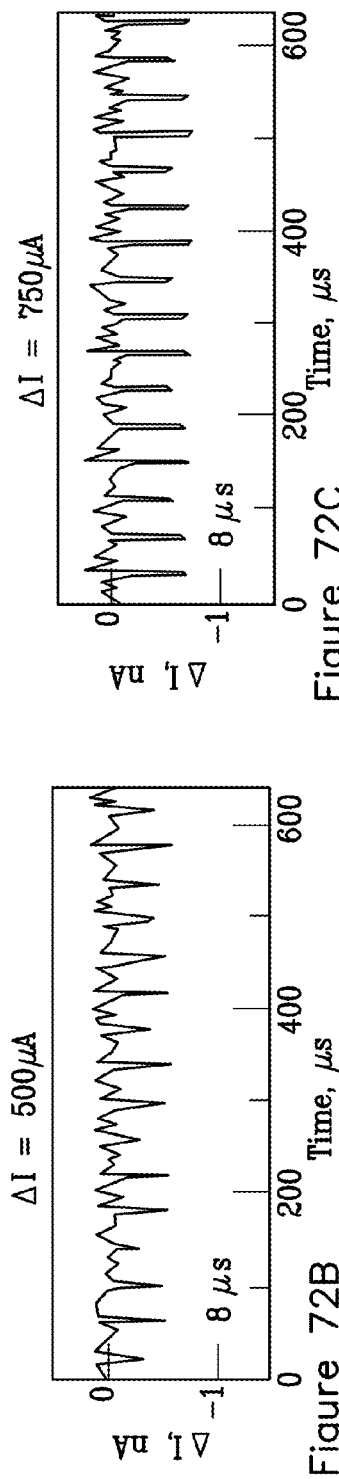
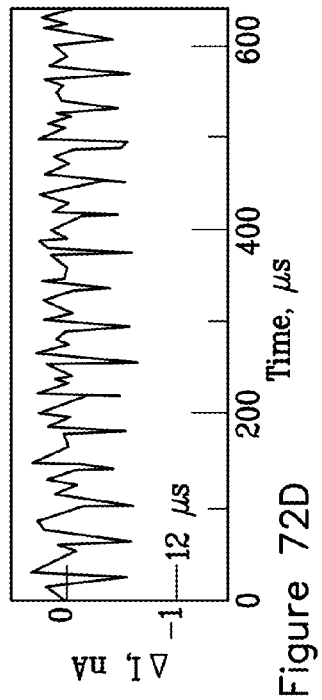
Figure 72A
Figure 72B
Figure 72C
Figure 72D
Figure 72E

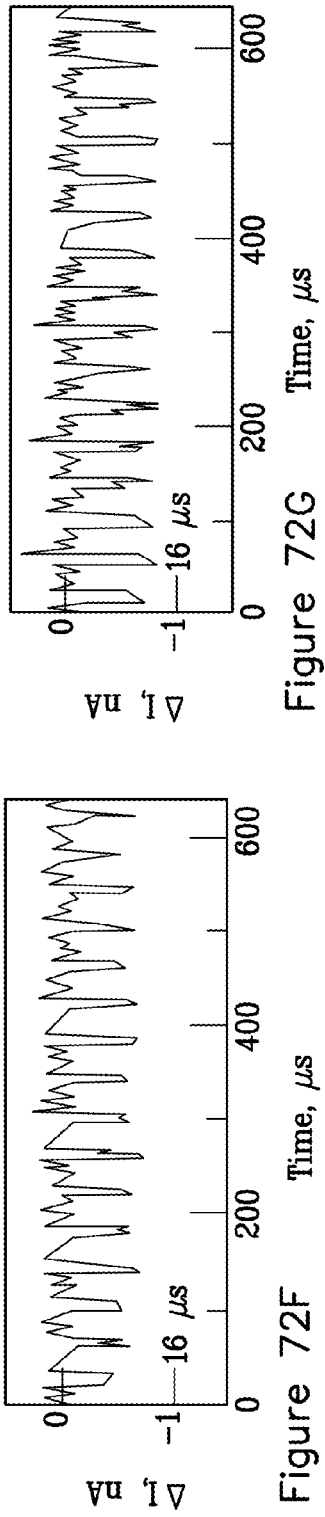
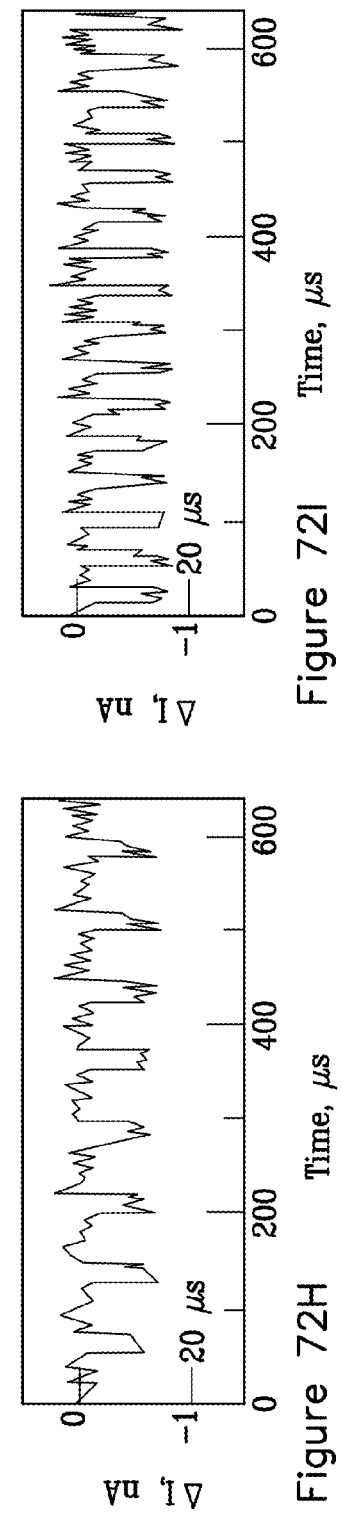
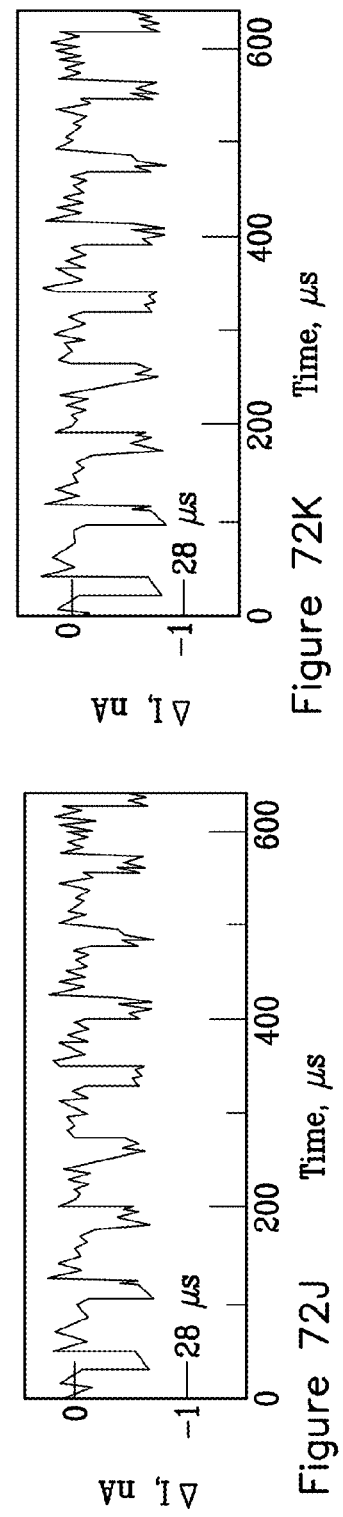
Figure 72F  Figure 72G  Figure 72H  Figure 72I  Figure 72J  Figure 72K

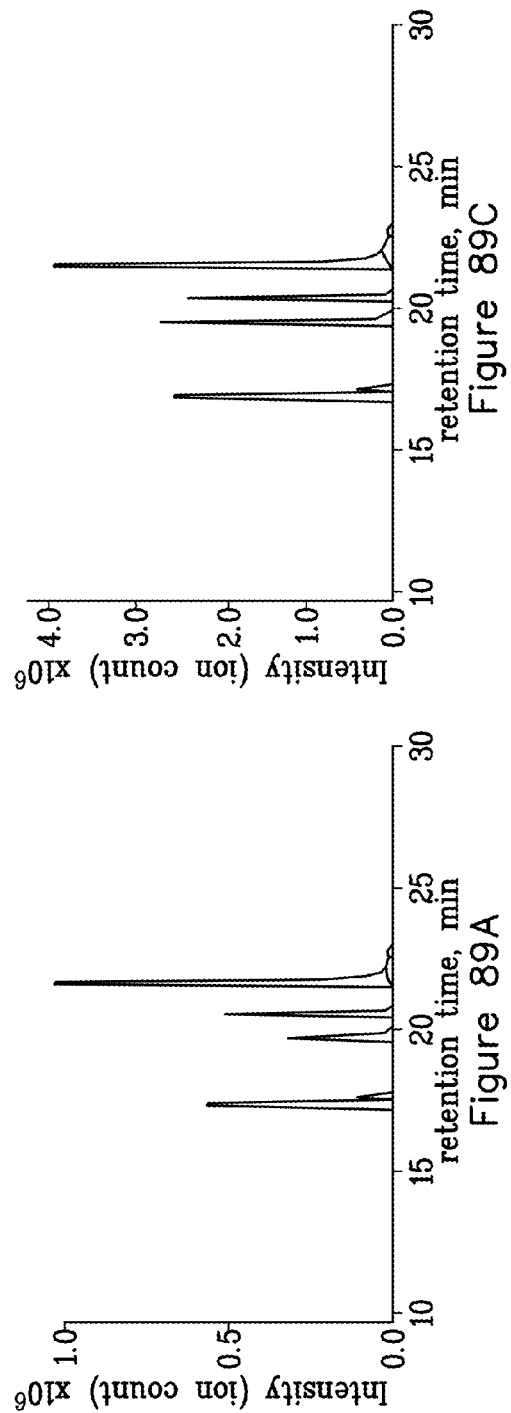
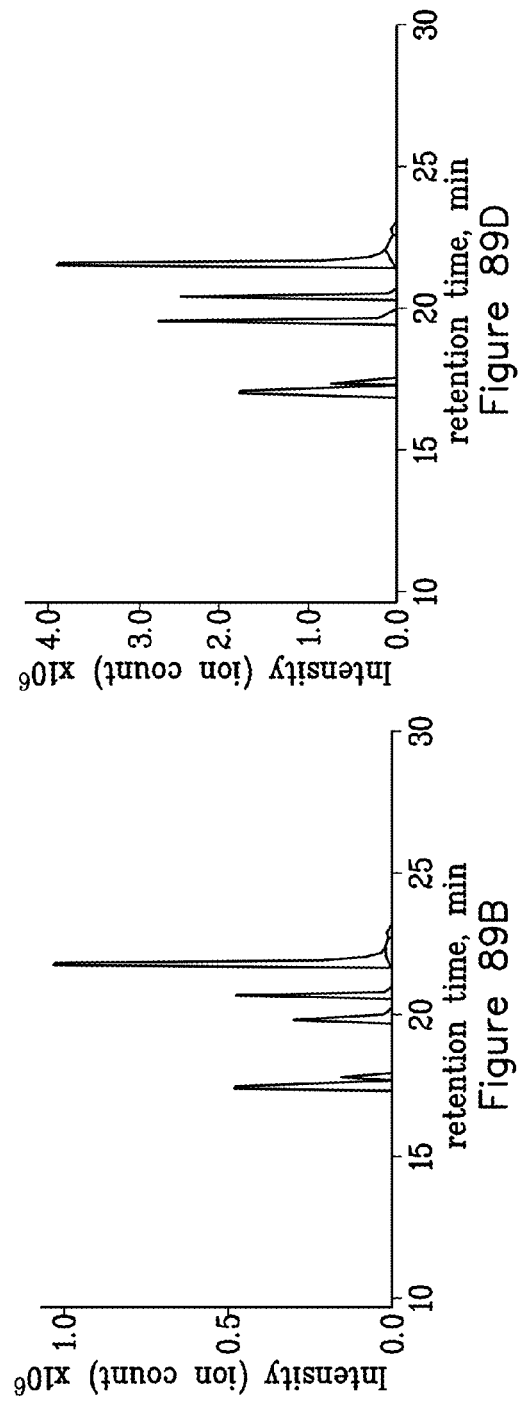
Figure 89A
Figure 89B
Figure 89C
Figure 89D

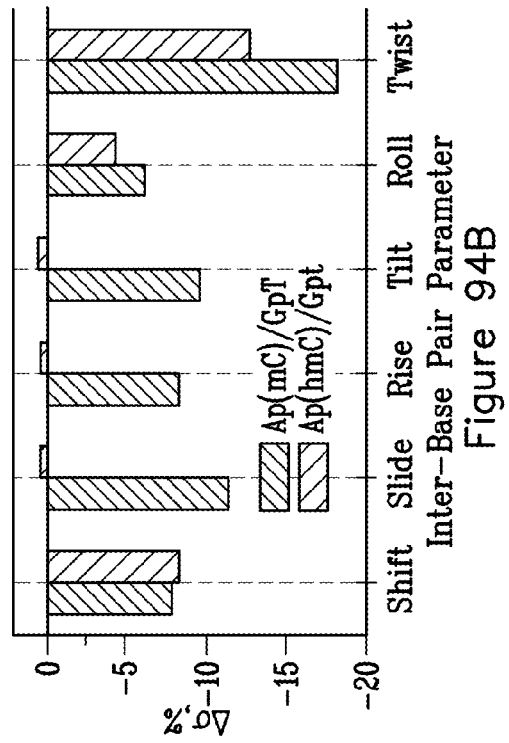
Figure 94A
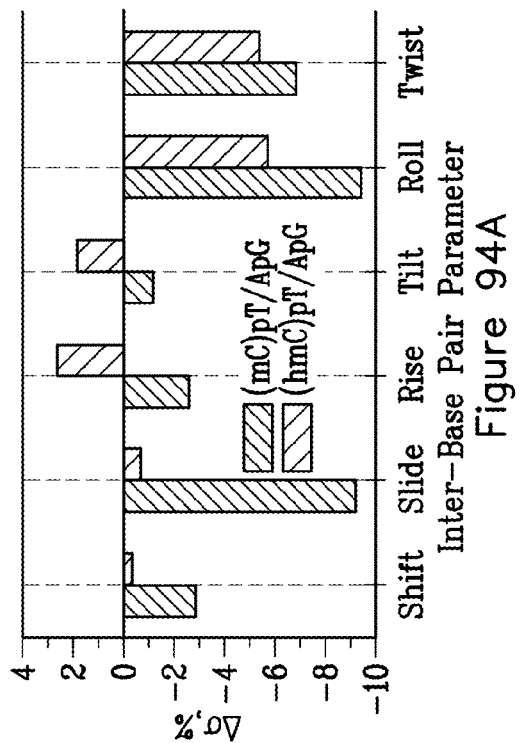
Figure 94C
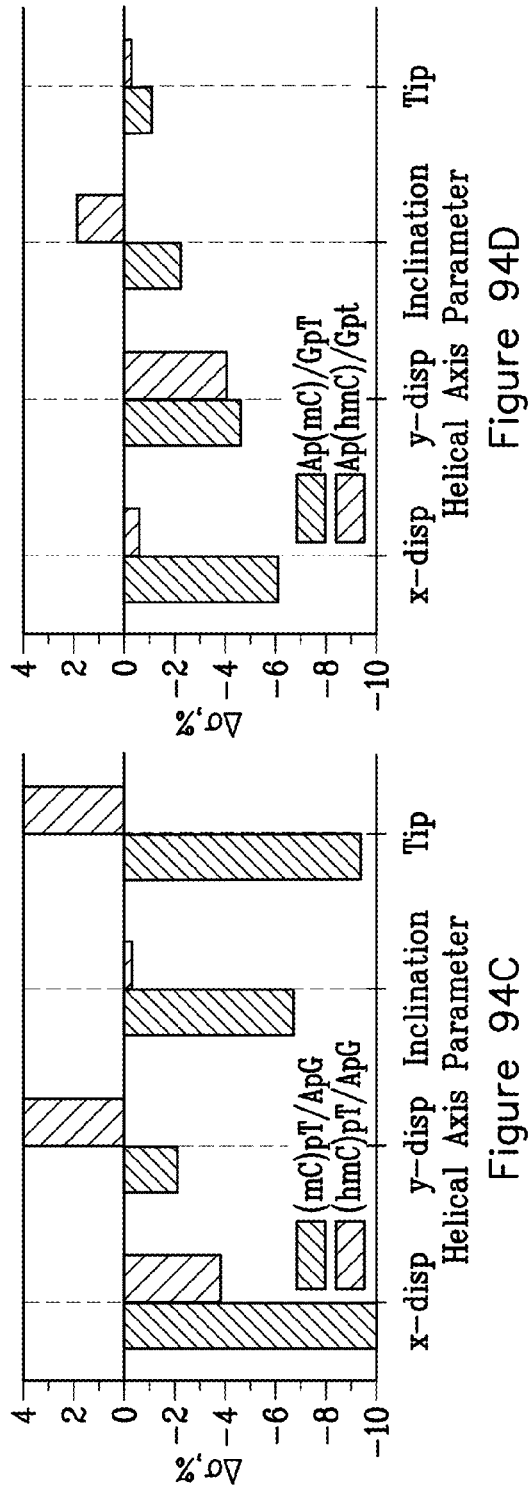

HIGH-RESOLUTION ANALYSIS DEVICES AND RELATED METHODS

RELATED APPLICATIONS

This application is a continuation-in-part of PCT application No. PCT/US2011/025434, "High-Resolution Analysis Devices and Related Methods", filed Feb. 18, 2011, which application claims the benefit of U.S. provisional application 61/306,114, "High-Resolution Analysis Devices and Related Methods," filed Feb. 19, 2010. This application also claims priority to U.S. provisional application 61/570,359, "DNA Base Discrimination Using High-Resolution Devices", filed on Dec. 14, 2011. All of the foregoing applications are incorporated herein by reference herein for any and all purposes.

STATEMENT OF GOVERNMENT RIGHTS

This invention was made with government support under grant 1R21HG004767-01, awarded by the National Institutes of Health. The government has certain rights in the invention.

TECHNICAL FIELD

The present invention relates to the fields of solid state nanopores and of macromolecular analysis.

BACKGROUND

Nanopores in synthetic membranes hold great promise as platforms for next-generation DNA sequencing, as well as for other applications in genomics. Solid-state nanopores have been playing a major role for realizing these efforts, as they exhibit reproducible structure, scale-up capabilities, stability, and robustness. Low-stress silicon nitride (SiN), silicon oxide, and aluminum oxide have been used as membranes for the fabrication of solid-state nanopores.

Nanopore-based applications rely on reading the ion current of an electrolyte through the nanopore as biomolecules are threaded through the pore. The ion current highly depends on voltage, salt concentration, temperature, and the pore geometry. Analogous to the sharpness of an AFM tip, the length of the nanopore determines the overall resolution of the nanopore technique.

The reported thickness values of solid-state nanopores lie in the range of 20-50 nm, which provides a maximum readout resolution for double-stranded DNA of around 60-150 basepairs. This resolution, however, hinders the quality of information that is recovered from ion-current signals. Fabrication of thinner membranes, however, poses its own challenges, and is limited by physical stability, resulting in cracks and holes through the membrane that render the devices unusable. In light of the demand for a cheaper DNA sequencing, genomic analysis, RNA analysis, protein analysis, and other methods for ultrasensitive molecular analysis, there is a need in the art for ultrathin (e.g., <10 nm) solid-state membrane substrates for nanopore analysis, and for related methods of fabricating and of using such devices.

SUMMARY

The present application provides approaches for fabricating sub-10 nm thick membrane devices, as well as the use of such membranes for nanopore-based nucleic acid analysis. This disclosure includes, inter alia, the steps of exposing a sub-micron region on a membrane (e.g., SiN) window, etching to locally thin the exposed region with sub-nanometer control, and the formation of a nanopore in the locally thinned region. Thereafter, the nanopore devices are treated using established protocols for subsequent biomolecular analysis.

In one aspect, the present invention provides analysis devices, the devices including a membrane having a thickness in the range of from about 0.2 to about 100 nm and comprising at least one pore extending therethrough, the pore having a characteristic cross-sectional in the range of from about 1 nm to about 1000 nm; and a supporting layer adjacent to the membrane.

In another aspect, provided are detection devices, the devices including a first capture material configured to bind preferentially to a first molecule; a membrane having a thickness in the range of from about 20 nm to about 100 nm, and the membrane having a thinned region, the thinned region having a thickness in the range of from about 0.1 nm to about 20 nm, and a first pore extending through the thinned region, the first pore being in fluid communication with the capture material; and a detector configured to detect a signal related to passage of the first molecule through the first pore.

The disclosure also provides methods of detecting an analyte, the methods including contacting a sample to a first capture material that preferentially binds to a first analyte; eluting the first analyte from the capture material; translocating the first analyte through a first pore disposed in a thinned region of a membrane, the thinned region having a thickness in the range of from about 0.1 nm to about 20 nm; and detecting a signal related to the translocation of the molecule through the first pore.

Also provided are methods of fabricating an analysis device, comprising removing at least a portion of a resist material disposed adjacent to a membrane so as to expose a target region of the membrane; etching at least a portion of the target region of the membrane material so as to reduce the thickness of the membrane material within the target region; and forming a pore that extends through the thinned target region of the membrane material.

Disclosed also are methods of fabricating an analysis device, the methods including removing at least a portion of a first material disposed adjacent to a membrane material having a thickness in the range of from about 20 nm to about 200 nm so as to expose at least one target region of the membrane material; and etching at least a portion of the at least one target region of the membrane material so as to reduce the thickness of the membrane material within the target region to from about 2 nm to about 30 nm.

The claimed invention also provides methods of analyzing a macromolecule, comprising translocating at least a portion of a macromolecule through a pore disposed in a membrane having a thickness in the range of from about 0.1 nm to about 20 nm; monitoring a signal related to the translocation of the macromolecule through the pore; and correlating the signal to a structural property of the macromolecule.

Additionally provided are membrane materials having a first region of from about 0.5 nm to about 20 nm in thickness; and a support layer disposed adjacent to the membrane material.

Further provided are analysis devices. These devices suitable include a membrane having a membrane thickness of from about 20 nm to about 1000 nm, the membrane having a thinned region thereon, and the thinned region having a thickness of between about 0.1 nm and about 20 nm.

Methods of analyzing a molecule are also provided. These methods include translocating at least a portion of a molecule through a pore disposed in a thinned region of a membrane, the thinned region having a thickness in the range of from about 0.1 nm to about 20 nm; and detecting a signal related to the translocation of the molecule through the pore.

The present application further provides detection devices. These devices suitably include a first capture material that binds specifically to a first molecule; a first membrane having a thickness in the range of from about 5 nm to about 100 nm; and a second membrane disposed adjacent the first membrane, the second membrane having a thickness in the range of from about 2 nm to about 20 nm, and the second membrane having at least one pore extending therethrough, the pore having a cross-sectional dimension in the range of from about 1 nm to about 100 nm, and the first membrane having a cavity formed thereon, the cavity being in register with at least one pore of the second membrane, the first pore being in fluid communication with the first capture material; a device configured to apply a gradient across the pore; and a detector configured to detect a signal related to passage of a molecule through the first pore.

Further included are methods of detecting an analyte. These methods include contacting a sample to a capture material that preferentially binds a first analyte; eluting the first analyte from the capture material; translocating the first analyte through a first pore formed in a first membrane disposed adjacent to a second membrane; the second membrane having a thickness in the range of from about 5 nm to about 100 nm and the second membrane having a cavity formed thereon, the cavity being in register with the first pore, the first membrane having a thickness in the range of from about 2 nm to about 20 nm, and the first pore extending through the first membrane, the pore having a cross-sectional dimension in the range of from about 1 nm to about 100 nm, the first pore being in fluid communication with the first capture material; and detecting a signal related to the translocation of the molecule through the pore.

Also provided are methods of fabricating a microscopy support. These methods include removing at least a portion of a first material disposed adjacent to a membrane so as to expose a first region of the membrane, the exposed region of the membrane having a thickness in the range of from 0.1 nm to about 20 nm.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

Figure 20A:
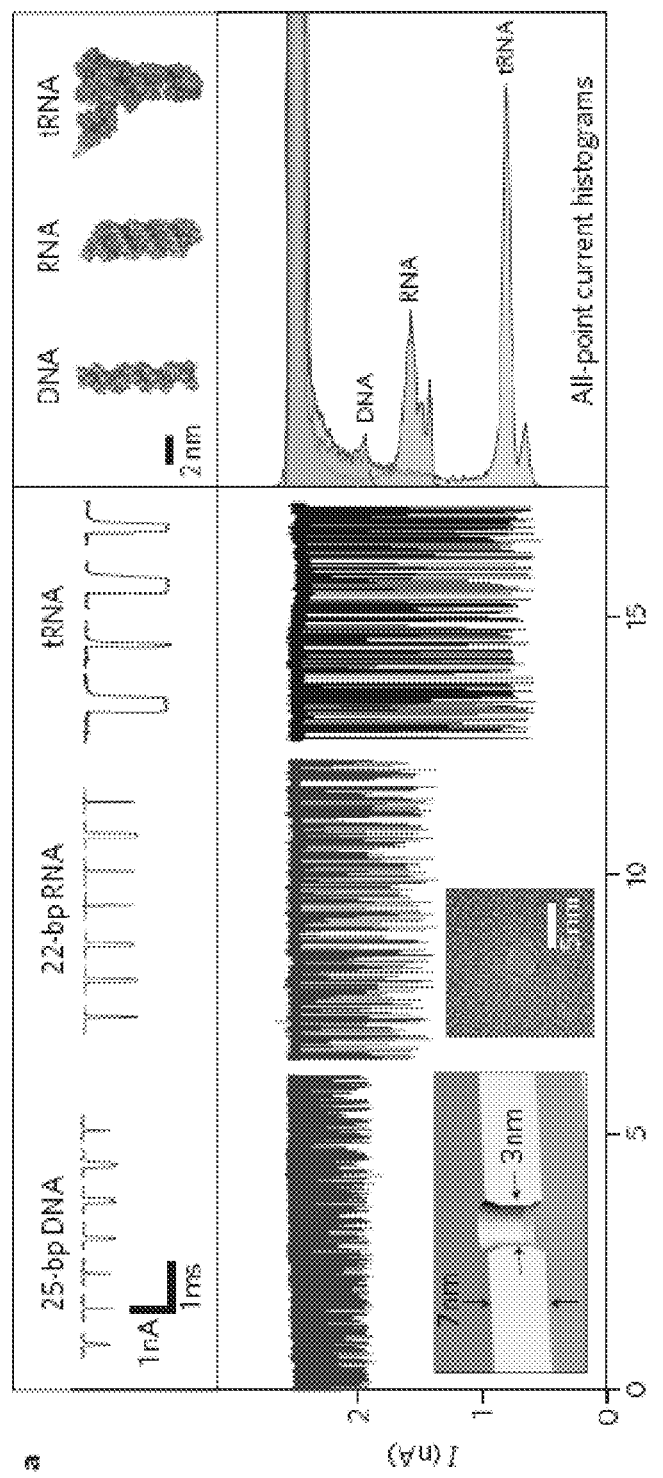
FIG. 20 illustrates discrimination among small nucleic acids using thin nanopores. (a) Continuous current vs. time traces from a 3 nm diameter pore in a 7 thick membrane measured at 0° C., V=500 mV (TEM image of pore is shown). Traces were median-filtered with rank of 1 in order to improve the signal-to-noise. Based on the conductance, the effective pore thickness heff=2.3 nm. The analyte chamber contains 25-bp dsDNA (left), 22-bp dsRNA (middle), or phenylalanine tRNA (right), at concentrations of ~80 fmol/μl. Sample events are shown above the continuous traces, and models based on crystal structures are shown to the right.

The all-point current histograms on the bottom right of FIG. 20a show that molecules can be distinguished based on their current amplitudes. The mean transport times for the DNA, RNA, and tRNA molecules are 20 μs, 50 μs, and 1.04 ms, respectively. Part (b) of this figure shows the relationship of the capture rate on applied voltage for 25-bp DNA and 22-bp RNA. The exponential dependence reveals that capture is voltage-activated. The lines in FIG. 20b are exponential fits to the data. Part (c) of the figure is a log-log plot of capture rate vs. DNA concentration. Linearity is observed for three orders of magnitude in DNA concentration, as indicated by a power-law fit exponent of 1.05+/−0.03;

FIG. 21 illustrates microRNA detection using solid-state molecular counters. Detection (of miRNA or of other analytes) can include counting events (e.g., analyte passages) at the nanopore. The counted events can be correlated to a property of the source of the analyte. For example, the user may construct a calibration curve that allows them to relate the number of passage events to the concentration of an analyte in a sample.

Figure 21A:
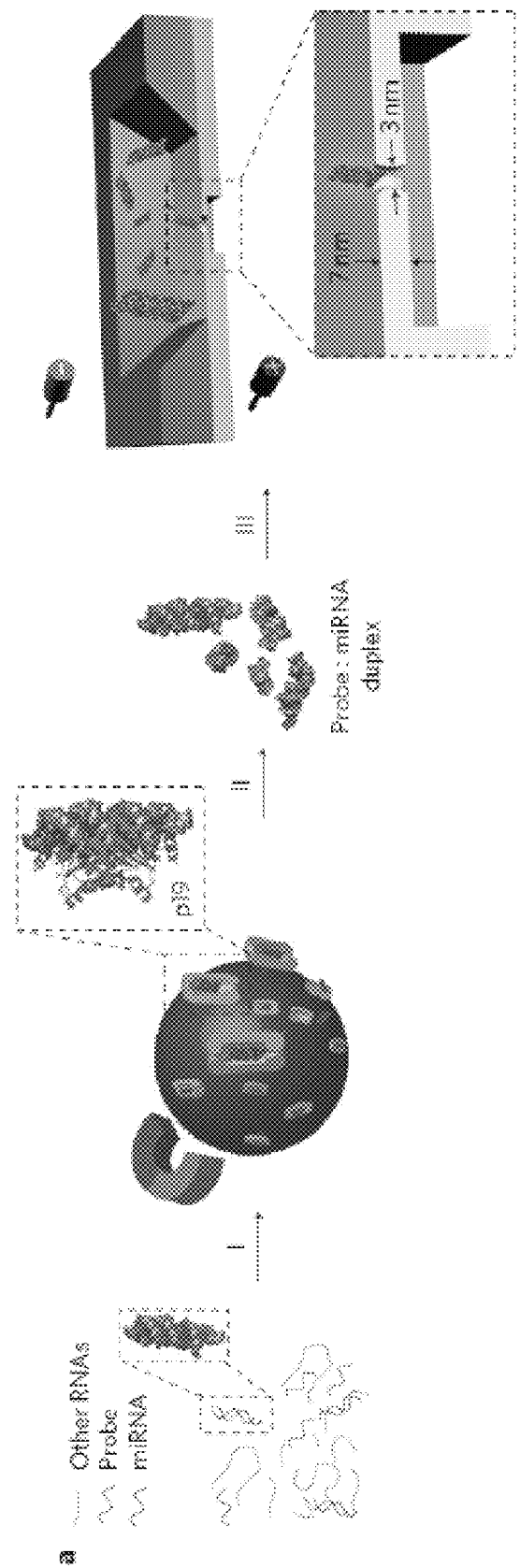
Figure 21B:
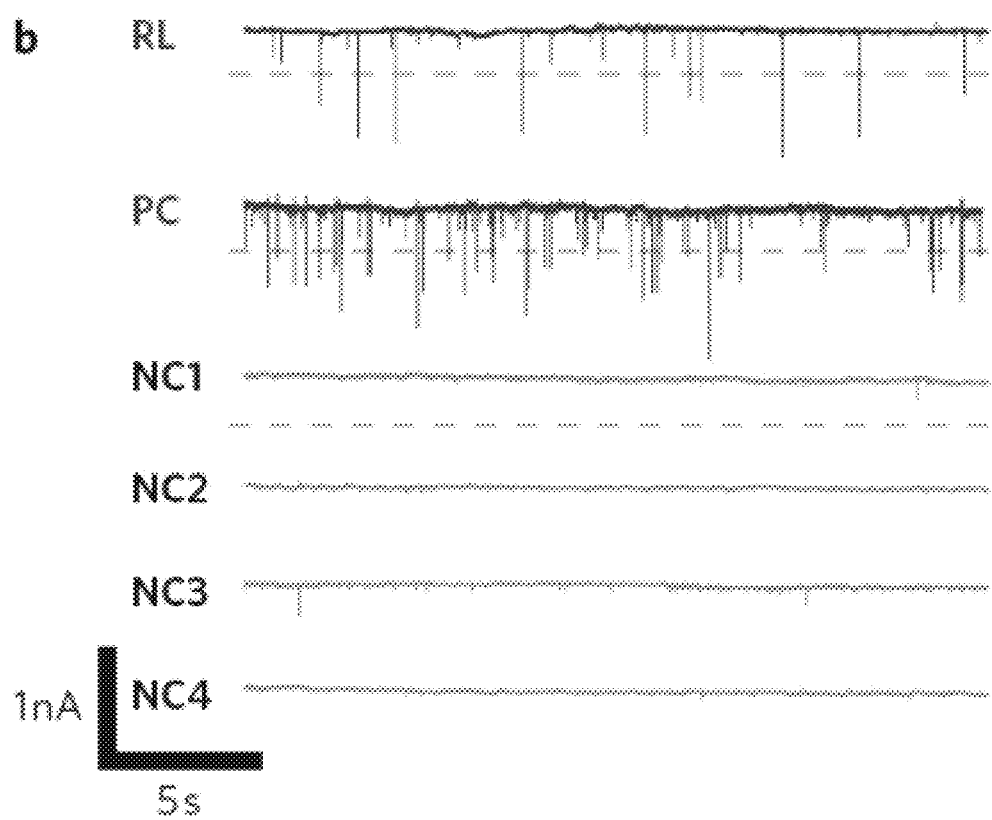
Figure 21D:
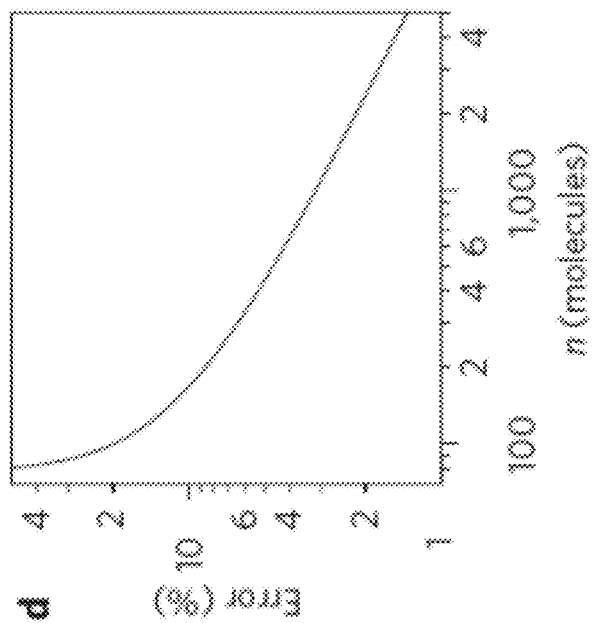
Figure 21C:
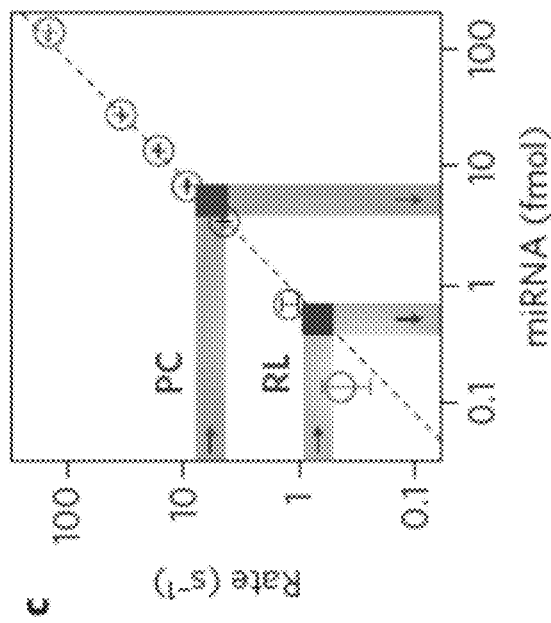
Figure 23:
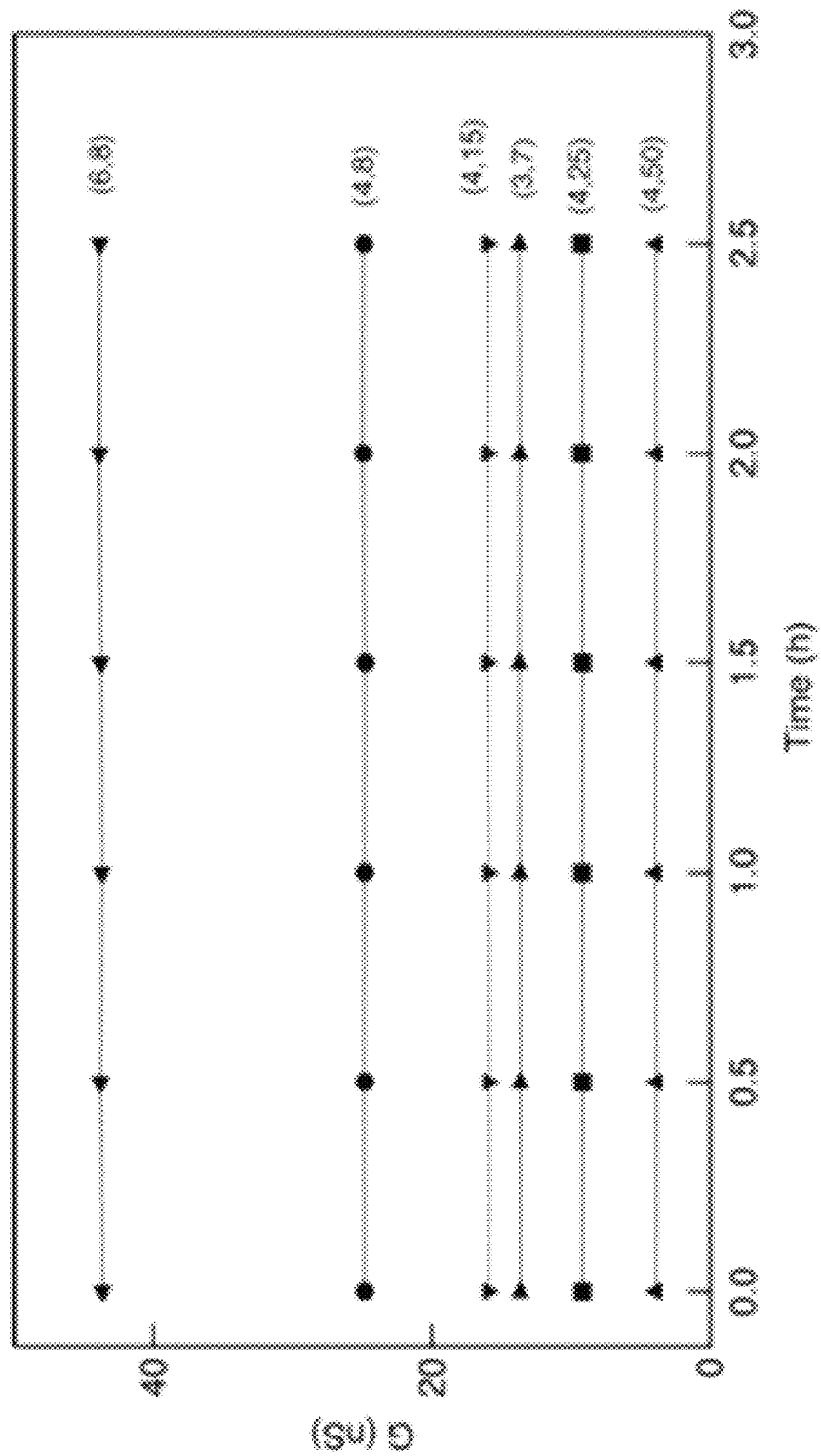
Figure 24:
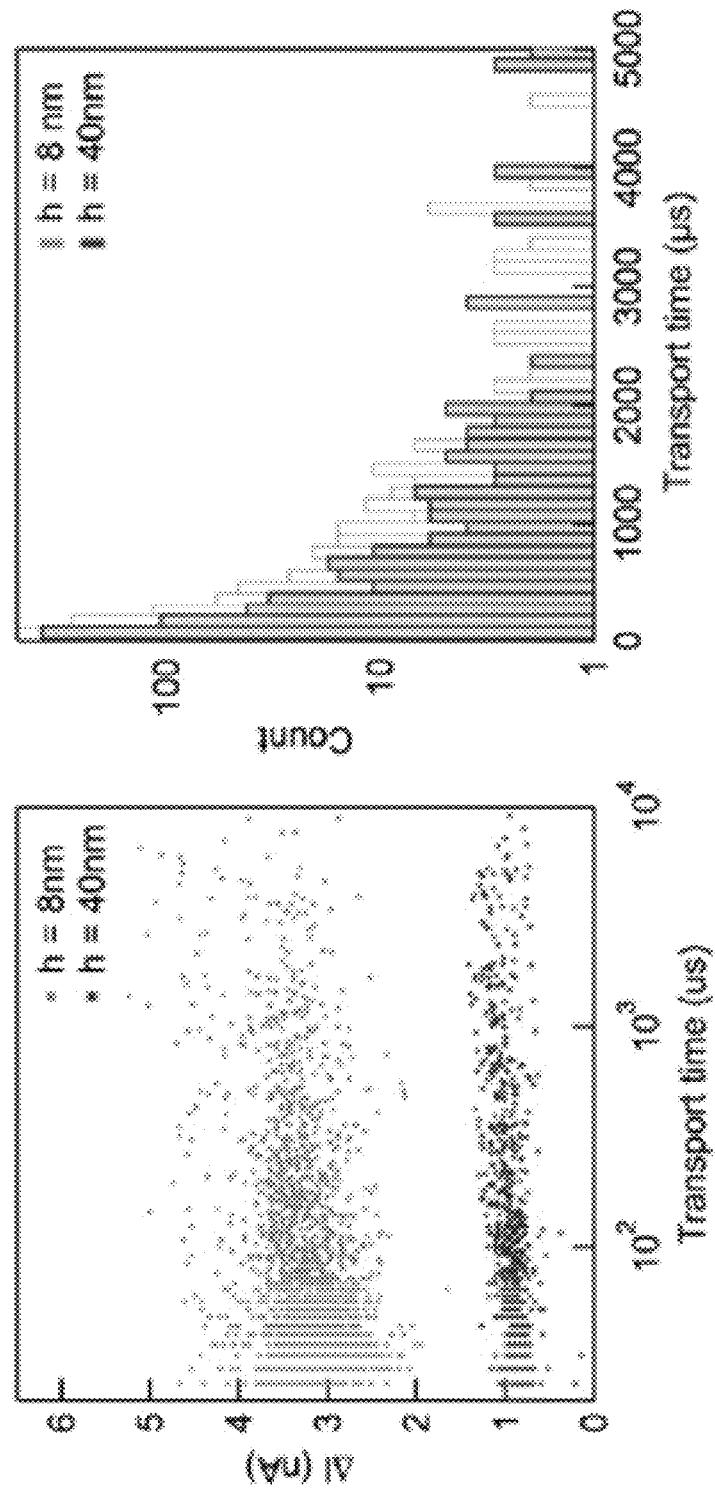
Figure 25:
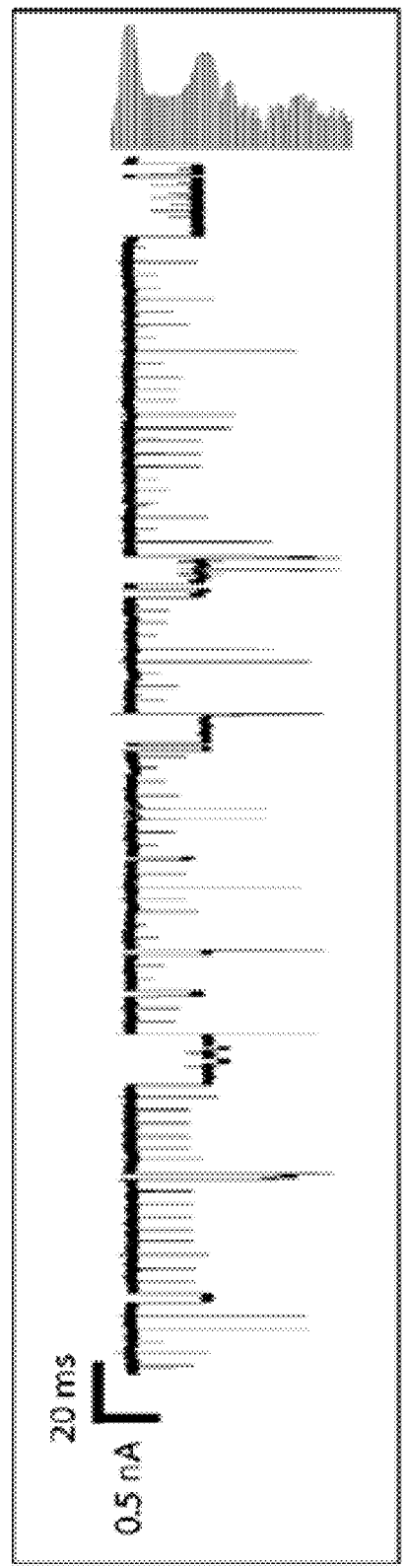
Figure 27:
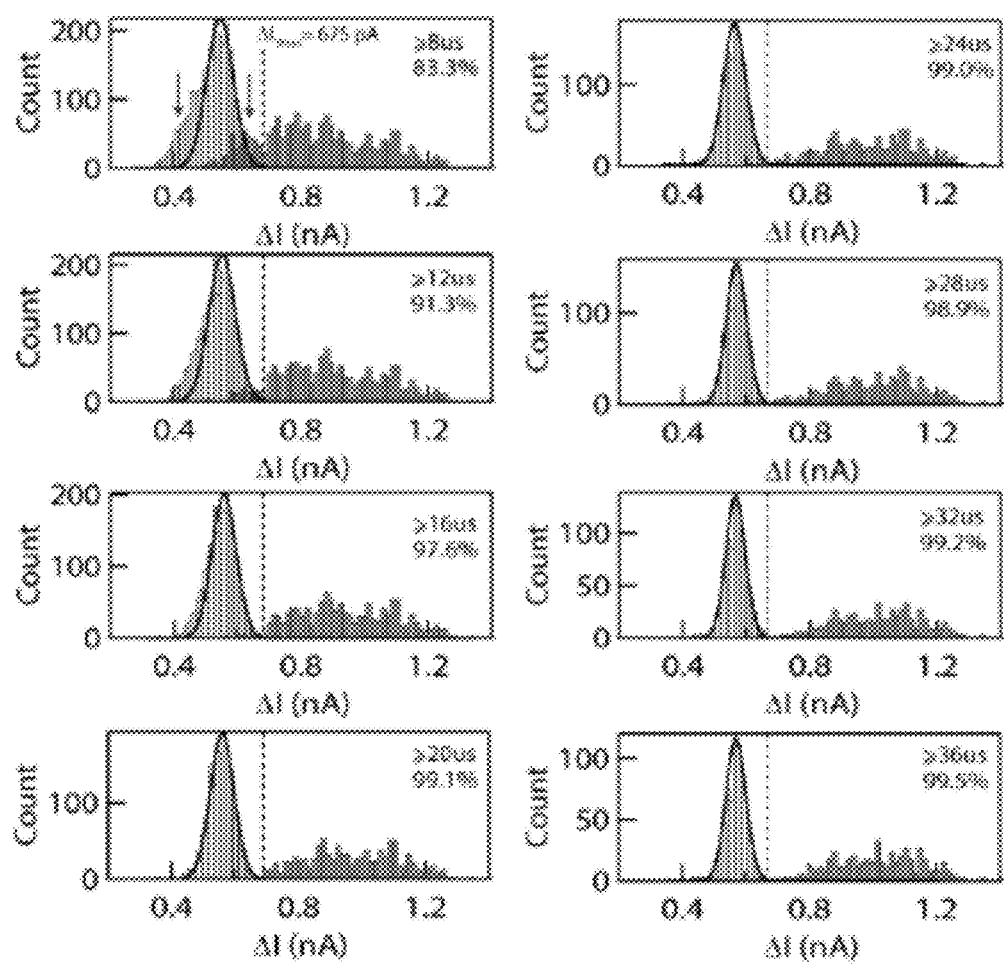
Figure 28:
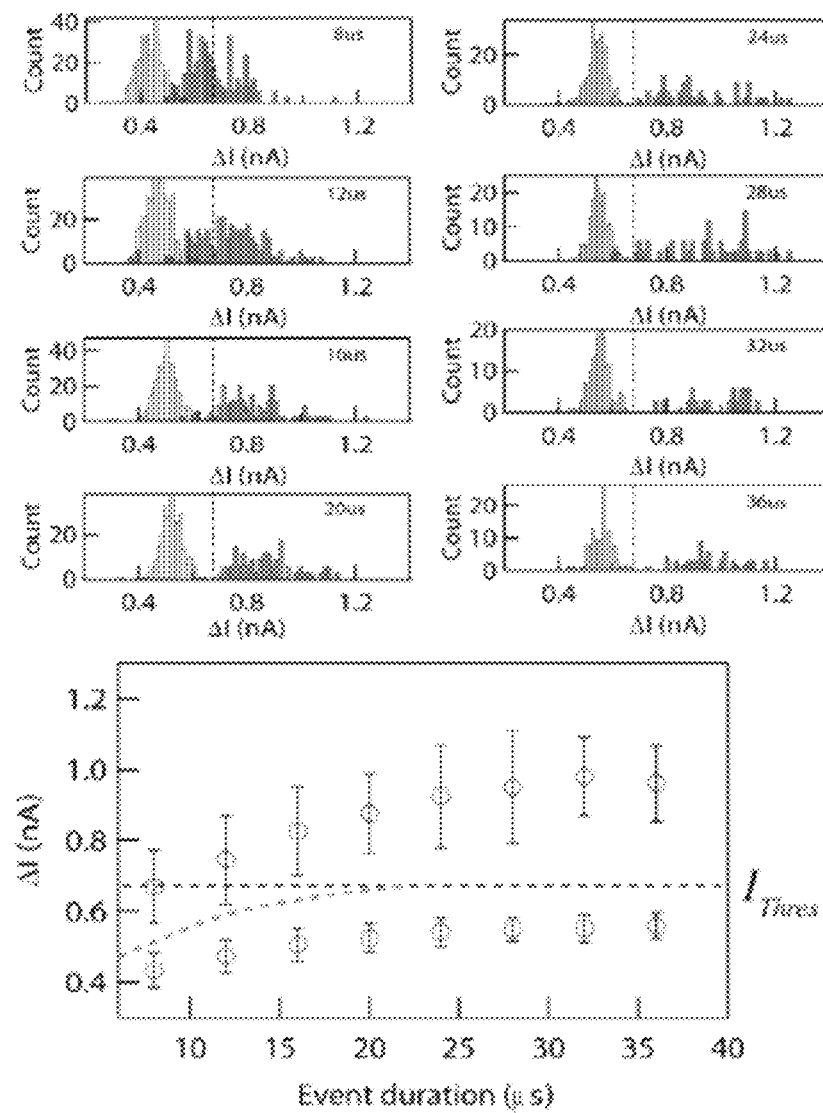
Figure 29:
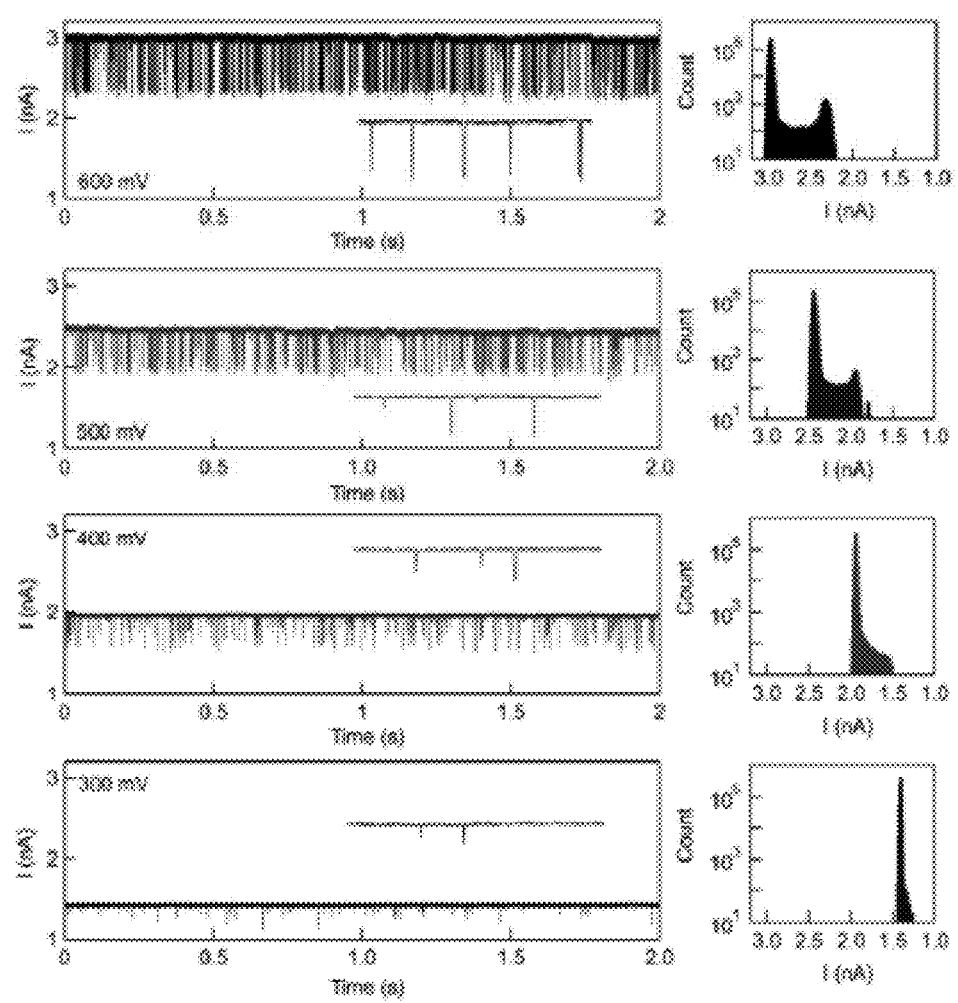
Figure 30:
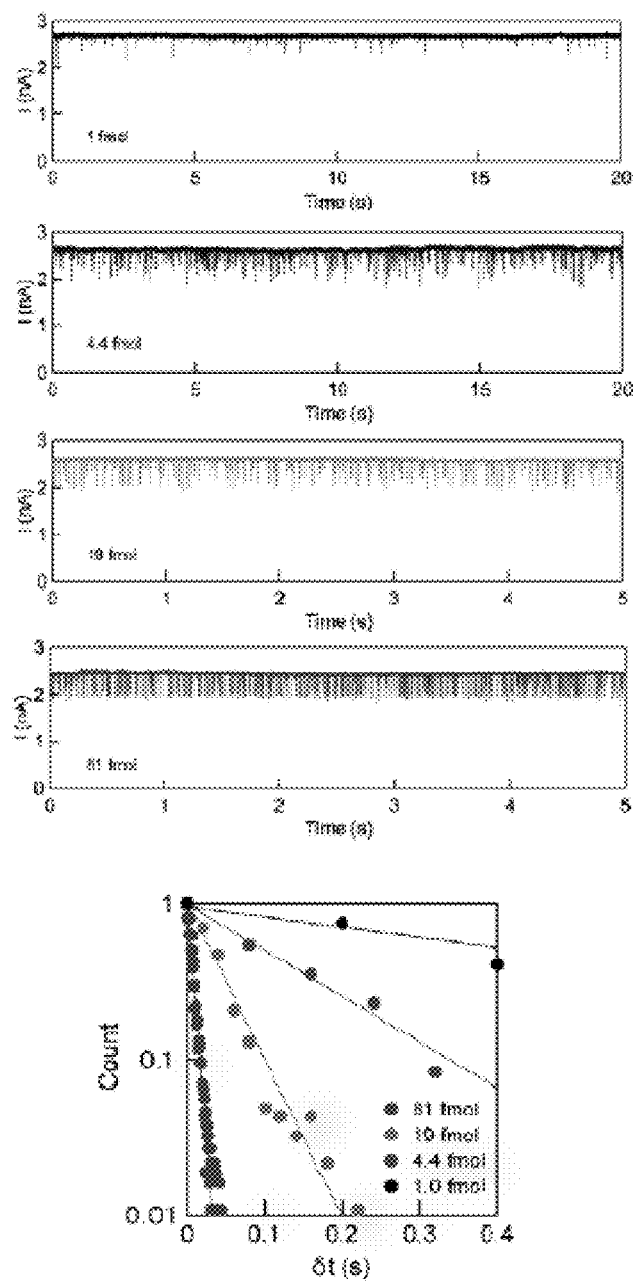
Figure 31:
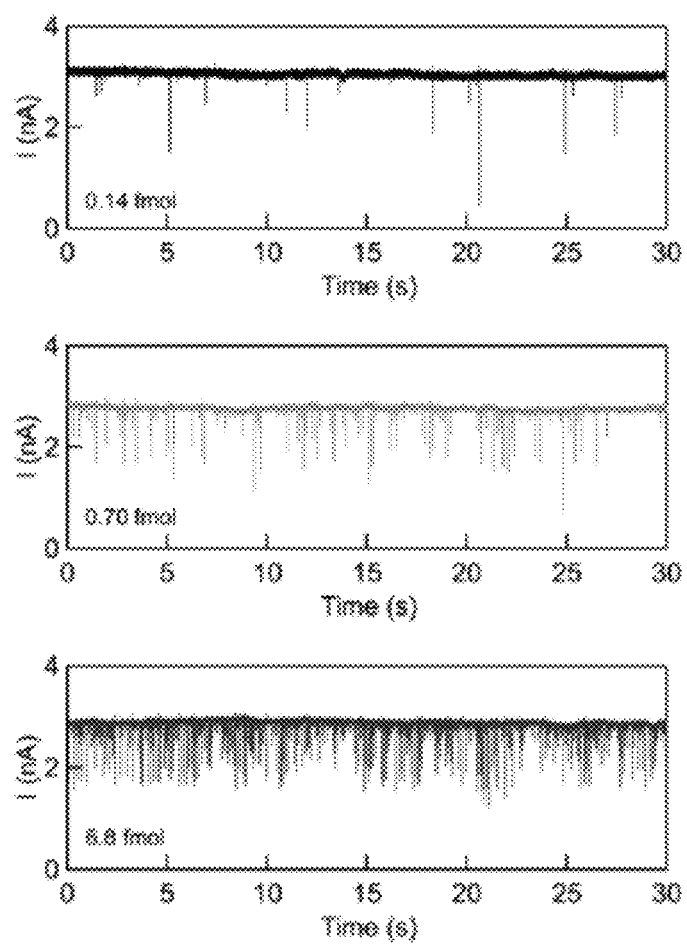
Figure 32:
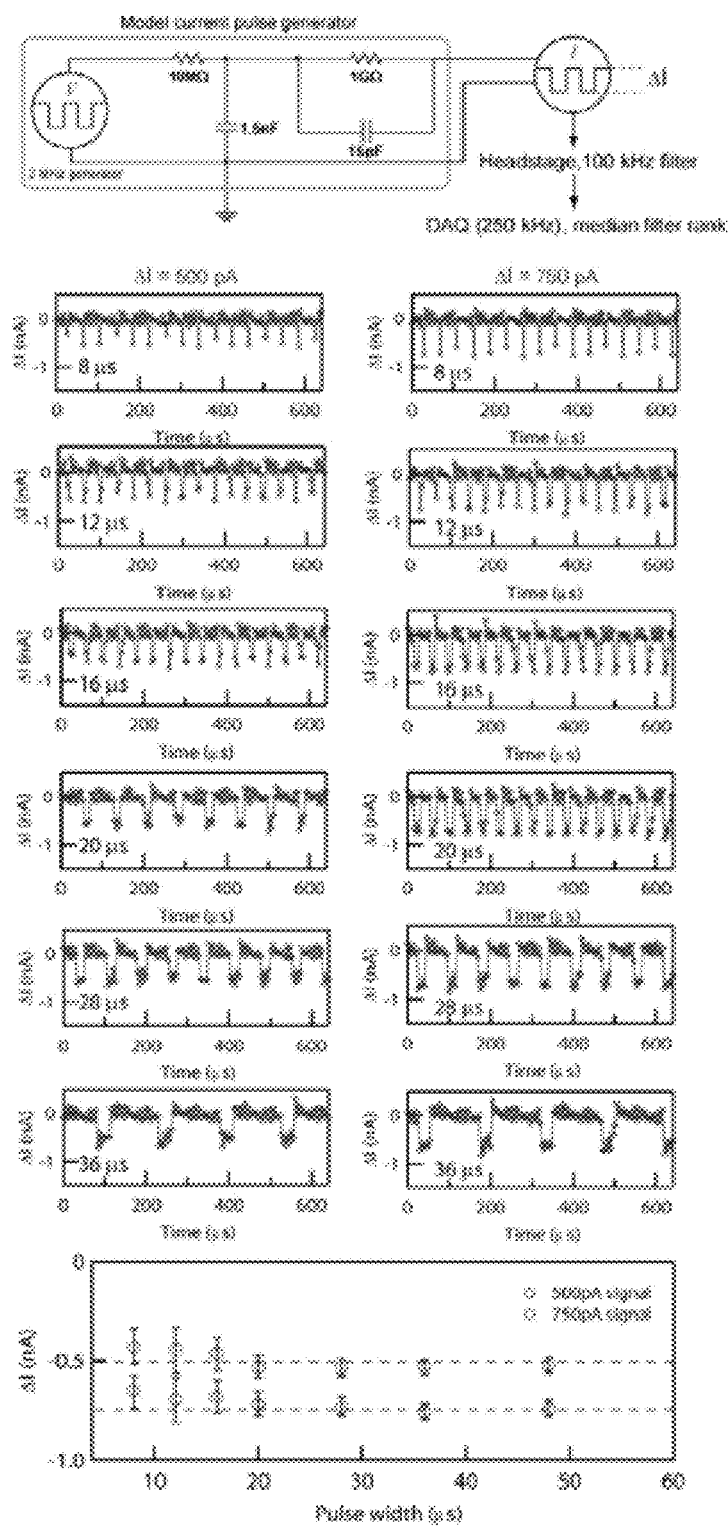
Figure 33:
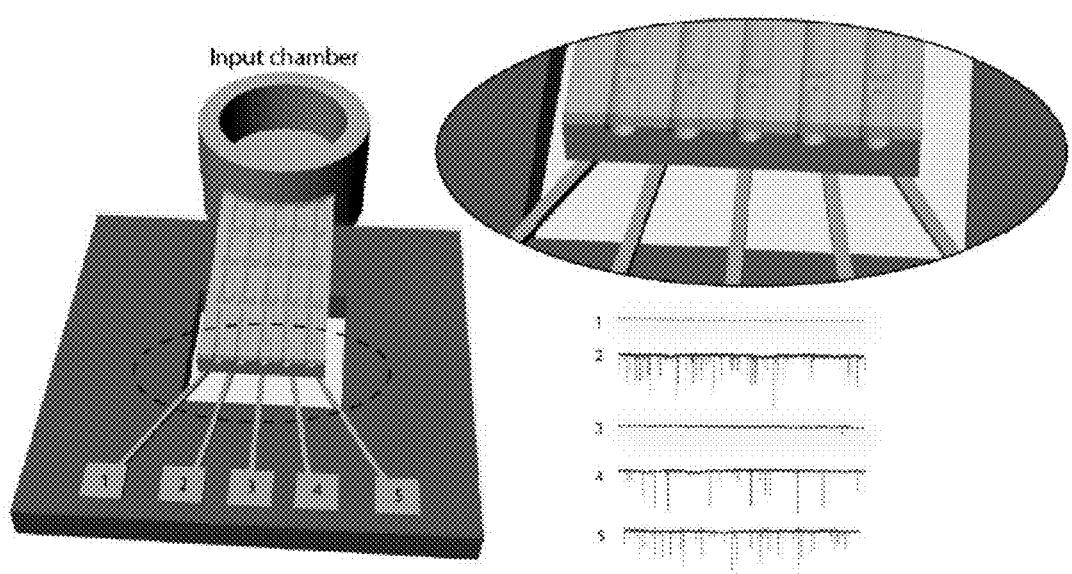
Figure 34:
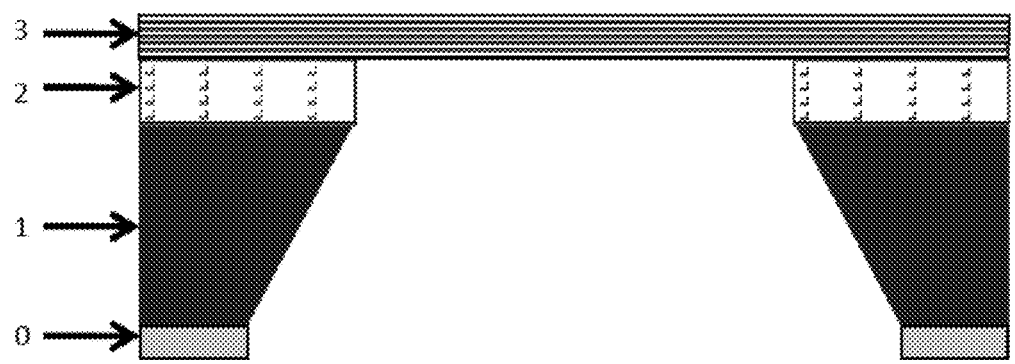
Figure 35:
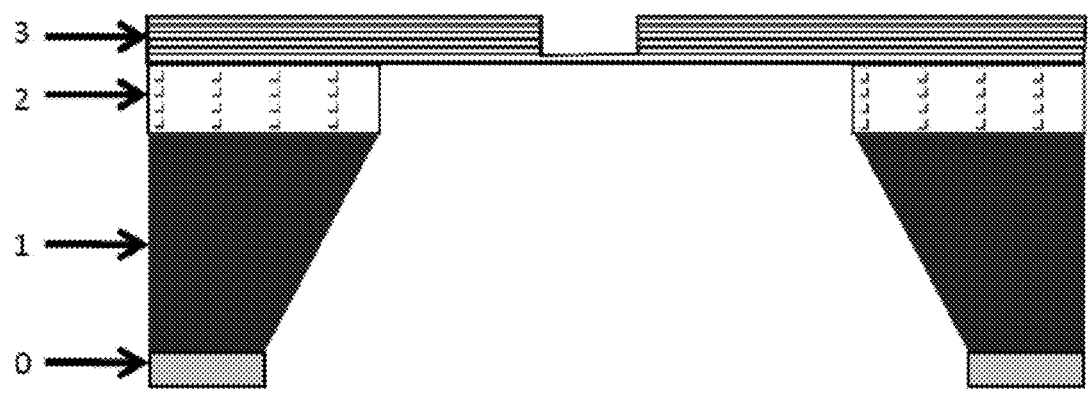
Figure 36:
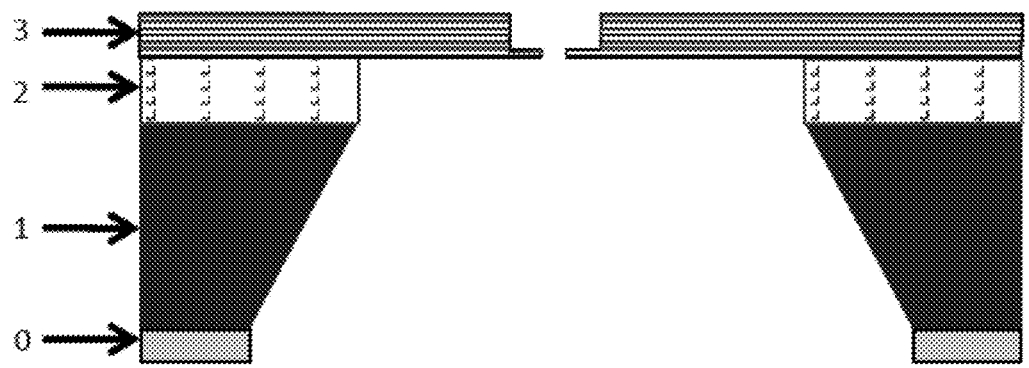
Figure 37:
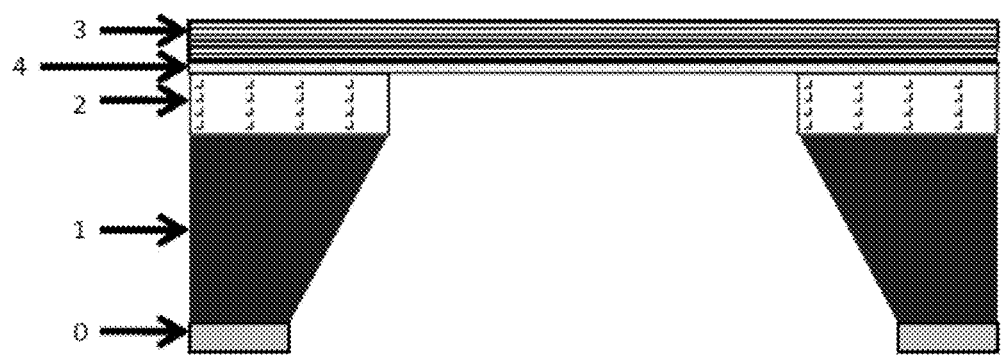
Figure 38:
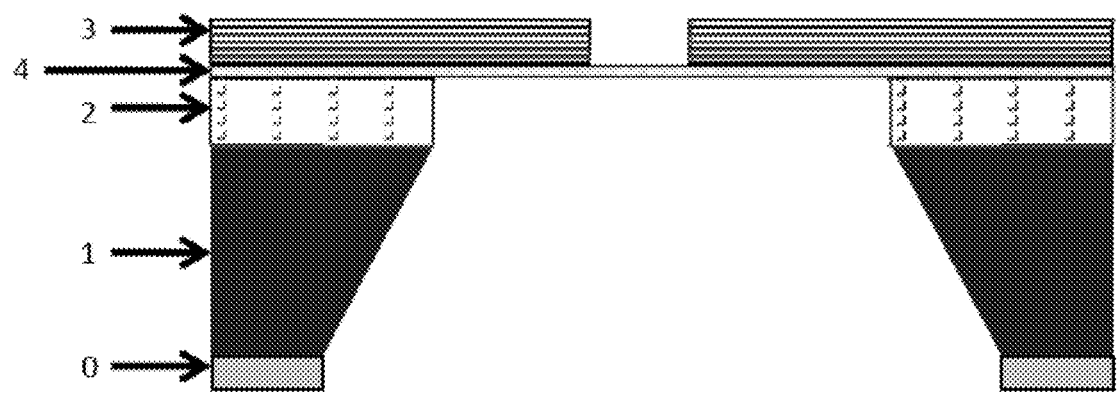
Figure 39:
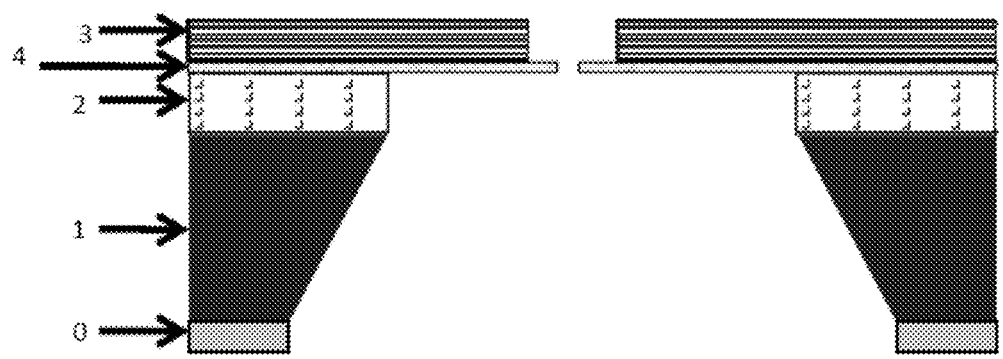
Figure 40:
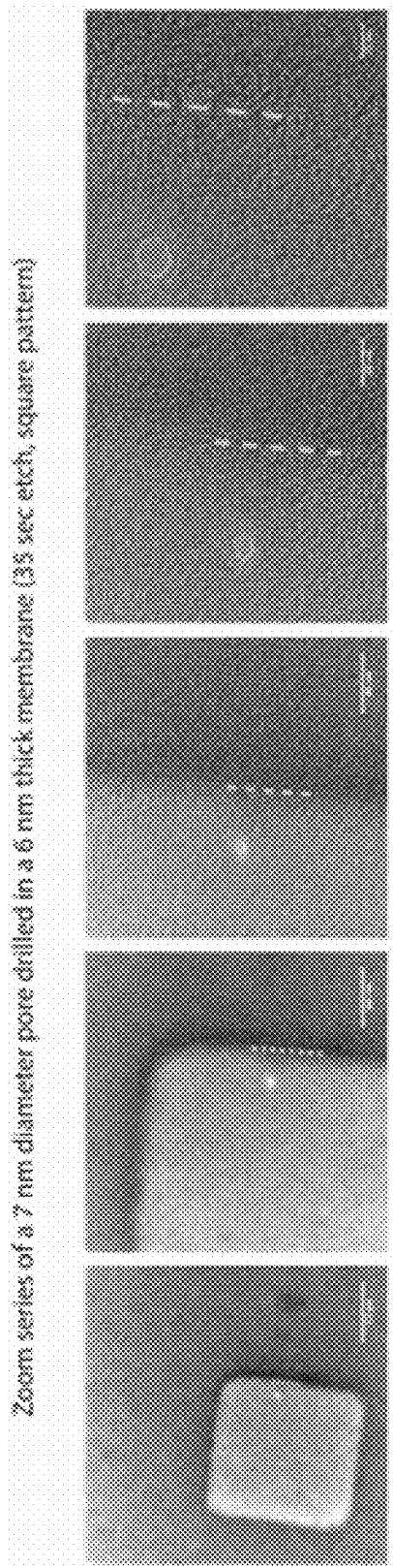

FIG. 21a illustrates a scheme for a miRNA-specific detection method. First, RNA is extracted from tissue (not shown; can be accomplished by lysing), and the extract is hybridized to a miRNA-specific oligonucleotide probe. In step (I), the probe:miRNA duplex is enriched by binding to p19-functionalized magnetic beads, followed by thorough washing in order to remove other RNAs from the mixture. In step (II) of FIG. 21a, the hybridized probe:miRNA duplex is eluted from the magnetic beads. While magnetic beads are illustrated here, other support materials—e.g., porous supports, strips, and the like—may also be used. In step (III), the eluted probe:miRNA duplex is electronically detected using a nanopore. FIG. 21b illustrates the detection of miR122a from rat liver RNA using a 3 nm diameter nanopore in a 7 nm thick membrane. The method shown in (a) was applied to detect miR122a from 1 μg of rat liver total RNA. Representative 30-second current vs. time traces are shown for a pore after the addition of the enriched miR122a (RL), a positive control containing a synthetic miR122a RNA duplex bound to magnetic beads, followed by washing, elution, and detection (PC), and four different negative controls (NC1-NC4, as described elsewhere herein). The negative controls did not produce any signal below the threshold, which was set to Io-0.4 nA (see dashed lines in FIG. 21b). FIG. 21c represents the quantification of miR122a from the mean capture rates. A calibration curve of capture rate vs. concentration was constructed (dashed line) using different concentrations of synthetic 22-bp RNA duplex, showing that capture rate scales linearly with concentration over three orders of magnitude. Determination of miR122a amounts (per μl solution) is based on the spike rate for sample RL ("RL" lines) and the positive control PC ("PC" lines). FIG. 21d illustrates the relative error in the determined RNA concentration as a function of the number of molecules counted by the nanopore. To achieve 95% accuracy under exemplary conditions, the time required for determination of 1 fmol RNA sample is 4 minutes, corresponding to ~250 translocation events;

FIG. 22 illustrates AFM images of the pattern shown in FIG. 18;

FIG. 23 illustrates the conductance as a function of time for pores with various diameters d and membrane thicknesses h, denoted as (d, h);

FIG. 24 illustrates a scatter plot of the mean current amplitude of each molecule (I) and the total transport time for 3 kbp dsDNA through 4 nm pores as a function of membrane thickness (h);

FIG. 25 illustrates a set of 10 bp translocations through a 3 nm diameter pore in a 7 nm thick membrane under 500 mV applied voltage, at a temperature of 0° C.;

FIG. 26 illustrates using a 3 nm diameter pore in a 7 nm thick membrane to discriminate among small nucleic acids of similar size, namely, 25 bp DNA (molecular weight=15 kD), 22 bp RNA (molecular weight=15 kD), and 76-nucleotide tRNA (molecular weight=25 kD);

FIG. 27 illustrates a quantitative analysis of a nanopore's ability to discriminate 25-bp DNA from 22-bp RNA based on current amplitudes;

FIG. 28 illustrates page/histograms for DNA and RNA events where in each plot is analyzed slices of the data that select all events with an indicated duration, in the range of 8-36 microseconds;

FIG. 29 illustrates shows 2-second current traces under different applied voltages of a 25 bp DNA sample analyzed using a 3 nm diameter pore fabricated in a 7 nm thick membrane (data taken at a temperature of 0° C.);

FIG. 30 illustrates current vs. time traces for a 3 nm diameter pore at a measured at a voltage of 500 mV and a temperature of 0° C., when different concentrations of DNA were added to the pore (expressed as fmol/µl solution);

FIG. 31 illustrates continuous time traces for a 3 nm diameter pore measured at a voltage of 500 mV and a temperature of 0° C., when different concentrations of RNA were added to the pore (expressed as fmol/µl solution);

FIG. 32 illustrates the response of an exemplary, non-limiting amplifier to synthetic current pulses in the range 8-48 s;

FIG. 33 illustrates an exemplary, non-limiting device analyte (e.g., miRNA) isolation and detection;

FIG. 34 illustrates a plan view of an exemplary device before processing, cross-section view;

FIG. 35 illustrates plan view of the device after processing/thinning the thin membrane;

FIG. 36 illustrates an exemplary device after processing a pore in a thinned membrane;

FIG. 37 illustrates an exemplary device;

FIG. 38 illustrates an exemplary device having a cavity formed above a thin membrane;

FIG. 39 illustrates the device of FIG. 39 having a nanopore formed in the thin membrane; and FIG. 40 illustrates images of a thin membrane region (light-color region; useful as a sample support in microscopy applications) and a thicker support material (darker color region).

Figure 6:
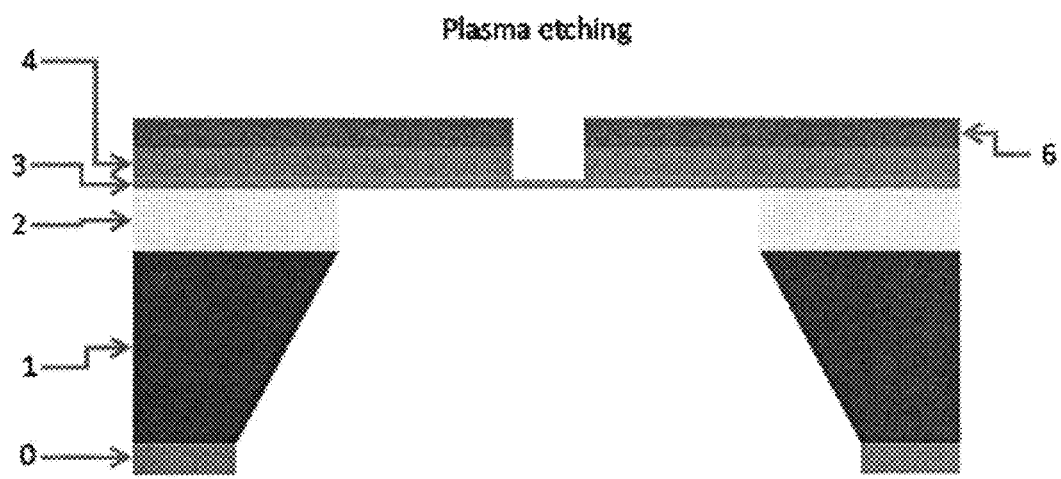
FIG. 6 depicts a device according to the claimed invention in an intermediate, nanopore-free stage of fabrication where capping material (4) is removed.
Figure 41:
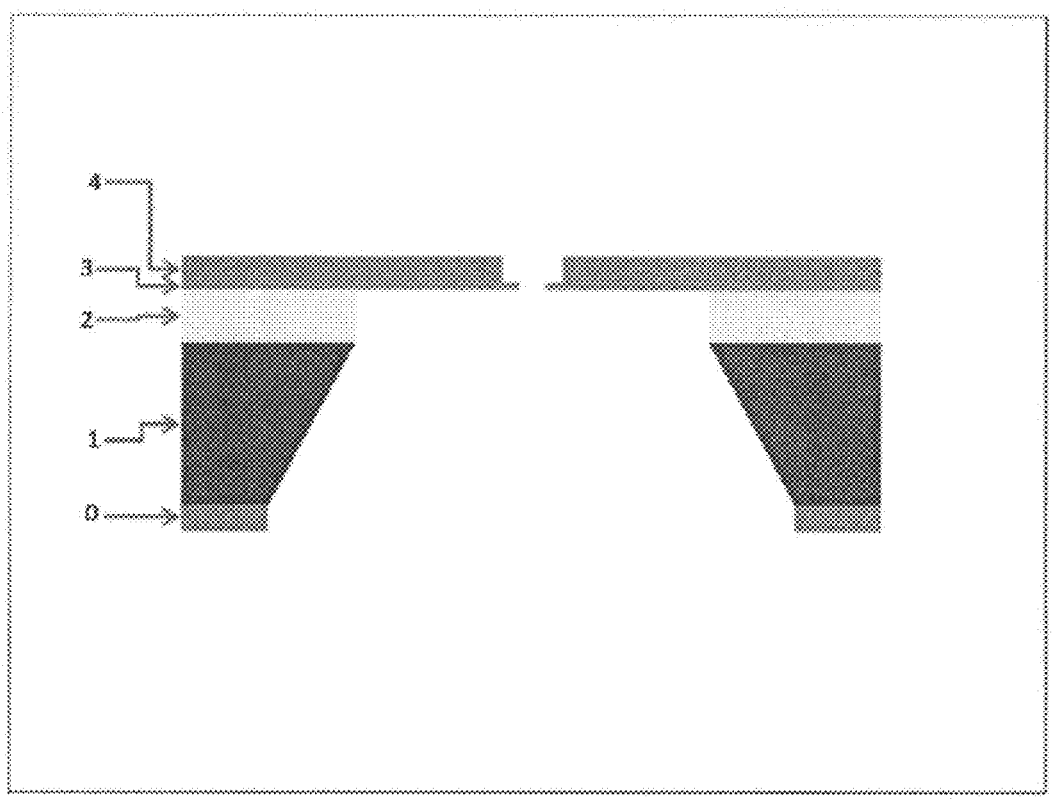
Figure 42:
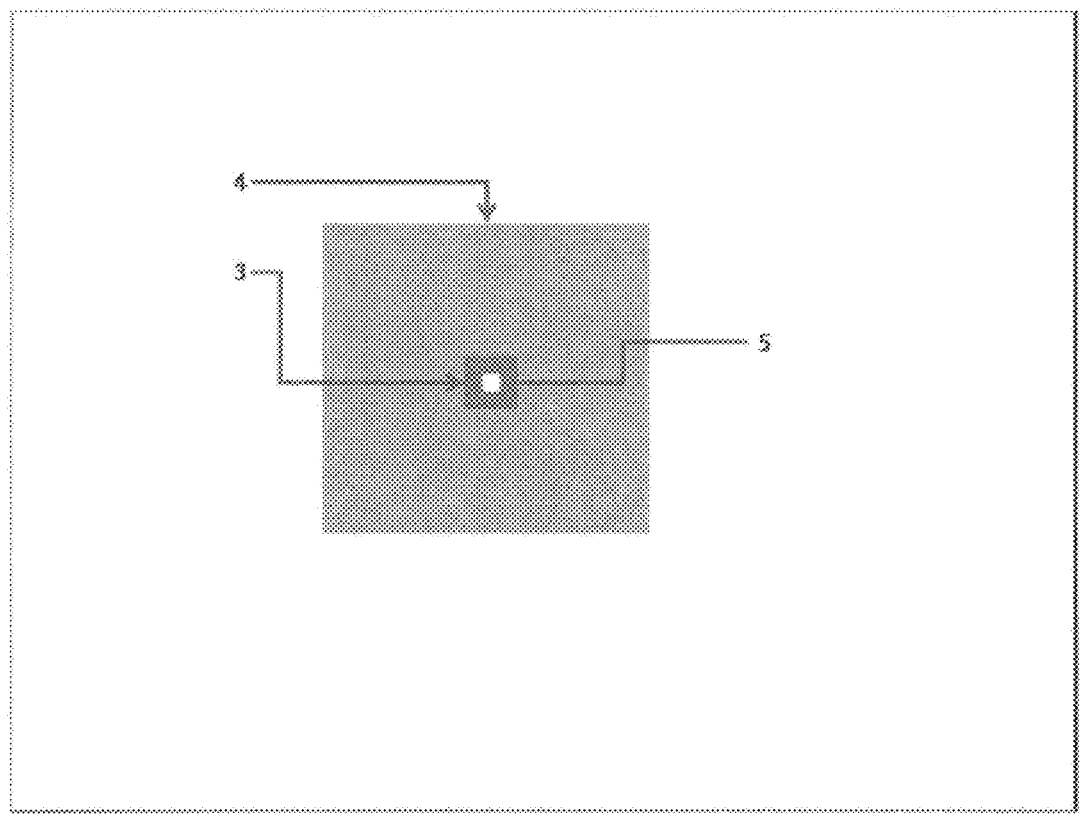
Figure 43:
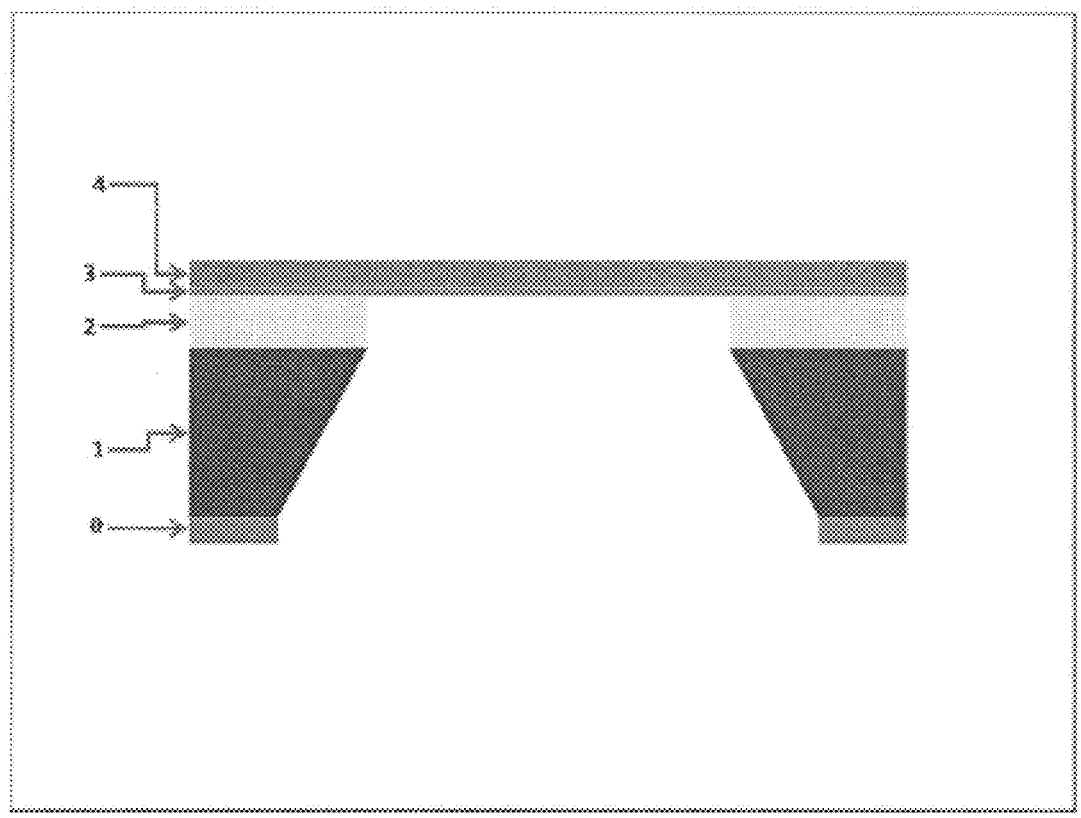
Figure 44:
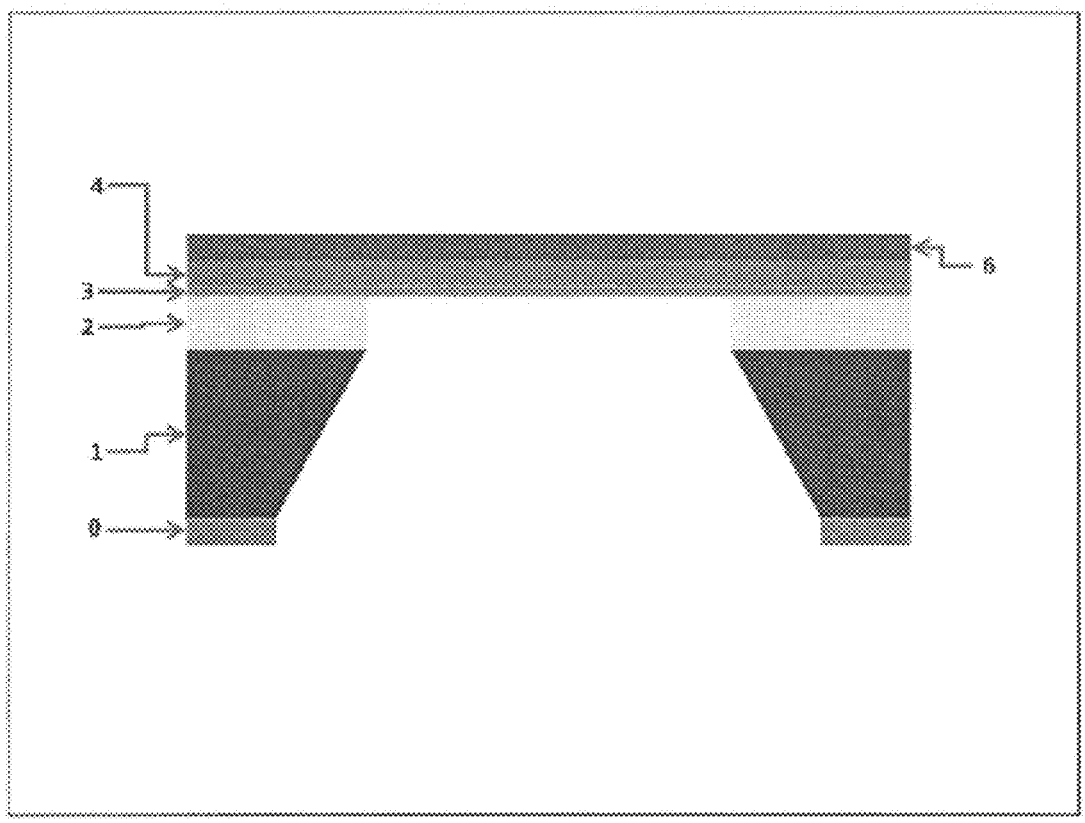
Figure 45:
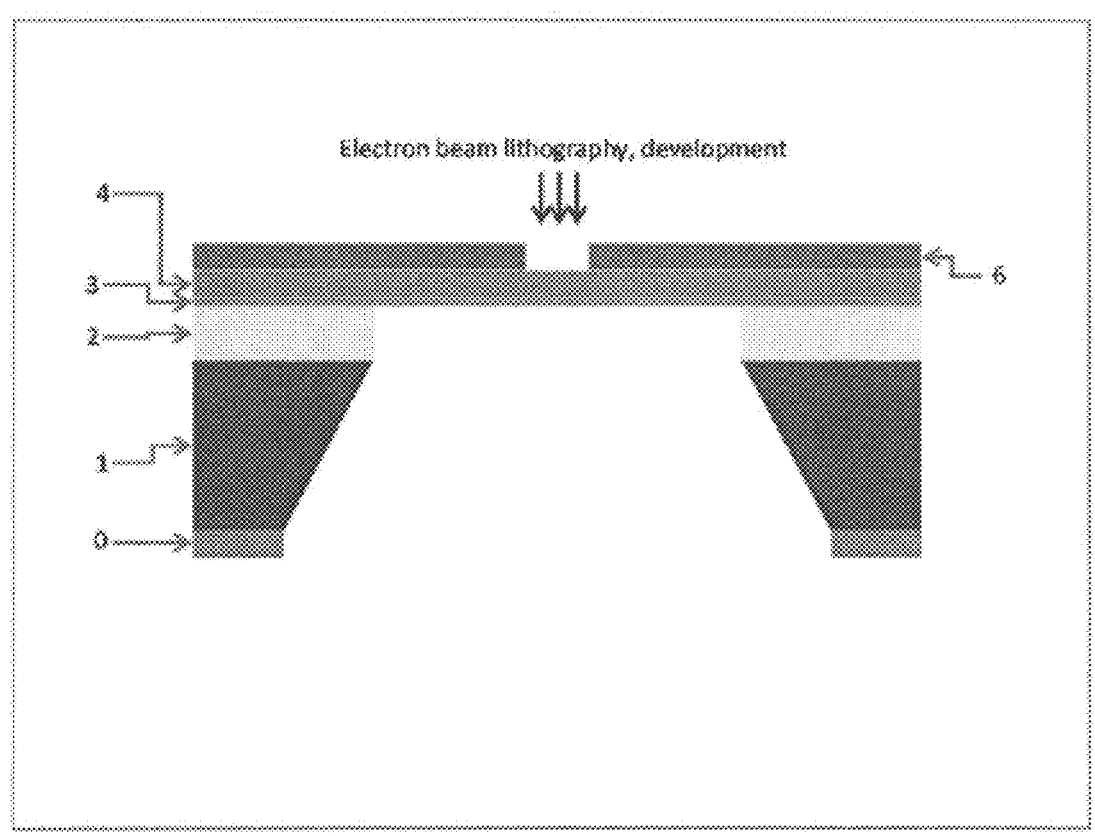
Figure 46:
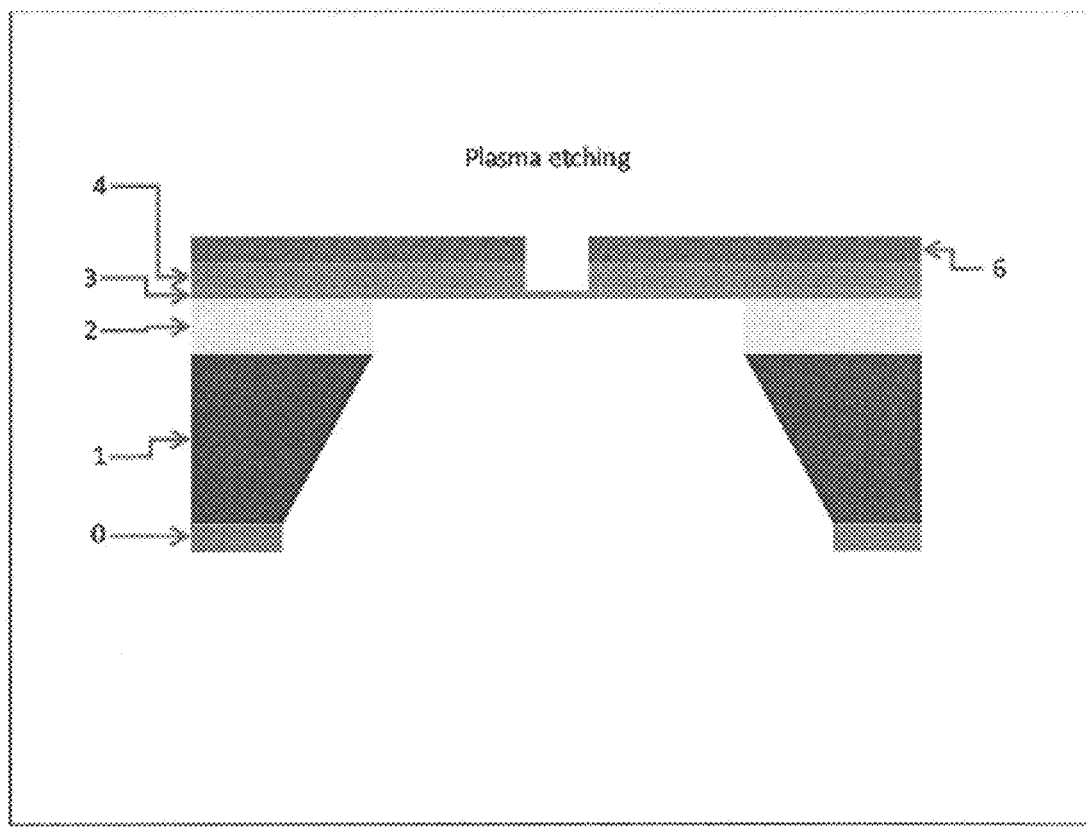
Figure 47:
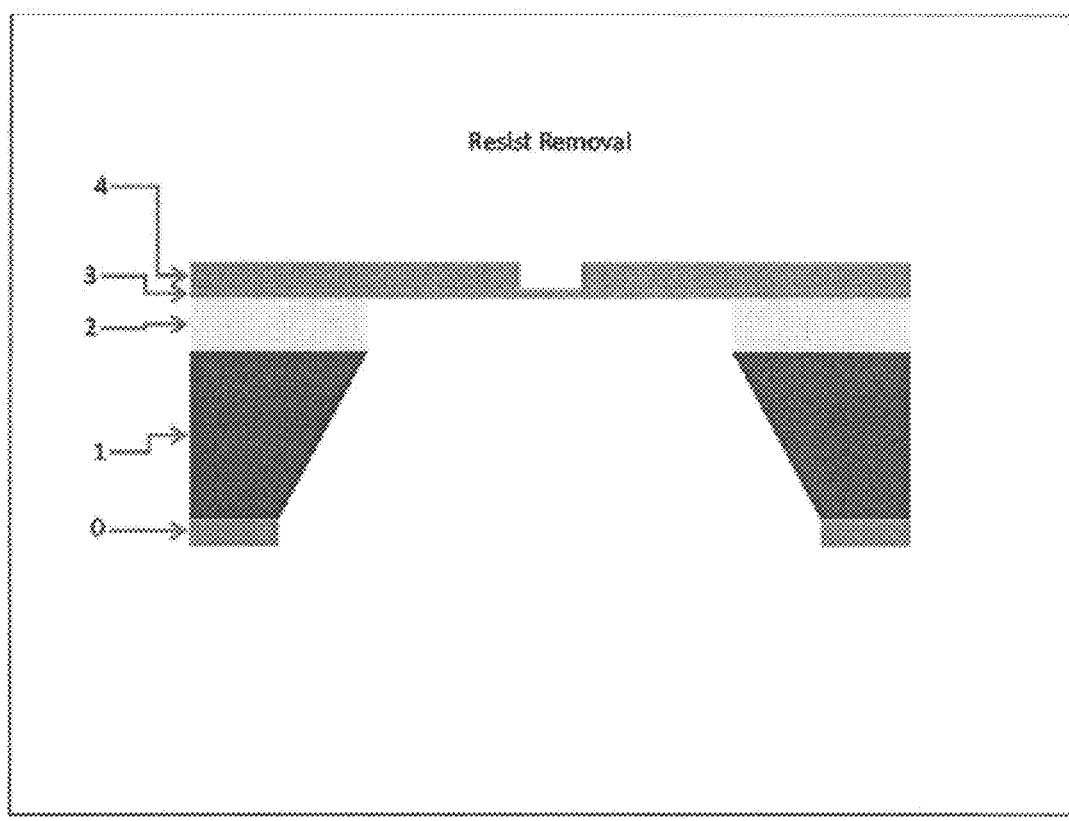
Figure 48:
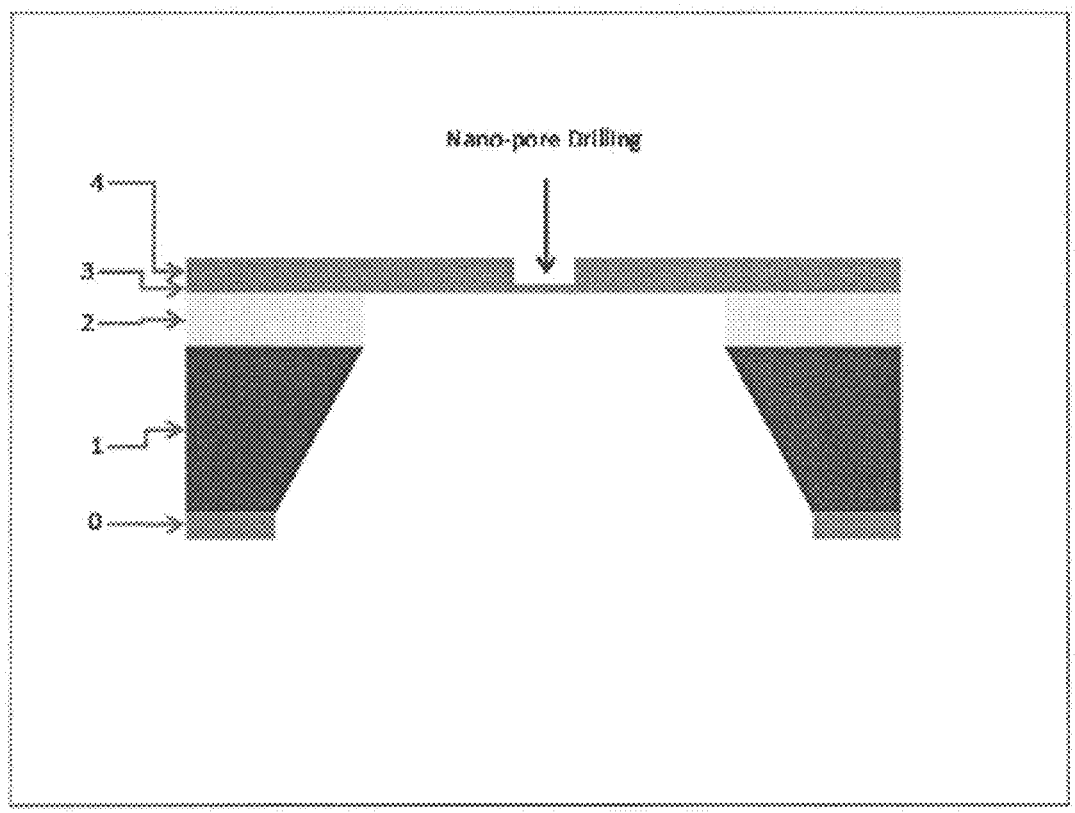
Figure 49:
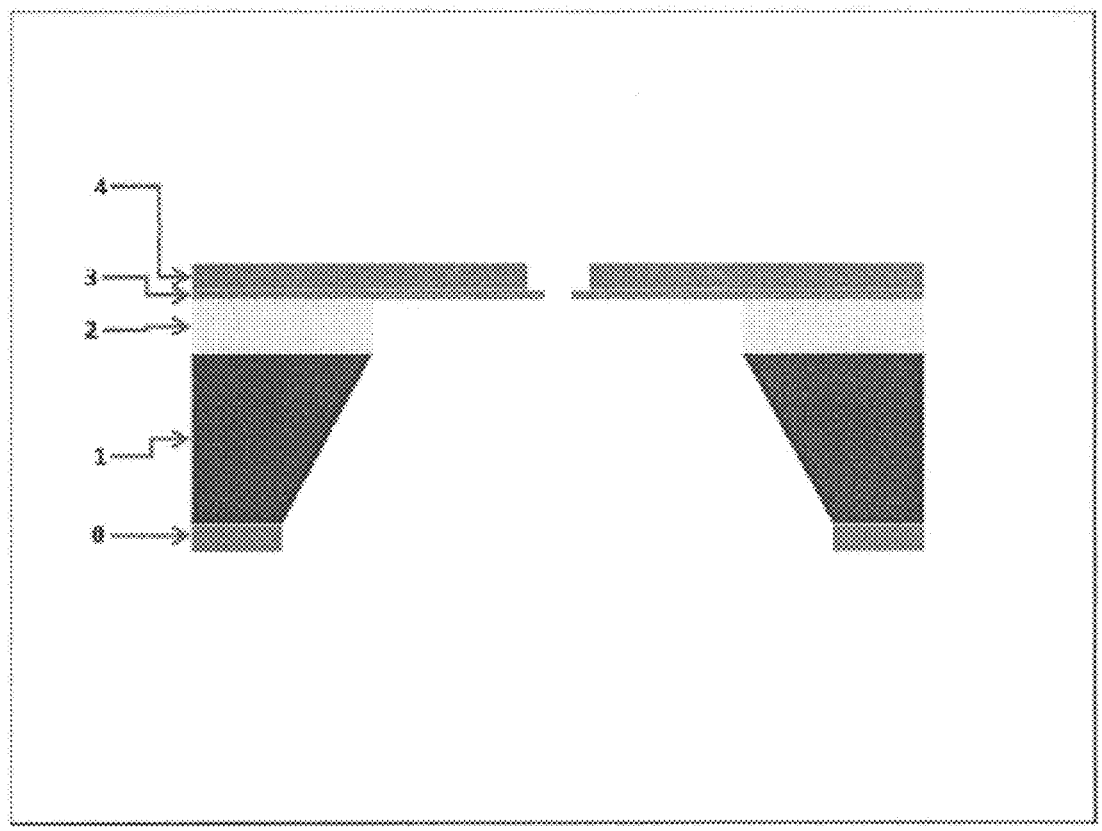
Figure 50:
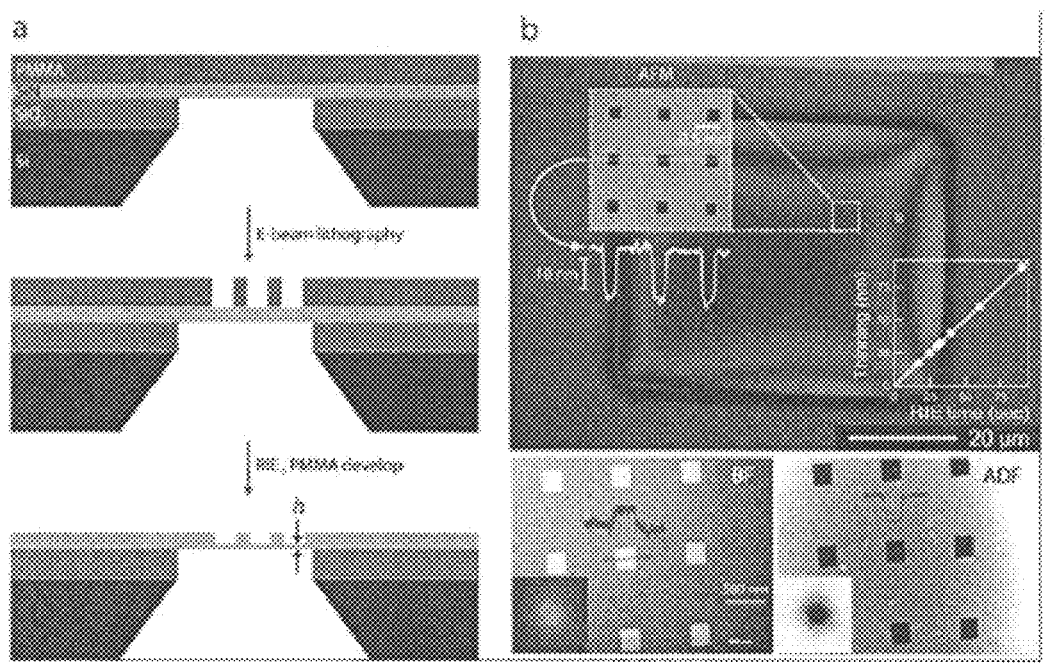

FIG. 41 depicts a completed device according to the claimed invention;

FIG. 42 depicts a top-down view of a device according to the claimed invention;

FIG. 43 depicts a device according to the claimed invention in an intermediate, nanopore-free stage of fabrication;

FIG. 44 depicts a device according to the claimed invention in an intermediate, nanopore-free stage of fabrication where resist material (6) is present atop the capping layer (4);

FIG. 45 depicts a device according to the claimed invention in an intermediate, nanopore-free stage of fabrication where resist material (6) is removed;

FIG. 46 depicts a device according to the claimed invention in an intermediate, nanopore-free stage of fabrication where capping material (4) is removed;

FIG. 47 depicts a device according to the claimed invention in an intermediate, nanopore-free stage of fabrication where resist material present in FIG. 6 has been removed;

FIG. 48 depicts a device according to the claimed invention in an intermediate, nanopore-free stage of fabrication where nanopore drilling has been initiated;

FIG. 49 depicts a device according to the claimed invention where a nanopore has been formed in the membrane (3);

FIG. 50 illustrates (a) a process for local thinning of solid-state membranes for improving the nanopore resolution, (b) optical microscope image of a pattern of squares used for thinning experiments. Following RIE process and lift-off, AFM image of the 250 nm squares is shown in the inset (17 nm thinning). The thinning was checked for different RIE times and shows excellent linearity (slope: 1 nm/sec). The bottom shows bright-field (BF) and annular dark field (ADF) images of the etched membranes, as well as corresponding images for a 10 nm pore (inset). The intensity profiles shown adjacent to the square-shaped pores highlight the exceptional contrast of ADF imaging, useful for accurate thickness determination.

Figure 51:
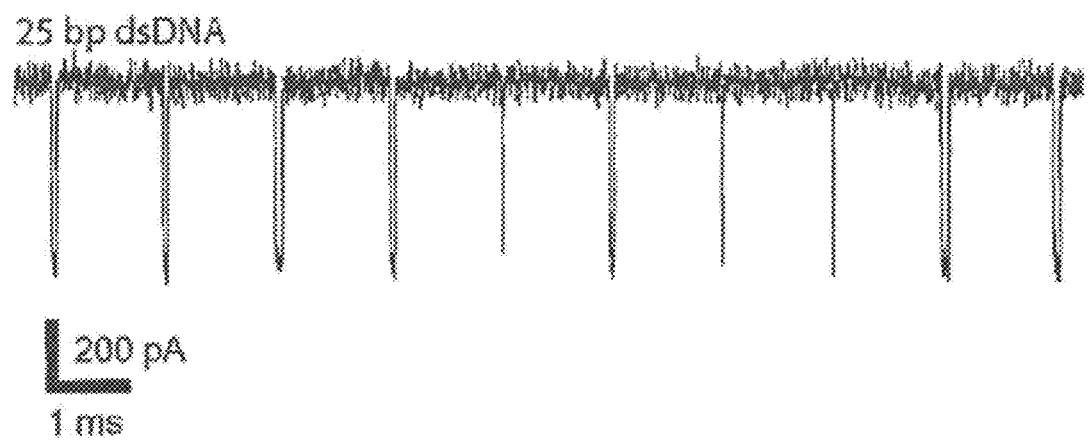

FIG. 51 illustrates the detection of 25 bp dsDNA using a 3 nm solid-state nanopore according to the claimed invention in a 20 nm thick SiN membrane (T=0° C., V=300 mV). Concatenated single-molecule traces are shown. The small pore and low temperature combination facilitates detection of these short molecules (mean transport time=80 microseconds), an important step for detecting RNA-drug complexes in design-RNA sequences, such as the ribosomal A-site and the TAR site of HIV RNA;

FIG. 52 illustrates Increasing the measurement resolution by nanopore thinning. (a) Concatenated sets of ~200 translocations of 3 kb linear double-stranded DNA through 4 nm diameter pores fabricated in membranes with different h values; $h_{eff}$ is the nanopore's effective thickness used in the geometric model discussed in the text. In decreasing h from 60 nm to 6 nm, the open pore current increased and the DNA signal amplitude increased. All traces were filtered using the Axopatch 100 kHz filter setting. For h=60 nm, the data was low-pass filtered at 10 kHz using the Axopatch filter to make events visible. (b) A magnified view of the traces in (a). (c) Semi-log histograms of the blocked current amplitudes normalized by subtracting delta I, which show increased current amplitudes for thinner nanopores. While the most probable blocked current $\Delta I_p$ increased with decreasing h, open pore noise values were similar. (d) Dependence of average experimental $<I_o>$ (circles) and the most probable DNA current amplitude $\Delta I_p$ (triangles) on h. The dashed line is a fit using Eqn. 1 to the average $I_o$ data from combined data of ~20 pores, which yields an effective pore thickness $h_{eff}=h/(3.04\pm0.30)$ ($h_{eff}$ scale shown on top x-axis). The fit to $\Delta I_p$ values (dashed line) is based on a geometric model described in detail herein. The inset shows $\Delta I_p/<I_o>$, which did not change appreciably with h. The inset's dashed line is the ratio of the fits to $\Delta I_p$ and $<I_o>$ from the main plot. (e) The signal-to-noise (S/N) and mean transport time as a function of h ($h_{eff}$ shown on top x-axis). One may define S/N=$\Delta I/I_{RMS}$, where $I_{RMS}$ at 100 kHz bandwidth is 75±5 pA. Mean transport times were obtained from the dwell-time distributions.

Figure 16:
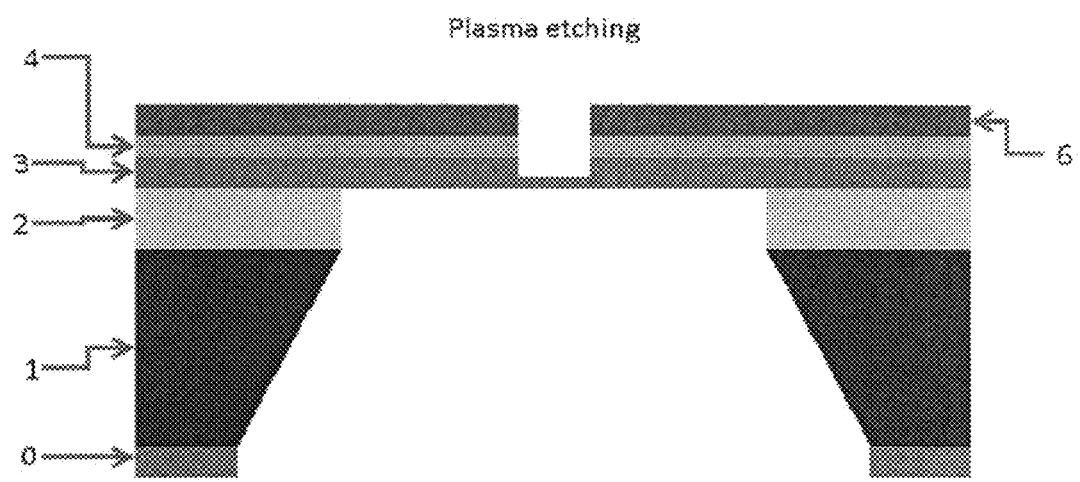
FIG. 16 illustrates removal of the capping layer (4) and membrane (3) so as to "thin" a region of the membrane layer (3)
Figure 53:
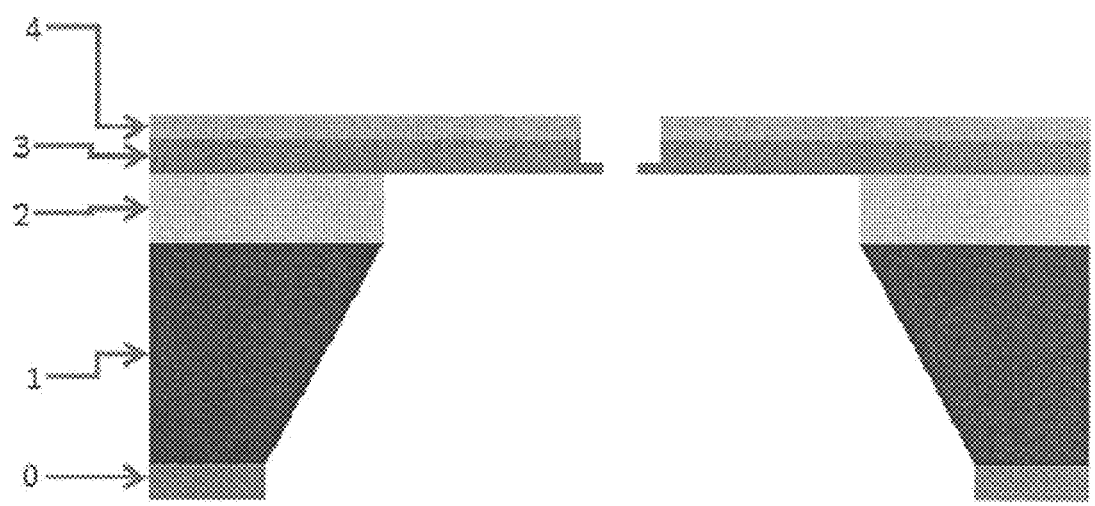
Figure 54:
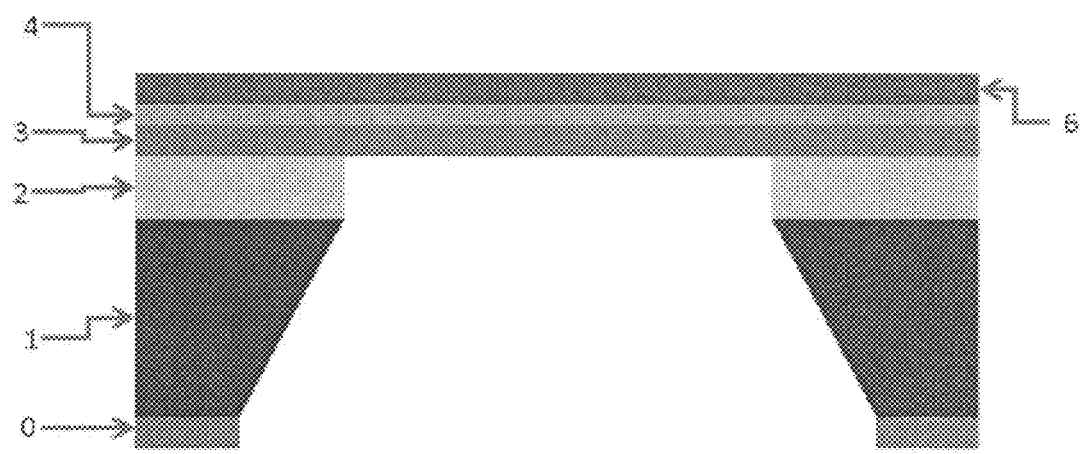
Figure 55:
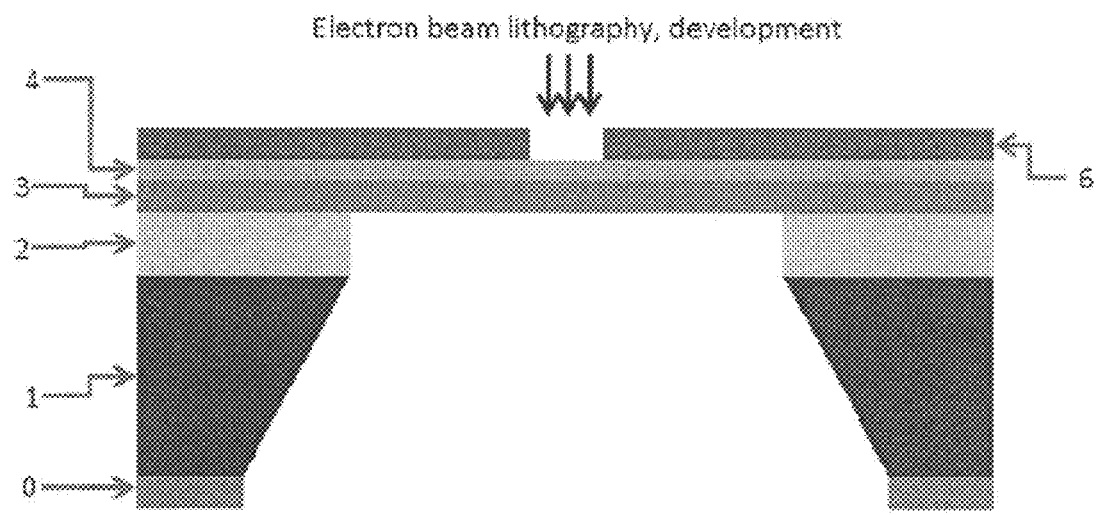
Figure 56:
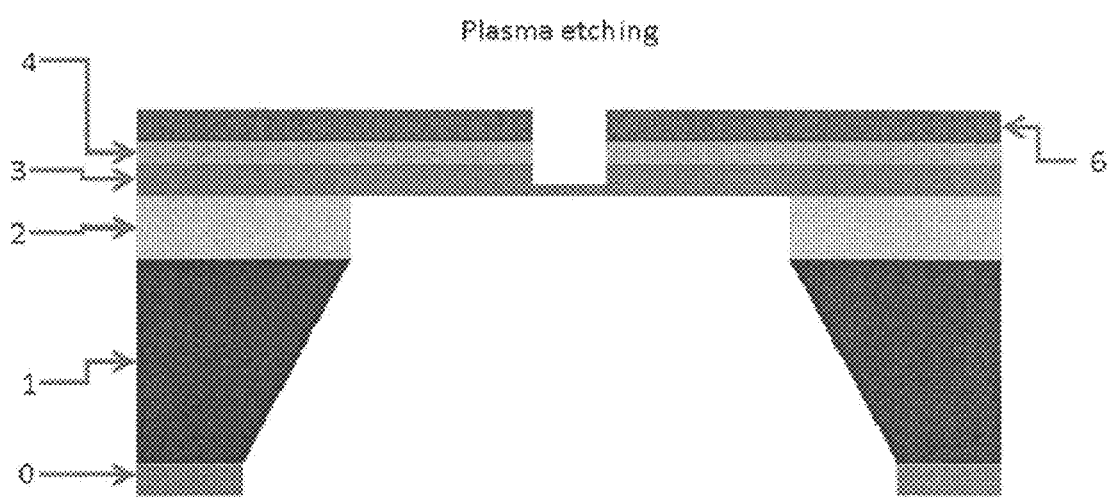
Figure 57:
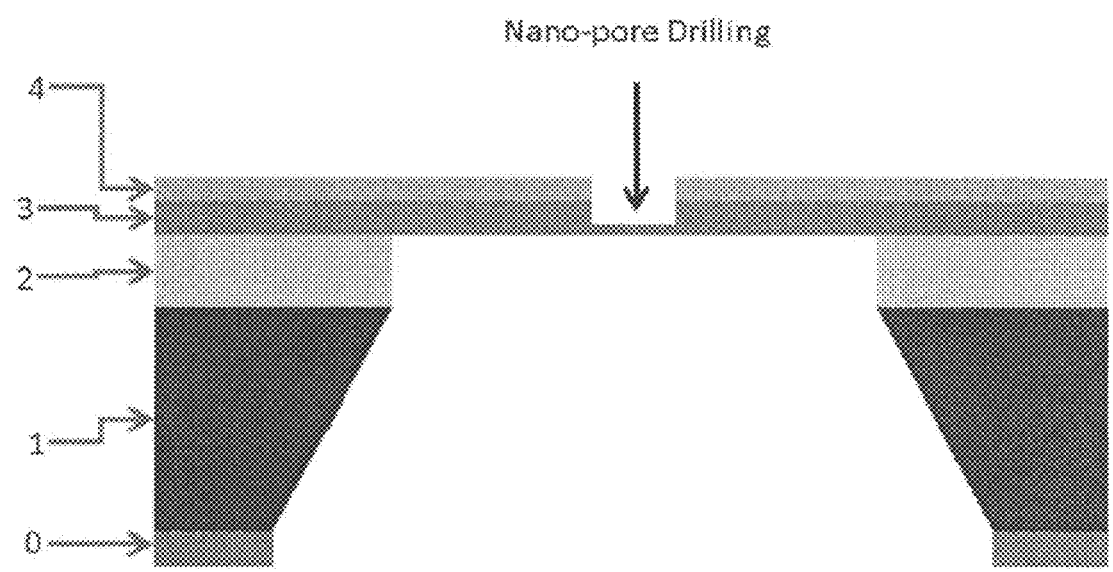

FIG. 53 depicts an embodiment of the claimed invention wherein a nanopore has been formed in a locally thinned region of the membrane material (3);

FIG. 54 depicts an intermediate stage of nanopore device fabrication where a resist (6) is disposed atop a capping layer (4) and a membrane material (3). A dielectric layer (2), support layer (1), and additional support (0) are also present;

FIG. 55 illustrates electron beam removal of the resist material;

FIG. 56 illustrates removal of the capping layer (4) and membrane (3) so as to "thin" a region of the membrane layer (3);

FIG. 57 illustrates the formation ("drilling") of a nanopore in the thinned membrane region of FIG. 16;

FIG. 58 illustrates sub-10 nm thick solid-state nanopore sensors. (a) Scheme of a nanopore sensor showing a DNA molecule translocating through the pore (not to scale). The sensor consists of a 5×5 mm2 Si chip that contains a free-standing silicon nitride (SiN) membrane (~50×50 µm2). After locally thinning the membrane using the process shown in (b), a nanopore is drilled using a TEM (see TEM image of a 4 nm diameter nanopore in 6 nm thick membrane). Electrolyte solution is added above and below the nanopore, each contacted by a Ag/AgCl electrode, and voltage is applied to drive charged biomolecules through the pore. (b) The membrane thinning process involves coating the membrane with a PMMA resist, followed by e-beam exposure and development, and controlled dry etching using SF6 plasma. (c) Optical image of the membrane after thinning (before removal of the PMMA). The inset shows an AFM topography image of a 3×3 square array following PMMA removal, as well as a line profile that shows uniform, 17 nm deep trenches. The inset shows that the etch depth, measured by AFM, is a linear function of the etch time and that the etch rate is 1 nm/s. (d) Epi-fluorescence image of a 41 nm thick SiN membrane in which 5 μm squares were thinned to 8 nm ($\lambda$ex=488 nm, $\lambda$em=525±25 nm). The fluorescence intensity histograms show lower fluorescence background in the thinned region;

FIG. 59 illustrates scanning TEM (STEM) characterization of a 4.5 nm diameter pore in a 7 nm thick membrane (STEM probe size=0.2 nm). (Left) A bright-field STEM (BF-STEM) image shows the etched 250×250 nm square as a brighter area with uniform intensity. (Right) Annular dark-field STEM (ADF-STEM) of a zoomed-in portion of the nanopore on the left. The height profile (data trace line on FIG. 19a) of a line through the center of the pore is shown. The membrane thickness h (y-axis) was measured from the difference of the initial membrane thickness and the etch depth (see text), normalized by assigning a thickness of 0 nm to the signal intensity at the pore (i.e., in vacuum).

FIG. 60 illustrates discrimination among small nucleic acids using thin nanopores. (a) Continuous current vs. time traces from a 3 nm diameter pore in a 7 thick membrane measured at 0° C., V=500 mV (TEM image of pore is shown). Traces were median-filtered with rank of 1 in order to improve the signal-to-noise. Based on the conductance, the effective pore thickness heff=2.3 nm. The analyte chamber contains 25-bp dsDNA (left), 22-bp dsRNA (middle), or phenylalanine tRNA (right), at concentrations of ~80 fmol/μl. Sample events are shown above the continuous traces, and models based on crystal structures are shown to the right.

Figure 60A:
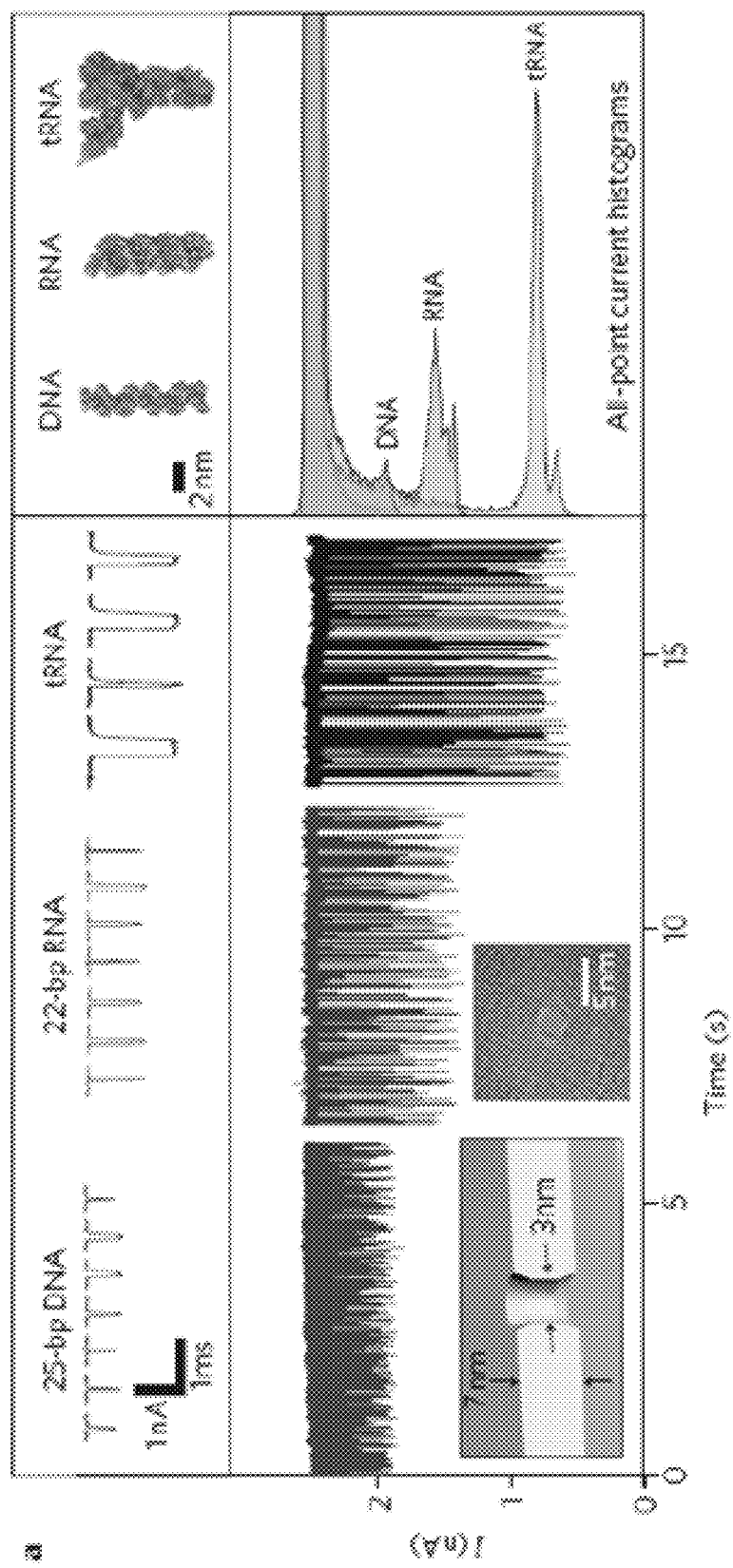

The all-point current histograms on the bottom right of FIG. 60a show that molecules can be distinguished based on their current amplitudes. The mean transport times for the DNA, RNA, and tRNA molecules are 20 μs, 50 μs, and 1.04 ms, respectively. Part (b) of this figure shows the relationship of the capture rate on applied voltage for 25-bp DNA and 22-bp RNA. The exponential dependence reveals that capture is voltage-activated. The lines in FIG. 60b are exponential fits to the data. Part (c) of the figure is a log-log plot of capture rate vs. DNA concentration. Linearity is observed for three orders of magnitude in DNA concentration, as indicated by a power-law fit exponent of 1.05+/−0.03;

FIG. 61 illustrates microRNA detection using solid-state molecular counters. Detection (of miRNA or of other analytes) can include counting events (e.g., analyte passages) at the nanopore. The counted events can be correlated to a property of the source of the analyte. For example, the user may construct a calibration curve that allows them to relate the number of passage events to the concentration of an analyte in a sample.

Figure 61A:
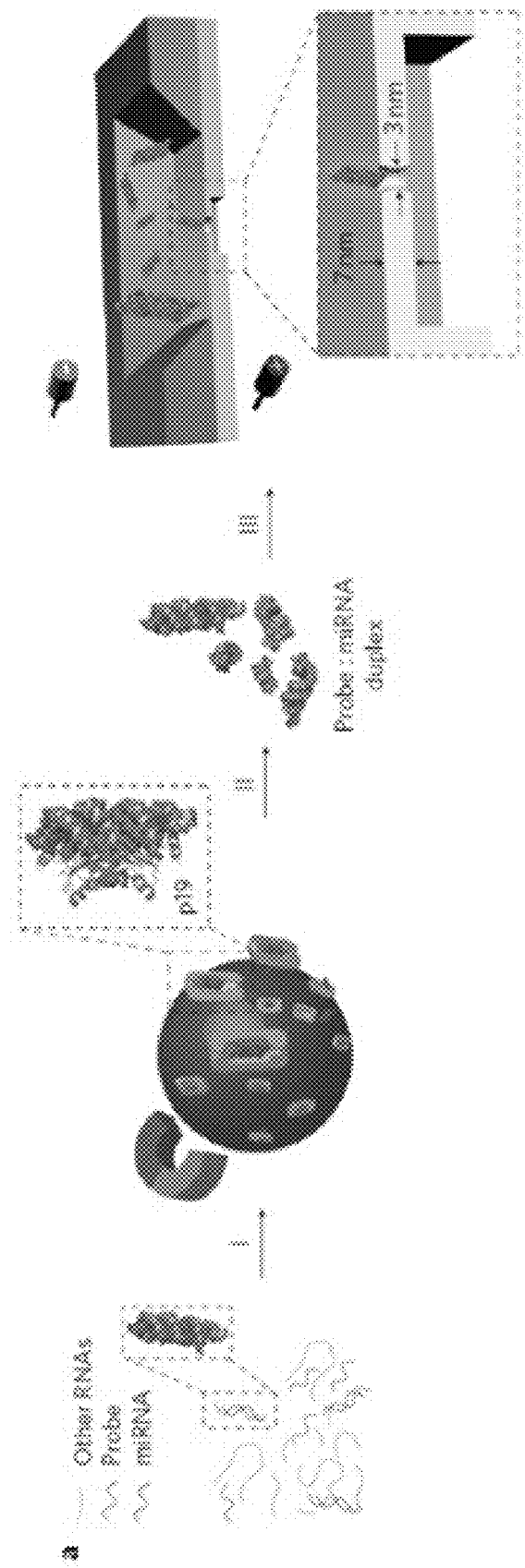
Figure 61B:
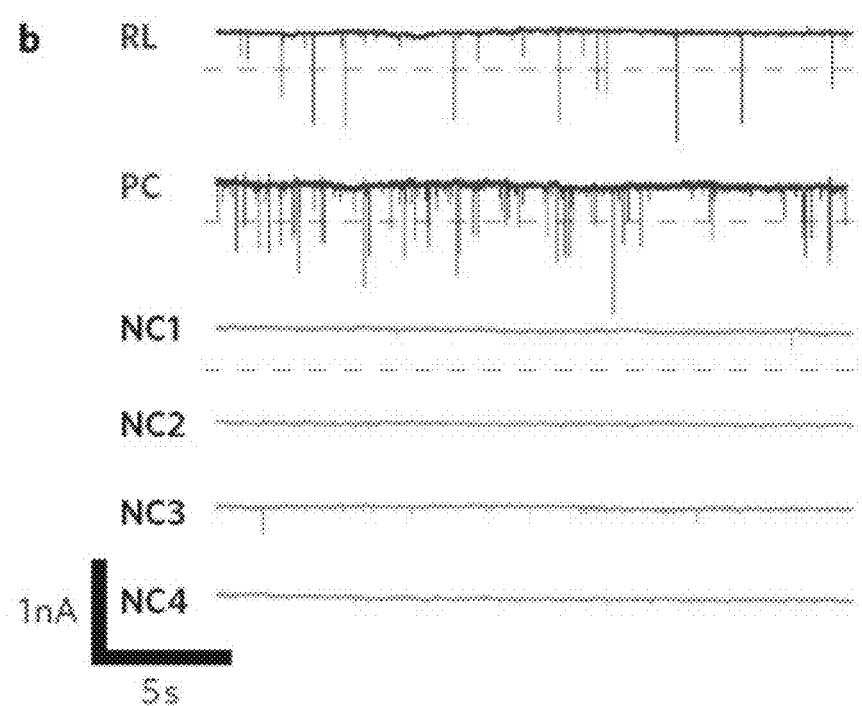
Figure 61D:
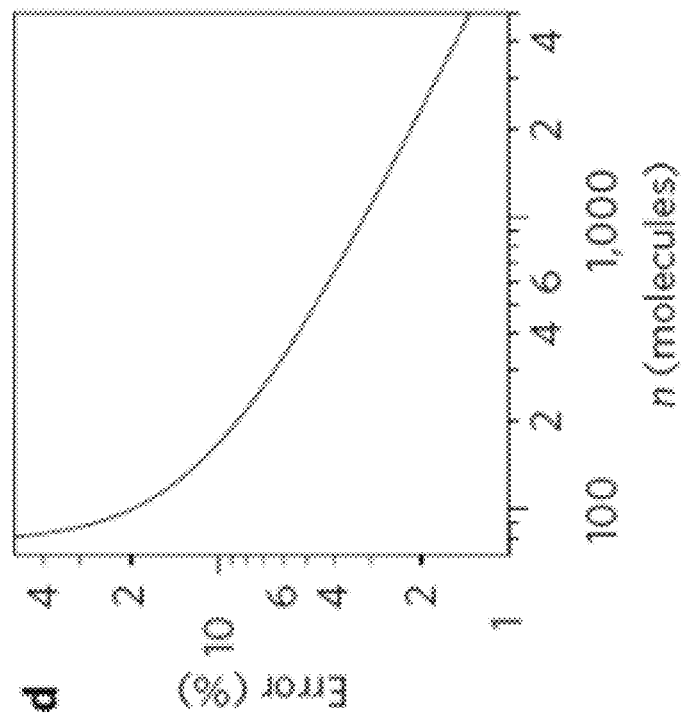
Figure 61C:
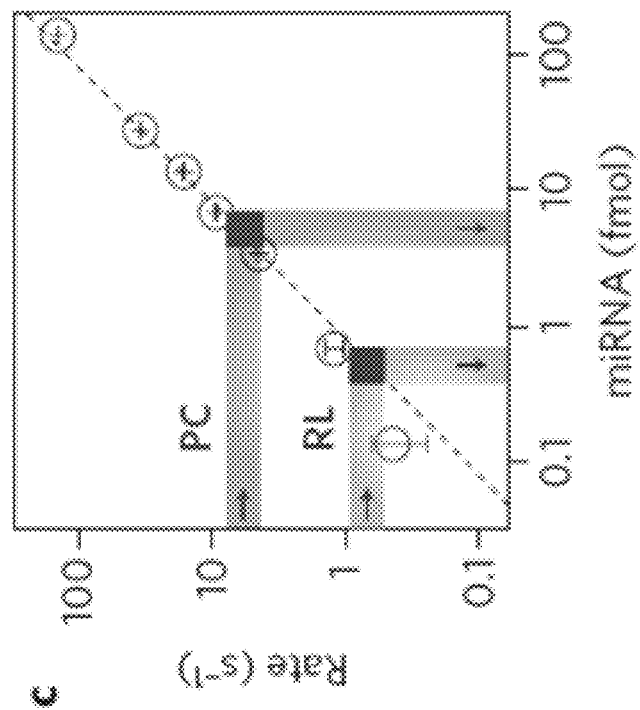
Figure 62:
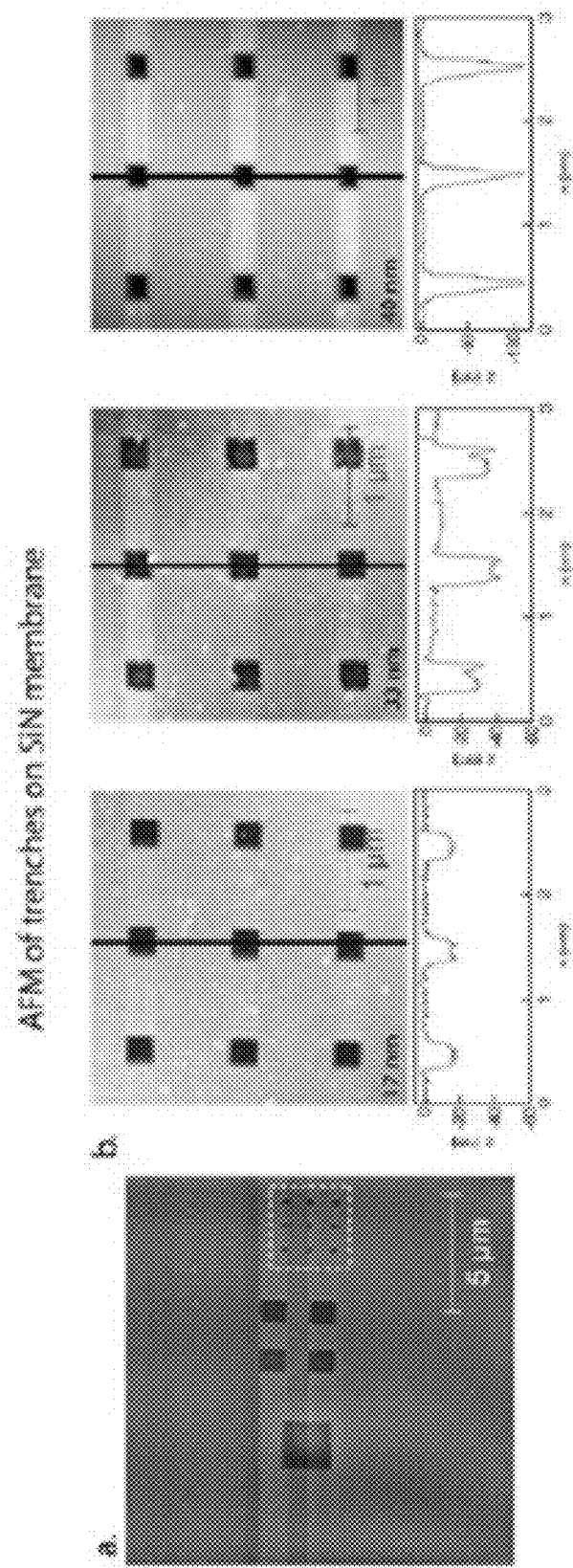
Figure 63:
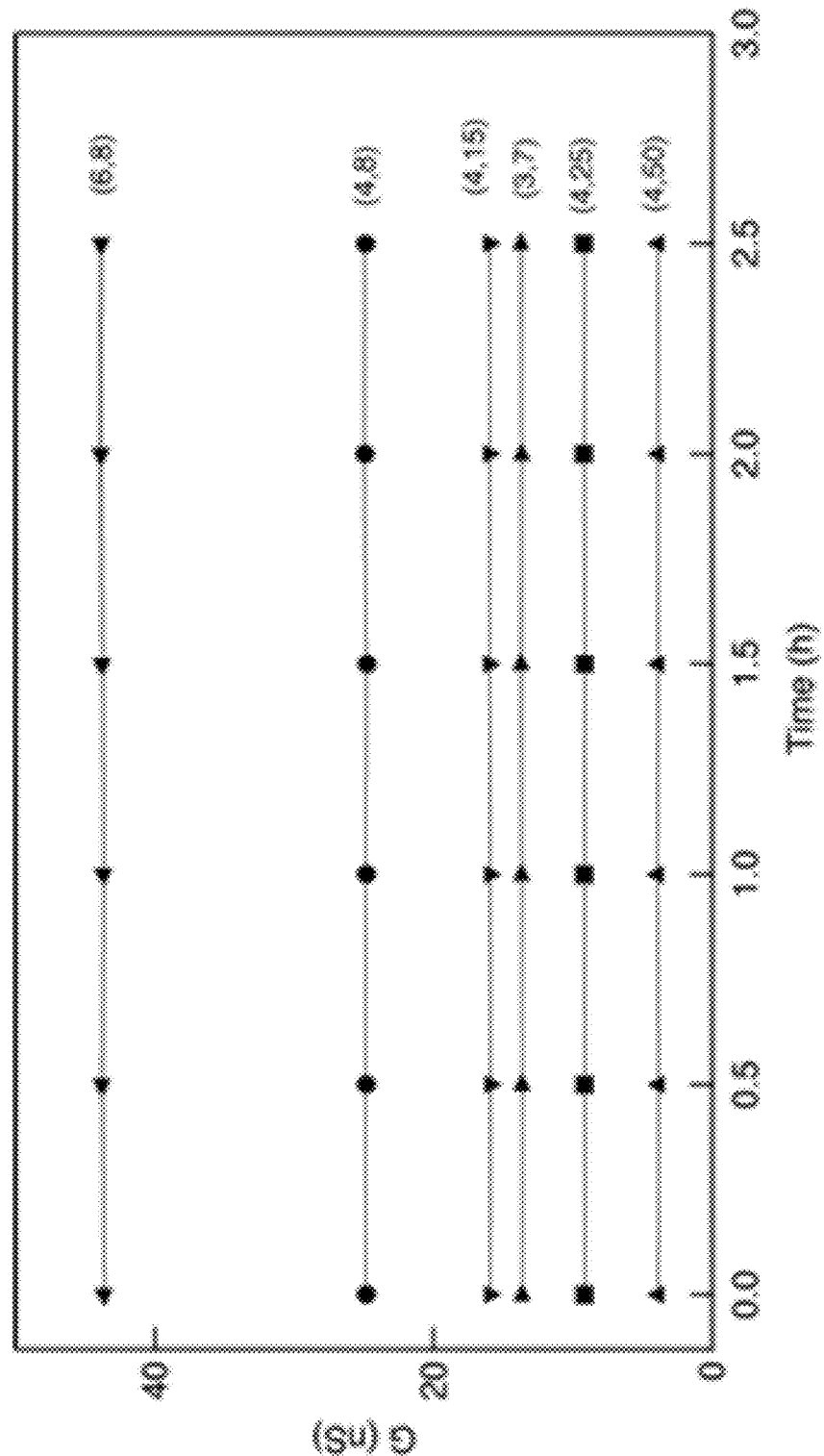
Figure 64:
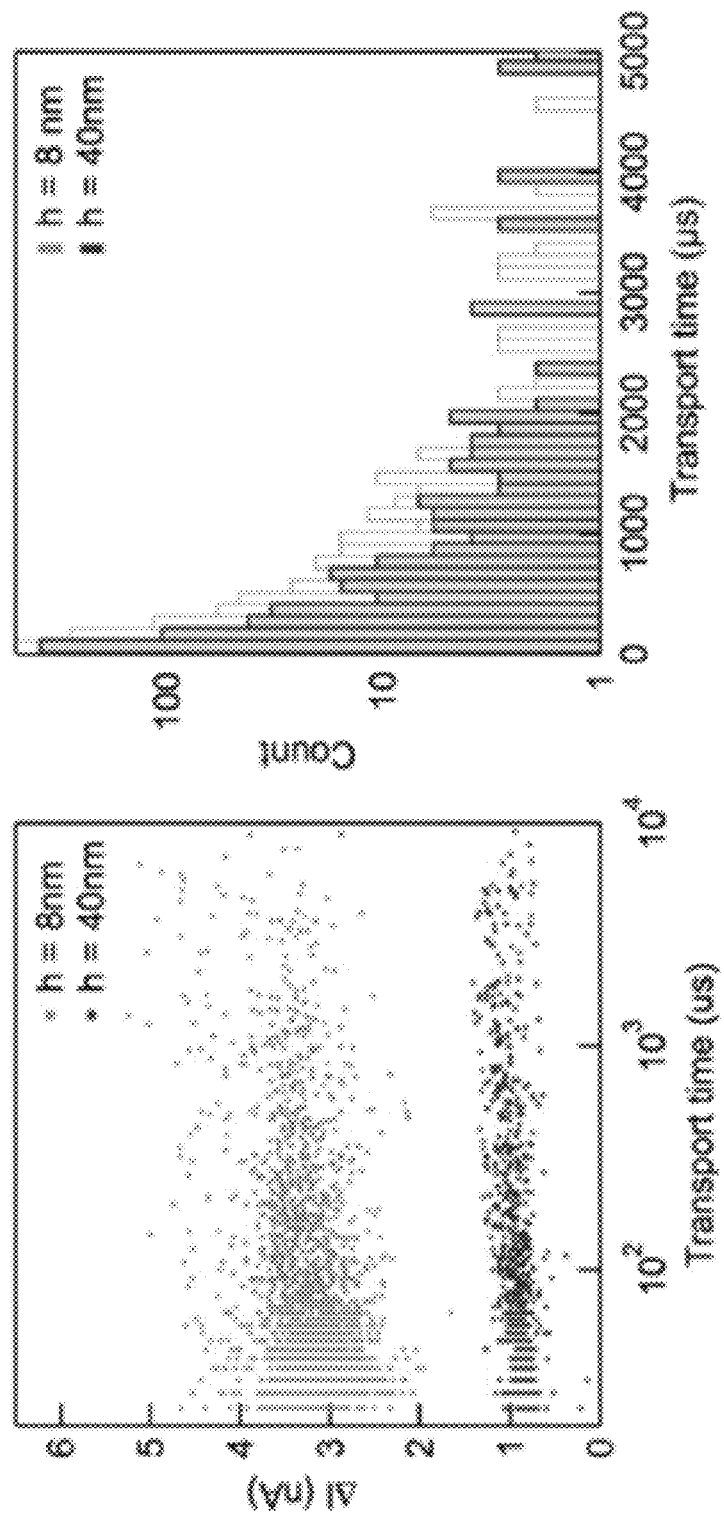
Figure 65:
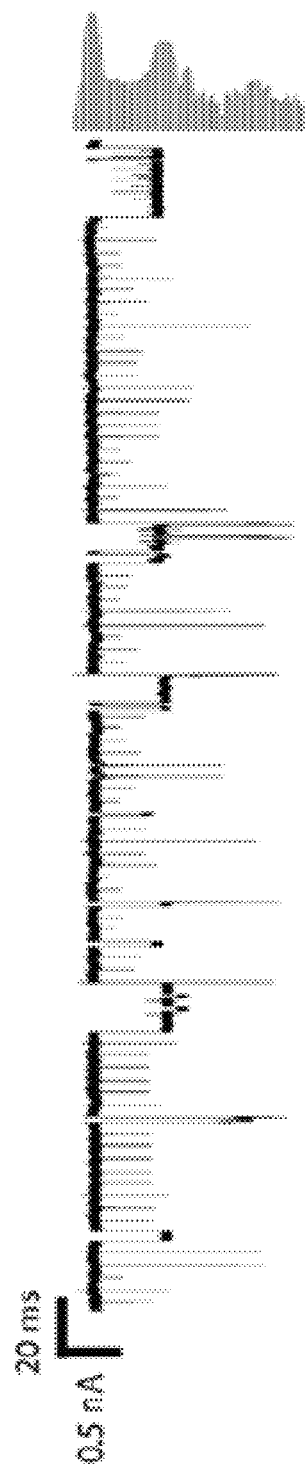
Figure 67:
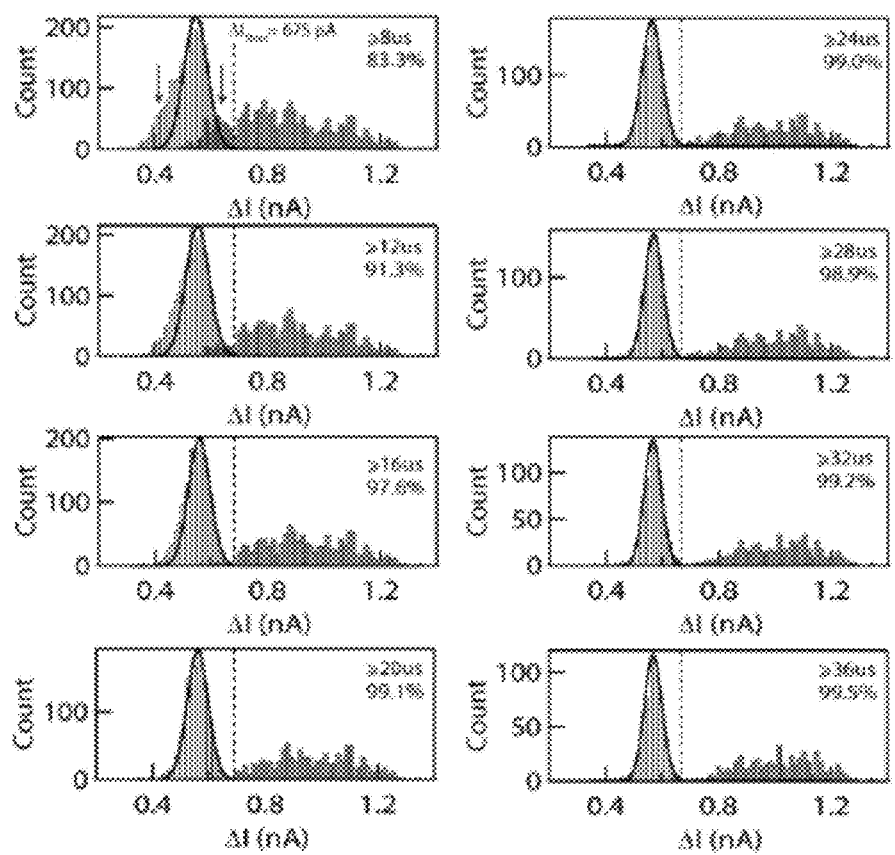
Figure 68:
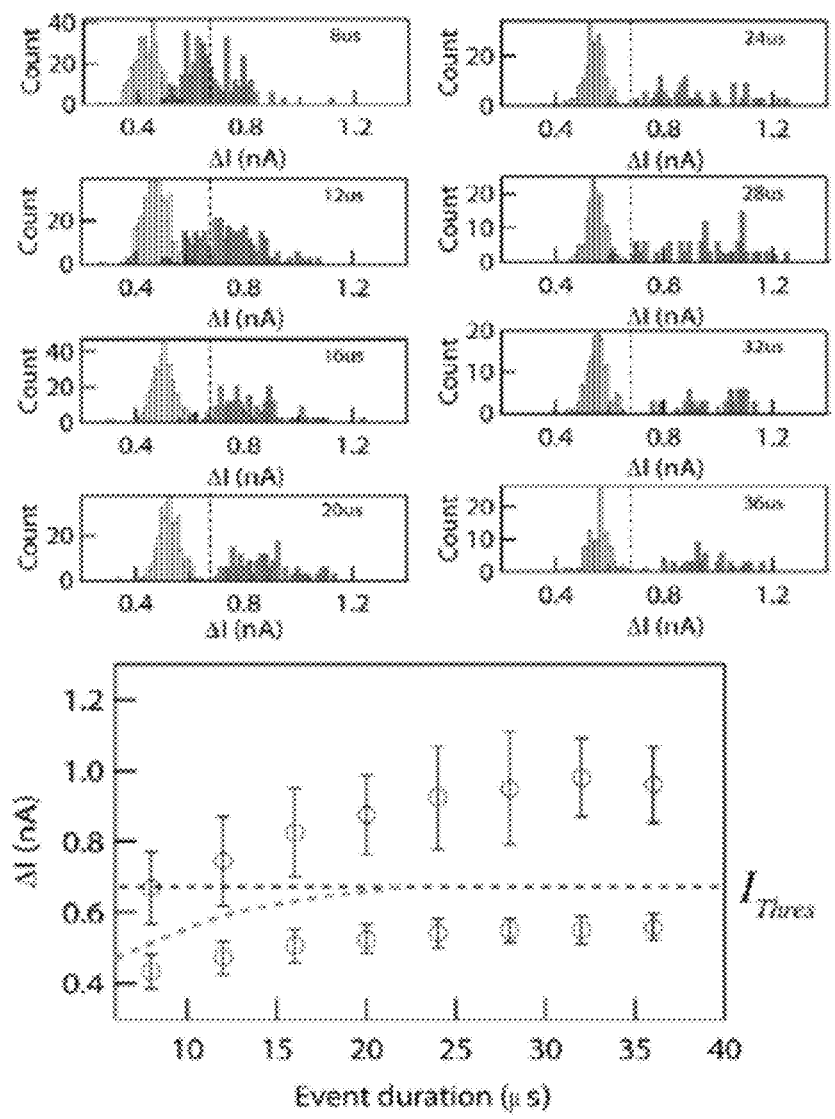
Figure 69:
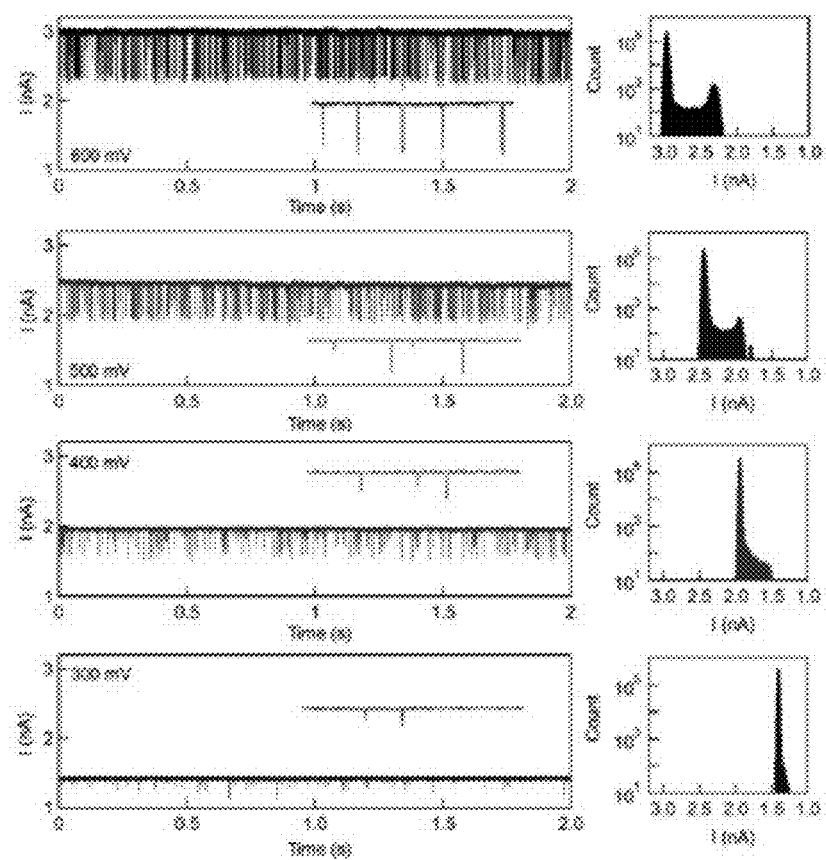
Figure 70:
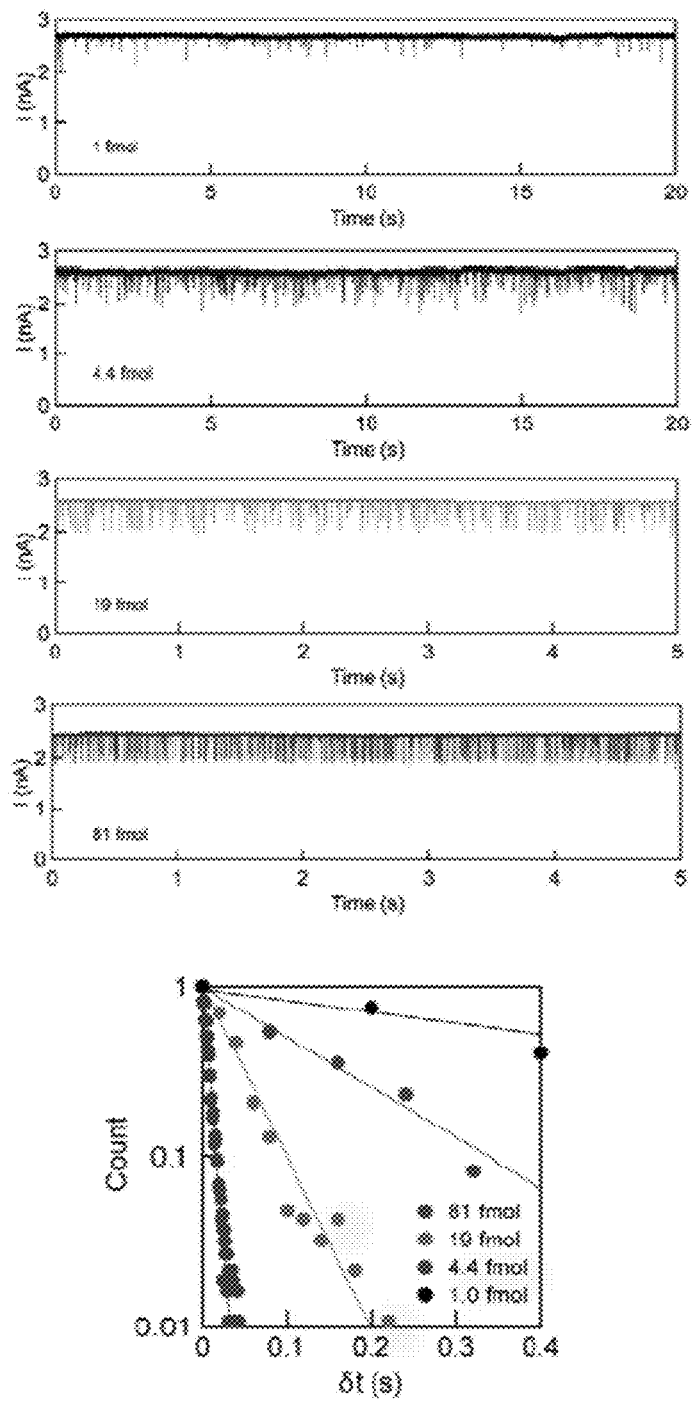
Figure 71:
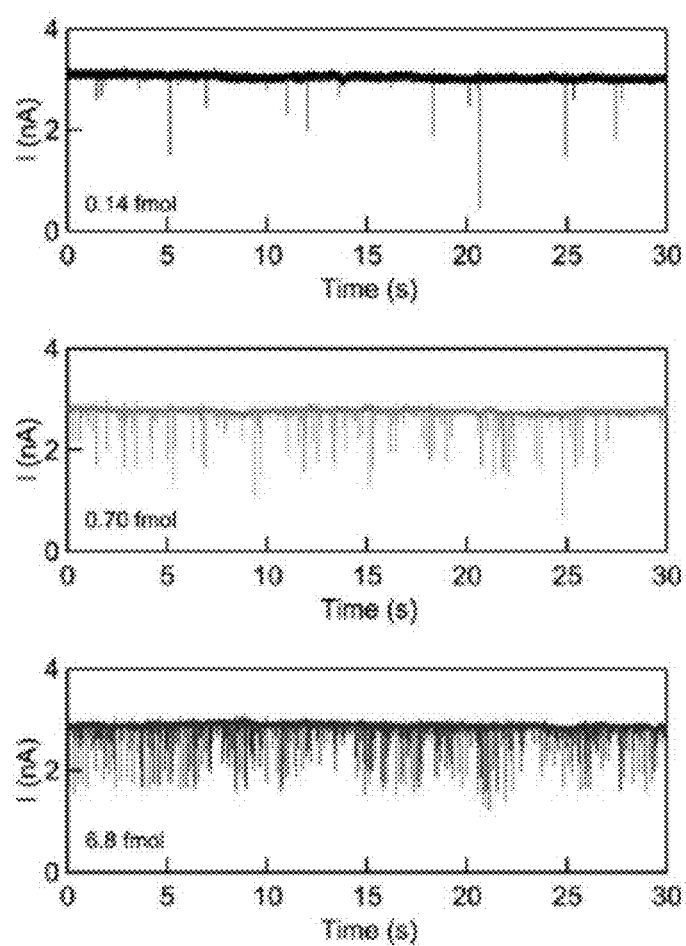
Figure 72L:
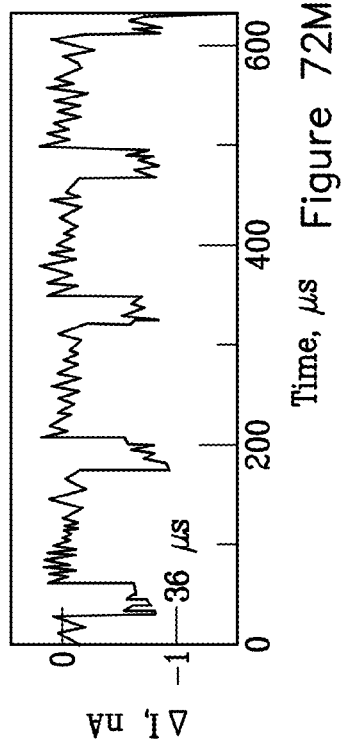
Figure 72M:
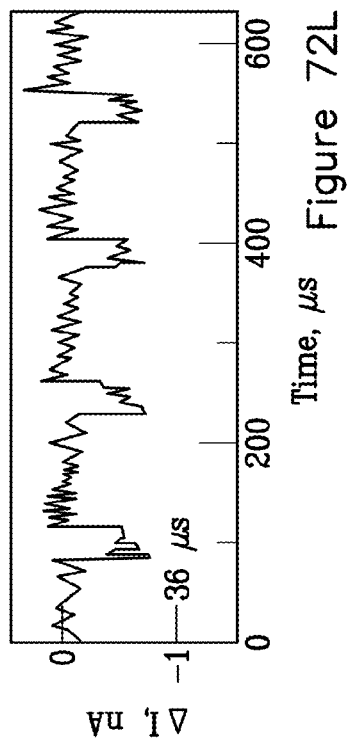
Figure 72N:
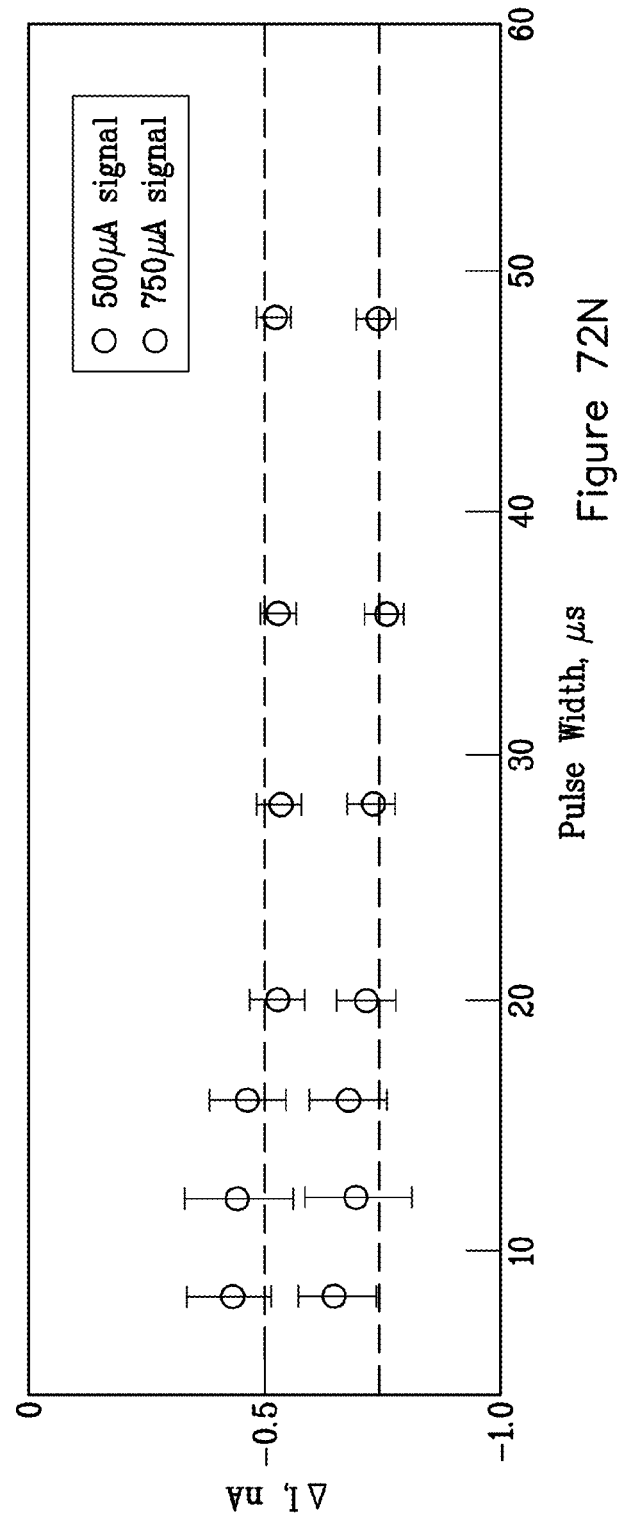
Figure 73:
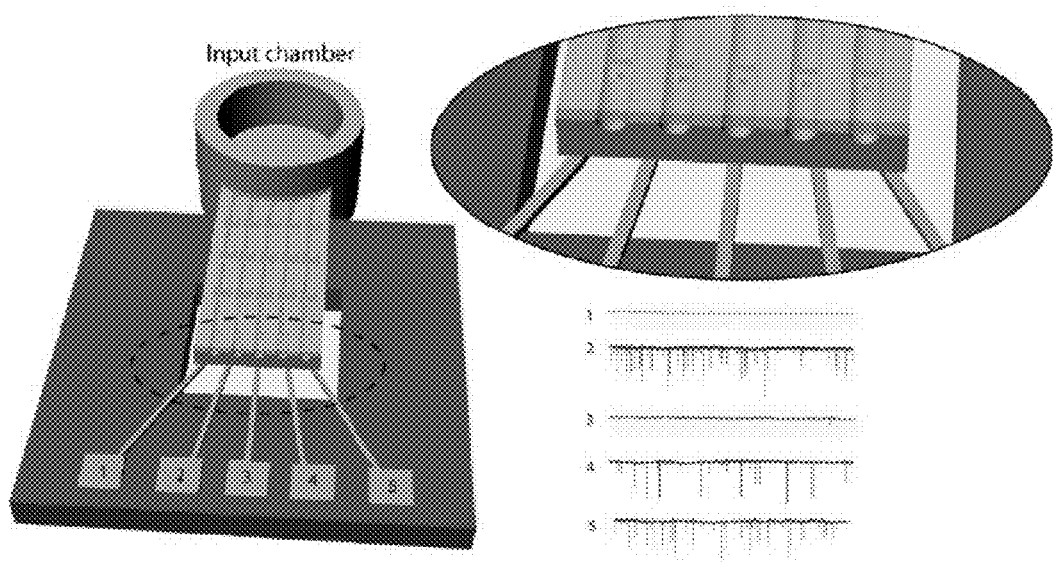
Figure 74:
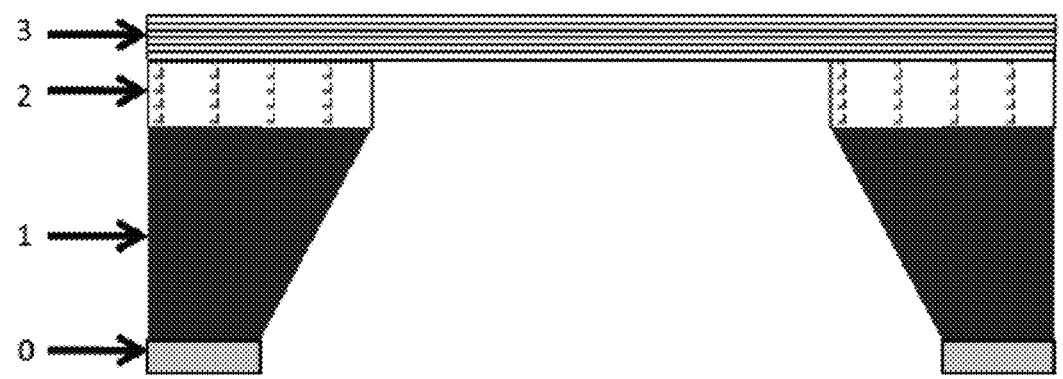
Figure 75:
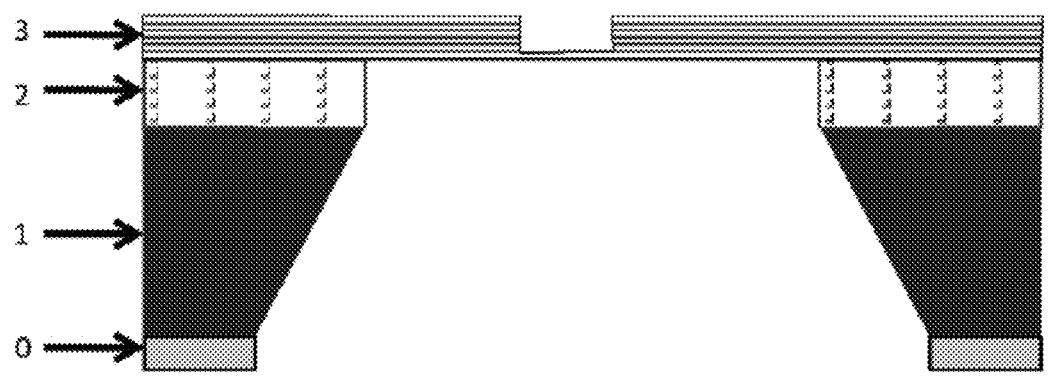
Figure 76:
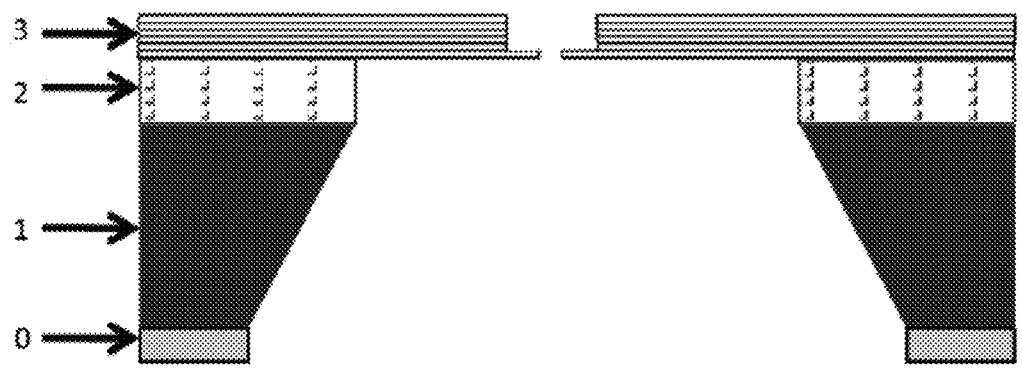
Figure 77:
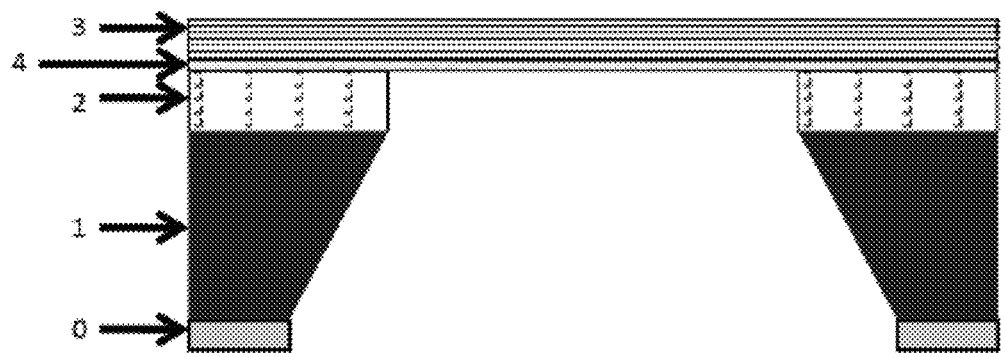
Figure 78:
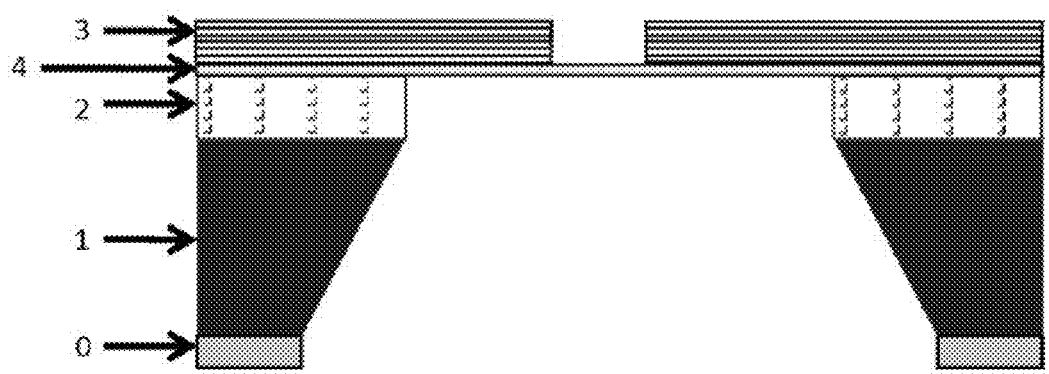
Figure 79:
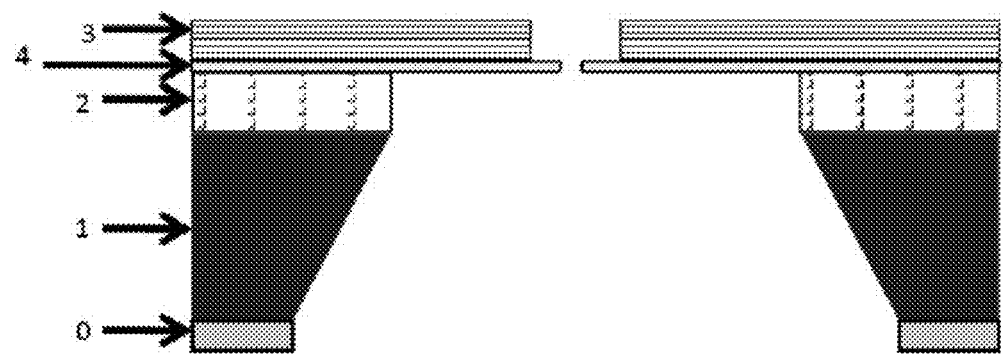
Figure 80:
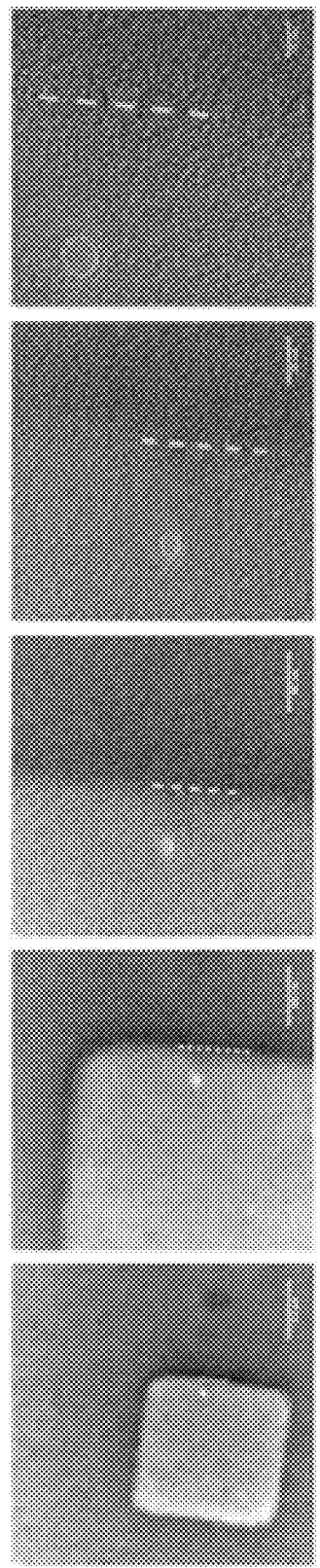

FIG. 61a illustrates a scheme for a miRNA-specific detection method. First, RNA is extracted from tissue (not shown; can be accomplished by lysing), and the extract is hybridized to a miRNA-specific oligonucleotide probe. In step (I), the probe:miRNA duplex is enriched by binding to p19-functionalized magnetic beads, followed by thorough washing in order to remove other RNAs from the mixture. In step (II) of FIG. 61a, the hybridized probe:miRNA duplex is eluted from the magnetic beads. While magnetic beads are illustrated here, other support materials—e.g., porous supports, strips, and the like—may also be used. In step (III), the eluted probe:miRNA duplex is electronically detected using a nanopore. FIG. 61b illustrates the detection of miR122a from rat liver RNA using a 3 nm diameter nanopore in a 7 nm thick membrane. The method shown in (a) was applied to detect miR122a from 1 μg of rat liver total RNA. Representative 30-second current vs. time traces are shown for a pore after the addition of the enriched miR122a (RL), a positive control containing a synthetic miR122a RNA duplex bound to magnetic beads, followed by washing, elution, and detection (PC), and four different negative controls (NC1-NC4, as described elsewhere herein). The negative controls did not produce any signal below the threshold, which was set to Io-0.4 nA (see dashed lines in FIG. 61b). FIG. 61c represents the quantification of miR122a from the mean capture rates. A calibration curve of capture rate vs. concentration was constructed (dashed line) using different concentrations of synthetic 22-bp RNA duplex, showing that capture rate scales linearly with concentration over three orders of magnitude. Determination of miR122a amounts (per μl solution) is based on the spike rate for sample RL ("RL" lines) and the positive control PC ("PC" lines). FIG. 61d illustrates the relative error in the determined RNA concentration as a function of the number of molecules counted by the nanopore. To achieve 95% accuracy under exemplary conditions, the time required for determination of 1 fmol RNA sample is 4 minutes, corresponding to ~250 translocation events;

FIG. 62 illustrates AFM images of the pattern shown in FIG. 18;

FIG. 63 illustrates the conductance as a function of time for pores with various diameters d and membrane thicknesses h, denoted as (d, h);

FIG. 64 illustrates a scatter plot of the mean current amplitude of each molecule (I) and the total transport time for 3 kbp dsDNA through 4 nm pores as a function of membrane thickness (h);

FIG. 65 illustrates a set of 10 bp translocations through a 3 nm diameter pore in a 7 nm thick membrane under 500 mV applied voltage, at a temperature of 0° C.;

FIGS. 66a-66d illustrate using a 3 nm diameter pore in a 7 nm thick membrane to discriminate among small nucleic acids of similar size, namely, 25 bp DNA (molecular weight=15 kD), 22 bp RNA (molecular weight=15 kD), and 76-nucleotide tRNA (molecular weight=25 kD);

FIG. 67 illustrates a quantitative analysis of a nanopore's ability to discriminate 25-bp DNA from 22-bp RNA based on current amplitudes;

FIG. 68 illustrates page I histograms for DNA and RNA events where in each plot is analyzed slices of the data that select all events with an indicated duration, in the range of 8-36 microseconds;

FIG. 69 illustrates shows 2-second current traces under different applied voltages of a 25 bp DNA sample analyzed using a 3 nm diameter pore fabricated in a 7 nm thick membrane (data taken at a temperature of 0° C.);

FIG. 70 illustrates current vs. time traces for a 3 nm diameter pore at a measured at a voltage of 500 mV and a temperature of 0° C., when different concentrations of DNA were added to the pore (expressed as fmol/μl solution);

FIG. 71 illustrates continuous time traces for a 3 nm diameter pore measured at a voltage of 500 mV and a temperature of 0° C., when different concentrations of RNA were added to the pore (expressed as fmol/μl solution);

FIG. 72 illustrates the response of an exemplary, non-limiting amplifier to synthetic current pulses in the range 8-48 s;

FIG. 73 illustrates an exemplary, non-limiting device analyte (e.g., miRNA) isolation and detection;

FIG. 74 illustrates a plan view of an exemplary device before processing, cross-section view;

FIG. 75 illustrates plan view of the device after processing/thinning the thin membrane;

FIG. 76 illustrates an exemplary device after processing a pore in a thinned membrane;

FIG. 77 illustrates an exemplary device;

FIG. 78 illustrates an exemplary device having a cavity formed above a thin membrane;

FIG. 79 illustrates the device of FIG. 39 having a nanopore formed in the thin membrane; and FIG. 80 illustrates images of a thin membrane region (light-color region; useful as a sample support in microscopy applications) and a thicker support material (darker color region).

Figure 81:
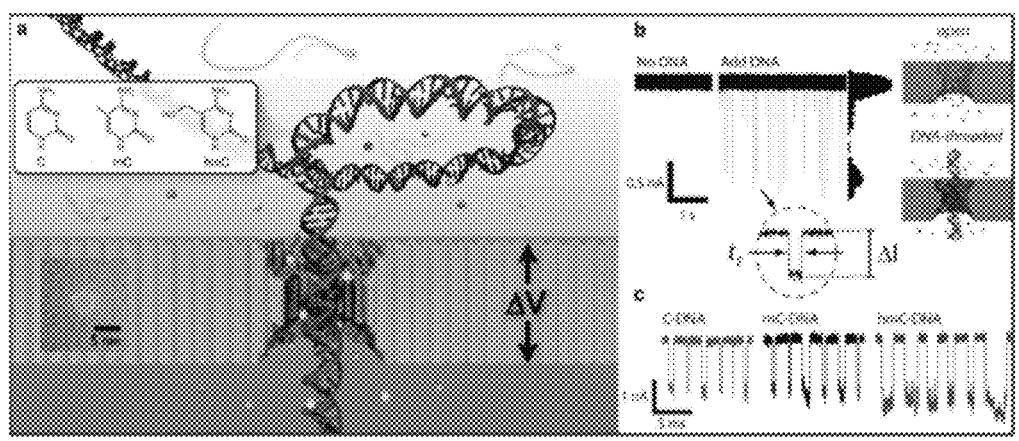

FIG. 81 illustrates nanopore detection of modified cytosines. (a) Scheme of a nanopore in a thin silicon nitride membrane, showing a DNA molecule being driven through it by an applied voltage ΔV. A TEM image of a 4 nm diameter pore in a 20 nm thick SiN membrane is also shown. The measured signal is the ion current of an electrolyte through the pore (e.g., KCl), represented by the yellow and green spheres. Three types of DNA molecules are driven through the pore, with the only difference between them being the chemical structure of cytosine residues in their sequence, shown in the inset. (b) Ion current traces of a 4 nm pore at 21 C under 300 mV applied voltage, before and after the addition of 3 kbp DNA to the analyte chamber (i.e., the chamber with the negative electrode). The deep spikes after the addition of DNA correspond to transport of DNA across the pore. The all-point histogram to the right of the current trace shows characteristic peaks for the open and DNA-occluded pores. A magnified event is shown in which ΔI and tT are defined. (c) Typical events that correspond to transport of C-DNA, mC-DNA, and hmC-DNA through the pore in (a). Transport of hmC-DNA exhibits larger ΔI and tT values than that of C-DNA or mC-DNA.

Figure 82:
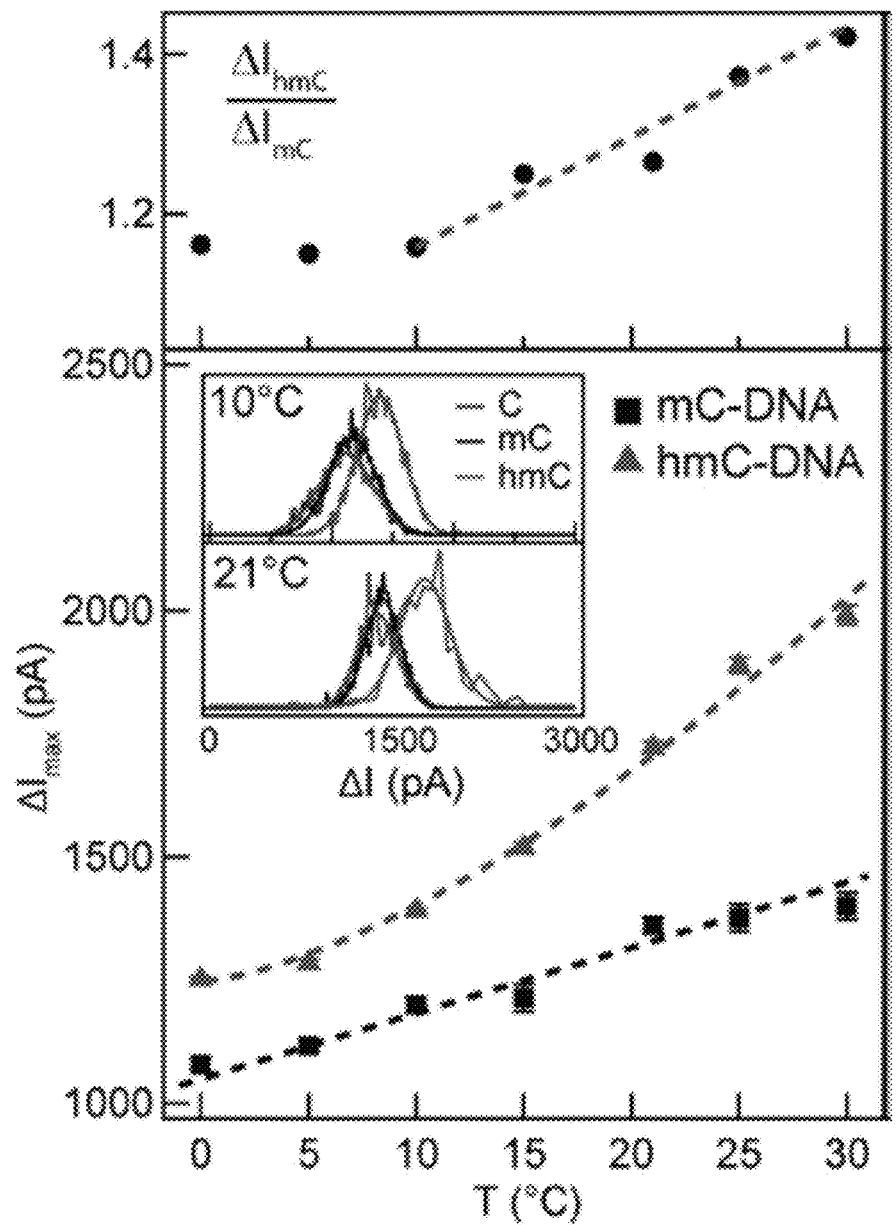

FIG. 82 illustrates signal amplitude dependence on bath temperature for mC-DNA and hmC-DNA. Each point in the graph represents the peak ΔI value (ΔImax) obtained from Gaussian fits to ΔI distributions for each experiment. Dashed lines are guides to the eye. The inset shows ΔI distributions for C-DNA, mC-DNA, and hmC-DNA at 10 and 21 deg. C. The ratio ΔIhmC/ΔImC is shown above the graph. C-DNA exhibited temperature dependence similar to that of mC-DNA. Each point is based on a measurement of 1560-2900 molecules, and all data were obtained using a single pore.

Figure 83:
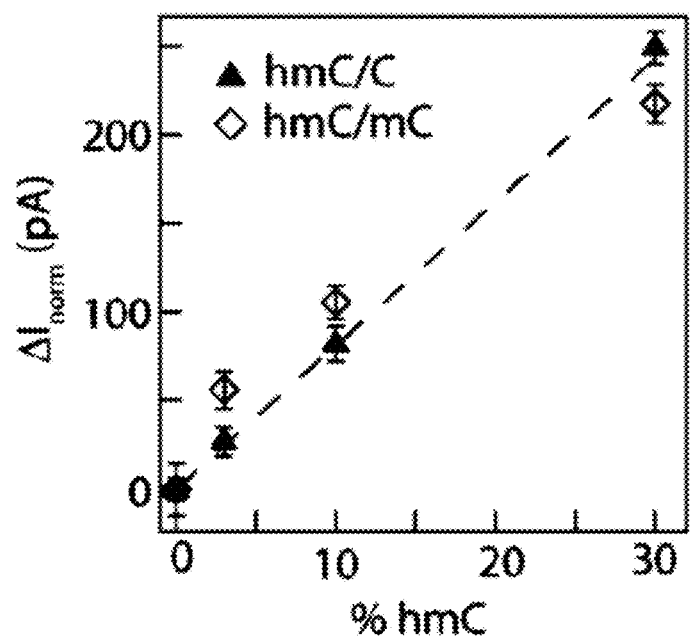

FIG. 83. Normalized ΔImax values for 3 kbp DNA with mixed cytosines (ΔInorm). Different cytosine modification ratios hmC/C and hmC/mC were tested, and ΔImax values were found from Gaussian fits to the ΔI distributions. The values in the plots represent the difference in ΔImax values from 0% hmC samples. The dashed line is a best global regression fit to the data, with slope of 8 (0.5 pA per percent hmC. Our lowest confidence is distinguishing 0% hmC-DNA from 3% hmC-DNA is 91% according to a Student's t test. Each point is based on a measurement of 1000-2040 molecules, and the two data sets were obtained using different pores with similar diameters.

Figure 84:
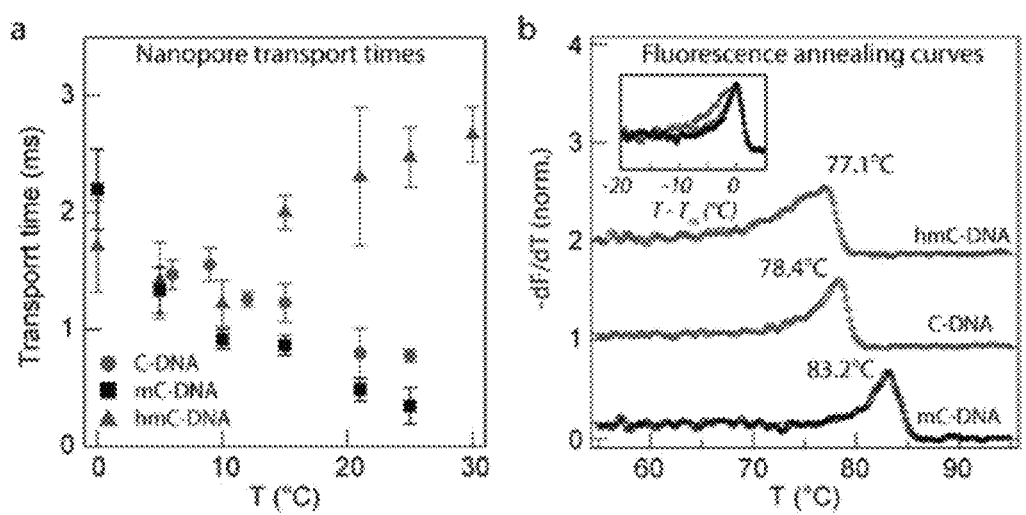

FIG. 84 presents temperature dependence on stability of duplexes with different cytosine modifications. (a) Mean transport times for 3 kbp C-DNA, mcDNA, and hmC-DNA samples as a function of bath temperature. With increasing temperatures in the range of 10-30 deg. C., mean transport times decrease for mC-DNA and C-DNA while increasing for hmC-DNA. (b) Fluorescence annealing curves for three DNA molecules. The curves were obtained by differentiating the fluorescence signal from SYBR Green I in the presence of DNA while cooling from 98 to 54 deg. C. in decrements of 0.2 deg. C. using a realtime PCR instrument (curves were vertically shifted for clarity). The peak positions represent the annealing temperatures Tm, written above each curve. Tm values follow the trend hmC-DNA>C-DNA>mCDNA. In addition, annealing of hmC-DNA occurs more gradually with temperature than for C-DNA or mC-DNA, as shown in the inset plot of T-Tm.

Figure 85:
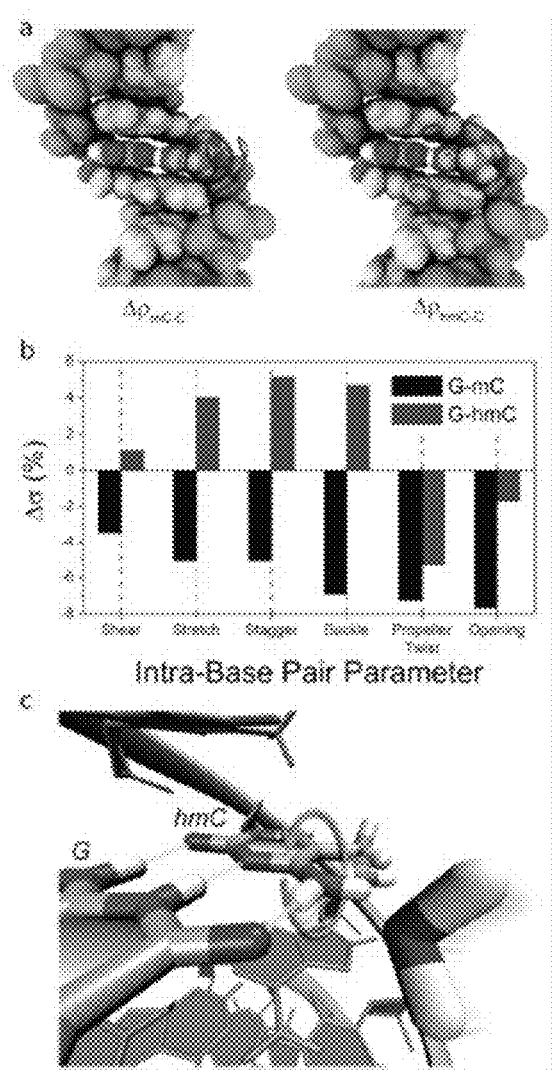

FIG. 85 presents results of molecular dynamics simulations of duplexes containing modified cytosines. (a) Water density in the major groove of mC (left) and hmC (right) relative to C. Cyan and magenta isosurfaces indicate regions of increased and diminished solvent density, respectively. (b) Differences in standard deviations (fluctuations) of G-mC and G-hmC intra-base-pair parameters relative to G-C. Overall, G-hmC experiences the largest fluctuations in internal motion. (c) Rotation of the position 4 amine in hmC due to a colliding water molecule. These rotations occur most frequently in hmC bases (see text).

Figure 86:
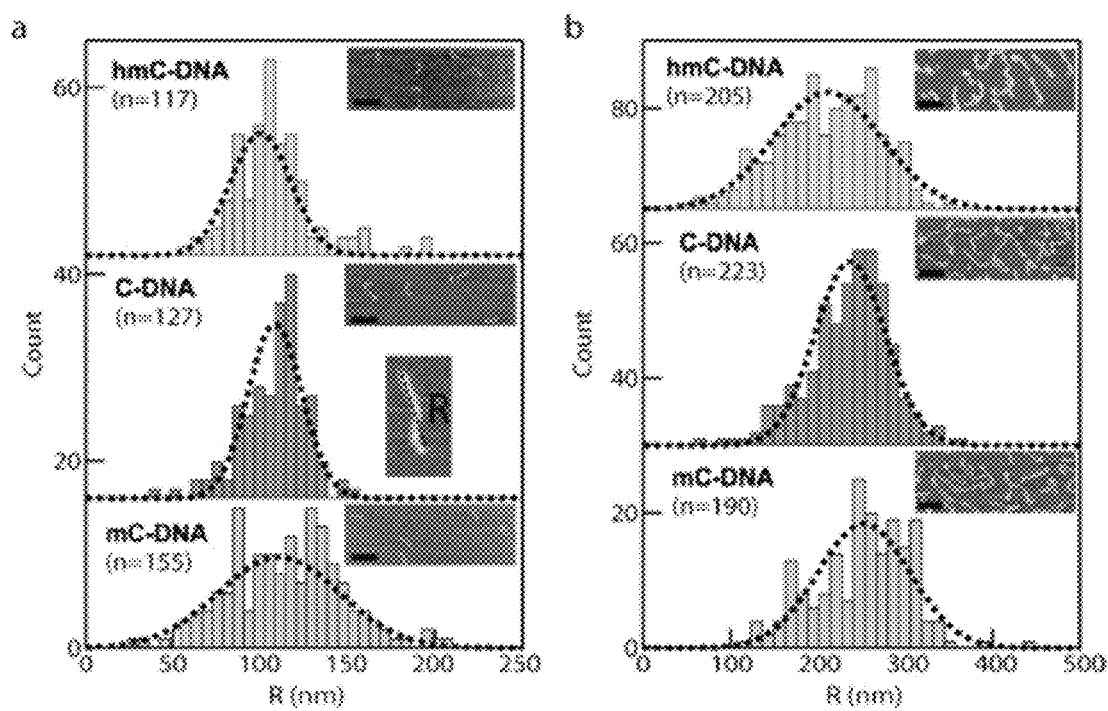

FIG. 86 presents AFM analysis of DNA with modified cytosines. (a) End-to-end distances R measured by tapping mode AFM of 410 bp fragments immobilized on mica by incubation with a solution of DNA containing 2 mM Tris and 1 mM Mg2+. Insets show representative AFM images for each of the samples (scale bar) 200 nm). The number of molecules n in each distribution is indicated. (b) Similar analysis as in (a) for an 1100 bp DNA fragment. For both DNA lengths, R follows hmC-DNA C-DNA mC-DNA.

Figure 87:
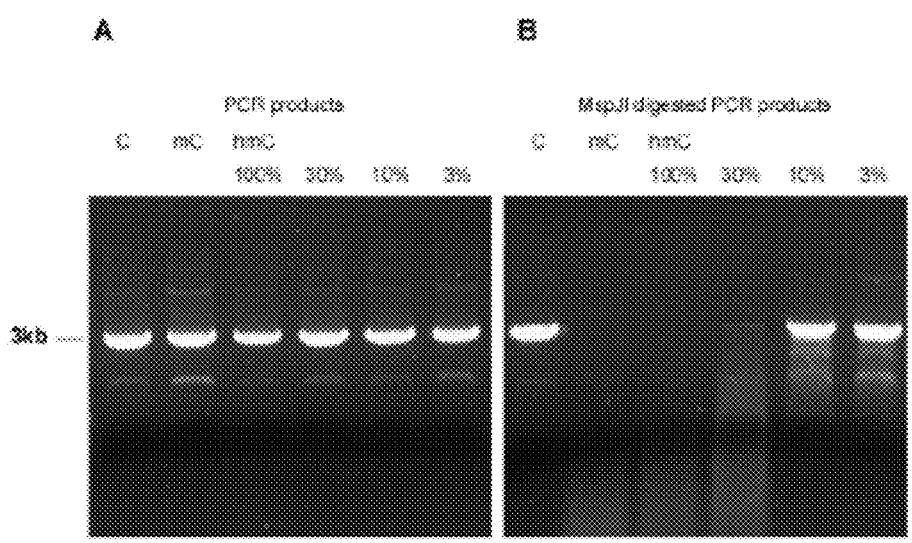

FIG. 87 presents mC and hmC incorporated 3 kbp DNA PCR products. (A) Purified 3 kb PCR product on 1% agarose gel. (B) Digested by a cytosine-modification dependent restriction enzyme (MspJI, NEB). Sites containing mC or hmC are digested (lane 2, 3), while unmodified C remains intact (lane 1). Qualitatively, samples that contain more hmC than C are more extensively digested (lanes 4, 5, 6).

Figure 88:
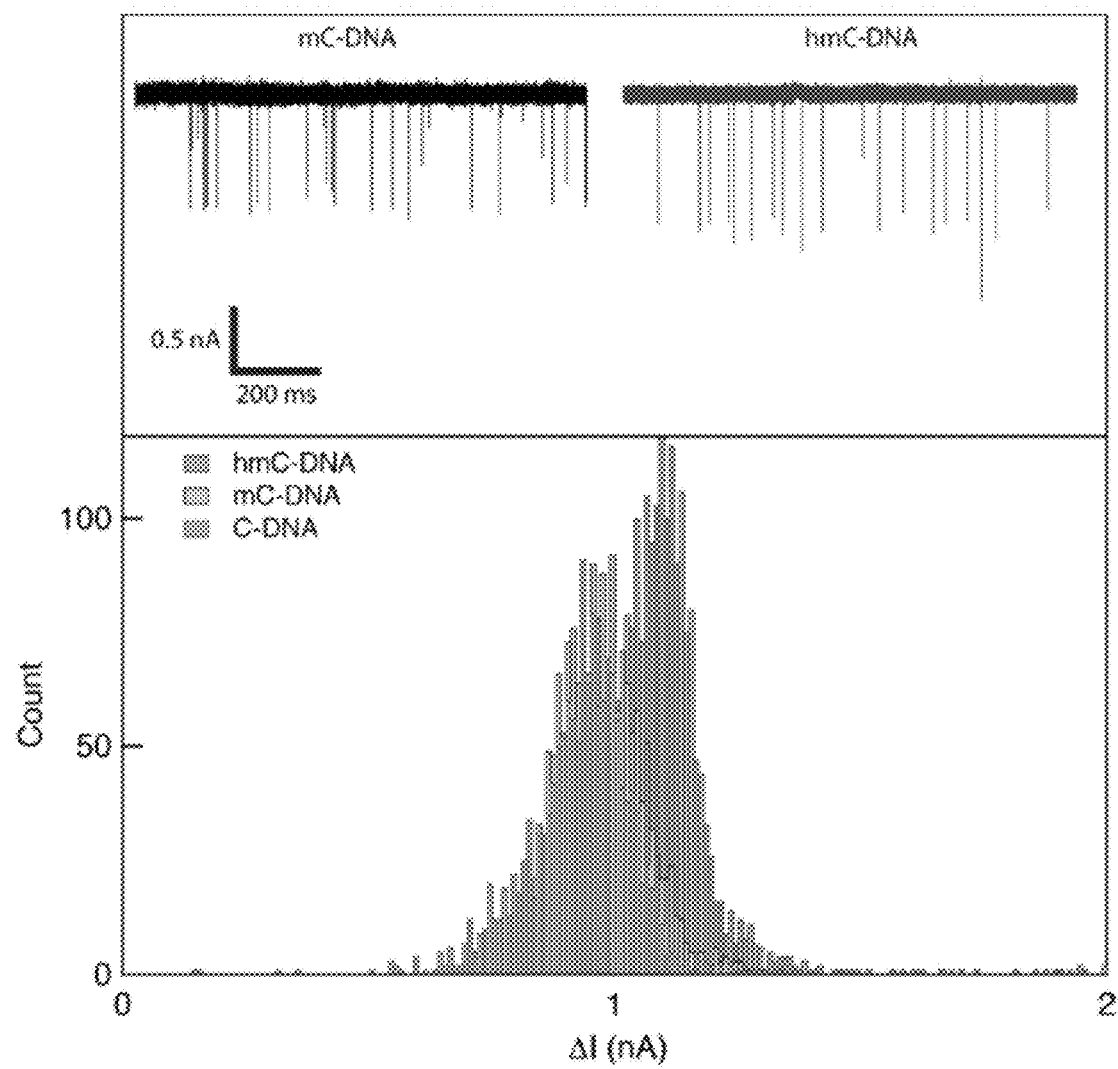

FIG. 88 presents current amplitude histograms for 410 bp DNA fragments with different cytosine modifications. (Top) Continuous 1-second current traces for 410 bp mC-DNA (black) and hmC-DNA (red), as obtained using a 4 nm pore at 21° C. and 300 mV applied voltage. (Bottom) Histograms of the mean current amplitudes (ΔI) for >1,000 events for each of the three modified cytosine variants. The histograms clearly show that hmC-DNA produces deeper amplitudes than C-DNA and mC-DNA.

FIG. 89 presents extracted ion chromatograms for different mononucleosides. The different nucleosides have different retention times. Colors: C (red), mC (black), G (green), T (blue), and A (purple). A) Analysis of the digested 3 kb PCR product that used 30% hmC in the PCR mix (30% with respect to cytosines). B) Analysis of the 3 kb PCR product with 60% hmC. C) analysis of a standard dNTP mix that contains 30% hmC. D) Analysis of a standard dNTP mix with 60% hmC.

Figure 90:
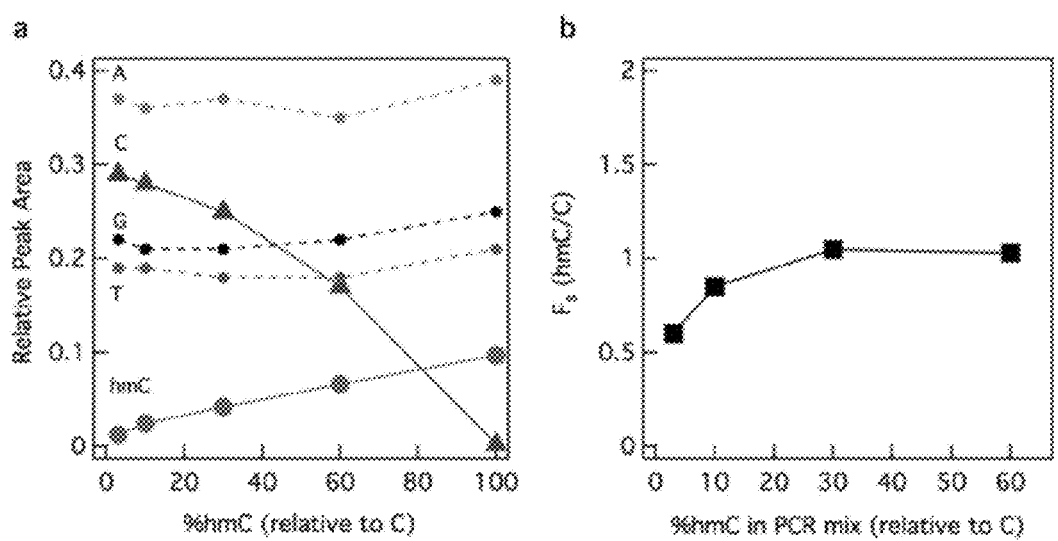

FIG. 90 presents LC/MS analysis of PCR-amplified DNA with modified cytosines. (a) Normalized relative peak areas for the indicated nucleoside bases at different proportions of hmC and C in a nucleotide mix (see text, each point represents the average of three experiments). (b) Comparison of % hmC over C in the PCR samples as compared to the standard calibration curve.

Figure 91:
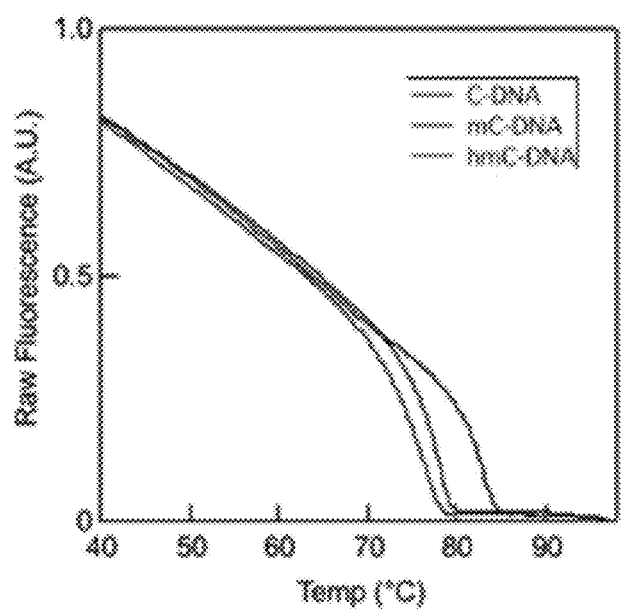

FIG. 91 presents annealing curves for DNA with different cytosine modifications.

Figure 92:
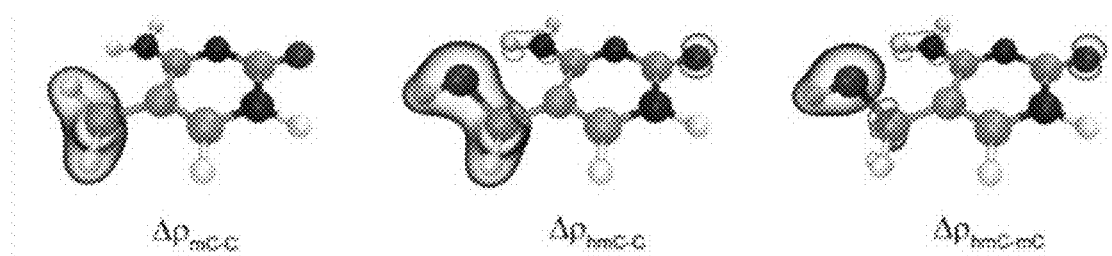

FIG. 92 presents electron density of mC relative to C (left), hmC relative to C (middle) and hmC relative to mC (right).

Blue and red isosurfaces indicate regions of increased and diminished electron density, respectively. The change in electronic structure is localized around the modification itself. The hydroxyl group in hmC polarizes the position 4 amine and position 2 keto groups causing minor geometric changes. However, a Mulliken population analysis reveals no appreciable differences in charge around these atoms. Additionally, counterpoise corrected calculations of G-*C base pair binding energy show that these small structural differences have negligible effect on binding. Thus, using the existing CHARMM charge parameters from C in mC and hmC is justified.

Figure 93:
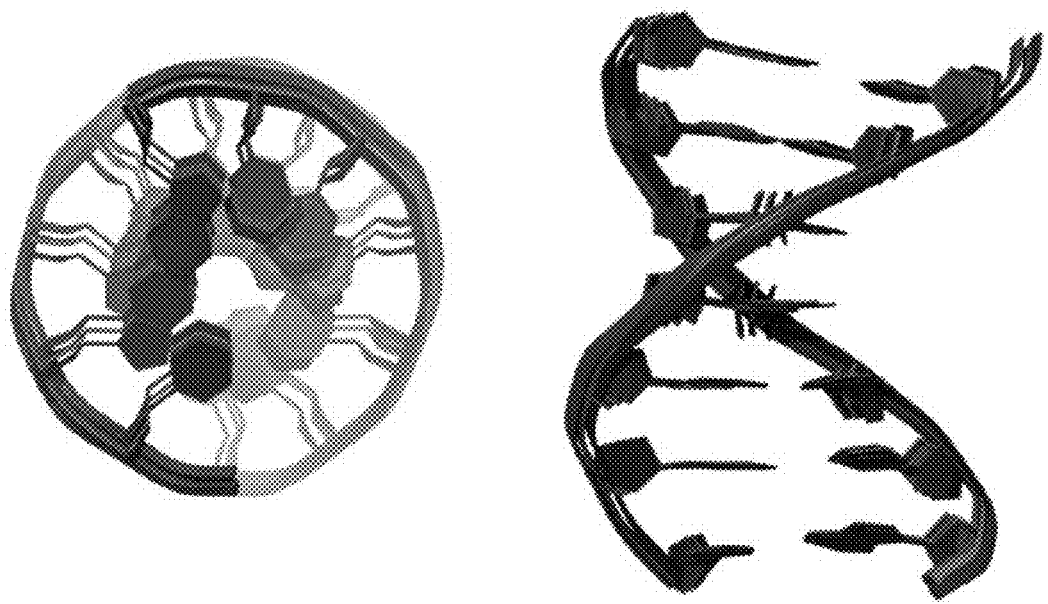

FIG. 93 presents superimposed average structures of C-DNA (blue), mC-DNA (gray), hmC-DNA (red). The structure changes systematically from C-DNA to hmC-DNA with mC-DNA intermediate. These changes are due to steric effects and, thus, follow the size of the chemical modification.

FIG. 94 illustrates differences in standard deviations (fluctuations) of inter-base pair and helical axis parameters for Ap(*C)/GpT and (*C)pT/ApG steps relative to unmodified ApC/GpT and CpT/ApG steps. Fluctuations in these parameters depend on both the steric effects and polarity of the modifications. These plots show that these two effects oppose one another: increasing the size of the modification increases the local rigidity of the duplex while increasing the modification's polarity decreases rigidity. Because of these opposite effects, these parameters follow the trend G-C>≈G-hmC>G-mC. The intra-base pair fluctuations, on the other hand, are affected less by steric effects and tend to follow the modifications polarity. Thus, the fluctuations in G-*C base pairs follows G-hmC>G-C>G-mC.

Figure 95:
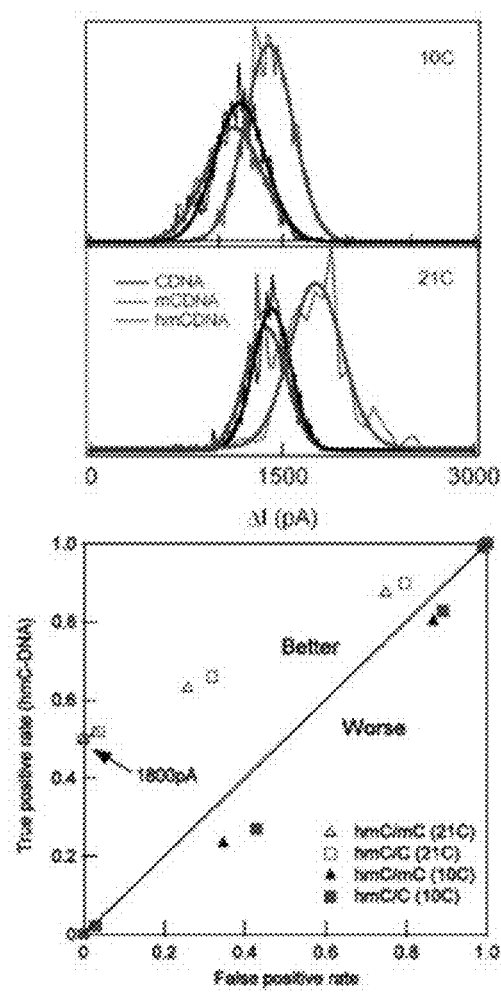

FIG. 95 illustrates (top) histograms of $\Delta I$ values for the three molecules at 21° C. and 10° C. and (bottom) receiver operating characteristic (ROC) curves for the three different 3 kbp cytosine variants at these two temperatures.

Figure 96:
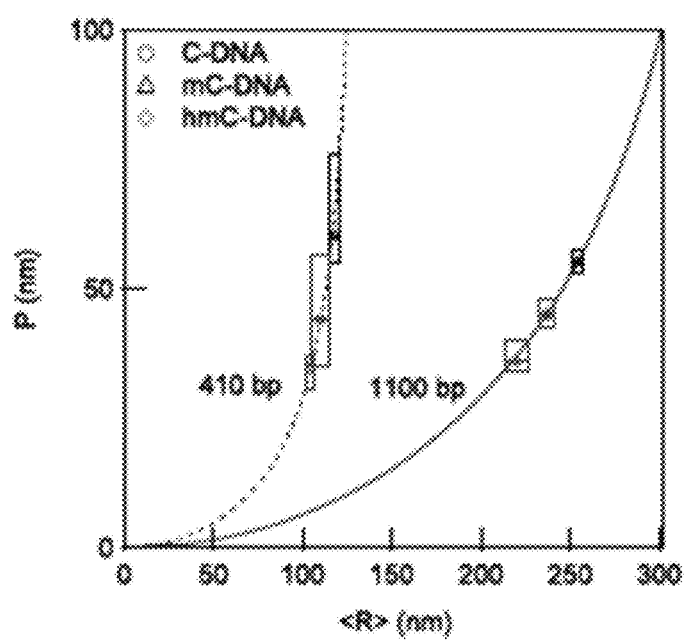

FIG. 96 illustrates shows curves of P as a function of R based on Eqn 1.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first aspect, the claimed invention provides analysis devices. These devices suitably include a membrane having a thickness of from about 20 nm to about 100 nm having a thinned region with a thickness in the range of from about 1 to about 20 nm. The device suitably includes at least one pore extending through this region of the membrane. The pore suitably has a characteristic cross-sectional dimension (e.g., a diameter) in the range of from about 1 nm to about 1000 nm. The devices also suitably include a supporting layer adjacent to the membrane.

The membranes of the disclosed devices (shown as layer 3 in the attached figures) are formed of a number of materials. Nitrides, oxides, and the like are all considered suitable. Nitrides may be silicon nitride, boron nitride, titanium nitride, gallium nitride, and the like; silicon nitride is considered especially suitable. Suitable oxides include silicon oxide, hafnium oxide, titanium oxide, aluminum oxide, and the like. Membrane materials that can be processed by standard lithography techniques are considered especially suitable. Any of the methods, analysis, and/or processes presented in the present disclosure may be performed on any of the articles, devices, systems, and/or apparatuses presented in the present disclosure.

The membrane may also include a carbonaceous material, such as a carbide, graphite, graphene, diamond, and the like. Silicon, gold, silver, platinum, gallium arsenide, and the like are all suitable, as are polymeric materials. Polymeric materials useful in the claimed invention include polymethyl methacrylate, polystyrene, polyimide, and the like. The polymeric material may be used in the membrane, but may also be present as a supporting layer or a capping layer of the device. The supporting layer may be fabricated from any of these materials, and may suitably include silicon, germanium, gallium arsenide, glass, quartz, or alumina.

The thinned region of the membrane suitably has a thickness in the range of the sub-nanometer range, or from about 0.1 nm to about 20 nm, but may have a thickness in the range of from about 1 nm to about 15 nm, or even in the range of from about 2 nm to about 6 nm. The thinned region may have a cross-sectional dimension (e.g., diameter, width) in the range of from about 1 nm to about 1000 nm, or from 10 nm to about 100 nm, or from about 20 nm to about 50 nm. Larger thinned regions are within the scope of the present disclosure.

A supporting layer suitably has a thickness in the range of from about 1 micron to about 2000 microns, or even in the range of from about 10 microns to about 200 microns. The optimal thickness of the supporting layer will depend of the specific uses of the device, and the user of ordinary skill in the art will encounter little difficulty in fabricating a supporting layer of the proper thickness.

The pores of the devices suitably have a characteristic cross-sectional dimension (e.g., diameter) in the range of from about 0.1 nm (i.e., a sub-nanometer size) or even 0.5 nm to about 500 nm, or from about 1 nm to about 200 nm. The optimal pore size will be apparent to the user, based on their needs. As non-limiting embodiments, pores having a diameter of from about 1 nm to about 3 nm are considered suitable for analyzing ssDNA, and pores having a diameter of from about 2 nm to about 10 nm are considered suitable for analyzing dsDNA. DNA samples may have both ss and ds portions. The ratio of the membrane thickness to the thickness of the thinned region is in the range of from about 100:99 to about 100:1, or even 100:51 to 100:5.

Figure 13:
FIG. 13 depicts an embodiment of the claimed invention wherein a nanopore has been formed in a locally thinned region of the membrane material (3)

As shown in the attached figures, the nanopore may extent through the entire thickness of a membrane layer (FIG. 1), or may extend through a locally thinned region of the membrane layer (FIG. 13). The optimal configuration will depend on the user's needs.

Figure 1:
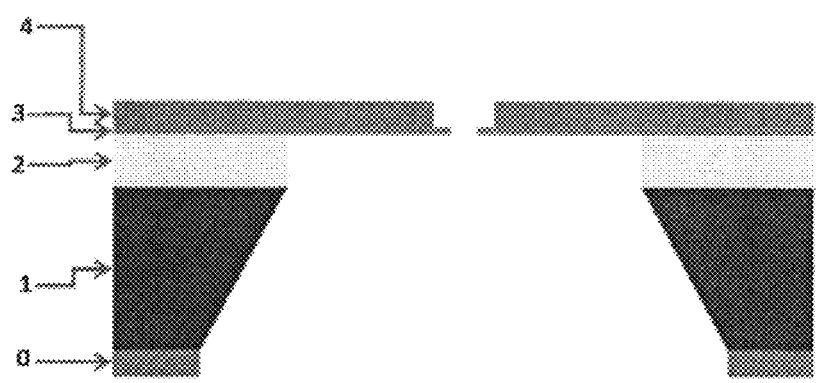
FIG. 1 depicts a completed device according to the claimed invention.

As shown in FIG. 1, a device may include a base 0, a support 1, a dielectric 2, a thin membrane 3, and a upper membrane 4. A pore may be formed in the thin member 3, as shown in the figure. The thin membrane may have a thickness of only a few nanometers, or of tens of nanometers. The upper membrane 4 may have a thickness of a few nanometers, tens of nanometers, or even 100-1000 nanometers, depending on the user's needs. Because free standing (unsupported) membranes having a thickness of about 5 nm or less may experience mechanical instability or may not always be sufficiently robust for all applications. The devices shown in FIG. 1 thus enable the user to overcome this challenge, as a pore is formed in the membrane 3, which membrane may have a thickness of 5 nm or less, but which membrane is reinforced by the upper membrane 4. A variety of materials are suitable for layers 0-4, which materials are described elsewhere herein in more detail.

Figure 2:
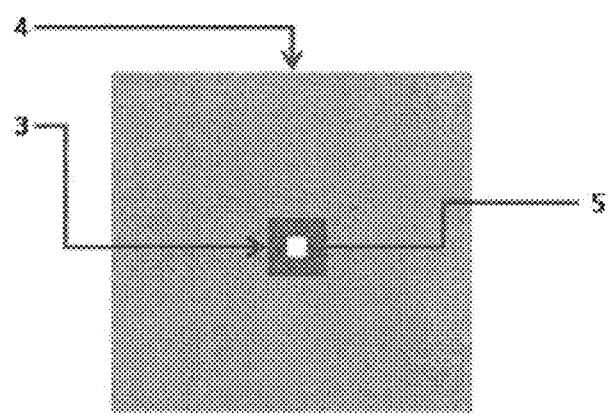
FIG. 2 depicts a top-down view of a device according to the claimed invention.

FIG. 2 illustrates a top-down view of a device according to FIG. 1. As shown in FIG. 2, the upper membrane 4 includes a window that exposes thin membrane 3, in which membrane is formed a pore 3. As explained elsewhere herein, the pore need not be square; it can be of virtually any shape. The thin membrane need not necessarily include a pore. In such embodiments, the thin membrane may serve as a stage or support for microscopy or other application. As shown in FIG. 40, the thinned membrane provides a reduced background for observing or measuring a sample; the sample of interest is deposited on the window substrate, and one or more of the optical methods above is used to image the sample. Some substrates have intrinsic fluorescence (e.g., SiN is known to be "noisy" for blue-green fluorescence measurements. The reduction of the thickness for local imaging reduces the background extinction or fluorescence from the substrate, enabling better signal and contrast from the sample of interest. A user may accordingly use such a device as a sample stage in a microscopy application.

Figure 3:
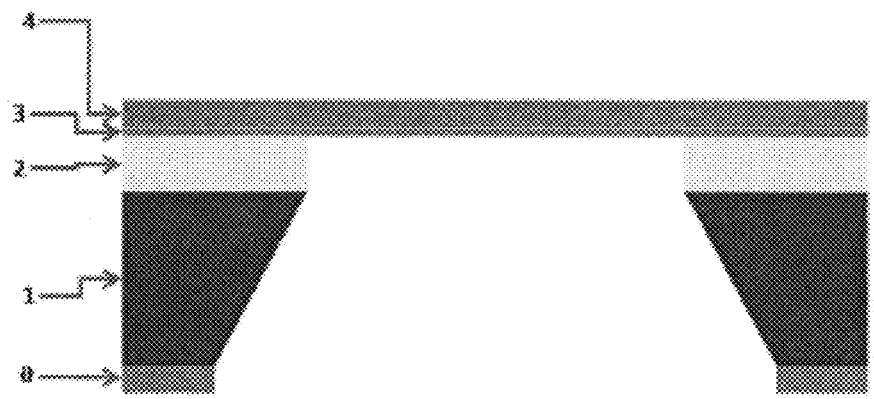
FIG. 3 depicts a device according to the claimed invention in an intermediate, nanopore-free stage of fabrication.
Figure 4:
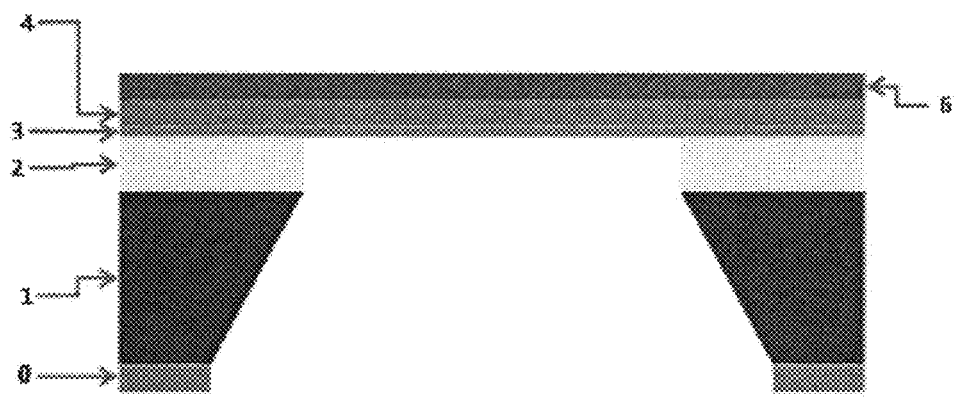
FIG. 4 depicts a device according to the claimed invention in an intermediate, nanopore-free stage of fabrication where resist material (6) is present atop the capping layer (4)
Figure 7:
FIG. 7 depicts a device according to the claimed invention in an intermediate, nanopore-free stage of fabrication where resist material present in FIG. 6 has been removed.

FIGS. 3-9 illustrate an exemplary fabrication process. As shown in FIGS. 3 and 4, a resist material 6 may be applied atop the upper membrane 4. The resist may be developed/removed to open a window in the resist that defines a region of the upper membrane 4. Plasma etching may be used to remove material from the upper membrane 4, which effectively defines a cavity or void above the thin membrane 3. The resist 6 may be removed (FIGS. 6-7). The user may then form a nanopore in the thin membrane 3 (FIG. 8) to give rise to the completed device shown in FIG. 9.

Figure 14:
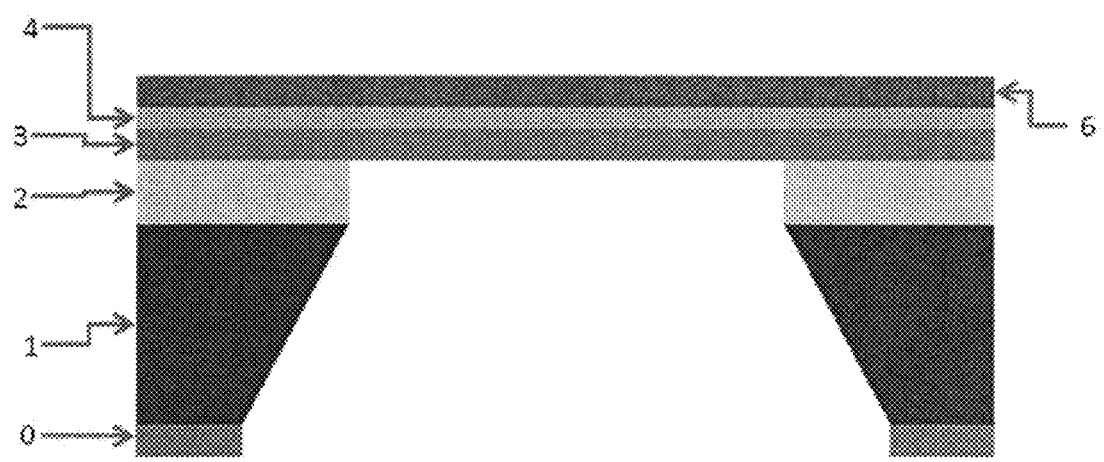
FIG. 14 depicts an intermediate stage of nanopore device fabrication where a resist (6) is disposed atop a capping layer (4) and a membrane material (3). A dielectric layer (2), support layer (1), and additional support (0) are also present.
Figure 15:
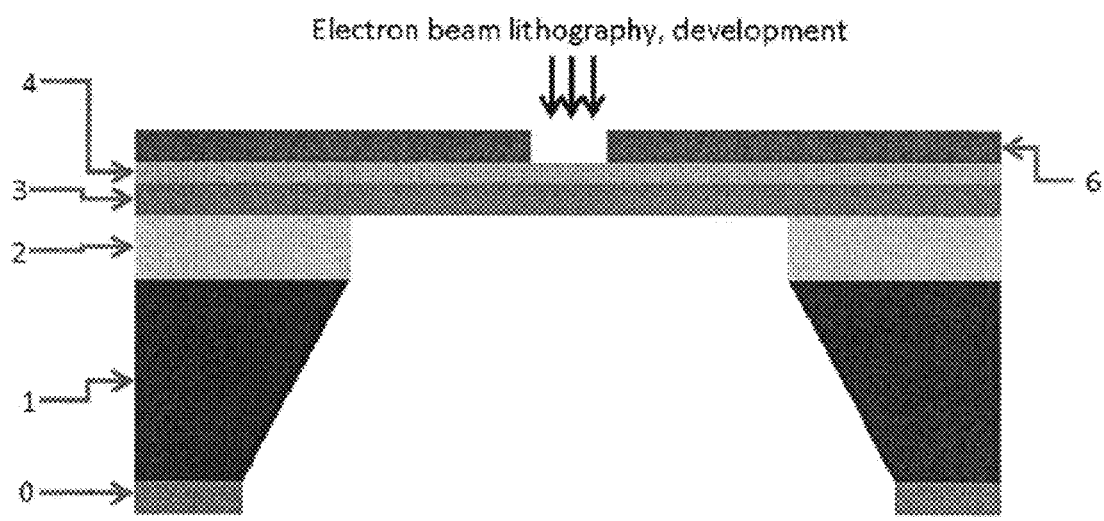
FIG. 15 illustrates electron beam removal of the resist material.

FIGS. 13-17 depict one non-limiting manner of fabricating the devices shown in FIG. 13. Briefly, FIG. 14 depicts a workpiece having resist (6), a capping layer (4), a membrane (3), a dielectric (2), a support (1), and an additional support (0) layer. The support layer (0) is suitably a hard material, such as silicon. The support layer (1) is suitably silicon, GaAs, and the like. The dielectric (2) may suitably be silicon oxide or other dielectric material. The dielectric layer is optional, and is not necessary to the devices' function.

Figure 17:
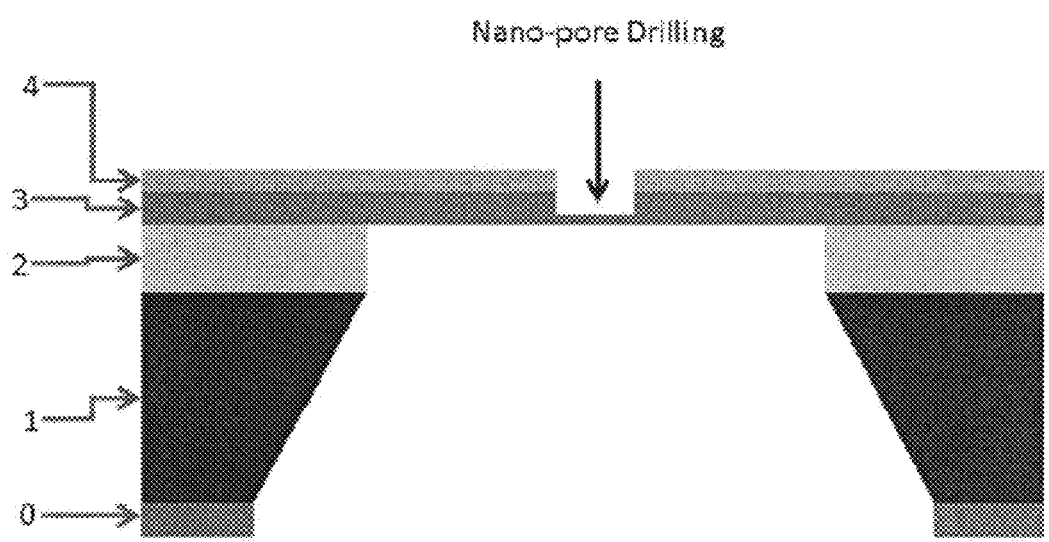
FIG. 17 illustrates the formation ("drilling") of a nanopore in the thinned membrane region of FIG. 16.

A portion of the resist is selectively removed (FIG. 15), and then portions of the capping layer and the membrane layer are removed (FIG. 16-17). The nanopore is then formed in the locally-thinned region of the membrane layer (FIGS. 17, 13).

Figure 5:
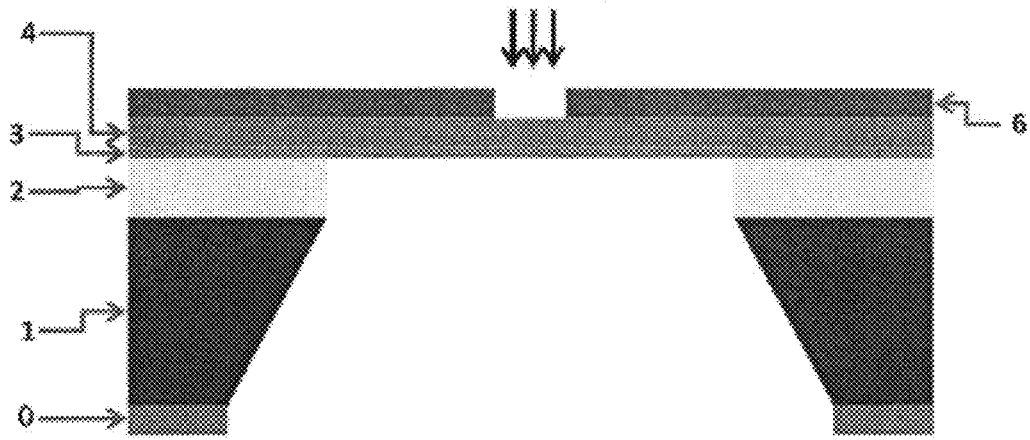
FIG. 5 depicts a device according to the claimed invention in an intermediate, nanopore-free stage of fabrication where resist material (6) is removed.
Figure 8:
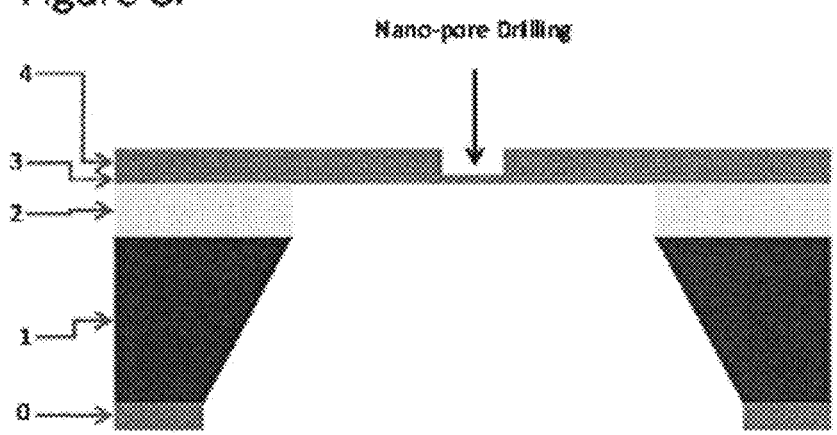
FIG. 8 depicts a device according to the claimed invention in an intermediate, nanopore-free stage of fabrication where nanopore drilling has been initiated.
Figure 9:
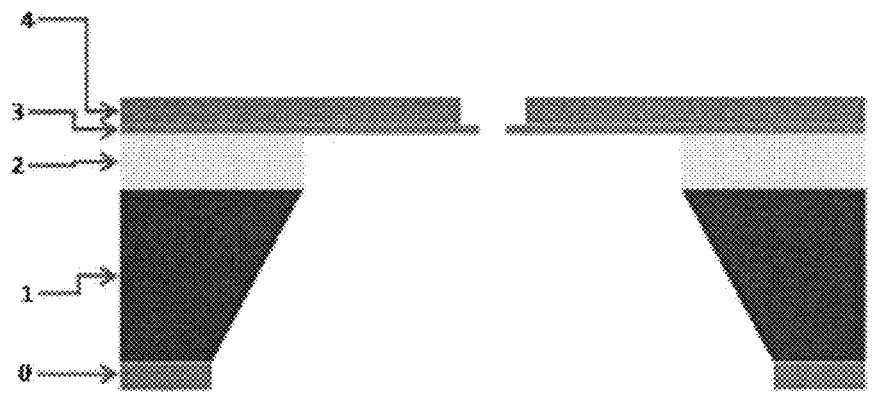
FIG. 9 depicts a device according to the claimed invention where a nanopore has been formed in the membrane (3)

In some embodiments (FIGS. 1-9), the fabrication process entails first removing a portion of the resist (6) disposed atop the device workpiece via electron beam lithography (or other etching method) and corresponding development (FIGS. 4-5). Plasma etching, for example, is used to remove a portion of the capping layer (4) (FIG. 6) to expose the comparatively thin membrane material (3). Resist (6) may be removed (FIG. 7), and a nanopore may be formed—as described elsewhere herein—in the now-exposed membrane (FIGS. 8-9).

Figure 10:
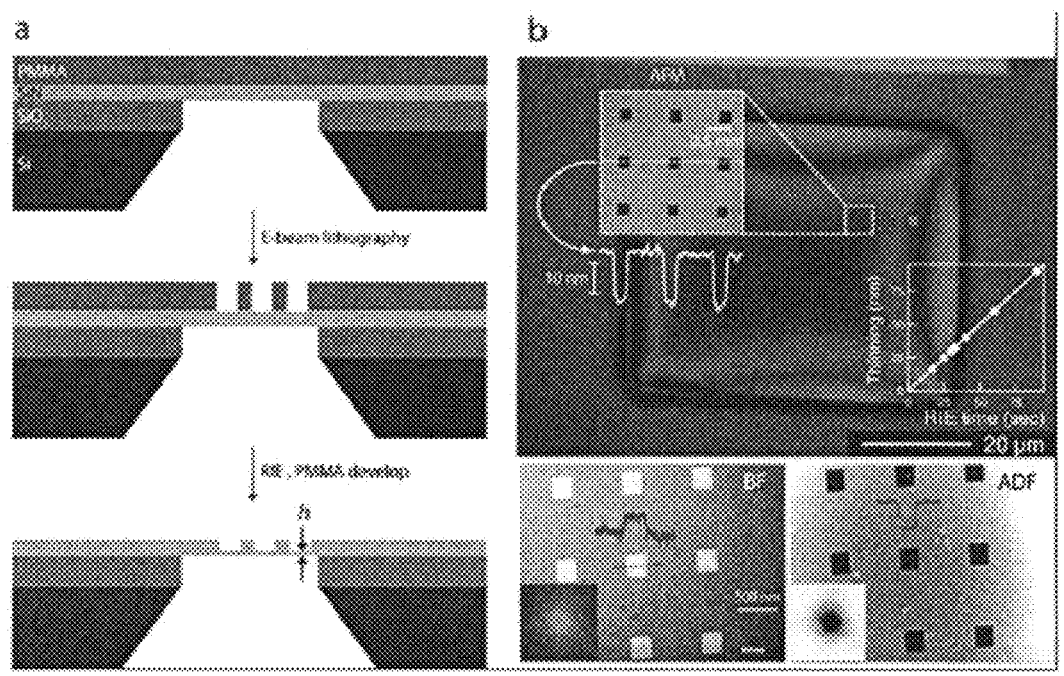
FIG. 10 illustrates (a) a process for local thinning of solid-state membranes for improving the nanopore resolution, (b) optical microscope image of a pattern of squares used for thinning experiments. Following RIE process and lift-off, AFM image of the 250 nm squares is shown in the inset (17 nm thinning). The thinning was checked for different RIE times and shows excellent linearity (slope: 1 nm/sec). The bottom shows bright-field (BF) and annular dark field (ADF) images of the etched membranes, as well as corresponding images for a 10 nm pore (inset). The intensity profiles shown adjacent to the square-shaped pores highlight the exceptional contrast of ADF imaging, useful for accurate thickness determination.

FIG. 10(*a*) depicts another embodiment of nanopore device fabrication. As shown in that figure, PMMA resist (topmost layer) is removed via electron beam lithography. Reactive ion etching (RIE) and PMMA development then follows to thin local regions of the SiN membrane to a thickness defined by (h). A silicon oxide layer is disposed (in this figure) below the membrane, and a silicon support (bottommost layer) is also present.

FIG. 10(*b*) depicts AFM and optical microscopy images of a device according to the claimed invention. Following RIE process and lift-off, the AFM image of the 250 nm squares is shown in the inset (17 nm thinning). In this example, the thinning was checked for different RIE times and showed excellent linearity (slope: 1 nm/sec). In this way, the user can, by considering the etch rate, effect a desired degree of thinning in The bottom right-hand images in FIG. 10 show bright-field (BF) and annular dark field (ADF) images of the etched membranes, as well as corresponding images for a 10 nm pore (inset). The intensity profiles shown adjacent to the square-shaped pores highlight the exceptional contrast of ADF imaging, which is useful for accurate thickness determination.

A device may include single or multiple pores, as shown in FIG. 10. Arrays or rows/strips of nanopores may be used. Arrayed pores are suitably spaced far apart enough from one another so as to avoid cross-talk between neighboring pores. Pores may be present in square (n×n) arrays. The arrays may include several pores, tens of pores, or even hundreds of pores, if the user so desires. The pores may be present in rows or strips, depending on the configuration of the device.

Pores are suitably circular or elliptical in conformation, but may also be polygonal. The pores may be square, pentagonal, rectangular, or other polygons having from 3 to 12 sides.

In some embodiments, a dielectric layer is disposed adjacent to the membrane. Without being bound to any particular theory, the dielectric layer improves the performance of the devices. The dielectric layer (layer 2 in the attached figures) suitably contacts the pore-bearing membrane where the supporting layer is present. Suitable materials for the dielectric layer include silicon oxide, aluminum oxide, silicon nitride, and the like. The dielectric layer, however, is optional, and need not be present.

In some embodiments, the devices include a capping layer (layer 4 in the attached figures). The capping layer is suitably disposed adjacent to the membrane. The capping layer material is suitably selected from the set of materials that are suitable for use in the membrane. In some embodiments, the capping layer and the membrane are formed of the same material.

The capping layer suitably includes an opening that overlaps, at least in part, a pore of the membrane. This opening may, in some embodiments, be used to assist the user in locating one or more pores of the membrane, as the pores are nanometer-scale. The opening suitably has a characteristic cross-sectional dimension greater than the corresponding cross-sectional dimension of the at least one pore of the membrane. The opening suitably has a characteristic cross-sectional dimension in the range of from about 10 nm to about 10 microns, or from about 50 nm to about 1 micron, or from about 100 nm to about 500 nm, or even about 250 nm. The opening in the capping layer may be circular, but can also be elliptical or polygonal in configuration.

The devices also may include a device capable of applying a gradient across the pore. Batteries, magnets, voltage generators, and the like are all considered suitable. The gradient may be an electrical gradient, a magnetic gradient, an ionic gradient, a pressure gradient, and the like. An electrolytic fluid is suitably present on both sides of the pore, so as to allow an electrical gradient to be passed across the pore to drive (or pull) a macromolecule across the pore. The fluid not necessarily be electrolytic, as non-conducting fluids may be useful where a pressure, magnetic, or other gradient is used to translocate the analyte across the pore.

The devices also suitably include a monitoring device capable of detecting a signal related to passage of a macromolecule across the pore, such as a change in electrical current related to passage of an analyte across the pore. The device may also be a device that detects an optical signal, such as a signal related to the passage of a fluorophore or other label that may pass through the nanopore.

The devices may further include a device (suitably a computer) capable of comparing the signal related to passage of a macromolecule across the pore to a signal evolved from passage of a macromolecule of known structure across the pore. In this way, the user may match the signal generated by a macromolecule of unknown structure to a signal generated by a macromolecule of known structure to determine the structure of the macromolecule being tested.

The devices may also include a device (e.g., a computer) that correlates a signal detected from the analyte or nanopore to a property of the analyte, the concentration of the analyte, or both. For example the device may correlate the number of passage events to the concentration of the analyte in the sample. This may be accomplished by comparing the number of passage events (or even the number of passage events per time) to calibration curve. The device may also output (e.g., display) the passage events, or may save a record of the events to a computer readable medium. The devices may display the signals detected at the pore as the signals are detected, i.e., in real-time.

Alternatively, the user may correlate the detected signal or signals to a property of the analyte. The user may do so by comparing a signal or signals evolved from the translocation of the analytes through the pores to a calibration curve or other standard.

Also provided are methods of fabricating devices. These methods include removing at least a portion of a first material disposed adjacent to a membrane material having a thickness in the range of from about 20 nm to about 200 nm so as to expose at least one target region of the membrane material; and etching at least a portion of the at least one target region of the membrane material so as to reduce the thickness of the membrane material within the target region to from about 0.1 nm to about 50 nm, or even from about 3 nm to about 30 nm. This can, in some embodiments, be conceptualized as thinning the targeted region of the membrane material.

The membrane may, in some embodiments, have a thickness in the range of even 5 nm to about 20 nm. The membrane may also have a thickness in excess of 200 nm, e.g., from about 200 nm to about 500 nm, or even to about 1000 nm. The first material—which may be a resist—may have virtually any thickness; the optimal thickness will depend on the user's needs and will be determined without undue experimentation.

The user may form at least one pore that extends through the target region of the membrane material. The pore may be formed by methods known in the art, e.g., application of an electron beam, a focused ion beam, heavy ion irradiation, chemical etching, or any combination thereof. The first material may be removed by electron beam lithography, application of etching or dissolution reagents, ion beams, and the like—suitable techniques will be known to those of ordinary skill in the art.

A variety of materials may be used as the first material. Polymethyl methacrylate, polymethyl glutarimide, styrene methyl acrylate, and the like are all suitable. Etching to reduce the thickness of the membrane may be accomplished by plasma etching, wet etching, focused ion beam etching, reactive ion etching, and the like, or any combination thereof.

The resist (first) material is suitably removed by electron beam lithography, optical lithography followed by development using an appropriate developing solvent, optical interference lithography followed by development using the appropriate developing solvent, nanoimprint lithography followed by development using the appropriate developing solvent, and the like. The resist suitably comprises polymethyl methacrylate, polymethyl glutarimide, styrene methyl acrylate, and the like; suitable resist materials will be known to those of ordinary skill in the art.

Resist material remaining after the first removal (FIG. 7) may also be removed, if the user desires. A capping layer may be present adjacent to the membrane (pore-bearing) layer, and a portion of the capping layer may be removed (FIG. 6) so as to expose the target region of the membrane material. This removal is suitably accomplished by wet-etching, dry etching, plasma etching, or any combination thereof.

Exemplary device fabrication is illustrated in FIG. 34, FIG. 35, and FIG. 36. In FIG. 34, a mask layer 0 (e.g., silicon nitride) is disposed adjacent to a silicon or other substrate material 1. A dielectric material 2 (e.g., silicon oxide) is disposed adjacent to a thinnable membrane material 3. The thinnable membrane material 3 may be silicon nitride. As shown in FIG. 35, a portion of the membrane 3 is removed so as to give rise to a thinned region of the membrane, which thinned region has a thickness smaller than that of the unthinned portion of the membrane 3. As shown in FIG. 36, a pore is then formed in the thinned region of the membrane 3.

This technique thus enables formation of thin (or, short) pores in a thicker membrane material. In this way, the user may create advantageously thin pores—which have useful properties, as described elsewhere herein—in a comparatively thick membrane 3, which membrane lends structural rigidity to the device. Methods of forming pores are well-known to those of ordinary skill in the art. A reduced area of the thinned membrane of a sub-micron scale is useful (but not necessary). It may also be useful—but not necessary—to reduce the membrane thickness in patterned areas that are at a distance from the edge of the support of the larger membrane. This may reduce stress in the thin membrane that results from the interface between the freestanding membrane and the supported membrane.

Also provided are methods of analyzing an analyte. These methods include translocating at least a portion of an analyte (e.g., miRNA or a macromolecule) through a pore disposed in a membrane having a thinned region with a thickness in the range of from about 0.1 nm to about 20 nm and detecting a signal related to the translocation of the molecule through the pore.

Translocation is suitably effected by application of a gradient, such as an electrical field, a magnetic field, an ionic gradient, or any combination thereof. The thickness of the pore is suitably between about 0.1 to about 20 nm, or from about 1 nm to about 10 nm, or even from about 2 nm to about 5 nm. The optimal thickness of the pore will depend on the needs of the user and on the characteristics of the macromolecule being analyzed.

The user may monitor an electrical signal, a visual signal, or even some combination of these. Electrical signals—such as current—are considered especially suitable. Microscopy instruments are suitably used to gather optical or visual signals from the macromolecules under analysis. The detection of the signal may be accomplished by electrodes, as shown in the exemplary embodiments herein.

In some embodiments, correlating comprises comparing the signal related to the translocation of the macromolecule through the pore to a signal generated from the translocation of a macromolecule of known structure through a pore. For example, a user may know that a particular sequence of six bases yields a particular electrical current signal when that sequence is passed through a detector nanopore. If the user then observes that same current signal when analyzing a macromolecule of unknown structure, the user can conclude that the macromolecule undergoing testing has the six base sequence. The signal can also be used as a measure of the size of the molecule being analyzed, and the correlating aspect may thus include directly measuring the signal and correlating the signal to the size of the molecule being analyzed.

Also provided are additional analysis devices. These devices suitably include a first membrane having a thickness in the range of from about 5 nm to about 100 nm; and a second membrane disposed adjacent the first membrane, the second membrane having a thickness in the range of from about 2 nm to about 20 nm. The second membrane may include at least one pore extending therethrough, the pore having a cross-sectional dimension in the range of from about 1 nm to about 100 nm. The second membrane may include hafnium oxide, silicon oxide, titanium oxide, aluminum oxide, and the like. The first membrane suitably includes a cavity in register with the pore of the second membrane.

The construction of exemplary devices is shown in FIGS. 37-39. As shown in those figures, a thinnable membrane material 3 is disposed adjacent another membrane material 4. The membrane material 4 suitably has a thickness of a only one or a few nanometers, although thicknesses of 5, 10, 20, or even 30 nm are considered suitable. The membrane material 4 is suitably disposed adjacent to an insulator 2, which is in turn adjacent to a dye or support 1, which is in turn adjacent to a mask layer 0. The user suitably etches a cavity in the thinnable material 3 (as shown in FIG. 38, so as to expose a region of the membrane material 4. The user may then form a nanopore (FIG. 39) in the exposed region of the membrane material 4. In this way, the user may construct a thin (short) nanopore in a structurally robust assembly, which assembly has a rigidity conferred on it by the thinnable material 3. While the figures are not necessarily to scale, it is useful (but not necessary) to form the cavities and pores in regions that are relatively distant from the interface of the membrane 4 and the supporting material 2.

Further disclosed are detection devices. These devices suitably include a first capture material configured to bind specifically to a first molecule (e.g., miRNA); a membrane having a thickness in the range of from about 20 nm to about 100 nm having a thinned region thereon, the thinned region having a thickness in the range of from about 1 nm to about 20 nm, and a first pore extending through the thinned region, the first pore being in fluid communication with the capture material; and a detector configured to detect a signal related to passage of the first molecule through the first pore. Suitable membranes and pores formed therein are described elsewhere herein in further detail.

The capture material may include a protein, a porous support (e.g., a monolith), a bead, and the like. The porous support may be polymeric in nature. The capture material is suitably configured so as to bind to the first molecule (or to a molecule that is itself bound to the first molecule). For example, the capture material may include a protein—e.g., p19—that preferentially binds to a probe-miRNA duplex, as shown in FIG. 21(*a*). The capture material may include one or more nucleotides that bind to the first molecule or a species that is itself bound to the first molecule.

In some embodiments, the first molecule is bound—as shown in FIG. 21*a*—to a probe that is specifically complementary to that molecule. Such a probe may be a nucleotide-containing probe that includes a nucleic acid sequence that is complementary to a sequence on the first (target) molecule. The capture material may be selected to as to bind preferentially to a predetermined first miRNA molecule.

In some embodiments, the devices include a second capture material. This second capture material may be one that binds preferentially to a second miRNA molecule that differs in at least one aspect (e.g., size, nucleic acid sequence) from the first miRNA molecule. In some embodiments, the user may contact a sample with a second probe that is complementary to a second molecule (e.g., a miRNA molecule) that differs in some respect from a first miRNA molecule.

The capture material may be positioned such that it is in fluid communication with a pore. The first and second capture materials may be in fluid communication with the same or different pores. This may be accomplished by using different channels to connect the different capture materials to different probes. The devices may, of course, include 3 or more different capture materials, channels, or even pores. By utilizing multiple channels or pores, the devices may perform multiplexed analysis or detection for multiple analytes.

The devices may also include a sample storage chamber or input chamber. This chamber may be placed into fluid communication with the first capture material. A valve, septum, or other fluidic element may be used to modulate flow between the input chamber and the capture material.

The present disclosure also provides additional detection devices. These devices suitably include a first capture material that binds specifically to a first molecule, a first membrane having a thickness in the range of from about 5 nm to about 100 nm; and a second membrane disposed adjacent the first membrane, the second membrane having a thickness in the range of from about 2 nm to about 20 nm, and the second membrane having at least one pore extending therethrough, the pore having a cross-sectional dimension in the range of from about 1 nm to about 100 nm, and the first membrane having a cavity formed thereon, the cavity being in register with at least one pore of the second membrane, the first pore being in fluid communication with the first capture material; a device configured to apply a gradient across the pore; and a detector configured to detect a signal related to passage of a molecule through the first pore.

Suitable membranes and pores are described in additional detail herein, as are suitable capture materials. An exemplary membrane/pore device is shown in FIGS. 37-39, which figures show a nanopore formed in a thin layer 4, the thin layer 4 being supported by a mask layer 0, a dye 1, and dielectric insulator 3. As shown in those figures, a cavity is formed in the membrane material 3 in register with the pore formed in layer 4.

These devices are considered especially suitable for miRNA detection. The devices are also useful for detection of DNA, RNA, and other biological entities. The sample may be present in a storage chamber (e.g., the input chamber shown in FIG. 33), which chamber may be in fluid communication with a capture material. The devices may include more than one capture material, and the configuration of the capture materials and pores is described herein in connection with the other disclosed devices.

The present disclosure also provides methods of detecting an analyte. These methods include contacting a sample to a first capture material that preferentially binds to a first analyte, eluting the first analyte from the capture material, translocating the first analyte through a first pore disposed in a thinned region of a membrane, the thinned region having a thickness in the range of from about 0.1 nm to about 20 nm; and detecting a signal related to the translocation of the analyte through the first pore.

The first analyte may be miRNA, DNA, RNA, tRNA, and the like. Biological analytes are considered especially suitable for the provided methods. The signal evolved from the translocation of the analyte (e.g., a molecule, such as miRNA) through the pore. Electrical signals, such as current, are suitably monitored.

In some embodiments, the capture material preferentially binds the analyte. In other embodiments, the capture material preferentially binds an analyte-probe combination or duplex. As shown in FIG. 21a, the user may contact a target molecule with a probe that binds specifically to the target. The probe-target duplex then binds to a capture material, such as p19 or other protein. The capture material may be part of a bead or a porous support. The beads may be of virtually any size; they may be of sub-micron size, micron size, tens of microns, or even hundreds of microns or even millimeter-scale in size. Washing may be performed to remove other analyte (e.g., unbound miRNA) from the mixture. The hybridized probe:miRNA complex may then be eluted from the capture material, by application of salt, heat, or other reagents that effect elution.

In some embodiments, the user may contact the analyte-containing sample to a second probe. This second probe is suitably selected so as to bind preferentially to an analyte (e.g., second analyte) that differs from the first analyte. The user may then bind the second analyte to a capture material, wash away other analytes, and elute the second analyte for detection by the pore, where the user detects a signal related to the translocation of the second analyte through the second pore.

The foregoing may also be accomplished by translocating an analyte through a first pore formed in a first membrane. The first membrane is suitably disposed adjacent to a second membrane; the second membrane having a thickness in the range of from about 5 nm to about 100 nm and the second membrane having a cavity formed thereon, the cavity being in register with the first pore, the first membrane having a thickness in the range of from about 2 nm to about 20 nm, and the first pore extending through the first membrane, the pore having a cross-sectional dimension in the range of from about 1 nm to about 100 nm, the first pore being in fluid communication with the first capture material; and detecting a signal related to the translocation of the molecule through the pore.

Exemplary Embodiments

The following is an exemplary, non-limiting embodiment of the claimed invention. The specific materials and techniques recited here are exemplary only and should not be taken as limiting the scope of the invention to these particular materials and techniques.

The present invention presents a unique approach for fabricating sub-10 nm thick membrane devices, as well as the use of such membranes for nanopore-based nucleic acid analysis. This innovation involves, inter alia, the steps of (1) electron-beam lithography is used to expose a sub-micron region on a 50 nm-thick SiN window, (2) reactive ion etch is used to locally thin the exposed SiN region with sub-nanometer control, (3) the electron-beam of a transmission electron microscope is used to drill a nanopore in the thinned SiN region. Thereafter, the nanopore devices are treated using established protocols for subsequent biomolecular analysis. Analysis of macromolecular translocation through solid-state nanopores is described in, e.g., Wanunu et al., *Biophys. J.*, August 2008, vol. 95, and Wanunu et al., *Nature Nanotechnology*, Vol. 5, November 2010, the entireties of which are incorporated herein for all purposes.

An exemplary, non-limiting fabrication scheme is shown in FIG. 1 (plan view) and FIG. 2 (top view). The ultrathin nanopore is supported by, e.g., a ca. 500 μm thick <100> p-type silicon (Si) wafer (layer 1 in FIG. 1), which may contain a several μm thick thermal oxide on one or both of its sides (layer 2 in FIG. 1).

Using low-pressure chemical vapor deposition (LPCVD), ca. 40 nm of low-stress SiN is deposited on both sides of the wafer. Standard photolithography followed by anisotropic etch using KOH is used to divide the wafer into a square array of 5×5 mm$^2$ chips, as well as to define in each chip a free-standing square SiN window with dimensions ranging from 1×1 to 500×500 μm$^2$. If oxide is present in the free-standing window, the oxide is removed by treatment with hydrofluoric acid or by buffered oxide etch using standard protocols. This yields a workpiece as shown in FIG. 3.

The top side of the substrate in FIG. 3 is then spun-coated with an electron beam resist C2 950 PMMA (950 molecular weight polymethyl methacrylate, 2% in chlorobenzene) at 5000 rpm for 50 seconds to achieve a resist layer of ~100 nm thickness, and then baked on a hotplate at 180° C. for 10 minutes (FIG. 4).

Electron beam lithography is then used to write a square of 50×50 to 1000×1000 nm2 onto the resist-coated SiN window, using a 20 pA electron beam of 50 kV (Elionix 7500-ELS) and a beam dose of 750 μC/cm$^2$. The device is then developed in 1:3 volume ratio of MIBK (methyl isobutyl ketone) and isopropanol, respectively, for 60 seconds (FIG. 5).

The exposed areas of the SiN are further thinned by $SF_6$ plasma etching using a 50 watt RF source and 0.4 mtorr SF6 chamber pressures (FIG. 6). The duration of the RF source determines the etch depth, which is suitably 1 nm per second under the indicated conditions. Other etch rates are within the scope of the claimed invention, and the optimal etch rate will depend on the user's needs and capabilities. The etch rate can be modulated or chosen so as to enable the user to achieve devices of the desired configuration.

In another, non-limiting embodiment, the user etches a SiN layer (shown as layer 4 in the attached figures) so as to expose a layer (layer 3) of hafnium oxide. The hafnium oxide may have a thickness of from about 2 nm to about 5 nm, in some embodiments.

Atomic force microscopy is used to accurately measure the etched depth in a given batch of etched chips. This process can be simultaneously carried out on a set of 1-300 chips. Following the thinning, PMMA resist is removed by incubation in warm acetone, yielding a device shown in FIG. 7.

Each chip is then inserted into a transmission electron microscope equipped with a field emission gun (e.g., a JEOL model 2010F) and a nanopore in the range 1-100 nm is drilled by focusing the electron beam onto the thinned region of the membrane using previously reported protocols (see FIG. 8), yielding a nanopore device as shown in FIG. 9. Formation of nanopores in membranes is well-characterized in the art, and is described in, e.g., Storm et al., *Nature Materials*, August 2003, vol. 2, the entirety of which is incorporated herein by reference for all purposes.

Figure 11:
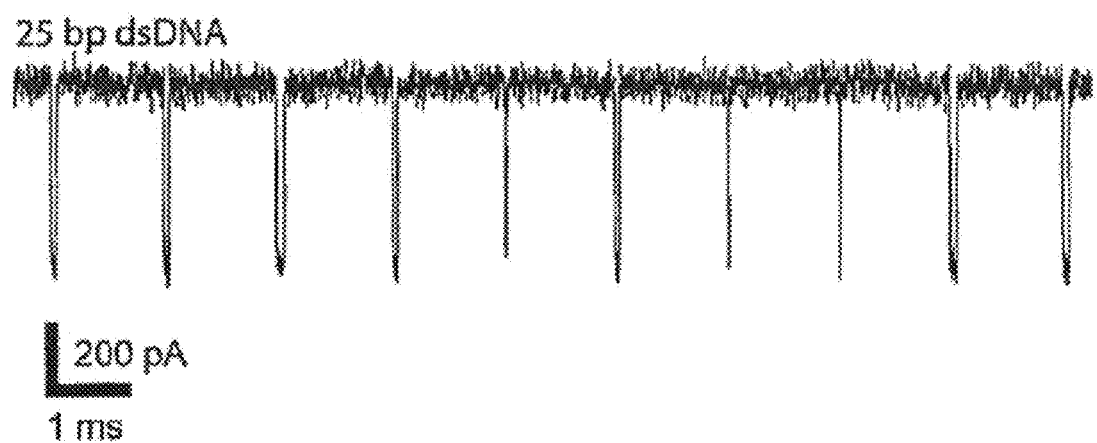
FIG. 11 illustrates the detection of 25 bp dsDNA using a 3 nm solid-state nanopore according to the claimed invention in a 20 nm thick SiN membrane (T=0° C., V=300 mV). Concatenated single-molecule traces are shown. The small pore and low temperature combination facilitates detection of these short molecules (mean transport time=80 microseconds), an important step for detecting RNA-drug complexes in design-RNA sequences, such as the ribosomal A-site and the TAR site of HIV RNA.

FIG. 11 illustrates the detection of 25 bp dsDNA using a 3 nm solid-state nanopore according to the claimed invention in a 20 nm thick SiN membrane (T=0° C., V=300 mV). In the figure, concatenated single-molecule traces are shown; the small pore and low temperature combination facilitates detection of these short molecules (mean transport time=80 microseconds), which is an important step for detecting RNA-drug complexes in design-RNA sequences, such as the ribosomal A-site and the TAR site of HIV RNA; and The improved resolution achieved by the claimed invention is shown by FIG. 12, which figure illustrates DNA translocation through 4 nm pores in SiN membranes of various thickness values.

Figure 12A:
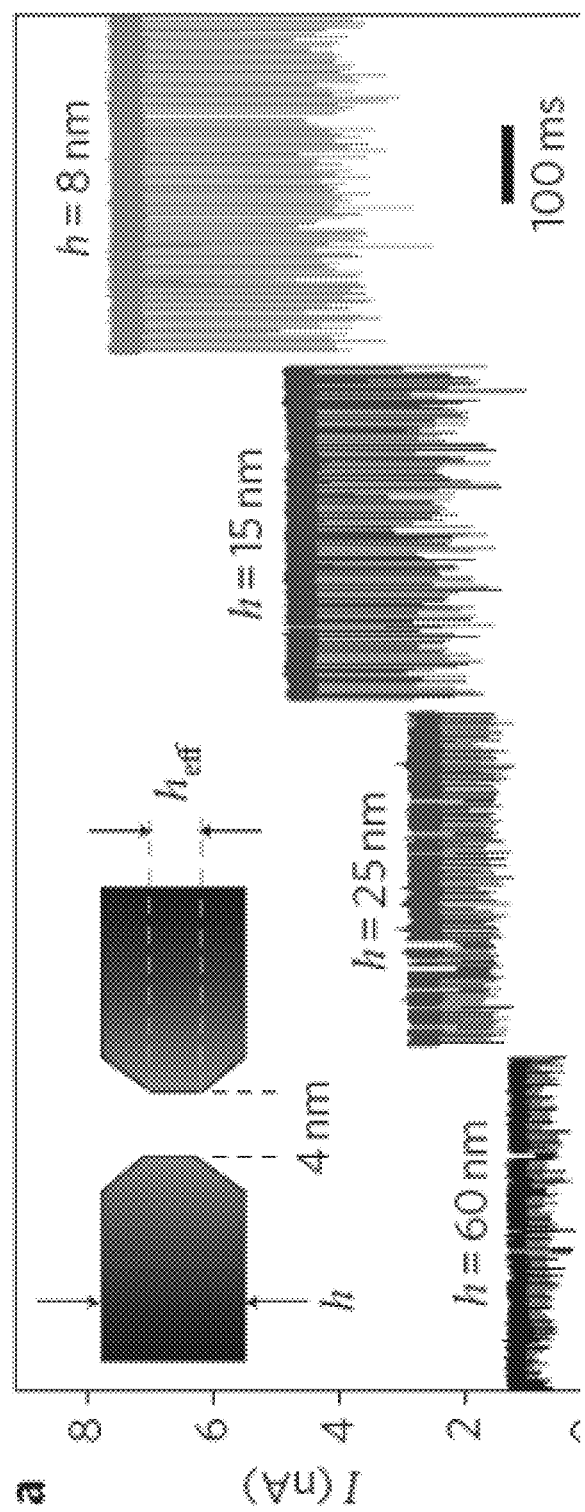
FIG. 12 illustrates increasing measurement resolution by nanopore thinning. (a) Concatenated sets of ~200 translocations of 3 kb linear double-stranded DNA through 4 nm diameter pores fabricated in membranes with different h values; $h_{eff}$ is the nanopore's effective thickness used in the geometric model discussed in the text. In decreasing h from 60 nm to 6 nm, the open pore current increased and the DNA signal amplitude increased. All traces were filtered using the Axopatch 100 kHz filter setting. For h=60 nm, the data was low-pass filtered at 10 kHz using the Axopatch filter to make events visible. (b) A magnified view of the traces in (a). (c) Semi-log histograms of the blocked current amplitudes normalized by subtracting delta I, which show increased current amplitudes for thinner nanopores. While the most probable blocked current $\Delta I_p$ increased with decreasing h, open pore noise values were similar. (d) Dependence of average experimental $<I_o>$ (circles) and the most probable DNA current amplitude $\Delta I_p$ (triangles) on h. The dashed line is a fit using Eqn. 1 to the average $I_o$ data from combined data of ~20 pores, which yields an effective pore thickness $h_{eff}$=h/(3.04±0.30) ($h_{eff}$ scale shown on top x-axis). The fit to $\Delta I_p$ values (dashed line) is based on a geometric model described in detail herein. The inset shows $\Delta I_p/<I_o>$, which did not change appreciably with h. The inset's dashed line is the ratio of the fits to $\Delta I_p$ and $<I_o>$ from the main plot. (e) The signal-to-noise (S/N) and mean transport time as a function of h ($h_{eff}$ shown on top x-axis). One may define S/N=$\Delta I/I_{RMS}$, where $I_{RMS}$ at 100 kHz bandwidth is 75±5 pA. Mean transport times were obtained from the dwell-time distributions.

FIG. 12a shows concatenated events for 3 kbp dsDNA translocations, as a function of membrane thickness (h) (V=300 mV, T=21° C., 1M KCl, pH 8). As shown at the top of the figure, the detected current increases with decreasing h values, such that a nanopore having a thickness of 8 nm is more than four times more sensitive than a nanopore having a thickness of 60 nm. These data underscore the performance advantages achieved by the thinned membranes and thin (low-h) nanopores of the present disclosure.

FIG. 12b shows expanded events from the traces shown in the upper quadrant of the figure. As shown, nanopores having a thickness of 8 nm enable the user to resolve individual translocation events at a far greater resolution than nanopores having thickness values of 15, 25, or even 60 nm. FIG. 12c shows semi-log all-point current histograms from the events shown at the top of the figure, illustrating the ability of the thinned nanopores to resolve DNA translocation at improved resolution.

Figures 12D, 12E:
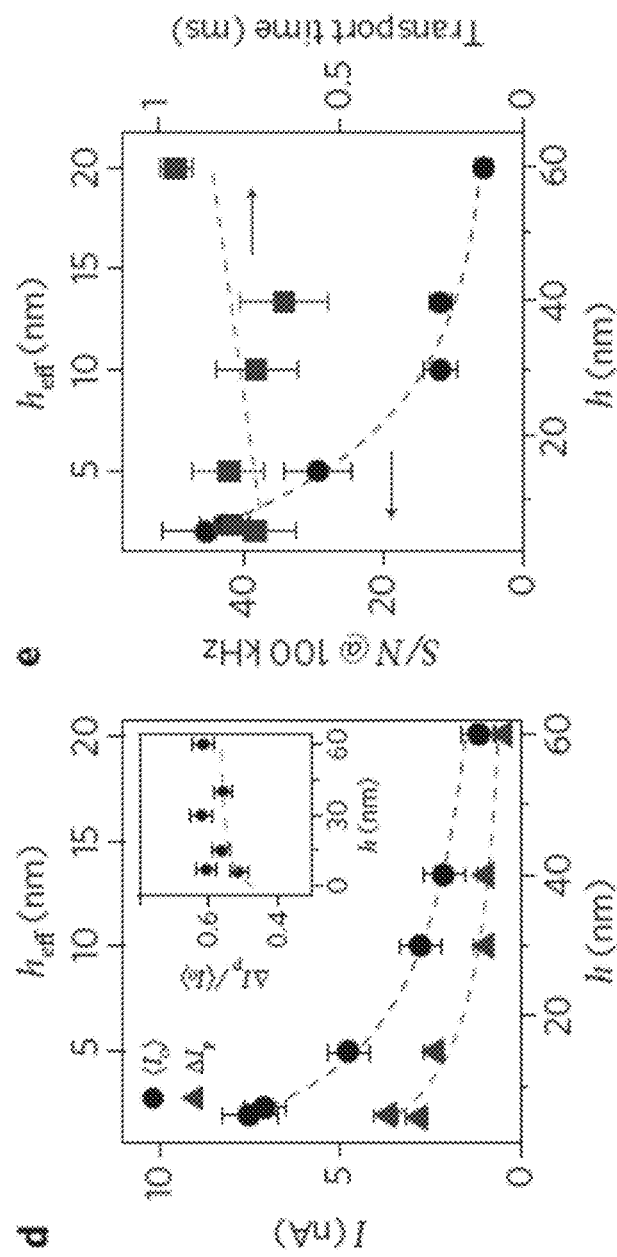

FIG. 12d illustrates the relationship average experimental $<I_o>$ (circles) and the most probable DNA current amplitude $\Delta I_p$ (triangles) on h. The dashed line among the circles is a fit using Eqn. 1 to the average $I_o$ data from combined data of ~20 pores, which yields an effective pore thickness $h_{eff}$=h/(3.04±0.30) ($h_{eff}$ scale shown on top x-axis). The fit to $\Delta I_p$ values (dashed line with triangles) is based on a geometric model described in detail herein. The inset shows $\Delta I_p/<I_o>$, which did not change appreciably with h. The dashed line in the inset is the ratio of the fits to $\Delta I_p$ and $<I_o>$ from the main plot.

FIG. 12e illustrates the signal-to-noise (S/N) and mean transport time as a function of h ($h_{eff}$ shown on top x-axis). S/N=$\Delta I/I_{RMS}$, where $I_{RMS}$ at 100 kHz bandwidth is 75±5 pA. Mean transport times were obtained from the dwell-time distributions.

Thinned pores presents many advantages, including improved signal-to-noise (improving from when the nanopore thickness goes from 60 nm to 8 nm), as well as improved resolution by contraction of the resistive sensing zone to a few nm, which contributes greatly to RNA-drug complex detection and footprinting.

Without being bound to any single theory of operation, the advantage of the disclosed thinned nanopores can be described by reference to existing, thicker nanopores. As a non-limiting example, if a DNA molecule enters a pore with a thickness of about 20 nm, approximately 40 to 50 base pairs would reside within the pore at a given moment. If, however, the pore is reduced in thickness such that only 5-6 base pairs reside within the pore at a given moment, the detected current (or other signal) related to the DNA passage across the pore would be averaged over far fewer bases than where the pore accommodates 40-50 base pairs.

Ultrathin nanopores have been fabricated and were evaluated for their performance in DNA analysis. The locally thinned SiN membranes offer tremendous advantages, such as greater signal-to noise values and improved resolution, with similar DNA transport velocities as with thicker membranes. This method can be applied on a wafer scale, enabling the production of hundreds of substrates at a time, essential for success in this proposal.

Microscopy

In another aspect, the present invention provides stages or platforms suitable for high-resolution microscopy. These stages or platforms suitably include a membrane having a locally thinned region (e.g., FIG. 13 and FIG. 6), which thinned region confers enhanced microscopy properties on the membrane. The thin membranes may be used as sample stages or supports. These are especially suitable for supporting cells, cell contents, or other biological entities for observation.

As one example, the thin membranes may be used in Transmission Electron Microscopy (TEM)-based and scanning TEM (STEM)-based imaging and analysis, which includes: bright field imaging, annular dark field (ADF) and high-angle annular dark field (HAADF) imaging, electron diffraction analysis, electron energy loss spectroscopy (EELS), and energy dispersive spectroscopy (EDS). One advantage presented by the thin membranes are that the ultrathin support enables higher contrast (relative signal) from samples deposited onto the ultrathin region, then the contrast from sample deposited onto a thicker region. An additional advantage is that the wide choice of materials suitable for the ultrathin membranes enables elemental spectroscopy (e.g., EELS and EDS above) with little or no interference from the substrate.

The thinned membranes are also suitable for Scanning Electron Microscopy (SEM)-based imaging, which includes imaging using a secondary electron detector, backscattering detector, a transmission detector, and a so called STEM detector. The ultrathin substrates exhibit an extremely low backscattering cross-section, which results in the substrates being practically SEM-invisible. Such devices exhibit a much better contrast than normal (thick) counterparts, enabling better contrast and EDS signal. This is illustrated in FIG. 40, which figure illustrates (from left to right) a series of zoomed images of a 6 nm thinned membrane formed in a thicker support. (The thinned membrane also includes a pore formed therethrough; the pore is shown by the bright spot at the edge of the thinned region.

The membranes are also advantageous for optical microscopy, which includes wide field white light imaging, or confocal fluorescence, or epifluorescence, or total-internal reflection mode fluorescence, or luminescence mode (in which light from a light-emitting source is collected). In such applications, the sample of interest is deposited on the window substrate, and one or more of the optical methods above is used to image the sample. Many substrates have intrinsic fluorescence (e.g., SiN is known to be "noisy" for blue-green fluorescence measurements. The reduction of the thickness for local imaging reduces the background extinction or fluorescence from the substrate, enabling better signal and contrast from the sample of interest.

Accordingly, the microscopy supports suitably include a membrane material having a first region of from about 0.5 nm to about 20 nm in thickness and a support layer disposed adjacent to the membrane material. The membrane and support layers may include the materials described elsewhere herein, e.g., silicon nitride and the like. The first region may have a thickness of from about 2 nm to about 12 nm, or even from about 6 nm to about 10 nm.

Also provided are methods of fabricating a microscopy supports. These methods suitably include removing at least a portion of a material disposed adjacent to a membrane so as to expose a first region of the membrane. This is shown by, e.g., FIGS. 4-7, which figures illustrate removal of material adjacent to a membrane (3) having the claimed thickness. FIG. 7 illustrates a device wherein a thin, lower membrane is exposed by formation of a cavity or other void in the material atop the lower membrane. The thin, exposed lower membrane may be used as a stage or support for samples undergoing optical microscopy, TEM, STEM, and other similar measurements. A pore may be formed in the lower, thin membrane, as shown in FIG. 8.

In some embodiments, the methods include etching at least a portion of the first region of the membrane material so as to reduce the thickness of the membrane material within the target region. This is shown by, e.g., FIGS. 10 and 14-16, which depict removal of a material adjacent to the membrane and then etching of the membrane material (3) itself so as to thin a localized region of the membrane.

ADDITIONAL DESCRIPTION

In one exemplary platform described herein, a target microRNA is first hybridized to a probe; this probe:microRNA duplex is then enriched through binding to the viral protein p19; and, lastly, the abundance of the duplex is quantified using a nanopore. Reducing the thickness of the membrane containing the nanopore to 6 nm leads to increasing signal amplitudes from biomolecules, while reducing the diameter of the nanopore to 3 nm allows the detection of and discrimination among small nucleic acids based on differences in their physical dimensions. This approach detects picogram levels of a liver-specific miRNA from rat liver RNA.

Forming Nanopores in Substrates

Figure 18A:
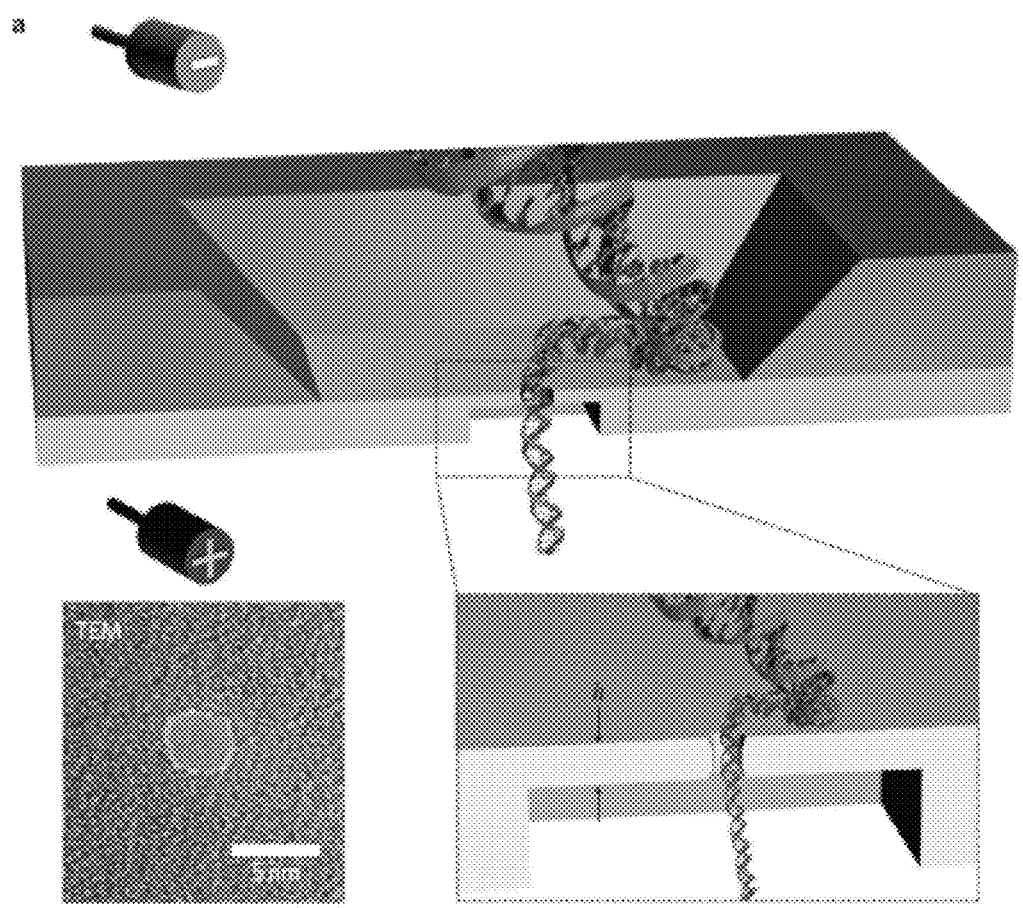
FIG. 18 illustrates sub-10 nm thick solid-state nanopore sensors. (a) Scheme of a nanopore sensor showing a DNA molecule translocating through the pore (not to scale). The sensor consists of a 5×5 mm2 Si chip that contains a free-standing silicon nitride (SiN) membrane (~50×50 μm2). After locally thinning the membrane using the process shown in (b), a nanopore is drilled using a TEM (see TEM image of a 4 nm diameter nanopore in 6 nm thick membrane). Electrolyte solution is added above and below the nanopore, each contacted by a Ag/AgCl electrode, and voltage is applied to drive charged biomolecules through the pore. (b) The membrane thinning process involves coating the membrane with a PMMA resist, followed by e-beam exposure and development, and controlled dry etching using SF6 plasma. (c) Optical image of the membrane after thinning (before removal of the PMMA). The inset shows an AFM topography image of a 3×3 square array following PMMA removal, as well as a line profile that shows uniform, 17 nm deep trenches. The inset shows that the etch depth, measured by AFM, is a linear function of the etch time and that the etch rate is 1 nm/s. (d) Epi-fluorescence image of a 41 nm thick SiN membrane in which 5 μm squares were thinned to 8 nm ($\lambda_{ex}$=488 nm, $\lambda_{em}$=525±25 nm). The fluorescence intensity histograms show lower fluorescence background in the thinned region.

FIG. 18a depicts an exemplary thin solid-state molecular counter. In this embodiment, a region of a freestanding SiN membrane supported by a Si chip is thinned, after which a nanopore is fabricated using a transmission electron microscope (TEM). Biomolecular translocations (depicted in the inset) through the nanopore appear as transient reductions in the ion current. A TEM image of a ca. 4 nm diameter pore in a ca. 6 nm thick membrane is shown in the inset. As shown in the figure, an electrical gradient is applied across the pore so as to drive the analyte through the pore for detection.

The reduction of membrane thickness h is described in FIG. 18b. An optical micrograph of a processed membrane is shown in FIG. 1c, in which a pattern of 1, 4, and 9 squares of different sizes has been exposed and etched. An AFM image of the thinned 3×3 array is shown in the inset. Knowledge of the initial membrane thickness and the etch depth allows calculation of the resulting membrane thickness. AFM characterization of the depth vs. etch time reveals an etch rate of 1.0 nm/sec, which is illustrated in FIG. 18c inset and FIG. 22.

Figure 18D:
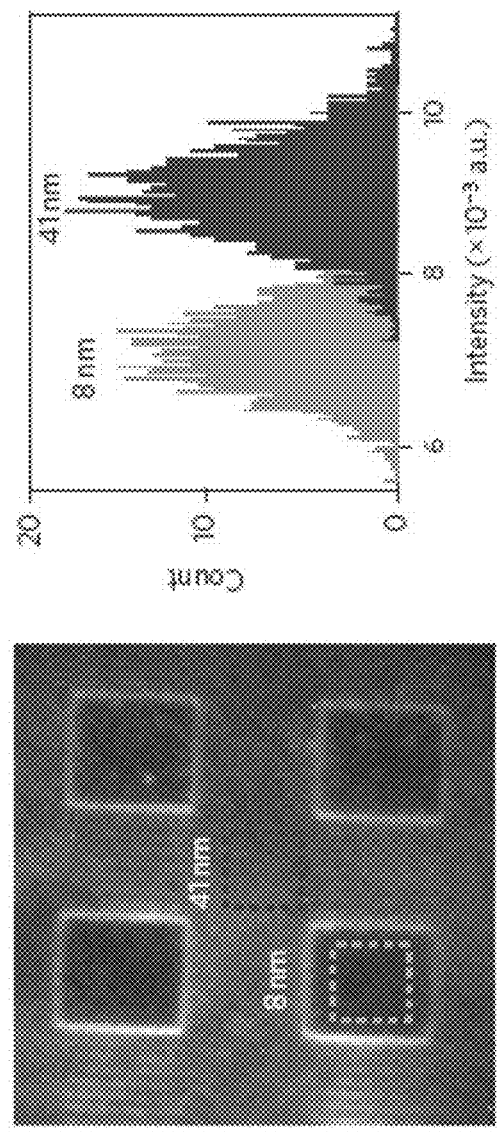

The intrinsic fluorescence of SiN membranes from embedded nano-Si structures was also measured. FIG. 18d shows that fluorescence background is reduced in the thinned regions, consistent with a reduced number of fluorescent structures. The thinnest nanopores were fabricated in 6 nm thick membranes (see FIG. 12d), which are comparable in thickness to lipid bilayers. Nanopores may, as described herein, be fabricated in membranes that are thinner and thicker than 6 nm.

Figures 19A, 19B:
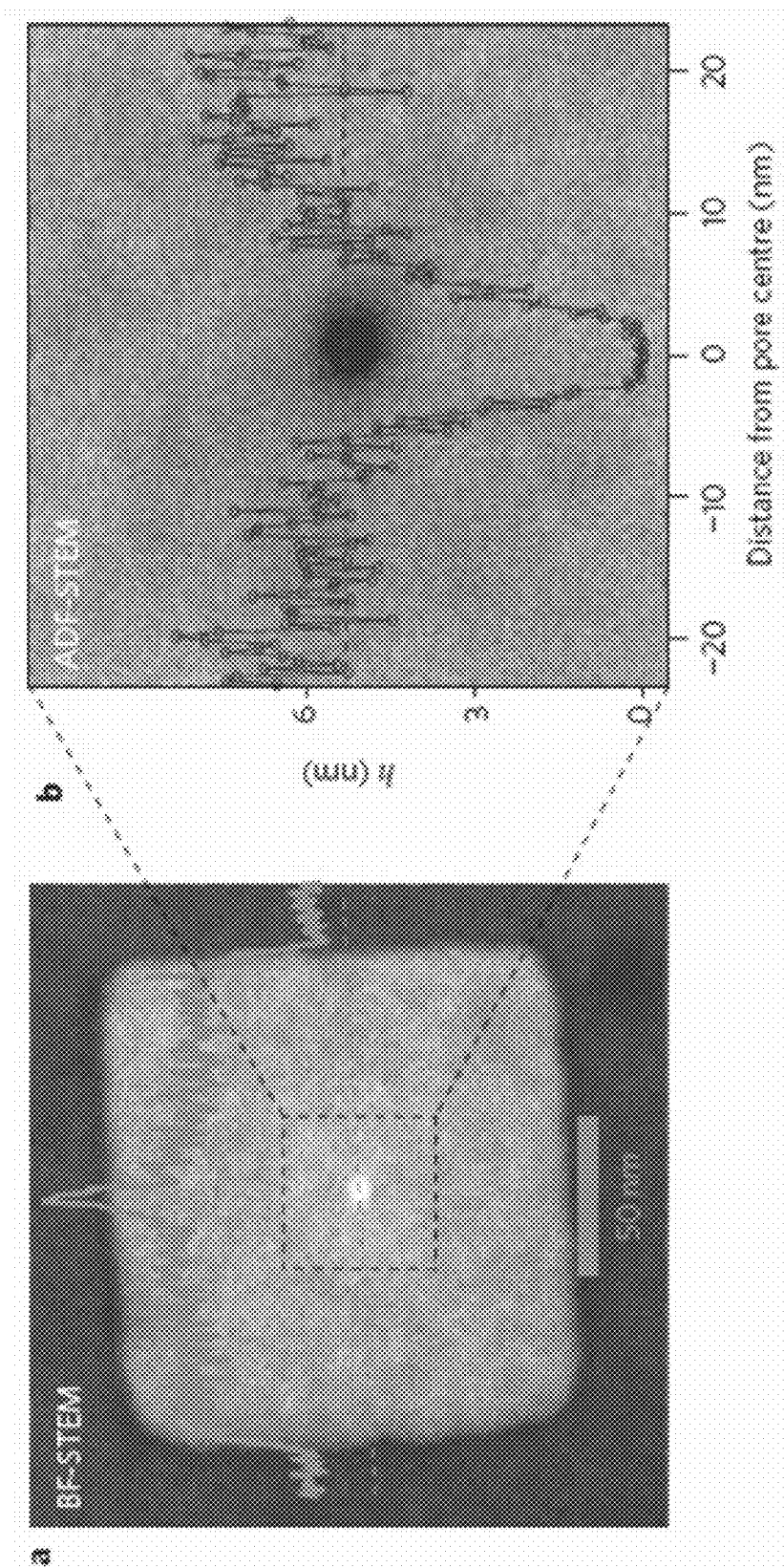
FIG. 19 illustrates scanning TEM (STEM) characterization of a 4.5 nm diameter pore in a 7 nm thick membrane (STEM probe size=0.2 nm). (Left) A bright-field STEM (BF-STEM) image shows the etched 250×250 nm square as a brighter area with uniform intensity. (Right) Annular dark-field STEM (ADF-STEM) of a zoomed-in portion of the nanopore on the left. The height profile (data trace line on FIG. 19a) of a line through the center of the pore is shown. The membrane thickness h (y-axis) was measured from the difference of the initial membrane thickness and the etch depth, normalized by assigning a thickness of 0 nm to the signal intensity at the pore (i.e., in vacuum).

To characterize the sub-10 nm thick nanopores, bright-field (BF) and annular dark-field (ADF) scanning transmission electron microscopy (STEM) images of a 4.5 nm diameter pore in a 7 nm thick membrane are shown in FIG. 19. Both BF and ADF STEM provide contrast that is very sensitive to membrane thickness. In BF-STEM, the thinned membrane region is a brighter area. The uniformity of the etched region is indicated by the line profile intensity (line in FIG. 19a). A zoomed-in ADF-STEM image reveals a sharp drop in the intensity near the pore (line in FIG. 19b). The contrast is reversed from BF to ADF, so that the pore appears dark.

Based on previous TEM and ion conductance measurements and the ADF-STEM measurements, nanopore shapes deviate from a perfect cylinder. However, a simplified geometric model using an equivalent cylinder of reduced thickness and equal diameter to the measured pore diameter can quantitatively explain the data. This reduced thickness is defined as the effective pore thickness $h_{eff}$, as illustrated in FIG. 12a.

To a first approximation, $h_{eff}$ can be used to quantitatively explain electrolyte transport through the pore. Systematically changing the membrane thickness h by controlled thinning should have a predictable influence on electrolyte transport through a pore fabricated in such a membrane. When voltage V is applied, the ion current $I_0$ through a cylindrical pore with diameter d and thickness $h_{eff}$ is approximated in high ionic strength solutions (>100 mM) by:

$$I_0 = V([\mu_{K^+} + \mu_{Cl^-}]n_{KCl}e)\left(\frac{4h_{eff}}{\pi d^2} + \frac{1}{d}\right)^{-1} \quad \text{Eqn. 1}$$

where μ is the electrophoretic mobility of a species, $n_{KCl}$ is the number density of KCl, and e is the elementary charge. This equation includes the access resistance, which dominates the conductance in the limit of $h_{eff} \rightarrow 0$. Passage of analytes through the pore transiently reduces the ion current because the ion flux is hindered. Therefore, for similar diameter pores, reducing the pore thickness should yield two experimental outcomes, increased $I_o$ (see Eqn. 1), and increased difference I between the open pore current and the current upon occlusion with biomolecules.

To test this, one may use similar TEM conditions to fabricate dozens of 4 nm diameter pores in membranes with h=6-60 nm. FIG. 12a shows a set of ~200 concatenated translocations of 3 kb linear double-stranded DNA (dsDNA) molecules for 4 nm diameter pores of different thicknesses, recorded at 21° C. and 300 mV. Upon decreasing h, it is founds that: (1) open pore currents increase, and (2) amplitudes of the DNA translocation signals increase. Decreasing h vastly improves the signal from biomolecules, as illustrated by the close-up view of representative events in FIG. 12b. All-point current histograms from the traces shown in FIG. 3a are plotted on a semi-log scale in FIG. 12c. The histograms were normalized by subtracting the mean open pore current $<I_o>$ from each distribution. As predicted, the most probable current amplitude $\Delta I_p$ (dashed white lines) increases as h decreases. Also, the broadness of the ΔI distributions is augmented in thinner pores. Broad ΔI distributions were previously observed for pores in lipid bilayers and solid-state membranes, and are likely a result of the varying transport speeds, interactions, and/or initial configurations of each molecule prior to translocation.

In FIG. 12d is shown experimental mean open pore currents $<I_o>$ (circles) and the most probable DNA current amplitudes $\Delta I_p$ (triangles). Both quantities increase with decreasing h. The dashed line among the circles is a fit of $\langle I_o \rangle$ based on Eqn. 1, where $h_{eff}$ is a fitting parameter. Using d=4.0 nm, $\mu_{K+}$=6.95×10$^{-8}$ m$^2$ V$^{-1}$ s$^{-1}$, and $\mu_{Cl-}$=7.23×10$^{-8}$ m$^2$ V$^{-1}$ s$^{-1}$, a best fit to the data is obtained using $h_{eff}$=h/(3.04±10.30), in good agreement with previous measurements for thicker membranes (see top x-axis of FIG. 12d). Based on the fit, the thinnest pores shows here with h=6 nm have a calculated $h_{eff}$≈2 nm.

To fit the experimental $\Delta I_p$ values, one uses a geometric model to compute the residual current through the pore when occupied by a DNA strand (see FIG. 23 and related discussion). In this model, dsDNA is assumed to be a cylinder 2.2 nm in diameter, and I is computed from the unobstructed area of the DNA-occluded pore. Once can add to this model a parameter S that describes the fraction of chloride ions excluded from the nanopore vicinity by the highly charged DNA coil. A previous report that $\Delta I$ increases as a function of DNA length in 4 nm pores suggests that the highly charged DNA coil excludes Cl$^-$ from the pore vicinity, therefore reducing [Cl$^-$] near the pore. Using a single parameter of 20±5% Cl$^-$ exclusion for 3 kb DNA, the results match the model for $\Delta I$ (Eqn. 2 herein) for all tested $h_{eff}$ values (see dashed curve). The inset to FIG. 12d shows the experimental (markers) and calculated (dashed line) blockage fractions $\Delta I_p/\langle I_o \rangle$ as a function of h. In the regime where access resistance does not dominate, i.e., for h>10 nm, $\Delta I_p/\langle I_o \rangle$ is independent of h.

FIG. 12e displays signal-to-noise ratios S/N $I_p/I_{RMS}$ as a function of h, where $I_{RMS}$ is the open pore current RMS at 100 kHz bandwidth. $I_{RMS}$ is independent of h ($I_{RMS}$~70-80 pA at 100 kHz bandwidth), which results in increasing S/N values with decreasing h because $\Delta I$ increases with decreasing h. S/N=46 for h=6 nm, a marked improvement over S/N~10 in similar diameter pores with h=25 nm.

Finally, a potential concern in this study was that reducing h would also reduce DNA interactions with the pore surface, thereby speeding up DNA transport and presenting detection challenges. The right axis of FIG. 12e shows that the mean transport times for the 3 kb DNA molecules are approximately independent of h, with less than 30% decrease in transport times when h is reduced from 60 nm to 6 nm. The weak dependence of transport times on h indicates that parameters other than surface interactions, for example, electro-osmotic drag, influence the transport dynamics.

DISCRIMINATION AMONG SMALL NUCLEIC ACIDS

Using the increased signal amplitude in thin nanopores, thin pore (d=3 nm, h=7 nm) were tested to discriminate among small nucleic acids. First were compared 22-bp RNA and 25-bp DNA, because the two molecules have similar effective solvation volumes (~35 nm$^3$ and ~32.3 nm$^3$, respectively) and molecular weights (~15 kD), while differing in cross-sectional areas by ~35% due to their different helicities (see in FIG. 20a PDB files 1RPU and 2BNA from http://www.rcsb.org). Continuous current traces, as well as magnified sets of representative events are shown in FIG. 20a. To quantify the difference between the molecular signatures, also shown are all-point current histograms for DNA and RNA, which highlight the characteristic signal from longer events. The histograms reveal peaks at characteristic current amplitudes of $I_{DNA}$=0.54 nA and $I_{RNA}$=0.92 nA. Similar amplitudes were obtained for 10-bp DNA and 25-bp DNA, although the 10-bp molecule often stuck to the pore for >1 ms timescales because the 10-bp molecule is comparable in length to the pore dimensions.

The difference in current amplitudes between short DNA and RNA is ~40%, in good agreement with their cross-sectional area differences. The mean transport times for the RNA molecule (50 μs) was significantly longer than the DNA molecule (20 μs). This, in addition to a broader $\Delta I$ distribution for RNA may be due to drag forces on the wider helical structure of RNA, and a greater extent of interactions between RNA and the nanopore. The differences in current amplitudes between DNA and RNA persist even for events with ≤16 μs duration, for which the signal amplitude is attenuated by as much as 20% due to use of a rank 1 median filter. Using a discrimination threshold of $\Delta I_{Thres}$=675 pA, one can discern DNA from RNA with >97% certainty by considering events with ≥16 μs durations, which represent >75% of the total detected events. Analysis of events with duration of ≤16 μs shows that the signal is attenuated by the same factor for both DNA and RNA, enabling discrimination even for events with this duration range. It was also checked whether discrimination based on I is not a result of the faster mean transport times for DNA by comparing events for DNA and RNA with similar durations, in which <10% overlap in the two $\Delta I$ distributions is seen.

The pores could also distinguish linear nucleic acids from more complex structures. For example, transfer-RNA (tRNA) is structurally more complex than duplex RNA and DNA due to the presence of unpaired bases and loops, which give rise to a bent structure (see in FIG. 20a the structure of phenylalanine tRNA from PDB file 4TNA). The traces in FIG. 20a shows events with amplitudes of 1.8 nA for the tRNA, a factor of 2 greater than for the 22-bp RNA molecule (0.92 nA). The mean transport time of the tRNA molecule is 1.04 ms, much longer than that of the linear nucleic acids (see expanded events in FIG. 20a). These differences in signals between the three molecules show that one can discriminate among populations of different nucleic acids with certainty.

The disclosed devices and methods are, as described elsewhere herein, considered especially suitable for detection and/or quantification of miRNA. The devices may be used to detect miRNA that has a length of from 1 to about 10 base pairs, or from 1 to about 20 base pairs, or from 1 to about 50 base pairs, or even from 1 to about 100 base pairs. miRNA molecules may be 22 base pairs in length, which size is well within the capabilities of the disclosed devices and methods to detect or otherwise analyze.

FIG. 20b shows mean capture rates vs. voltage for 25-bp DNA and 22-bp RNA (see FIG. 29 and associated text). The mean capture rates are exponentially dependent on voltage in the range of 300-600 mV (curves are exponential fits to the data), suggesting that nucleic acid capture is a voltage-activated process. Based on the ratio of the observed event rate and the calculated arrival rate of molecules to the pore at 600 mV, one can estimate that >50% of the molecules that arrive at the pore are captured and detected.

The concentration of a sample can be measured from the frequency of molecular signals, provided that a calibration curve of capture rate vs. concentration is constructed. In FIG. 20c, a log-log plot of the mean capture rate vs. concentration of 25-bp DNA is shown (see FIG. 30 and associated text). The power-law fit to the data (line between data points) yields an exponent of 1.05±0.03, indicating linearity over three orders of magnitude in concentration. This dynamic range can be extended by orders of magnitude by increasing the measurement time and applied voltage, or by adjusting the electrostatic potential at the pore entrance.

Electronic Platform for Detection of Specific microRNAs

Electronic detection of small RNAs using a solid-state device may provide an alternative to existing methods for rapid and sensitive miRNA analysis. Microarray-based miRNA profiling, fluorescence, radioactive gel electrophoresis, and other novel techniques can detect sub-femtomole RNA levels, but none of these offer the unique aspects of nanopore detection, such as electronic sensing, single-molecule sensitivity, reusability, use of an unlabeled probe, and avoidance of surface immobilization. To detect a specific miRNA with a nanopore, a sequence-specific enrichment step of a particular miRNA may be useful (but not required), as miRNAs are <1% in concentration relative to other cellular RNAs.

To enrich a specific RNA, the p19 protein from the Carnation Italian ringspot virus was used. P19 binds 21-23 bp dsRNA in a size dependent, sequence independent manner. The p19 protein does not bind ssRNA, tRNA or rRNA.

To enhance isolation of the bound dsRNA C-terminal fusion of p19 with the chitin binding domain (CBD) was created, allowing linkage of the p19 fusion protein to chitin magnetic beads. The magnetic beads simplify the washing steps required to remove unbound RNA. Using p19 beads have achieved over 100,000-fold enrichment of the probe: miRNA duplex from total RNA. The protocol shown in FIG. 21a for nanopore-based miRNA detection was used. This begins with isolation of total RNA from tissue and hybridization to a miRNA-specific oligonucleotide RNA probe fully complementary to a target miRNA. In step (I), the probe-hybridized total RNA is incubated with the p19 protein immobilized on magnetic beads, followed by washing to remove the remaining RNA. In step (II), the purified probe: miRNA duplex is eluted from the p19 protein. In step (III), the duplex is detected using a nanopore (see FIG. 31 and associated text). A miRNA enrichment protocol may take several hours starting from isolated cellular RNA.

MiRNAs isolated with p19 may contain agents that interfere with nanopore detection of the probe:miRNA duplex. Along with the eluted duplex, other agents may be present, such as bovine serum albumin (BSA) that coats the beads, SDS used for dsRNA elution from the p19, and trace amounts of other RNAs. To eliminate the possibility of an artifact signal caused by these interfering agents, several controls were performed. The results are summarized in FIG. 21b showing 30 second current traces for different samples, all of which have been treated using p19 beads.

The first trace shown at the top of FIG. 21b is for the probe:miR122a duplex reacted with 1 µg rat liver RNA (RL). The second trace shown is for a positive control (PC), in which 30 ng of synthetic probe:miR122a duplex was bound to and eluted from p19 beads. In addition to the positive control samples, performed four negative controls NC1 to NC4 were performed, as described elsewhere herein. The traces show spikes with current amplitudes typical of dsRNA for samples PC and RL, whereas no spikes of amplitudes greater than 0.3 nA were present in the negative controls. The open pore current was stable to within 5% throughout the experiments.

To quantify the miRNA concentration, a calibration curve of capture rate vs. concentration was constructed using a synthetic probe:miR122a duplex, indicated by the open markers in FIG. 21c. For an unknown miRNA sample, one then counts ~250 current spikes that cross the threshold of $I_o$~0.4 nA (see dashed grey lines in the traces), computes the mean capture rate, and uses the calibration curve to determine the RNA concentration. The PC and RL lines in FIG. 21c show how the capture rates translate to RNA concentration for samples RL and PC, respectively. From the calibration curve, the concentration of the 20-fold diluted miR122a in sample RL is 0.7 fmol/µl, translating to an original abundance of 78±2 pg miR122a/µg liver RNA in rat liver cells, in close agreement with previous findings (58-67 pg miR122a/µg RNA). In addition, sample PC showed a concentration of 5.2 fmol/µl, indicating that the synthetic probe:miR122a duplex efficiently bound to and eluted from the p19 beads. The negative controls did not show any current spikes that cross the threshold over the measurement time (2 min each), indicating a background that is at least two orders of magnitude lower in spike frequency than sample RL (i.e., background noise <7 amol/µl).

FIG. 21d shows the relative error in measured concentration vs. the number of detected molecules. The plot was generated by computing the standard error in the mean capture rates for population subsets of sizes ranging from 100 to 4,000 events. Based on FIGS. 5c and d, one can obtain the time required to analyze a sample with a desired accuracy. For 1 fmol miRNA duplex per µl solution, the capture rate is ~1 molecule/sec, so detection of 250 molecules in ~4 minutes is sufficient to determine miRNA concentration with 93% certainty.

The foregoing demonstrates a process for fabricating uniform, robust and well-defined solid-state membranes that can be manufactured on a full Si wafer, which was used to make solid-state nanopore sensors with the thickness of lipid membranes. Reducing the nanopore thickness improves the signal amplitude from biomolecules, and the use of 3 nm pores in sub-10 nm membranes facilitates electronic discrimination among small nucleic acids. Moreover, nanopores in thin membranes are more easily hydrated than nanopores in thicker membranes, and remain stable over time. Three types of small nucleic acids with different structures were discriminated among with good signal contrast. The systematic study of thin nanopore properties allows development of an electronic detection process for counting individual small RNA molecules, which quantifies miRNA enriched from biological tissue. The inherent ability of these systems to electronically detect single molecules, combined with microfluidic-scale sample volumes (nl) exceeds the detection limits of conventional methods. The systems are capable of simultaneous detection of different molecular species in solution (peptides, miRNA, etc.) by multiplexed read-out of electronic signals from many pores.

Exemplary Methods

The substrates for device fabrication were 5×5 mm² Si chips that have a low-stress silicon nitride (SiN) film deposited on a 5-µm-thick thermally-grown $SiO_2$ layer, used to reduce the electrical noise. Electron beam lithography was used to write square patterns on the membranes, followed by developing the exposed areas and locally thinning the SiN membrane using an $SF_6$ plasma etcher. After lift-off of the resist and hot piranha cleaning, AFM was used to profile the etch depth (Enviroscope, Veeco). Epi-fluorescence was measured using an upright microscope (Nikon Eclipse 80i) with a Nikon Apo 100x 0.95 NA dry objective.

Laser excitation at 488 nm was blocked using a notch filter and detected behind a Chroma 525/50 emission filter using a cooled CCD (Princeton Instruments). Solid-state nanopores were fabricated and analyzed in a JEOL 2010FEG TEM equipped with an annular detector for ADF-STEM. The resulting geometry of nanopores fabricated in solid-state membranes is governed by an interplay between surface tension of the molten SiN and its ablation kinetics. Adjustment of the pore shape by tuning the e-beam fabrication process has been previously reported. In light of a recent report that the TEM beam size influences the nanopore shape, one can use an intense electron beam spot of 1-2 nm diameter to drill the nanopores. All nanopore experiments were carried out using 1M KCl+1 mM EDTA, Tris buffered to pH 8.

An exemplary fluoropolymer cell accommodated volumes of 1-20 μl and features temperature regulation using a thermoelectric device. The nanopore chip was installed between two buffered electrolyte solutions, each equipped with a Ag/AgCl electrode. After piranha cleaning, each chip was installed in a custom fluoropolymer cell that accommodates volumes as small as 1 μl. The fraction of pores that yield a steady ion conductance in good agreement with Eqn. 1 using $h_{eff}=h/3$ was ~100% for h<10 nm, compared to 40-60% for similarly treated pores with h=25 nm. Pores that exhibited fluctuating currents characterized by high 1/f noise and conductance <2 nS were not reported in FIG. 12d and were re-cleaned. When the electrolyte chamber was sealed using a PDMS gasket, or when the cell temperature was reduced to <10° C., the conductance of pores with different thicknesses was stable to within 5% for hours.

For translocation experiments, analyte was added to one of the chambers, and voltage was applied while monitoring current through the pore. Electrical current, measured using an Axopatch 200B amplifier, was digitized at 250 kHz and fed to a computer using custom LabVIEW collection/analysis software. For short nucleic acid analysis one digitally filters the data using a median filter with a rank of 1, in which one finds that events with duration ≥24 μs are undistorted. All DNA samples were purchased from Fermentas (NoLimits®). For the experiments in FIG. 12, 4.0±0.2 nm pores were used, ~1 nM DNA concentrations were placed in one chamber at 21±0.1° C., and 300 mV was applied to the opposite chamber. The miR122a probe was a 22 nucleotide complementary RNA to miR122a, phosphorylated at the 5' terminus (5'-AACACCAUUGUCACACUCCAUA-3'). The probe:miRNA duplex was enriched from RNA using the protocol described herein. For miRNA determination, ~1 μl sample was added to the negative chamber of a 3 nm nanopore in a 7 nm thick membrane, and current was recorded vs. time at 500 mV and 0° C. See FIG. 21 and associated text. In the first negative control (NC1), 1 μg of liver RNA was hybridized to a non-specific miRNA probe for miR153 (5'-CACUUUU-GUGACUAUGCAA-3'), which is absent in liver. In the second negative control (NC2), no probe was hybridized to 1 μg of liver RNA. In the third negative control (NC3), miR122a probe was hybridized to yeast RNA, which does not contain miR122a. In the fourth negative control (NC4), single-stranded miR122a was incubated without liver RNA. In Equation 1 in the geometrical model, one neglects the low SiN surface charge density because experiments were performed at high ionic strengths (1M KCl).

Fabricating Different Thickness SiN Membranes

Sub-10 nm thick membranes were fabricated in 5×5 mm² Si chips that contained a 5-μm-thick thermal $SiO_2$ oxide underneath a 41 nm thick low-stress SiN layer, deposited by low-pressure chemical vapor deposition (Center for Nanoscale Fabrication, Cornell University). For characterization of the etch rate (see FIG. 18c) and for studying DNA transport through 60 nm thick membranes (see FIG. 12), a Si wafer that has a 100 nm thick SiN membrane was used. Prior to processing, the thickness of the SiN membrane was measured at different points on the Si wafer using a Rudolph Research AutoEL III Ellipsometer at a wavelength of 632.8 nm and an incidence angle of 70°.

From the ellipsometric parameters, one can obtain for the SiN film optical parameters of n=2.24, k=0, as well as a film thickness of 41.5±0.3 nm. Standard photolithography followed by anisotropic KOH etch was used to produce a freestanding SiN membrane with approximate dimensions ~50×50 μm². A subsequent buffered-oxide etch step was then performed to remove the 5 μm $SiO_2$ layer from the KOH-etched side, in order to obtain freestanding SiN membranes. The SiN membrane was then spun-coated with a PMMA electron beam resist (a 2% solution of 950 kD molecular weight in chlorobenzene, MicroChem Inc.) followed by baking at 180° C. for 10 minutes. Electron beam lithography was then used to write a pattern of squares with sides ranging from 250 nm to 5 μm, using a 50 kV electron beam (Elionix 7500-ELS) and beam dose of 750 μC/cm². The irradiated device was developed in 1:3 methyl isobutyl ketone:isopropanol volume ratio for 60 seconds followed by rinsing with isopropanol and drying under a stream of compressed nitrogen gas. Thinning of the exposed SiN areas was accomplished using a Technics PEIIA plasma etcher, using a 50 W rf source and 400 mtorr $SF_6$ chamber pressures. The SiN etch rate under these conditions was 1.0±0.1 nm/s. The resist was finally removed by ~1 h incubation in warm acetone at 65° C., drying under a stream of $N_2$, and then heating at 100° C. in hot piranha solution for 10 minutes (made by mixing 1:3 of 30% $H_2O_2$ and conc. $H_2SO_4$); note that piranha is a strong oxidizer that reacts violently with most organic materials and must be handled with caution. The chips were then washed with water, dried, and stored until use.

AFM Characterization of Thinned SiN Membranes

Tapping-mode atomic force microscopy was carried out in order to characterize the process of localized membrane etching. All measurements were performed in ambient air using a Veeco EnviroScope to profile the etch depth and roughness of a given batch of processed chips. TESP Si tips (Veeco) with tip radii of <10 nm were used for all images. In FIG. 22, it is shown in panel (a) an AFM image of the pattern shown in FIG. 18c, following a 17 nm etch process (the membrane curvature has been subtracted using a polynomial in order to improve visibility of the pattern). The dashed yellow line represents the 3×3 array of 250×250 nm squares that is shown in FIG. 18c. In panel (b), three AFM images of 41 nm thick SiN windows in which a 3×3 array of 250 nm squares with a 1 μm pitch were plasma etched for 17, 33, and 40 seconds. Line profiles through a set of 3 squares can be seen below each image, showing step heights of 17±1 nm, 33±1 nm, and for the 40 nm thinning, the image shows a ~100 nm deep triangular profile that resembles the tip shape, indicating that the membrane is completely perforated. The membrane thickness h in the processed region is given by the difference between the initial membrane thickness and the etch depth, i.e., in this case, h=41 nm−etch depth. A membrane robust enough for experiments is a membrane that has been etched for 35 seconds, which yields a membrane thickness of ~6 nm. Membranes with thickness values h≤5 nm did always not survive the piranha cleaning step.

Conductance of Sub 10 nm Thick Nanopores as a Function of Time

FIG. 23 illustrates conductance as a function of time for pores with various diameters d and membrane thicknesses h, denoted as (d, h). The buffer used for all measurements was 1M KCl buffered to pH 8. Conductance values are reported in nS based on the current at 300 mV and an electrolyte temperature of 21° C.

Geometric Model for ΔI of DNA as a Function of Effective Pore Thickness

The values of ΔI upon DNA entry were calculated based on Equation 1 herein, with a modification that takes into account the displaced electrolyte current upon DNA occlusion of the pore. A hydrodynamic diameter for B-form DNA of 2.2 nm was assumed, as it was previously found to explain the observed relative conductance as a function of pore diameter d. The current difference between an open pore $I_o$ (see Eqn. 1) and a DNA-occluded pore $I_{DNA}$ is expressed as:

$$\Delta I = I_o - I_{DNA} = I_o - V([\mu_K + (1-S)\mu_{Cl}]n_{KCl}e)\left(\frac{4h_{eff}}{\pi d_{eff}^2} + \frac{1}{d_{eff}}\right)^{-1} \quad \text{Eqn. 2}$$

where the two added parameters are $d_{eff}$, the effective pore diameter of the DNA-occluded pore (calculated from a circle of an equivalent area that is available for KCl transport in the case of the DNA occluded pore case), and S, the fraction of excluded Cl⁻ ions in the DNA-occluded pore. This exclusion of Cl⁻ ions was modelled as a coefficient from 0-1 that reduces the mobility of Cl⁻ ions (this is equivalent to a reduced Cl⁻ concentration). The rational for chloride exclusion is based on previous results that showed an increase in ΔI with DNA length for a length >1,200 bp, which may be attributable to a decreased effective concentration of anions (e.g., Cl⁻) near the pore during translocation, due to electrostatic repulsion by the DNA coil. The dashed line in FIG. 12d is a best fit to ΔI for a pore diameter d=4 nm as a function of the effective thickness $h_{eff}$, which yields values of $d_{eff}$=2.83 nm and S=0.2 (i.e., 20% exclusion of Cl⁻).

Scatter Plots of ΔI Vs. Transport Time of 3 Kbp DNA for Two Pore Thicknesses

FIG. 24 shows a scatter plot of the mean current amplitude of each molecule (I) and the total transport time for 3 kbp dsDNA through 4 nm pores as a function of membrane thickness (h). Thinning the membrane has two observable consequences, one is increased I, which facilitates detection of the DNA, and the second is a minor decrease in transport times. Overall, transport times were ~30% smaller when reducing h from 60 to 6 nm, going from 0.95 ms to 0.72 ms. The plot on the right of FIG. 24 shows transport time distributions for two membrane thicknesses. Mean transport times are determined by fitting the distributions to exponentially decaying distributions.

Translocations of 10 bp DNA Through a 3 nm Diameter Pore in a 7 nm Thick Membrane FIG. 25 shows a set of 10 bp translocations through a 3 nm diameter pore in a 7 nm thick membrane under 500 mV applied voltage, at a temperature of 0° C. The events were concatenated by pasting together current spikes that include 2 ms current data before and after each spike. In contrast to events with the 25 bp DNA fragment, one observes many deep and long events for the 10 bp sample, which was observed for many different 3 nm diameter pores. This may be attributed to sideways jamming of the molecule at the pore entrance, which would cause the DNA to stall for a relatively long time (milliseconds). The contour length of the 10 bp DNA is 3.5 nm, slightly higher than the pore diameter. An all-point histogram is shown to the right of the concatenated trace. The difference in amplitude between the first blockade peak and the open pore peak is 0.6 nA, similar to that of the 25 bp DNA sample (see FIG. 20). The second peak (1.1 nA) may be due to entry of two molecules simultaneously or sideways entry of the molecule into the pore. The traces for 25 bp DNA and the 22 bp RNA samples in FIG. 20a show that such frequent blocking of the pore does not occur in double-stranded nucleic acids with contour lengths of at least 7 nm.

Discrimination Among 25 bp DNA, 22 bp RNA, and 76-Nucleotide tRNA

Figures 26A, 26B:
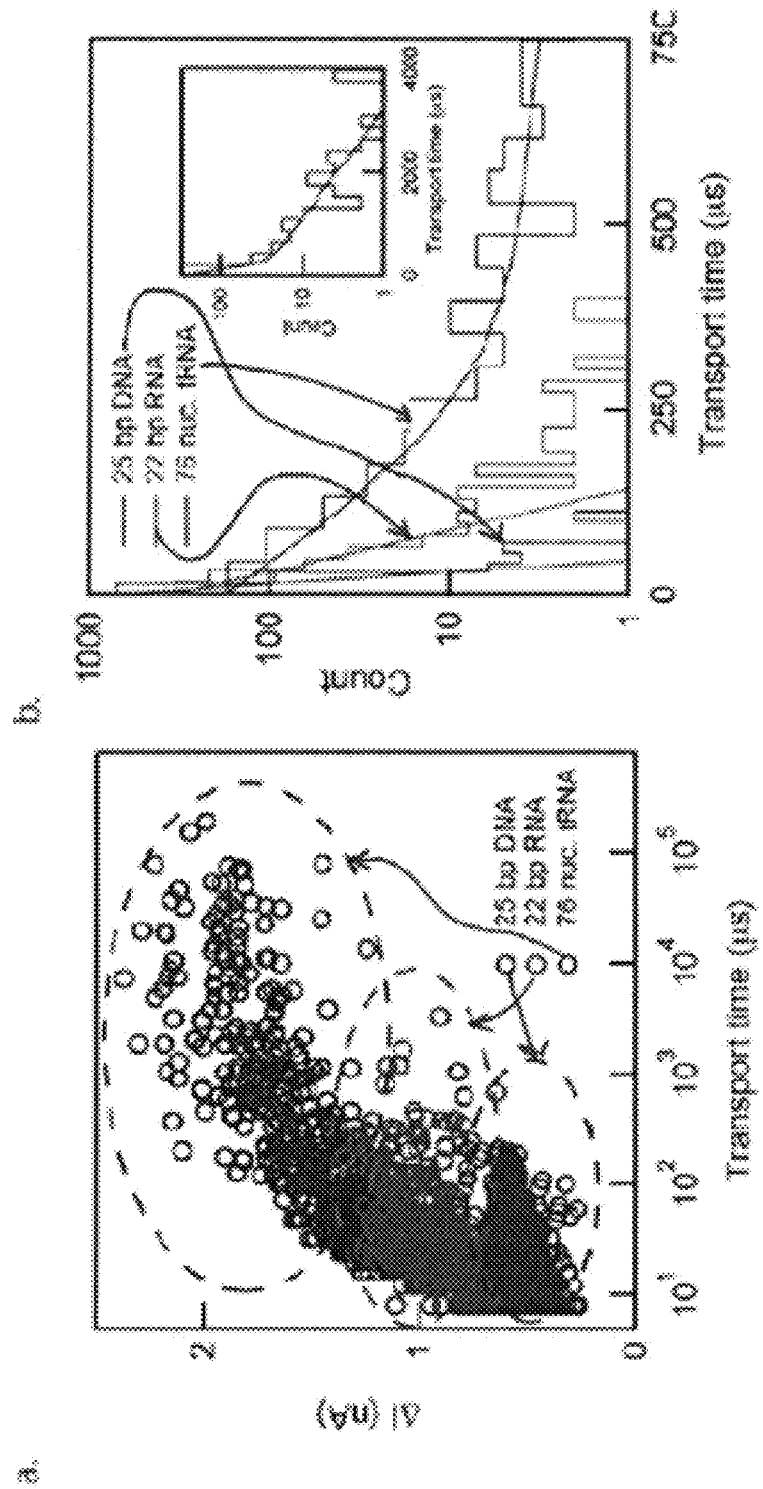
Figure 26C:
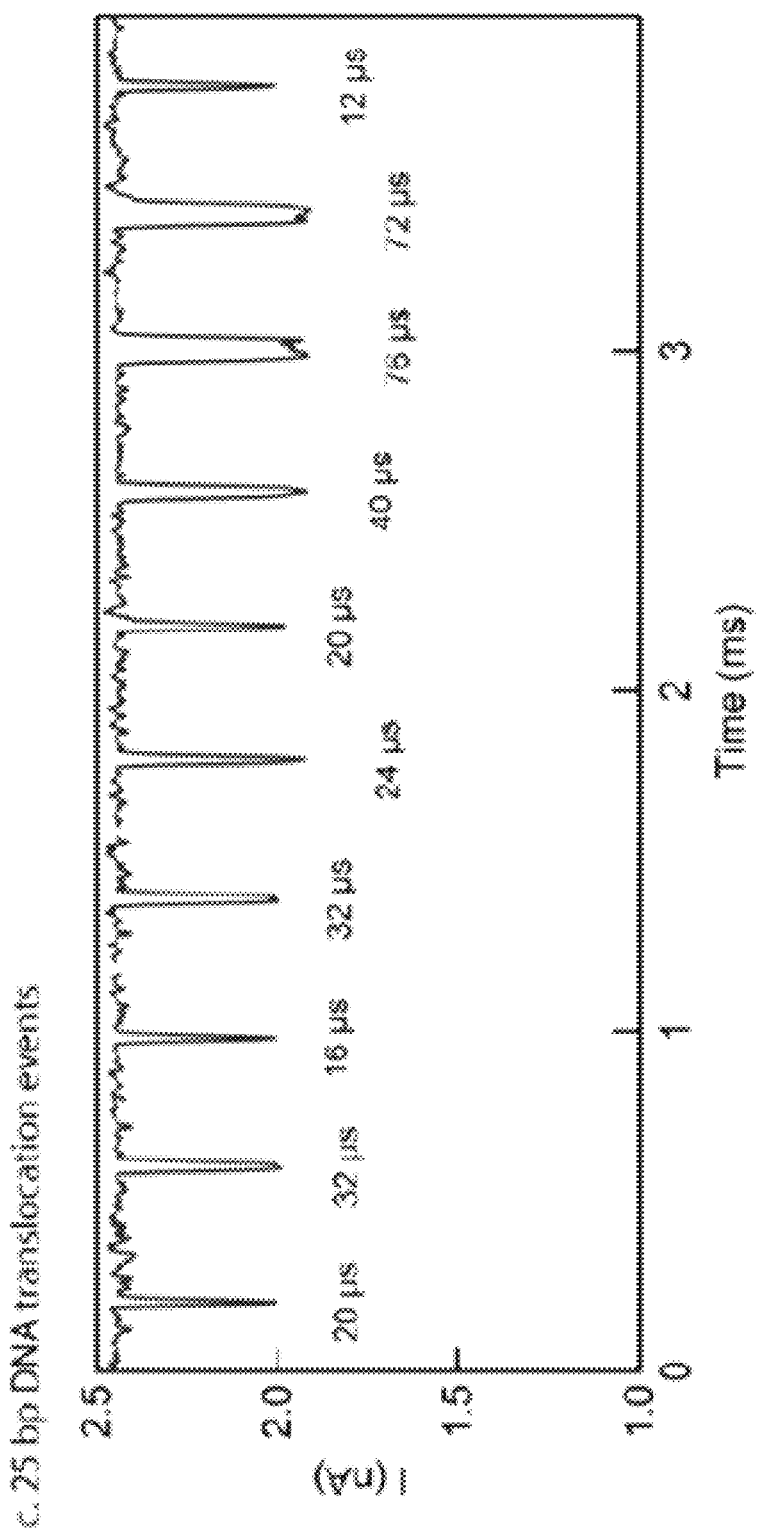

FIG. 26 provides more detail about using a 3 nm diameter pore in a 7 nm thick membrane to discriminate among small nucleic acids of similar size, namely, 25 bp DNA (molecular weight=15 kD), 22 bp RNA (molecular weight=15 kD), and 76-nucleotide tRNA (molecular weight=25 kD). FIG. 26a illustrates scatter plots of current amplitude (I) vs. transport time for the three molecules under the same measurement conditions (0° C., 500 mV, 3 nm diameter pore in a 7 nm thick SiN membrane). The dashed ovals represent regions containing >85% of detectable events for each molecule type. FIG. 26b illustrates transport-time distributions for >1,000 events of each molecule type. For the 25 bp DNA and 22 bp RNA, >90% of the data fits a single exponential decay, with timescales of 20 μs and 50 μs, respectively.

Figure 26D:
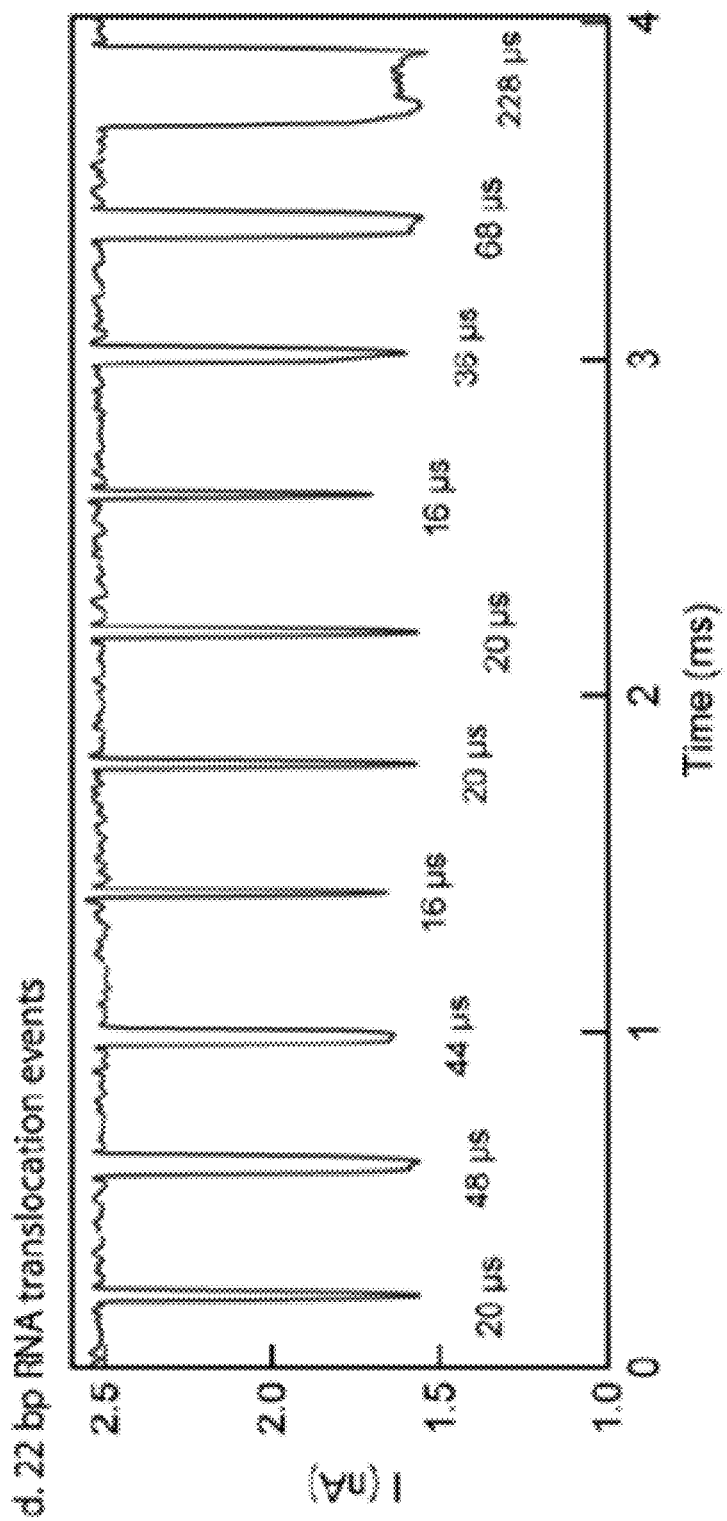

For tRNA, the data fits a two-exponential function, with timescales 80 μs and 1.04 ms (see inset of panel b for expanded view of the transport-time histogram for tRNA). While the short timescale may be due to collisions and fast translocations of the bulky tRNA molecule, the long timescale, in which the majority of events fall in, suggests that the tRNA must deform from its bent equilibrium structure in order to traverse the 3 nm diameter pore, a process that may stall transport, leading to longer dwell times and a broader dwell time distribution. Representative concatenated translocation events (FIG. 26c) in the dwell time range of 12-228 μs for 25 bp DNA (c) and 22 bp RNA. In FIG. 26d, events for the tRNA molecule are not shown here, because their duration is clearly longer, as seen in FIG. 20a. The corresponding transport times are noted below each event. These traces are shown in order to illustrate that the current amplitude for 25 bp DNA and 22 bp RNA are distinctly different, easily seen for events with duration longer than 30 μs. These results suggest that the different amplitude spikes are a result of the different molecular properties between the three nucleic acids, rather than an artifact of fast dwell times close to the detection limit that would distort the current amplitudes.

A more quantitative analysis of the nanopore's ability to discriminate 25-bp DNA from 22-bp RNA based on current amplitudes is shown in FIG. 27. First, in order to test the response of the system to short pulses, a simulation was performed of ideal square current pulses with different durations and current amplitudes in the range 8-48 micro-s. The simulated events indicate that all events with durations <20 micro-s are attenuated in terms of their amplitudes. For example, for pulse widths of 8 micro-s, the mean attenuation factor is 20%. That is, events with 500 pA and 750 pA amplitudes are detected as 400 pA and 600 pA amplitudes, respectively.

Next, is shown the effect of a rank 1 median filter on the real DNA and RNA data collected for the scatter plots shown in FIG. 26. Shown in the figure are ΔI distributions of for all the events in the scatter plots for 25-bp DNA and 22-bp RNA. In this series of histograms, one takes subsets of the dataset that contain events with duration equal to or longer than the indicated value in each plot.

Also indicated in the plots are % certainty values for the discrimination between DNA and RNA, calculated from the fraction of RNA events that lie above the $I_{Thres}$=675 pA threshold (shown as dashed line). The threshold was chosen because <0.1% DNA events were found with larger ΔI values. For example, including only events ≥8 s results in a certainty of 83.3%, because 16.7% of the RNA events have amplitudes that are lower than $I_{Thres}$. In other words, looking at all of the data in the range ≥8 s, one finds that 16.7% of the RNA molecules and mixed with the DNA population, and therefore cannot be distinguished from DNA events. Now, when one looks to data ≥12 microseconds, one finds that 91.3% of the RNA events lie above the threshold, resulting in only 8.7% error in discrimination. This certainty in discrimination improves to >97% when only events ≥16 μs are included. One notes that events with durations ≥16 μs constitute 75% and 73% of the total detected events for DNA and RNA, respectively. Finally, one notes that differences in duration between DNA and RNA cannot explain the differences in current amplitudes, because events longer than 36 μs, which represent about one half of the datapoints, have a clear plateau at the mean current amplitude value, unequivocally showing that DNA and RNA provide distinguishable current amplitude levels.

The bandwidth-limited data acquisition results in asymmetric shapes for the current amplitude distributions, which exhibit "bellies" or "shoulders" at 0.4 nA and 0.6 nA for DNA (left arrow) and RNA (right arrow), respectively. These "bellies", which deviate from Gaussian shapes (see curves), disappear completely for events with durations of ≥16 μs, and the distribution shapes are Gaussian thereafter. This asymmetry may be a result of attenuation by filter.

However, despite the signal attenuation, one still can discriminate among short DNA and RNA, provided that one chooses a suitable threshold amplitude for discrimination that considers the event duration. To illustrate this, shown are ΔI histograms for DNA and RNA events where in each plot are analyzed slices of the data that select all events with an indicated duration, in the range of 8-36 s. In each plot are drawn dashed lines for $\Delta I_{Thres}$=675 pA as a guide to the eye. In FIG. 28, below all the distributions are shown mean ΔI values as a function of event duration (the error bars show one standard deviation in each direction). As seen in these plots, the current amplitude signals for both RNA and DNA are distorted towards lower ΔI values for events in the range 8-16 s, after which there is no apparent shift in the position of the distributions. The magnitude of this distortion for short events is up to 150 pA for the 8 s events (or 22% of the ΔI value), in good agreement with the simulated data. The attenuation factor appears robust as a function of event duration, and therefore one can compensate for attenuated data by adapting the threshold (see lower arched, dashed line in FIG. 28 that connects up to straight dashed line at duration=22 microseconds), in order discriminate DNA from RNA in this regime with >90% confidence.

Continuous Traces for 25 bp DNA Through a 3 nm Pore for Different Voltages

FIG. 29 shows 2-second current traces under different applied voltages of a 25 bp DNA sample analyzed using a 3 nm diameter pore fabricated in a 7 nm thick membrane (data taken at a temperature of 0° C.). Pores are not, of course, limited to 3 nm diameters, as pores can have diameters of 1 nm, 5 nm, 10 nm, 25 nm, 50 nm, 100 nm, and of intermediate values therebetween. The analyte chamber contains 25 bp DNA at a concentration of 81 fmol/μl, and positive voltage is applied to the second chamber in order to drive DNA to the other side. The inset trace in each plot is a zoomed-in 7 ms view, with the same current amplitude scale as the y-axis. On the right-hand side of the figure, all-point current histograms are shown for each trace. Increasing the voltage greatly increases the capture rate, as seen by the increasing amount of deep events. The shallow events for the low voltage traces are presumably collisions of the DNA with the pore. The fraction of these collisions decreases with increasing voltages, in line with a voltage-activated barrier for threading.

Continuous Time Traces for 25 bp DNA at Different Concentrations

FIG. 30 shows current vs. time traces for a 3 nm diameter pore at a measured at a voltage of 500 mV and a temperature of 0° C., when different concentrations of DNA were added to the pore (expressed as fmol/μl solution). While the open pore current remains similar for different concentrations of DNA (~2.5 nA), the number of spikes increases as a function of the concentration. The rate of events shown in FIG. 12d were derived from the time-delay distributions (t) between two successive events (see plot below the traces), which fits a first arrival time distribution function $P_{capture}$=Aexp(-Rate*t), where the slope of the exponent (i.e., Rate) is the mean capture rate in $s^{-1}$.

Details of p19-Based miRNA Enrichment from Cellular RNA Extracts

The p19 protein binds tightly to double-stranded RNA that is 19 to 22 basepairs in length. There is no binding to single stranded RNA. This tight, selective binding of p19 to dsRNAs allows the enrichment from cellular RNA of probe-hybridized miRNAs that have a very low abundance. For example, miR153, a miRNA with very low abundance compared to other miRNAs, has been enriched by over 100.000-fold from cellular RNA.

The protocol of miRNA enrichment proceeds as follows: A synthetic 22 nucleotide RNA oligo probe of sequence 5'-AA-CACCAUUGUCACAC-UCCAUA-3' (Integrated DNA technologies, Inc.) complementary to miR122a was first phosphorylated at the 5' end using T4 polynucleotide kinase (New England Biolabs, Ipswich, Mass.). The miR122a-specific probe was then added to PCR tubes containing the different RNA samples (rat liver RNA, positive control, and the four negative controls) in 1× p19 binding buffer (20 mM Tris-HCl, pH 7.0, 1 mM EDTA, 1 mM tris(2-carboxyethyl) phosphine, 100 mM NaCl, 0.02% Tween-20) in a total volume of 10 μl. Hybridizations were carried out in a thermal cycler programmed to 75° C. for 5 min, followed by 52° C. for 5 hours. Each 10 μl of hybridization reaction was incubated with 10 μl of p19 beads suspended in 1× p19 binding buffer, 10 units of murine RNase inhibitor (NEB), and 1 mg of BSA in a total volume of 20 μl. The binding reaction was incubated by shaking for 1-2 h at RT in an Orbis shaker (MarketLab, Calcdonia, Mich., USA). Using a magnetic rock (NEB), the unbound RNA was removed by washing 6 times in 600 μl of 1× p19 wash buffer (20 mM Tris-HCl, pH 7.0, 1 mM EDTA, 100 mM NaCl). For each wash, the beads were shaken for 5 min. at 37° C. on a heated shaker. After the third wash, the washing temperature was increased to 42° C. to remove all of the non-specific unbound RNA. The probe:miR122a duplex was eluted from the p19 beads into 20 μl of 1× p19 elution buffer (20 mM Tris-HCl adjusted to pH 7.0, 100 mM NaCl, 1 mM EDTA and 0.5% SDS) by shaking for 20 min at 37° C. SDS was removed by adding 16 μl of 4 M KCl to the 160 μl eluate and cooling to 4° C. After centrifugation for 15 min. at 14,000 rpm in a microfuge, the solution was carefully decanted to a new tube to remove the white SDS pellet. The isolated miRNA were diluted into KCl solutions such that the total KCl concentration was 1M, and the solution was added to a 3 nm diameter nanopore in a 7 nm thick membrane for detection, which was carried out for all samples at 0° C. and 500 mV.

The sequence of experiments that led to the data for FIG. 21 is as follows: A calibration curve for different 22 bp duplex RNA concentrations was first performed using the synthetic probe:miR122a duplex, after which the negative controls NC1-NC4 were tested, and finally, samples RL and PC were tested. Between each sample, the chamber was rinsed 10 times by removing the chamber contents, adding 20 μl of fresh buffer, mixing the chamber contents using a pipette, and repeating the process. After each cleaning procedure, a 20 second trace was collected to verify that the baseline current was within 5% of the open pore current value, and that no detectable events are present. During data acquisition for the negative controls, evidence that the nanopore is active comes from the fact that occasionally shallow events occurred (<0.3 nA), which may be tied to trace amounts of single-stranded RNA (e.g., the hybridization probe) present in the p19-treated samples.

Continuous Time Traces of Different Concentrations of 22 bp RNA

FIG. 31 shows continuous time traces for a 3 nm diameter pore measured at a voltage of 500 mV and a temperature of 0° C., when different concentrations of RNA were added to the pore (expressed as fmol/μl solution). The calibration curve in FIG. 21c was constructed by calculating for each trace the mean capture rate as a function of the RNA concentration.

Response of System to Artificial Short Current Pulses

In order to test the system's response to very fast translocation events, the response of the amplifier tested to synthetic current pulses in the range 8-48 s was tested. The scheme for generating these pulses is shown in FIG. 32: A 2 MHz square wave generator with asymmetric pulse capabilities (TENMA Jupiter 2010) was fed into the compensated RC circuitry shown in FIG. 32. The circuitry converts the voltage signal of the generator into a current pulse train with specified durations and amplitudes, adjusted manually by reading the function generator's output using an oscilloscope. Next, were generated current pulses of durations in the range 8-48 microseconds, fed the signal into the amplifier's headstage, then digitized the output at a sampling rate of 250 kHz using a DAQ card and median filtered the data using a rank of 1. Combined with the 100 kHz bandwidth of the Axopatch 200B patch clamp amplifier, which is set by its internal 4-pole Bessel filter, a rank 1 median filter behaves as a low-pass filter with a corner frequency of $f_c$=37.8 Khz at 250 kHz sampling rate. The roll-off of this median filter is shallower than commercial low-pass filters.

Representative traces are shown for pulses of the indicated durations and two amplitudes, delta I=500 pA (left column of plots) and 750 pA (right column of plots), which model events from the short DNA and RNA molecules, respectively. A plot of the mean delta I values vs. pulse duration shows that events of duration ≤20 microseconds are attenuated. However, the attenuation factor is similar for the 500 pA and the 750 pA pulses: for the 8 microsecond pulses that are detected as a single sample point, the peak amplitude was attenuated by 14% for both pulse amplitudes.

Exemplary Embodiments

One exemplary embodiment of the disclosed devices is shown in FIG. 33. The device will be described here illustrating its use in detecting miRNA, but the device may be used for detecting other analytes, such as DNA and RNA.

In some embodiments, the devices may include a Si-chip. Such chips may have an area of only a few $mm^2$. For example, one may use a 5×5 $mm^2$ device, with a transparent SiN window that is 100×100 $\mu m^2$. The devices may integrate the disclosed nanopore/electrode devices with fluidics such that analyte isolation (e.g., p19-based miRNA isolation) can be performed in real time.

In some embodiments (illustrated by FIG. 21a), the device accepts an input sample (such as cell contents, including cellular RNA), hybridizes the sample to a probe (e.g., a miRNA probe), immobilizes the probe:analyte duplex (e.g., onto protein p19). The user may then wash, elute, and detect the analyte (miRNA) concentration. These devices thus enable multiplexed delivery and detection of miRNAs using a series of nanopores equipped with electrodes.

The signals (such as changes in electrical current) may be read using independent electrodes that are disposed proximal to each nanopore. The devices are suitably constructed such that nanopores are individually monitored or addressed by electrodes. In this way, the user may assign different analytes to different nanopores, enabling simultaneous, parallel analysis of multiple analytes.

By analyzing the current signal as a function of time, the concentration of each miRNA in each channel is quantified, which may be achieved by comparing the signal (or passage events per time) to a calibration curve. Exemplary electrodes are described in United States Published Applications US 2010/0142259 ("Nanogaps: Methods and Devices Containing Same") and US 2010/0009134 ("Beam Ablation Lithography"), the entireties of which are incorporated herein by reference.

In the exemplary embodiment shown in FIG. 33, a device includes an input chamber. The user may introduce sample material (e.g., the contents of a lysed cell or cells) into this input chamber. The chamber may itself be a lysis chamber, configured to apply or receive lysis reagents, heat, sonication, pressure, and the like to a cell or other sample placed within the chamber. Lysing techniques and reagents are known in the art, and suitable lysing techniques will be known to the user of ordinary skill in the art. The lysing may be accomplished, for example, on a porous membrane under pressure. Alternatively, lysing may be accomplished chemically. In some embodiments, cell contents may be introduced directly into the chamber.

The input chamber may be configured or disposed such that it is in fluid communication with one or more nanopores according to the claimed invention. The fluid communication may be accomplished by having tubes, conduits, channels, or other pathways between the input chamber and the nanopores. The input chamber may have multiple outlets, where each outlet is connected to one or more channels. Alternatively, the input chamber may include or be connected to a manifold, which manifold in turn distributes sample material to the channels. The manifold may be constructed so as to admit material into only a single channel or into multiple channels. The devices suitably include a device that applies a gradient (e.g., fluid pressure, voltage, magnetic) to transport sample or analyte from one location in the device to another.

The exemplary embodiment of FIG. 33 illustrates channels connecting the chamber to the nanopores. The chamber may suitably have an internal volume of 0.1-100 ml, or 1-10 ml, or even about 5 ml, depending on the needs of the user; although larger and smaller volumes are also suitable. The chambers are suitably constructed from polymers, silicon, and from other materials known and used in the fluidics field.

The devices may be constructed such that the capture material, nanopores, channels, or all of the foregoing, are disposed on a chip or other device that is then connected to a sample source or input chamber. In other embodiments, the chamber, nanopores, channels, electrodes and capture materials are all disposed on a single, integrated device, as shown in FIG. 33. The components may be configured as part of a system, where a base or other unit accepts chips having sample containers, capture materials, nanopores, and electrodes in a snap-in or slide-in configuration. The base may include electrode that contact electrical contacts in the chips so as to apply a gradient or to address individual pores. The system may also include pumps, syringes, and/or other means that deliver fluids and samples to the input chambers, channels, pores, or other components.

The devices may be constructed such that each channel has a length of from 0.1 mm to 1 cm or even 10 cm or more. Channels may have internal cross-sectional dimensions of from 0.1 mm to 1 cm, or 1 mm to 100 mm, or even about 5 mm to 10 mm. The channels may be made from a polymer, silicon, an oxide, or other materials used in the fluidics field and known to those of skill in the art.

In some embodiments, one or more channels may include a material that binds to a particular analyte or analytes. For example, in the case of miRNA, the capture material may be p19 (e.g., New England Biolabs, www.neb.com) protein or other material that binds specifically to miRNA. While the p19 protein is considered especially suitable, other proteins that resemble p19 in structure or in function are suitable, as well as mutants derived from the native viral sequence. The material may be cellulose, a Drosha-DGCR8 complex, the PAZ domain on the *C. elegans* genome, and the like. The capture material may be present on a bead, porous support, or other structure, as shown in FIG. 21. Beads are considered especially suitable, but are not necessary to the disclosed devices.

In this way, the user may transport cell contents to the capture materials so as to isolate an analyte (e.g., miRNA), if present, in the sample. Once the target binds to the capture material, the user may flush the channel (and capture material) to remove any unwanted materials.

In certain embodiments, the user may apply an analyte-specific probe to the analyte. Suitable probes include multi-nucleotide probes or even proteins; probes that specifically bind to the analyte of interest are considered especially suitable. The probe may be labeled with a fluorophore or phosphor. A probe may also be labeled magnetically or radioactively. In some embodiments, the analyte (e.g., miRNA) and probe are mixed together, and the capture material binds to the analyte-probe duplexes. In other case, a capture material—such as a bead or a porous support—has bound to it probes that are specific to a particular analyte. For example, a bead (or other support, such as a monolith or a strip) may be decorated with probes that are complementary to a nucleotide sequence on miRNA1. The sample is contacted to the bead, and miRNA1 in the sample—if present—binds to the probes on the bead. Excess sample may be washed away, and the bound miRNA1 may be eluted (in duplex miRNA1:probe form or as miRNA1 alone) and detected at a nanopore. The capture material may also be a microarray, which micro array includes spots or regions that bind specifically to only a particular analyte. For example, such a region on a microarray might include oligonucleotides or even proteins that are specifically complementary to an analyte of interest. Once the analyte binds and excess sample is washed away, the bound analyte is suitably eluted and then detected by a nanopore.

In this way, a device may detect multiple analytes, and may even do so in real time. In one embodiment, the sample chamber is in fluid communication with a first capture material (binding specifically to miRNA1) and a second capture material (binding specifically to miRNA2). Each of these capture materials may be disposed within its own channel, which channel is in turn in fluid communication with its own nanopore. The sample is contacted to the first and second capture materials, which materials bind specifically (respectively) to miRNA1 and miRNA2, if present. The user may then wash away excess sample. The bound miRNA1 and miRNA2 are then eluted into the channels associated with the respective capture materials and are detected by the nanopores associated with those channels, where the user detects the concentration (e.g., in the form of miRNA passages through the nanopore per unit time) of each miRNA.

The probe is suitably designed or selected so as to be complementary to only a particular target. By applying multiple probes to multiple capture materials, the user can simultaneously label multiple analytes. For example, capture material is disposed in channels 1 and 2 of a given device. The user then contacts the bound miRNA in channel 1 with a probe that is complementary only to miRNA1, and contacts the bound miRNA in channel 2 with a probe that is complementary only to miRNA2.

The user elutes any bound miRNA from the capture material (e.g., by application of heat, solvent, reagent, and the like), and the eluted miRNA then travels down the channels to a nanopore or nanopores. Once the eluted miRNA arrives at the nanopores, electrodes monitor the number of miRNA probe-target duplex passage events through the nanopore. In embodiments where the analyte is labeled with a fluorescent, magnetic, or radioactive probe, the nanopores may be used to count the number of visual, magnetic, or radioactive passage events per unit time. The number of passage events may be correlated to the concentration of the analyte; this may be done with the assistance of a calibration curve, as shown in FIG. 21c.

Target material of interest may be bound to a probe for enrichment, or may be in its natural form (i.e., not bound to a probe). The probe may be selected such that the probe binds specifically to the analyte of interest. The probe may also bind to the capture material; in this way, only analyte bound to a probe binds to the capture material, and unbound analyte may be washed away. In some embodiments, the probe is not labeled, and gives rise to a sample:probe duplex than is then isolated and detected by passage through a nanopore. (Nanopores are suitably configured according to any of the nanopore devices and membranes described herein.)

Each channel in a device may be separately addressable; the nanopores are also suitably individually addressable. For example, the first channel in a device may be used to detect the concentration of miRNA1. This may be accomplished by eluting into the nanopore only analyte material that has been exposed to a probe complementary to miRNA 1. If duplexes between that material and the probe are present, the user will observe passage events of the duplexes through the nanopore. If no such duplexes are present—e.g., because miRNA1 was not present in the cell sample and the miRNA1 probe consequently had nothing to bind to and was washed away—then the user will observe little to no passage events at the nanopore. The user may create a multiplexed device—as shown in FIG. 33—that includes multiple channels for application of multiple probes, which in turn allows for detection of multiple analytes. A device may be constructed having two, three, or more channels dedicated to a single analyte (e.g., three channels configured to detect miRNA1) so as to perform multiple, simultaneous detections for a single analyte.

The devices may include nanopores and membranes according to any of embodiment disclosed in this application. For example, the devices may include a first capture material that binds specifically to a first molecule; a first membrane having a thickness in the range of from about 5 nm to about 100 nm; and a second membrane disposed adjacent the first membrane, the second membrane having a thickness in the range of sub-nm thickness up to about 20 nm (and all values therebetween), with the second membrane having at least one pore extending therethrough, the pore having a cross-sectional dimension in the range of from about 1 nm to about 100 nm, and the first membrane having a cavity formed thereon, the cavity being in register with at least one pore of the second membrane, the first pore being in fluid communication with the first capture material; a device configured to apply a gradient across the pore; and a detector configured to detect a signal related to passage of a molecule through the first pore.

In another embodiment, the device includes a first capture material configured to bind preferentially to a first molecule; a membrane having a thickness in the range of from about 20 nm to about 100 nm, and the membrane having a thinned region, the thinned region having a thickness in the range of from about 0.1 nm to about 20 nm, and a first pore extending through the thinned region, the first pore being in fluid communication with the capture material; and a detector configured to detect a signal related to passage of the first molecule through the first pore.

While the foregoing examples pertain to miRNAs, the described devices and methods may be used to detect analytes other than miRNA. For example, the devices may be used to detect DNA, RNA, tRNA, mRNA, and the like.

Also provided herein are methods of obtaining sequence or structure information. In these methods, the user may translocate an analyte through a nanopore (described elsewhere herein), and detect a signal related to the structure of the analyte. The signal may be an electrical signal, an optical signal, a magnetic signal, and the like. The signal is suitably related to a structural feature of the analyte. For example, a user may contact a DNA molecule with a labeled probe that bind only to a specific sequence of nucleic acids, e.g., ATTCG. The user may then translocate the sample through a nanopore and detect—if present—a signal (e.g., an optical signal from a fluorescent probe) related to passage of the labeled probe through the nanopore. The signal may, as described elsewhere herein, be correlated to the concentration of the target analyte.

The presence of the signal will indicate that the sequence to which the probe is complementary is present on the analyte. The user may perform sequencing by contacting segments of a target analyte (e.g., segments that are generated by restriction enzyme or enzymes) with labeled, sequence specific probes, and then detecting the presence—or absence—of signals when the segments are translocated through the nanopore.

Alternatively, the user may apply restriction enzymes with known binding sequences to an analyte and detect the presence—or absence—of segments cleaved from the analyte by the restriction enzyme. In this way, if a segment is detected, the user will know that the analyte from which that segment was removed included the sequence of nucleic acids to which the restriction enzyme bound.

In one aspect, the claimed invention provides analysis devices. These devices suitably include a membrane having a thickness of from about 20 nm to about 100 nm having a thinned region with a thickness in the range of from about 1 to about 20 nm. The device suitably includes at least one pore extending through this region of the membrane. The pore suitably has a characteristic cross-sectional dimension (e.g., a diameter) in the range of from about 1 nm to about 1000 nm. The devices also suitably include a supporting layer adjacent to the membrane.

The membranes of the disclosed devices (shown as layer 3 in the attached figures) are formed of a number of materials. Nitrides, oxides, and the like are all considered suitable. Nitrides may be silicon nitride, boron nitride, titanium nitride, gallium nitride, and the like; silicon nitride is considered especially suitable. Suitable oxides include silicon oxide, hafnium oxide, titanium oxide, aluminum oxide, and the like. Membrane materials that can be processed by standard lithography techniques are considered especially suitable.

The membrane may also include a carbonaceous material, such as a carbide, graphite, graphene, diamond, and the like. Silicon, gold, silver, platinum, gallium arsenide, and the like are all suitable, as are polymeric materials. Polymeric materials useful in the claimed invention include polymethyl methacrylate, polystyrene, polyimide, and the like. The polymeric material may be used in the membrane, but may also be present as a supporting layer or a capping layer of the device. The supporting layer may be fabricated from any of these materials, and may suitably include silicon, germanium, gallium arsenide, glass, quartz, or alumina.

The thinned region of the membrane suitably has a thickness in the range of the sub-nanometer range, or from about 0.1 nm to about 20 nm, but may have a thickness in the range of from about 1 nm to about 15 nm, or even in the range of from about 2 nm to about 6 nm. The thinned region may have a cross-sectional dimension (e.g., diameter, width) in the range of from about 1 nm to about 1000 nm, or from 10 nm to about 100 nm, or from about 20 nm to about 50 nm. Larger thinned regions are within the scope of the present disclosure.

A supporting layer suitably has a thickness in the range of from about 1 micron to about 2000 microns, or even in the range of from about 10 microns to about 200 microns. The optimal thickness of the supporting layer will depend of the specific uses of the device, and the user of ordinary skill in the art will encounter little difficulty in fabricating a supporting layer of the proper thickness.

The pores of the devices suitably have a characteristic cross-sectional dimension (e.g., diameter) in the range of from about 0.1 nm (i.e., a sub-nanometer size) or even 0.5 nm to about 500 nm, or from about 1 nm to about 200 nm. The optimal pore size will be apparent to the user, based on their needs. As non-limiting embodiments, pores having a diameter of from about 1 nm to about 3 nm are considered suitable for analyzing ssDNA, and pores having a diameter of from about 2 nm to about 10 nm are considered suitable for analyzing dsDNA. DNA samples may have both ss and ds portions. The ratio of the membrane thickness to the thickness of the thinned region is in the range of from about 100:99 to about 100:1, or even 100:51 to 100:5.

As shown in the attached figures, the nanopore may extent through the entire thickness of a membrane layer (FIG. 41), or may extend through a locally thinned region of the membrane layer (FIG. 53). The optimal configuration will depend on the user's needs.

As shown in FIG. 41, a device may include a base 0, a support 1, a dielectric 2, a thin membrane 3, and a upper membrane 4. A pore may be formed in the thin member 3, as shown in the figure. The thin membrane may have a thickness of only a few nanometers, or of tens of nanometers. The upper membrane 4 may have a thickness of a few nanometers, tens of nanometers, or even 100-1000 nanometers, depending on the user's needs. Because free standing (unsupported) membranes having a thickness of about 5 nm or less may experience mechanical instability or may not always be sufficiently robust for all applications. The devices shown in FIG. 41 thus enable the user to overcome this challenge, as a pore is formed in the membrane 3, which membrane may have a thickness of 5 nm or less, but which membrane is reinforced by the upper membrane 4. A variety of materials are suitable for layers 0-4, which materials are described elsewhere herein in more detail.

FIG. 42 illustrates a top-down view of a device according to FIG. 41. As shown in FIG. 42, the upper membrane 4 includes a window that exposes thin membrane 3, in which membrane is formed a pore 3. As explained elsewhere herein, the pore need not be square; it can be of virtually any shape. The thin membrane need not necessarily include a pore. In such embodiments, the thin membrane may serve as a stage or support for microscopy or other application. As shown in FIG. 80, the thinned membrane provides a reduced background for observing or measuring a sample; the sample of interest is deposited on the window substrate, and one or more of the optical methods above is used to image the sample.

Some substrates have intrinsic fluorescence (e.g., SiN is known to be "noisy" for blue-green fluorescence measurements. The reduction of the thickness for local imaging reduces the background extinction or fluorescence from the substrate, enabling better signal and contrast from the sample of interest. A user may accordingly use such a device as a sample stage in a microscopy application.

FIGS. 43-49 illustrate an exemplary fabrication process. As shown in FIGS. 43 and 44, a resist material 6 may be applied atop the upper membrane 4. The resist may be developed/removed to open a window in the resist that defines a region of the upper membrane 4. Plasma etching may be used to remove material from the upper membrane 4, which effectively defines a cavity or void above the thin membrane 3. The resist 6 may be removed (FIGS. 46-47). The user may then form a nanopore in the thin membrane 3 (FIG. 48) to give rise to the completed device shown in FIG. 49.

FIGS. 53-57 depict one non-limiting manner of fabricating the devices shown in FIG. 53. Briefly, FIG. 54 depicts a workpiece having resist (6), a capping layer (4), a membrane (3), a dielectric (2), a support (1), and an additional support (0) layer. The support layer (0) is suitably a hard material, such as silicon. The support layer (1) is suitably silicon, GaAs, and the like. The dielectric (2) may suitably be silicon oxide or other dielectric material. The dielectric layer is optional, and is not necessary to the devices' function.

A portion of the resist is selectively removed (FIG. 55), and then portions of the capping layer and the membrane layer are removed (FIG. 56-57). The nanopore is then formed in the locally-thinned region of the membrane layer (FIGS. 57, 53).

In some embodiments (FIGS. 41-49), the fabrication process entails first removing a portion of the resist (6) disposed atop the device workpiece via electron beam lithography (or other etching method) and corresponding development (FIGS. 44-45). Plasma etching, for example, is used to remove a portion of the capping layer (4) (FIG. 46) to expose the comparatively thin membrane material (3). Resist (6) may be removed (FIG. 47), and a nanopore may be formed—as described elsewhere herein—in the now-exposed membrane (FIGS. 48-49).

FIG. 50(*a*) depicts another embodiment of nanopore device fabrication. As shown in that figure, PMMA resist (topmost layer) is removed via electron beam lithography. Reactive ion etching (RIE) and PMMA development then follows to thin local regions of the SiN membrane to a thickness defined by (h). A silicon oxide layer is disposed (in this figure) below the membrane, and a silicon support (bottom-most layer) is also present.

FIG. 50(*b*) depicts AFM and optical microscopy images of a device according to the claimed invention. Following RIE process and lift-off, the AFM image of the 250 nm squares is shown in the inset (17 nm thinning). In this example, the thinning was checked for different RIE times and showed excellent linearity (slope: 1 nm/sec). In this way, the user can, by considering the etch rate, effect a desired degree of thinning in The bottom right-hand images in FIG. 50 show bright-field (BF) and annular dark field (ADF) images of the etched membranes, as well as corresponding images for a 10 nm pore (inset). The intensity profiles shown adjacent to the square-shaped pores highlight the exceptional contrast of ADF imaging, which is useful for accurate thickness determination.

A device may include single or multiple pores, as shown in FIG. 50. Arrays or rows/strips of nanopores may be used. Arrayed pores are suitably spaced far apart enough from one another so as to avoid cross-talk between neighboring pores. Pores may be present in square (n×n) arrays. The arrays may include several pores, tens of pores, or even hundreds of pores, if the user so desires. The pores may be present in rows or strips, depending on the configuration of the device.

Pores are suitably circular or elliptical in conformation, but may also be polygonal. The pores may be square, pentagonal, rectangular, or other polygons having from 3 to 12 sides.

In some embodiments, a dielectric layer is disposed adjacent to the membrane. Without being bound to any particular theory, the dielectric layer improves the performance of the devices. The dielectric layer (layer 2 in the attached figures) suitably contacts the pore-bearing membrane where the supporting layer is present. Suitable materials for the dielectric layer include silicon oxide, aluminum oxide, silicon nitride, and the like. The dielectric layer, however, is optional, and need not be present.

In some embodiments, the devices include a capping layer (layer 4 in the attached figures). The capping layer is suitably disposed adjacent to the membrane. The capping layer material is suitably selected from the set of materials that are suitable for use in the membrane. In some embodiments, the capping layer and the membrane are formed of the same material.

The capping layer suitably includes an opening that overlaps, at least in part, a pore of the membrane. This opening may, in some embodiments, be used to assist the user in locating one or more pores of the membrane, as the pores are nanometer-scale. The opening suitably has a characteristic cross-sectional dimension greater than the corresponding cross-sectional dimension of the at least one pore of the membrane. The opening suitably has a characteristic cross-sectional dimension in the range of from about 10 nm to about 10 microns, or from about 50 nm to about 1 micron, or from about 100 nm to about 500 nm, or even about 250 nm. The opening in the capping layer may be circular, but can also be elliptical or polygonal in configuration.

The devices also may include a device capable of applying a gradient across the pore. Batteries, magnets, voltage generators, and the like are all considered suitable. The gradient may be an electrical gradient, a magnetic gradient, an ionic gradient, a pressure gradient, and the like. An electrolytic fluid is suitably present on both sides of the pore, so as to allow an electrical gradient to be passed across the pore to drive (or pull) a macromolecule across the pore. The fluid not necessarily be electrolytic, as non-conducting fluids may be useful where a pressure, magnetic, or other gradient is used to translocate the analyte across the pore.

The devices also suitably include a monitoring device capable of detecting a signal related to passage of a macromolecule across the pore, such as a change in electrical current related to passage of an analyte across the pore. The device may also be a device that detects an optical signal, such as a signal related to the passage of a fluorophore or other label that may pass through the nanopore.

The devices may further include a device (suitably a computer) capable of comparing the signal related to passage of a macromolecule across the pore to a signal evolved from passage of a macromolecule of known structure across the pore. In this way, the user may match the signal generated by a macromolecule of unknown structure to a signal generated by a macromolecule of known structure to determine the structure of the macromolecule being tested.

The devices may also include a device (e.g., a computer) that correlates a signal detected from the analyte or nanopore to a property of the analyte, the concentration of the analyte, or both. For example the device may correlate the number of passage events to the concentration of the analyte in the sample. This may be accomplished by comparing the number of passage events (or even the number of passage events per time) to calibration curve. The device may also output (e.g., display) the passage events, or may save a record of the events to a computer readable medium. The devices may display the signals detected at the pore as the signals are detected, i.e., in real-time.

Alternatively, the user may correlate the detected signal or signals to a property of the analyte. The user may do so by comparing a signal or signals evolved from the translocation of the analytes through the pores to a calibration curve or other standard.

Also provided are methods of fabricating devices. These methods include removing at least a portion of a first material disposed adjacent to a membrane material having a thickness in the range of from about 20 nm to about 200 nm so as to expose at least one target region of the membrane material; and etching at least a portion of the at least one target region of the membrane material so as to reduce the thickness of the membrane material within the target region to from about 0.1 nm to about 50 nm, or even from about 3 nm to about 30 nm. This can, in some embodiments, be conceptualized as thinning the targeted region of the membrane material.

The membrane may, in some embodiments, have a thickness in the range of even 5 nm to about 20 nm. The membrane may also have a thickness in excess of 200 nm, e.g., from about 200 nm to about 500 nm, or even to about 1000 nm. The first material—which may be a resist—may have virtually any thickness; the optimal thickness will depend on the user's needs and will be determined without undue experimentation.

The user may form at least one pore that extends through the target region of the membrane material. The pore may be formed by methods known in the art, e.g., application of an electron beam, a focused ion beam, heavy ion irradiation, chemical etching, or any combination thereof. The first material may be removed by electron beam lithography, application of etching or dissolution reagents, ion beams, and the like—suitable techniques will be known to those of ordinary skill in the art.

A variety of materials may be used as the first material. Polymethyl methacrylate, polymethyl glutarimide, styrene methyl acrylate, and the like are all suitable. Etching to reduce the thickness of the membrane may be accomplished by plasma etching, wet etching, focused ion beam etching, reactive ion etching, and the like, or any combination thereof.

The resist (first) material is suitably removed by electron beam lithography, optical lithography followed by development using an appropriate developing solvent, optical interference lithography followed by development using the appropriate developing solvent, nanoimprint lithography followed by development using the appropriate developing solvent, and the like. The resist suitably comprises polymethyl methacrylate, polymethyl glutarimide, styrene methyl acrylate, and the like; suitable resist materials will be known to those of ordinary skill in the art.

Resist material remaining after the first removal (FIG. 47) may also be removed, if the user desires. A capping layer may be present adjacent to the membrane (pore-bearing) layer, and a portion of the capping layer may be removed (FIG. 46) so as to expose the target region of the membrane material. This removal is suitably accomplished by wet-etching, dry etching, plasma etching, or any combination thereof.

Exemplary device fabrication is illustrated in FIG. 74, FIG. 75, and FIG. 76. In FIG. 74, a mask layer 0 (e.g., silicon nitride) is disposed adjacent to a silicon or other substrate material 1. A dielectric material 2 (e.g., silicon oxide) is disposed adjacent to a thinnable membrane material 3. The thinnable membrane material 3 may be silicon nitride. As shown in FIG. 75, a portion of the membrane 3 is removed so as to give rise to a thinned region of the membrane, which thinned region has a thickness smaller than that of the unthinned portion of the membrane 3. As shown in FIG. 76, a pore is then formed in the thinned region of the membrane 3.

This technique thus enables formation of thin (or, short) pores in a thicker membrane material. In this way, the user may create advantageously thin pores—which have useful properties, as described elsewhere herein—in a comparatively thick membrane 3, which membrane lends structural rigidity to the device. Methods of forming pores are well-known to those of ordinary skill in the art. A reduced area of the thinned membrane of a sub-micron scale is useful (but not necessary). It may also be useful—but not necessary—to reduce the membrane thickness in patterned areas that are at a distance from the edge of the support of the larger membrane. This may reduce stress in the thin membrane that results from the interface between the freestanding membrane and the supported membrane.

Also provided are methods of analyzing an analyte. These methods include translocating at least a portion of an analyte (e.g., miRNA or a macromolecule) through a pore disposed in a membrane having a thinned region with a thickness in the range of from about 0.1 nm to about 20 nm and detecting a signal related to the translocation of the molecule through the pore.

Translocation is suitably effected by application of a gradient, such as an electrical field, a magnetic field, an ionic gradient, or any combination thereof. The thickness of the pore is suitably between about 0.1 to about 20 nm, or from about 1 nm to about 10 nm, or even from about 2 nm to about 5 nm. The optimal thickness of the pore will depend on the needs of the user and on the characteristics of the macromolecule being analyzed.

The user may monitor an electrical signal, a visual signal, or even some combination of these. Electrical signals—such as current—are considered especially suitable. Microscopy instruments are suitably used to gather optical or visual signals from the macromolecules under analysis. The detection of the signal may be accomplished by electrodes, as shown in the exemplary embodiments herein.

In some embodiments, correlating comprises comparing the signal related to the translocation of the macromolecule through the pore to a signal generated from the translocation of a macromolecule of known structure through a pore. For example, a user may know that a particular sequence of six bases yields a particular electrical current signal when that sequence is passed through a detector nanopore. If the user then observes that same current signal when analyzing a macromolecule of unknown structure, the user can conclude that the macromolecule undergoing testing has the six base sequence. The signal can also be used as a measure of the size of the molecule being analyzed, and the correlating aspect may thus include directly measuring the signal and correlating the signal to the size of the molecule being analyzed.

Also provided are additional analysis devices. These devices suitably include a first membrane having a thickness in the range of from about 5 nm to about 100 nm; and a second membrane disposed adjacent the first membrane, the second membrane having a thickness in the range of from about 2 nm to about 20 nm. The second membrane may include at least one pore extending therethrough, the pore having a cross-sectional dimension in the range of from about 1 nm to about 100 nm. The second membrane may include hafnium oxide, silicon oxide, titanium oxide, aluminum oxide, and the like. The first membrane suitably includes a cavity in register with the pore of the second membrane.

The construction of exemplary devices is shown in FIGS. 77-79. As shown in those figures, a thinnable membrane material 3 is disposed adjacent another membrane material 4. The membrane material 4 suitably has a thickness of a only one or a few nanometers, although thicknesses of 5, 10, 20, or even 30 nm are considered suitable. The membrane material 4 is suitably disposed adjacent to an insulator 2, which is in turn adjacent to a dye or support 1, which is in turn adjacent to a mask layer 0. The user suitably etches a cavity in the thinnable material 3 (as shown in FIG. 78, so as to expose a region of the membrane material 4. The user may then form a nanopore (FIG. 79) in the exposed region of the membrane material 4. In this way, the user may construct a thin (short) nanopore in a structurally robust assembly, which assembly has a rigidity conferred on it by the thinnable material 3. While the figures are not necessarily to scale, it is useful (but not necessary) to form the cavities and pores in regions that are relatively distant from the interface of the membrane 4 and the supporting material 2.

Further disclosed are detection devices. These devices suitably include a first capture material configured to bind specifically to a first molecule (e.g., miRNA); a membrane having a thickness in the range of from about 20 nm to about 100 nm having a thinned region thereon, the thinned region having a thickness in the range of from about 1 nm to about 20 nm, and a first pore extending through the thinned region, the first pore being in fluid communication with the capture material; and a detector configured to detect a signal related to passage of the first molecule through the first pore. Suitable membranes and pores formed therein are described elsewhere herein in further detail.

The capture material may include a protein, a porous support (e.g., a monolith), a bead, and the like. The porous support may be polymeric in nature. The capture material is suitably configured so as to bind to the first molecule (or to a molecule that is itself bound to the first molecule). For example, the capture material may include a protein—e.g., p19—that preferentially binds to a probe-miRNA duplex, as shown in FIG. 61(*a*). The capture material may include one or more nucleotides that bind to the first molecule or a species that is itself bound to the first molecule.

In some embodiments, the first molecule is bound—as shown in FIG. 61*a*—to a probe that is specifically complementary to that molecule. Such a probe may be a nucleotide-containing probe that includes a nucleic acid sequence that is complementary to a sequence on the first (target) molecule. The capture material may be selected to as to bind preferentially to a predetermined first miRNA molecule.

In some embodiments, the devices include a second capture material. This second capture material may be one that binds preferentially to a second miRNA molecule that differs in at least one aspect (e.g., size, nucleic acid sequence) from the first miRNA molecule. In some embodiments, the user may contact a sample with a second probe that is complementary to a second molecule (e.g., a miRNA molecule) that differs in some respect from a first miRNA molecule.

The capture material may be positioned such that it is in fluid communication with a pore. The first and second capture materials may be in fluid communication with the same or different pores. This may be accomplished by using different channels to connect the different capture materials to different probes. The devices may, of course, include 3 or more different capture materials, channels, or even pores. By utilizing multiple channels or pores, the devices may perform multiplexed analysis or detection for multiple analytes.

The devices may also include a sample storage chamber or input chamber. This chamber may be placed into fluid communication with the first capture material. A valve, septum, or other fluidic element may be used to modulate flow between the input chamber and the capture material.

The present disclosure also provides additional detection devices. These devices suitably include a first capture material that binds specifically to a first molecule, a first membrane having a thickness in the range of from about 5 nm to about 100 nm; and a second membrane disposed adjacent the first membrane, the second membrane having a thickness in the range of from about 2 nm to about 20 nm, and the second membrane having at least one pore extending therethrough, the pore having a cross-sectional dimension in the range of from about 1 nm to about 100 nm, and the first membrane having a cavity formed thereon, the cavity being in register with at least one pore of the second membrane, the first pore being in fluid communication with the first capture material; a device configured to apply a gradient across the pore; and a detector configured to detect a signal related to passage of a molecule through the first pore.

Suitable membranes and pores are described in additional detail herein, as are suitable capture materials. An exemplary membrane/pore device is shown in FIGS. 77-79, which figures show a nanopore formed in a thin layer 4, the thin layer 4 being supported by a mask layer 0, a dye 1, and dielectric insulator 3. As shown in those figures, a cavity is formed in the membrane material 3 in register with the pore formed in layer 4.

These devices are considered especially suitable for miRNA detection. The devices are also useful for detection of DNA, RNA, and other biological entities. The sample may be present in a storage chamber (e.g., the input chamber shown in FIG. 73), which chamber may be in fluid communication with a capture material. The devices may include more than one capture material, and the configuration of the capture materials and pores is described herein in connection with the other disclosed devices.

The present disclosure also provides methods of detecting an analyte. These methods include contacting a sample to a first capture material that preferentially binds to a first analyte, eluting the first analyte from the capture material, translocating the first analyte through a first pore disposed in a thinned region of a membrane, the thinned region having a thickness in the range of from about 0.1 nm to about 20 nm; and detecting a signal related to the translocation of the analyte through the first pore.

The first analyte may be miRNA, DNA, RNA, tRNA, and the like. Biological analytes are considered especially suitable for the provided methods. The signal evolved from the translocation of the analyte (e.g., a molecule, such as miRNA) through the pore. Electrical signals, such as current, are suitably monitored.

In some embodiments, the capture material preferentially binds the analyte. In other embodiments, the capture material preferentially binds an analyte-probe combination or duplex. As shown in FIG. 61*a*, the user may contact a target molecule with a probe that binds specifically to the target. The probe-target duplex then binds to a capture material, such as p19 or other protein. The capture material may be part of a bead or a porous support. The beads may be of virtually any size; they may be of sub-micron size, micron size, tens of microns, or even hundreds of microns or even millimeter-scale in size. Washing may be performed to remove other analyte (e.g., unbound miRNA) from the mixture. The hybridized probe: miRNA complex may then be eluted from the capture material, by application of salt, heat, or other reagents that effect elution.

In some embodiments, the user may contact the analyte-containing sample to a second probe. This second probe is suitably selected so as to bind preferentially to an analyte (e.g., second analyte) that differs from the first analyte. The user may then bind the second analyte to a capture material, wash away other analytes, and elute the second analyte for detection by the pore, where the user detects a signal related to the translocation of the second analyte through the second pore.

The foregoing may also be accomplished by translocating an analyte through a first pore formed in a first membrane. The first membrane is suitably disposed adjacent to a second membrane; the second membrane having a thickness in the range of from about 5 nm to about 100 nm and the second membrane having a cavity formed thereon, the cavity being in register with the first pore, the first membrane having a thickness in the range of from about 2 nm to about 20 nm, and the first pore extending through the first membrane, the pore having a cross-sectional dimension in the range of from about 1 nm to about 100 nm, the first pore being in fluid communication with the first capture material; and detecting a signal related to the translocation of the molecule through the pore.

Exemplary Embodiment

The following is an exemplary, non-limiting embodiment of the claimed invention. The specific materials and techniques recited here are exemplary only and should not be taken as limiting the scope of the invention to these particular materials and techniques.

The present invention presents a unique approach for fabricating sub-10 nm thick membrane devices, as well as the use of such membranes for nanopore-based nucleic acid analysis. This innovation involves, inter alia, the steps of (1) electron-beam lithography is used to expose a sub-micron region on a 50 nm-thick SiN window, (2) reactive ion etch is used to locally thin the exposed SiN region with sub-nanometer control, (3) the electron-beam of a transmission electron microscope is used to drill a nanopore in the thinned SiN region. Thereafter, the nanopore devices are treated using established protocols for subsequent biomolecular analysis. Analysis of macromolecular translocation through solid-state nanopores is described in, e.g., Wanunu et al., *Biophys. J.*, August 2008, vol. 95, and Wanunu et al., *Nature Nanotechnology*, Vol. 5, November 2010, the entireties of which are incorporated herein for all purposes.

An exemplary, non-limiting fabrication scheme is shown in FIG. 41 (plan view) and FIG. 2 (top view). The ultrathin nanopore is supported by, e.g., a ca. 500 μm thick <100> p-type silicon (Si) wafer (layer 1 in FIG. 41), which may contain a several μm thick thermal oxide on one or both of its sides (layer 2 in FIG. 41).

Using low-pressure chemical vapor deposition (LPCVD), ca. 40 nm of low-stress SiN is deposited on both sides of the wafer. Standard photolithography followed by anisotropic etch using KOH is used to divide the wafer into a square array of 5×5 mm$^2$ chips, as well as to define in each chip a free-standing square SiN window with dimensions ranging from 1×1 to 500×500 μm$^2$. If oxide is present in the free-standing window, the oxide is removed by treatment with hydrofluoric acid or by buffered oxide etch using standard protocols. This yields a workpiece as shown in FIG. 43.

The top side of the substrate in FIG. 43 is then spun-coated with an electron beam resist C2 950 PMMA (950 molecular weight polymethyl methacrylate, 2% in chlorobenzene) at 5000 rpm for 50 seconds to achieve a resist layer of ~100 nm thickness, and then baked on a hotplate at 180° C. for 10 minutes (FIG. 44).

Electron beam lithography is then used to write a square of 50×50 to 1000×1000 nm2 onto the resist-coated SiN window, using a 20 pA electron beam of 50 kV (Elionix 7500-ELS) and a beam dose of 750 μC/cm$^2$. The device is then developed in 1:3 volume ratio of MIBK (methyl isobutyl ketone) and isopropanol, respectively, for 60 seconds (FIG. 45).

The exposed areas of the SiN are further thinned by $SF_6$ plasma etching using a 50 watt RF source and 0.4 mtorr SF6 chamber pressures (FIG. 46). The duration of the RF source determines the etch depth, which is suitably 1 nm per second under the indicated conditions. Other etch rates are within the scope of the claimed invention, and the optimal etch rate will depend on the user's needs and capabilities. The etch rate can be modulated or chosen so as to enable the user to achieve devices of the desired configuration.

In another, non-limiting embodiment, the user etches a SiN layer (shown as layer 4 in the attached figures) so as to expose a layer (layer 3) of hafnium oxide. The hafnium oxide may have a thickness of from about 2 nm to about 5 nm, in some embodiments.

Atomic force microscopy is used to accurately measure the etched depth in a given batch of etched chips. This process can be simultaneously carried out on a set of 1-300 chips. Following the thinning, PMMA resist is removed by incubation in warm acetone, yielding a device shown in FIG. 47.

Each chip is then inserted into a transmission electron microscope equipped with a field emission gun (e.g., a JEOL model 2010F) and a nanopore in the range 1-100 nm is drilled by focusing the electron beam onto the thinned region of the membrane using previously reported protocols (see FIG. 48), yielding a nanopore device as shown in FIG. 49. Formation of nanopores in membranes is well-characterized in the art, and is described in, e.g., Storm et al., *Nature Materials*, August 2003, vol. 2, the entirety of which is incorporated herein by reference for all purposes.

FIG. 51 illustrates the detection of 25 bp dsDNA using a 3 nm solid-state nanopore according to the claimed invention in a 20 nm thick SiN membrane (T=0° C., V=300 mV). In the figure, concatenated single-molecule traces are shown; the small pore and low temperature combination facilitates detection of these short molecules (mean transport time=80 microseconds), which is an important step for detecting RNA-drug complexes in design-RNA sequences, such as the ribosomal A-site and the TAR site of HIV RNA; and The improved resolution achieved by the claimed invention is shown by FIG. 52, which figure illustrates DNA translocation through 4 nm pores in SiN membranes of various thickness values.

Figure 52A:
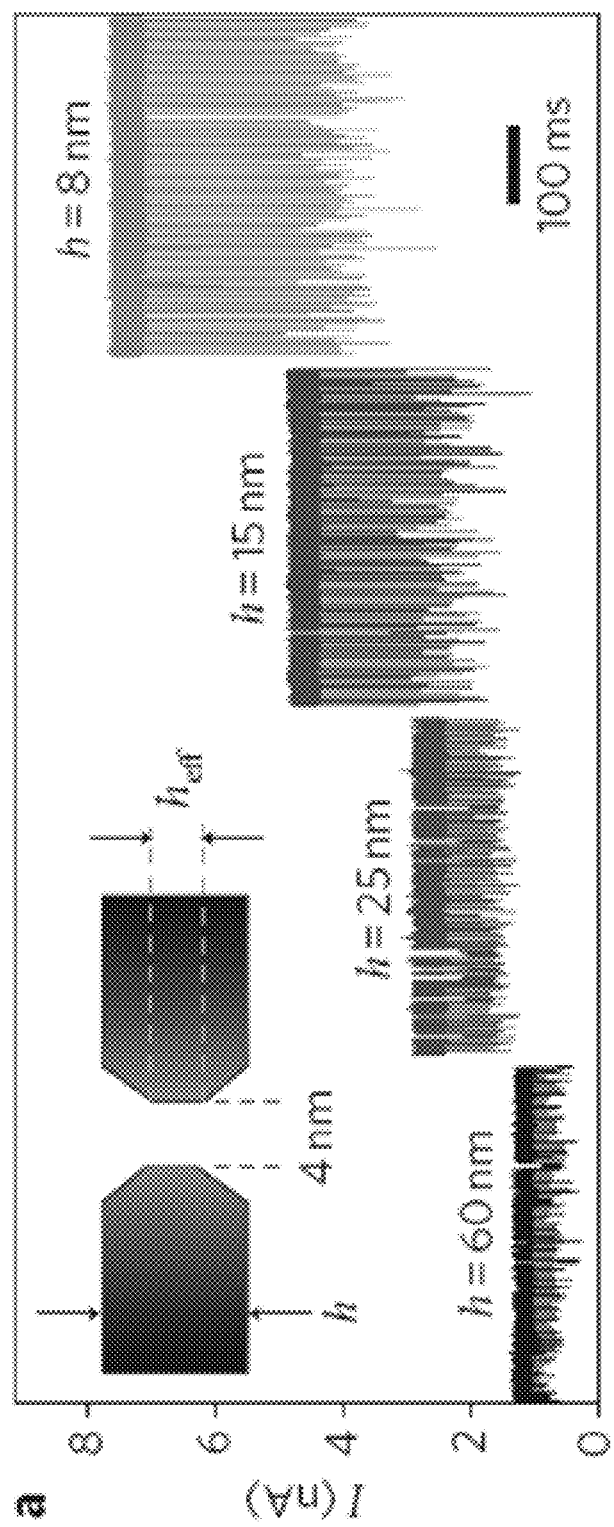

FIG. 52a shows concatenated events for 3 kbp dsDNA translocations, as a function of membrane thickness (h) (V=300 mV, T=21° C., 1M KCl, pH 8). As shown at the top of the figure, the detected current increases with decreasing h values, such that a nanopore having a thickness of 8 nm is more than four times more sensitive than a nanopore having a thickness of 60 nm. These data underscore the performance advantages achieved by the thinned membranes and thin (low-h) nanopores of the present disclosure.

Figure 52B:
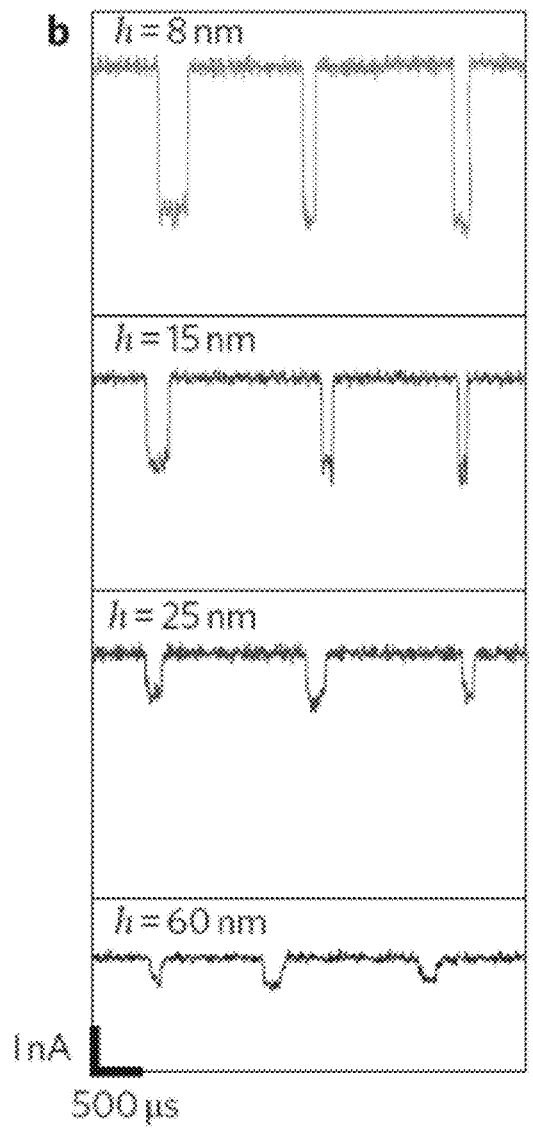
Figure 52C:
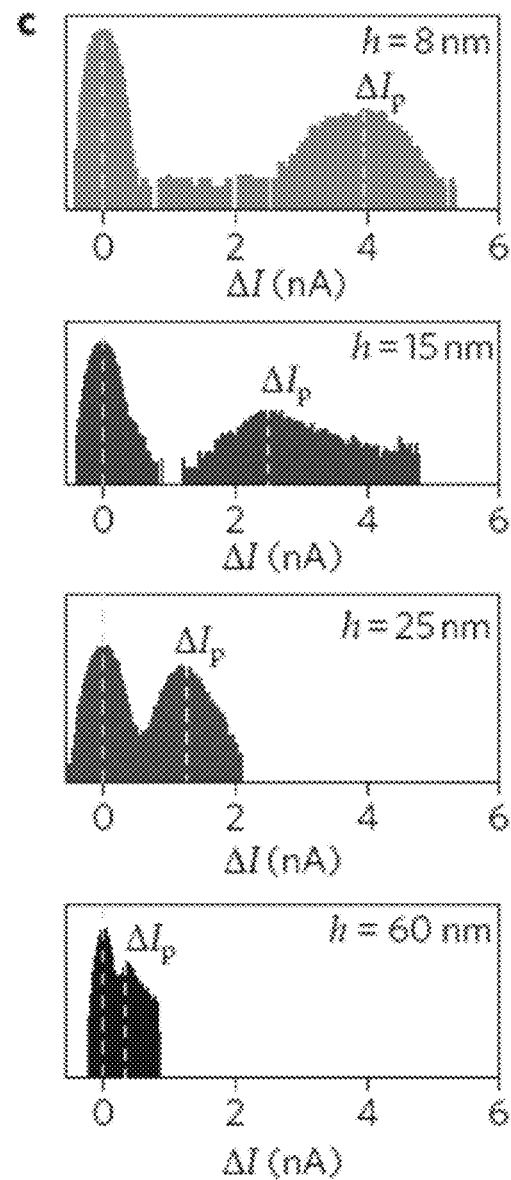

FIG. 52b shows expanded events from the traces shown in the upper quadrant of the figure. As shown, nanopores having a thickness of 8 nm enable the user to resolve individual translocation events at a far greater resolution than nanopores having thickness values of 15, 25, or even 60 nm. FIG. 52c shows semi-log all-point current histograms from the events shown at the top of the figure, illustrating the ability of the thinned nanopores to resolve DNA translocation at improved resolution.

Figure 52E:
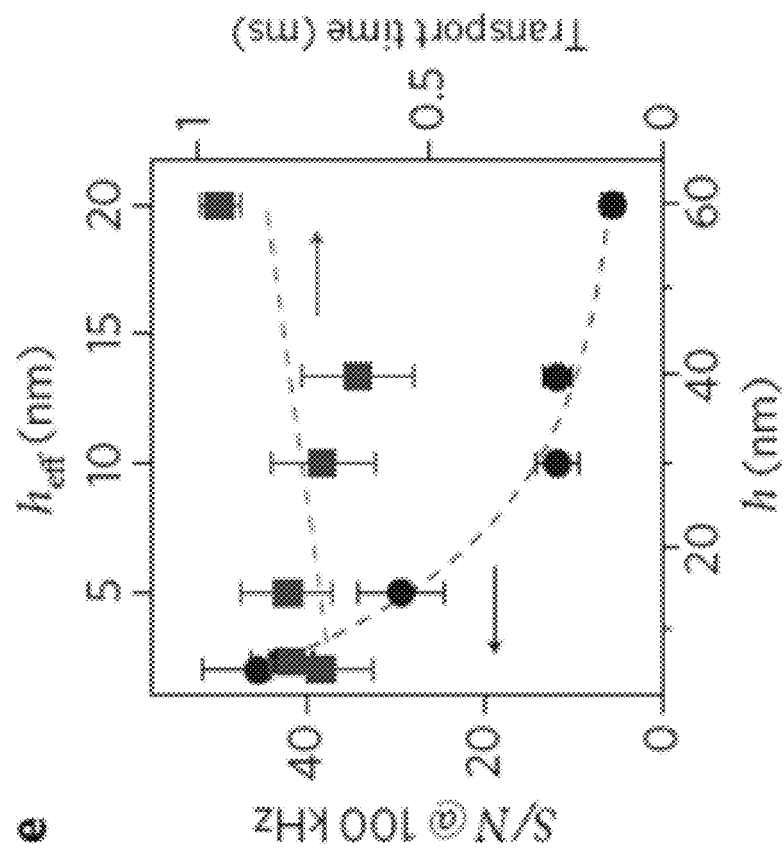
Figure 52D:
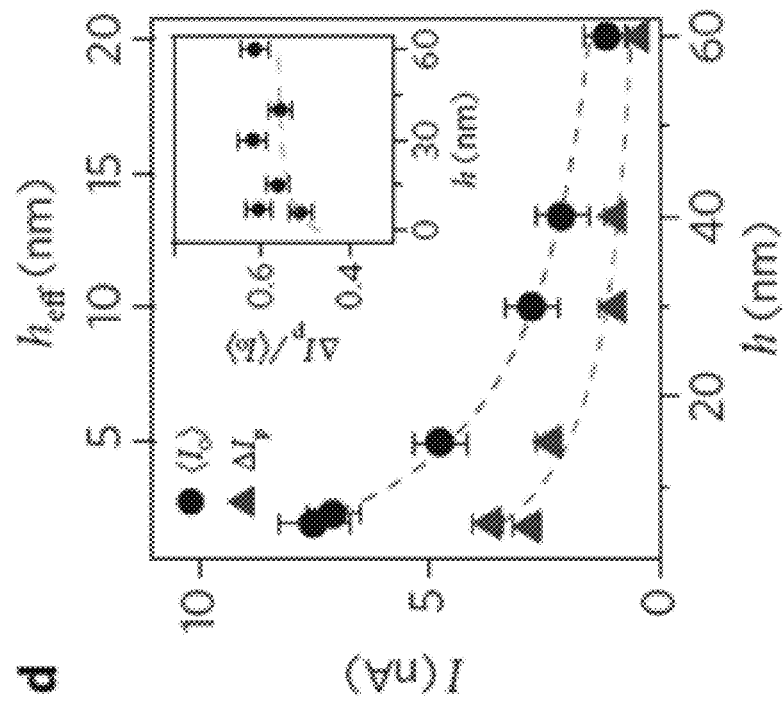

FIG. 52*d* illustrates the relationship average experimental $<I_o>$ (circles) and the most probable DNA current amplitude $\Delta I_p$ (triangles) on h. The dashed line among the circles is a fit using Eqn. 1 to the average $I_o$ data from combined data of ~20 pores, which yields an effective pore thickness $h_{eff}$=h/(3.04±0.30) ($h_{eff}$ scale shown on top x-axis). The fit to $\Delta I_p$ values (dashed line with triangles) is based on a geometric model described in detail herein. The inset shows $\Delta I_p/<I_o>$, which did not change appreciably with h. The dashed line in the inset is the ratio of the fits to $\Delta I_p$ and $<I_o>$ from the main plot.

FIG. 52*e* illustrates the signal-to-noise (S/N) and mean transport time as a function of h ($h_{eff}$ shown on top x-axis). S/N=$\Delta I/I_{RMS}$, where $I_{RMS}$ at 100 kHz bandwidth is 75±5 pA. Mean transport times were obtained from the dwell-time distributions.

Thinned pores presents many advantages, including improved signal-to-noise (improving from when the nanopore thickness goes from 60 nm to 8 nm), as well as improved resolution by contraction of the resistive sensing zone to a few nm, which contributes greatly to RNA-drug complex detection and footprinting.

Without being bound to any single theory of operation, the advantage of the disclosed thinned nanopores can be described by reference to existing, thicker nanopores. As a non-limiting example, if a DNA molecule enters a pore with a thickness of about 20 nm, approximately 40 to 50 base pairs would reside within the pore at a given moment. If, however, the pore is reduced in thickness such that only 5-6 base pairs reside within the pore at a given moment, the detected current (or other signal) related to the DNA passage across the pore would be averaged over far fewer bases than where the pore accommodates 40-50 base pairs.

Ultrathin nanopores have been fabricated and were evaluated for their performance in DNA analysis. The locally thinned SiN membranes offer tremendous advantages, such as greater signal-to noise values and improved resolution, with similar DNA transport velocities as with thicker membranes. This method can be applied on a wafer scale, enabling the production of hundreds of substrates at a time, essential for success in this proposal.

Microscopy

In another aspect, the present invention provides stages or platforms suitable for high-resolution microscopy. These stages or platforms suitably include a membrane having a locally thinned region (e.g., FIG. 53 and FIG. 46), which thinned region confers enhanced microscopy properties on the membrane. The thin membranes may be used as sample stages or supports. These are especially suitable for supporting cells, cell contents, or other biological entities for observation.

As one example, the thin membranes may be used in Transmission Electron Microscopy (TEM)-based and scanning TEM (STEM)-based imaging and analysis, which includes: bright field imaging, annular dark field (ADF) and high-angle annular dark field (HAADF) imaging, electron diffraction analysis, electron energy loss spectroscopy (EELS), and energy dispersive spectroscopy (EDS). One advantage presented by the thin membranes are that the ultrathin support enables higher contrast (relative signal) from samples deposited onto the ultrathin region, then the contrast from sample deposited onto a thicker region. An additional advantage is that the wide choice of materials suitable for the ultrathin membranes enables elemental spectroscopy (e.g., EELS and EDS above) with little or no interference from the substrate.

The thinned membranes are also suitable for Scanning Electron Microscopy (SEM)-based imaging, which includes imaging using a secondary electron detector, backscattering detector, a transmission detector, and a so called STEM detector. The ultrathin substrates exhibit an extremely low backscattering cross-section, which results in the substrates being practically SEM-invisible. Such devices exhibit a much better contrast than normal (thick) counterparts, enabling better contrast and EDS signal. This is illustrated in FIG. 40, which figure illustrates (from left to right) a series of zoomed images of a 6 nm thinned membrane formed in a thicker support. (The thinned membrane also includes a pore formed therethrough; the pore is shown by the bright spot at the edge of the thinned region.

The membranes are also advantageous for optical microscopy, which includes wide field white light imaging, or confocal fluorescence, or epifluorescence, or total-internal reflection mode fluorescence, or luminescence mode (in which light from a light-emitting source is collected). In such applications, the sample of interest is deposited on the window substrate, and one or more of the optical methods above is used to image the sample. Many substrates have intrinsic fluorescence (e.g., SiN is known to be "noisy" for blue-green fluorescence measurements. The reduction of the thickness for local imaging reduces the background extinction or fluorescence from the substrate, enabling better signal and contrast from the sample of interest.

Accordingly, the microscopy supports suitably include a membrane material having a first region of from about 0.5 nm to about 20 nm in thickness and a support layer disposed adjacent to the membrane material. The membrane and support layers may include the materials described elsewhere herein, e.g., silicon nitride and the like. The first region may have a thickness of from about 2 nm to about 12 nm, or even from about 6 nm to about 10 nm.

Also provided are methods of fabricating a microscopy supports. These methods suitably include removing at least a portion of a material disposed adjacent to a membrane so as to expose a first region of the membrane. This is shown by, e.g., FIGS. 44-47, which figures illustrate removal of material adjacent to a membrane (3) having the claimed thickness. FIG. 47 illustrates a device wherein a thin, lower membrane is exposed by formation of a cavity or other void in the material atop the lower membrane. The thin, exposed lower membrane may be used as a stage or support for samples undergoing optical microscopy, TEM, STEM, and other similar measurements. A pore may be formed in the lower, thin membrane, as shown in FIG. 48.

In some embodiments, the methods include etching at least a portion of the first region of the membrane material so as to reduce the thickness of the membrane material within the target region. This is shown by, e.g., FIGS. 50 and 54-56, which depict removal of a material adjacent to the membrane and then etching of the membrane material (3) itself so as to thin a localized region of the membrane.

ADDITIONAL DESCRIPTION

In one exemplary platform described herein, a target microRNA is first hybridized to a probe; this probe:microRNA duplex is then enriched through binding to the viral protein p19; and, lastly, the abundance of the duplex is quantified using a nanopore. Reducing the thickness of the membrane containing the nanopore to 6 nm leads to increasing signal amplitudes from biomolecules, while reducing the diameter of the nanopore to 3 nm allows the detection of and discrimination among small nucleic acids based on differences in their physical dimensions. This approach detects picogram levels of a liver-specific miRNA from rat liver RNA.

Forming Nanopores in Substrates

Figure 58A:
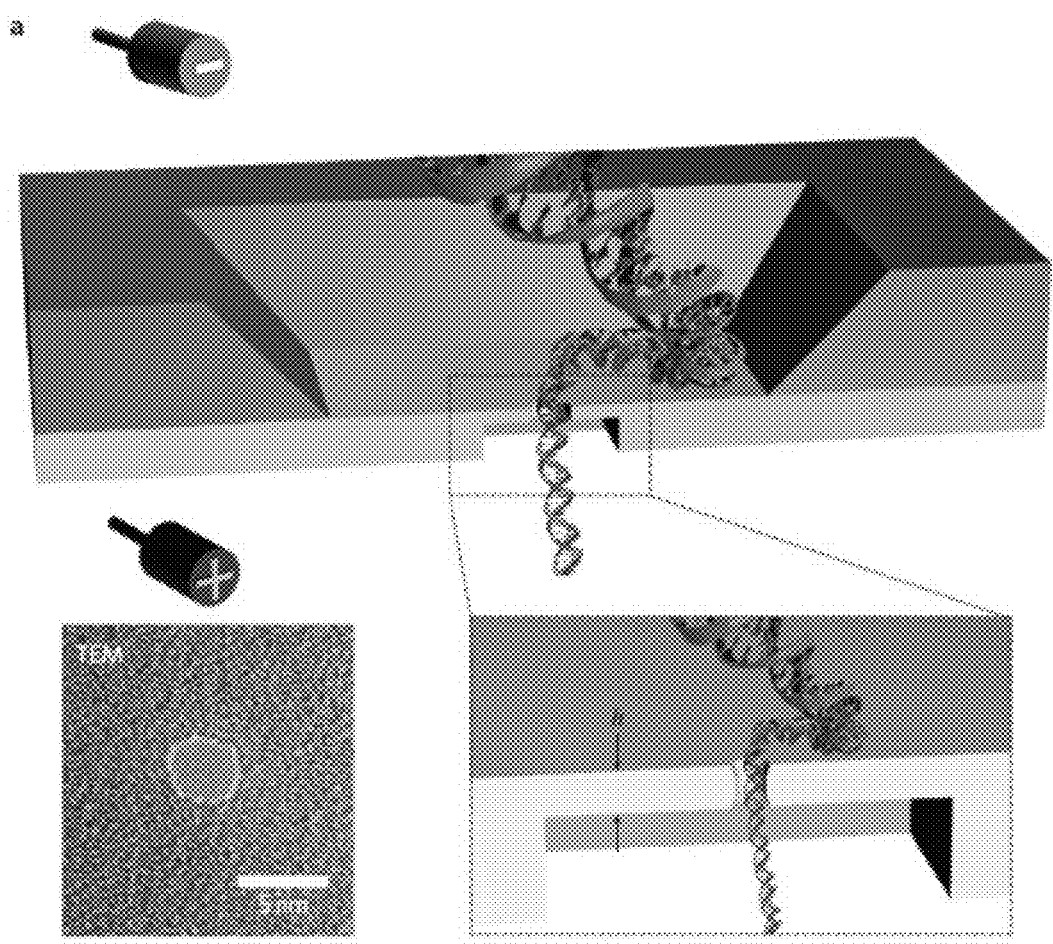

FIG. 58a depicts an exemplary thin solid-state molecular counter. In this embodiment, a region of a freestanding SiN membrane supported by a Si chip is thinned, after which a nanopore is fabricated using a transmission electron microscope (TEM). Biomolecular translocations (depicted in the inset) through the nanopore appear as transient reductions in the ion current. A TEM image of a ca. 4 nm diameter pore in a ca. 6 nm thick membrane is shown in the inset. As shown in the figure, an electrical gradient is applied across the pore so as to drive the analyte through the pore for detection.

The reduction of membrane thickness h is described in FIG. 58b. An optical micrograph of a processed membrane is shown in FIG. 1c, in which a pattern of 1, 4, and 9 squares of different sizes has been exposed and etched. An AFM image of the thinned 3×3 array is shown in the inset. Knowledge of the initial membrane thickness and the etch depth allows calculation of the resulting membrane thickness. AFM characterization of the depth vs. etch time reveals an etch rate of 1.0 nm/sec, which is illustrated in FIG. 58c inset and FIG. 62.

Figure 58D:
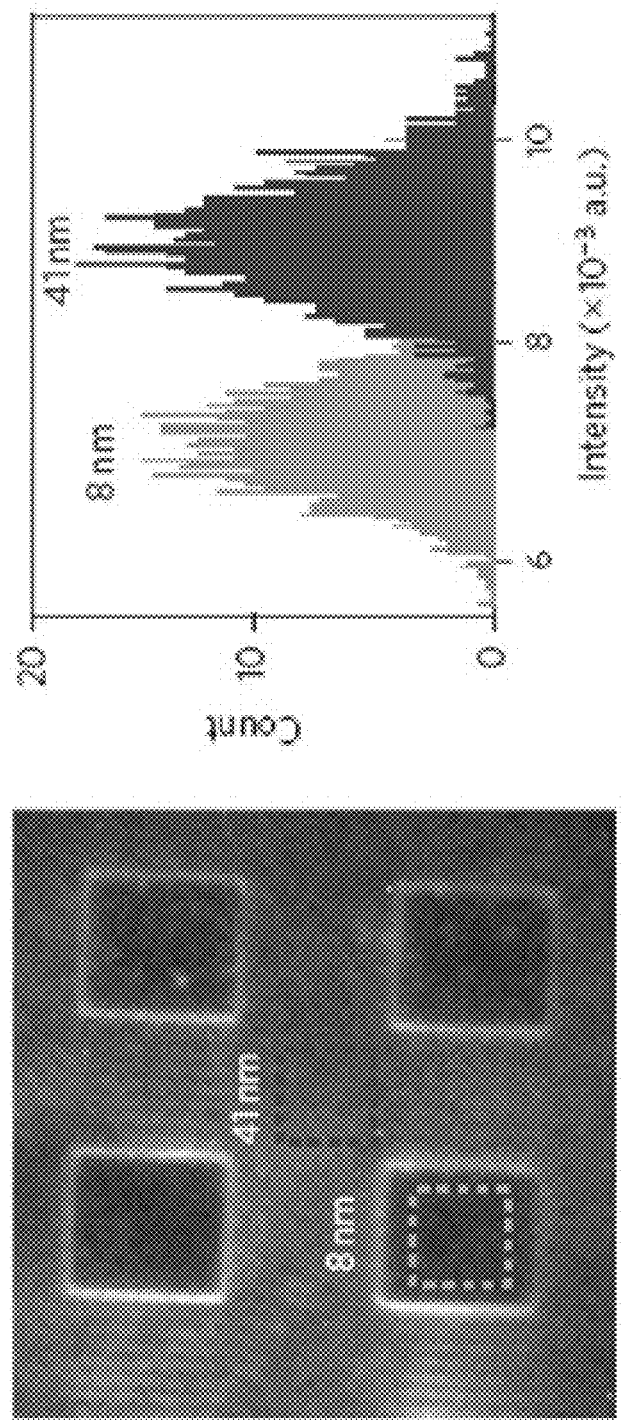

The intrinsic fluorescence of SiN membranes from embedded nano-Si structures was also measured. FIG. 58d shows that fluorescence background is reduced in the thinned regions, consistent with a reduced number of fluorescent structures. The thinnest nanopores were fabricated in 6 nm thick membranes (see FIG. 52d), which are comparable in thickness to lipid bilayers. Nanopores may, as described herein, be fabricated in membranes that are thinner and thicker than 6 nm.

To characterize the sub-10 nm thick nanopores, bright-field (BF) and annular dark-field (ADF) scanning transmission electron microscopy (STEM) images of a 4.5 nm diameter pore in a 7 nm thick membrane are shown in FIG. 59. Both BF and ADF STEM provide contrast that is very sensitive to membrane thickness. In BF-STEM, the thinned membrane region is a brighter area. The uniformity of the etched region is indicated by the line profile intensity (line in FIG. 59a). A zoomed-in ADF-STEM image reveals a sharp drop in the intensity near the pore (line in FIG. 59b). The contrast is reversed from BF to ADF, so that the pore appears dark.

Based on previous TEM and ion conductance measurements and the ADF-STEM measurements, nanopore shapes deviate from a perfect cylinder. However, a simplified geometric model using an equivalent cylinder of reduced thickness and equal diameter to the measured pore diameter can quantitatively explain the data. This reduced thickness is defined as the effective pore thickness $h_{eff}$, as illustrated in FIG. 12a.

To a first approximation, $h_{eff}$ can be used to quantitatively explain electrolyte transport through the pore. Systematically changing the membrane thickness h by controlled thinning should have a predictable influence on electrolyte transport through a pore fabricated in such a membrane. When voltage V is applied, the ion current $I_0$ through a cylindrical pore with diameter d and thickness $h_{eff}$ is approximated in high ionic strength solutions (>100 mM) by:

$$I_0 = V([\mu_{K^+} + \mu_{Cl^-}]n_{KCl}e)\left(\frac{4h_{eff}}{\pi d^2} + \frac{1}{d}\right)^{-1} \quad \text{Eqn. 1}$$

where μ is the electrophoretic mobility of a species, $n_{KCl}$ is the number density of KCl, and e is the elementary charge. This equation includes the access resistance, which dominates the conductance in the limit of $h_{eff} \rightarrow 0$. Passage of analytes through the pore transiently reduces the ion current because the ion flux is hindered. Therefore, for similar diameter pores, reducing the pore thickness should yield two experimental outcomes, increased $I_0$ (see Eqn. 1), and increased difference I between the open pore current and the current upon occlusion with biomolecules.

To test this, one may use similar TEM conditions to fabricate dozens of 4 nm diameter pores in membranes with h=6-60 nm. FIG. 12a shows a set of ~200 concatenated translocations of 3 kb linear double-stranded DNA (dsDNA) molecules for 4 nm diameter pores of different thicknesses, recorded at 21° C. and 300 mV. Upon decreasing h, it is founds that: (1) open pore currents increase, and (2) amplitudes of the DNA translocation signals increase. Decreasing h vastly improves the signal from biomolecules, as illustrated by the close-up view of representative events in FIG. 52b. All-point current histograms from the traces shown in FIG. 43a are plotted on a semi-log scale in FIG. 52c. The histograms were normalized by subtracting the mean open pore current $<I_o>$ from each distribution. As predicted, the most probable current amplitude $\Delta I_p$ (dashed white lines) increases as h decreases. Also, the broadness of the $\Delta I$ distributions is augmented in thinner pores. Broad $\Delta I$ distributions were previously observed for pores in lipid bilayers and solid-state membranes, and are likely a result of the varying transport speeds, interactions, and/or initial configurations of each molecule prior to translocation.

In FIG. 52d is shown experimental mean open pore currents $<I_o>$ (circles) and the most probable DNA current amplitudes $\Delta I_p$ (triangles). Both quantities increase with decreasing h. The dashed line among the circles is a fit of $<I_o>$ based on Eqn. 1, where $h_{eff}$ is a fitting parameter. Using d=4.0 nm, $\mu_{K^+}$=6.95×10$^{-8}$ m$^2$ V$^{-1}$ s$^{-1}$, and $\mu_{Cl^-}$=7.23×10$^{-8}$ m$^2$ V$^{-1}$ s$^{-1}$, a best fit to the data is obtained using $h_{eff}$=h/(3.04±0.30), in good agreement with previous measurements for thicker membranes (see top x-axis of FIG. 52d). Based on the fit, the thinnest pores shows here with h=6 nm have a calculated $h_{eff}$≈2 nm.

To fit the experimental $\Delta I_p$ values, one uses a geometric model to compute the residual current through the pore when occupied by a DNA strand (see FIG. 63 and related discussion). In this model, dsDNA is assumed to be a cylinder 2.2 nm in diameter, and I is computed from the unobstructed area of the DNA-occluded pore. Once can add to this model a parameter S that describes the fraction of chloride ions excluded from the nanopore vicinity by the highly charged DNA coil. A previous report that $\Delta I$ increases as a function of DNA length in 4 nm pores suggests that the highly charged DNA coil excludes CF from the pore vicinity, therefore reducing [Cl$^{-1}$] near the pore. Using a single parameter of 20±5% Cl$^-$ exclusion for 3 kb DNA, the results match the model for $\Delta I$ (Eqn. 2 herein) for all tested $h_{eff}$ values (see dashed curve). The inset to FIG. 52d shows the experimental (markers) and calculated (dashed line) blockage fractions $\Delta I_p/<I_o>$ as a function of h. In the regime where access resistance does not dominate, i.e., for h>10 nm, $\Delta I_p/<I_o>$ is independent of h.

FIG. 52e displays signal-to-noise ratios S/N $I_p/I_{RMS}$ as a function of h, where $I_{RMS}$ is the open pore current RMS at 100 kHz bandwidth. $I_{RMS}$ is independent of h ($I_{RMS}$~70-80 pA at 100 kHz bandwidth), which results in increasing S/N values with decreasing h because $\Delta I$ increases with decreasing h. S/N=46 for h=6 nm, a marked improvement over S/N~10 in similar diameter pores with h=25 nm.

Finally, a potential concern in this study was that reducing h would also reduce DNA interactions with the pore surface, thereby speeding up DNA transport and presenting detection challenges. The right axis of FIG. 52*e* shows that the mean transport times for the 3 kb DNA molecules are approximately independent of h, with less than 30% decrease in transport times when h is reduced from 60 nm to 6 nm. The weak dependence of transport times on h indicates that parameters other than surface interactions, for example, electro-osmotic drag, influence the transport dynamics.

Discrimination Among Small Nucleic Acids

Using the increased signal amplitude in thin nanopores, thin pore (d=3 nm, h=7 nm) were tested to discriminate among small nucleic acids. First were compared 22-bp RNA and 25-bp DNA, because the two molecules have similar effective solvation volumes (~35 nm$^3$ and ~32.3 nm$^3$, respectively) and molecular weights (~15 kD), while differing in cross-sectional areas by ~35% due to their different helicities (see in FIG. 60*a* PDB files 1RPU and 2BNA from http://www.rcsb.org). Continuous current traces, as well as magnified sets of representative events are shown in FIG. 60*a*. To quantify the difference between the molecular signatures, also shown are all-point current histograms for DNA and RNA, which highlight the characteristic signal from longer events. The histograms reveal peaks at characteristic current amplitudes of $I_{DNA}$=0.54 nA and $I_{RNA}$=0.92 nA. Similar amplitudes were obtained for 10-bp DNA and 25-bp DNA, although the 10-bp molecule often stuck to the pore for >1 ms timescales because the 10-bp molecule is comparable in length to the pore dimensions.

The difference in current amplitudes between short DNA and RNA is ~40%, in good agreement with their cross-sectional area differences. The mean transport times for the RNA molecule (50 µs) was significantly longer than the DNA molecule (20 µs). This, in addition to a broader ΔI distribution for RNA may be due to drag forces on the wider helical structure of RNA, and a greater extent of interactions between RNA and the nanopore. The differences in current amplitudes between DNA and RNA persist even for events with ≤16 µs duration, for which the signal amplitude is attenuated by as much as 20% due to use of a rank 1 median filter. Using a discrimination threshold of $\Delta I_{Thres}$=675 pA, one can discern DNA from RNA with >97% certainty by considering events with ≥16 µs durations, which represent >75% of the total detected events. Analysis of events with duration of ≤16 µs shows that the signal is attenuated by the same factor for both DNA and RNA, enabling discrimination even for events with this duration range. It was also checked whether discrimination based on I is not a result of the faster mean transport times for DNA by comparing events for DNA and RNA with similar durations, in which <10% overlap in the two ΔI distributions is seen.

The pores could also distinguish linear nucleic acids from more complex structures. For example, transfer-RNA (tRNA) is structurally more complex than duplex RNA and DNA due to the presence of unpaired bases and loops, which give rise to a bent structure (see in FIG. 60*a* the structure of phenylalanine tRNA from PDB file 4TNA). The traces in FIG. 60*a* shows events with amplitudes of 1.8 nA for the tRNA, a factor of 2 greater than for the 22-bp RNA molecule (0.92 nA). The mean transport time of the tRNA molecule is 1.04 ms, much longer than that of the linear nucleic acids (see expanded events in FIG. 60*a*). These differences in signals between the three molecules show that one can discriminate among populations of different nucleic acids with certainty.

The disclosed devices and methods are, as described elsewhere herein, considered especially suitable for detection and/or quantification of miRNA. The devices may be used to detect miRNA that has a length of from 1 to about 10 base pairs, or from 1 to about 20 base pairs, or from 1 to about 50 base pairs, or even from 1 to about 100 base pairs. miRNA molecules may be 22 base pairs in length, which size is well within the capabilities of the disclosed devices and methods to detect or otherwise analyze.

FIG. 60*b* shows mean capture rates vs. voltage for 25-bp DNA and 22-bp RNA (see FIG. 69 and associated text). The mean capture rates are exponentially dependent on voltage in the range of 300-600 mV (curves are exponential fits to the data), suggesting that nucleic acid capture is a voltage-activated process. Based on the ratio of the observed event rate and the calculated arrival rate of molecules to the pore at 600 mV, one can estimate that >50% of the molecules that arrive at the pore are captured and detected.

The concentration of a sample can be measured from the frequency of molecular signals, provided that a calibration curve of capture rate vs. concentration is constructed. In FIG. 60*c*, a log-log plot of the mean capture rate vs. concentration of 25-bp DNA is shown (see FIG. 70 and associated text). The power-law fit to the data (line between data points) yields an exponent of 1.05±0.03, indicating linearity over three orders of magnitude in concentration. This dynamic range can be extended by orders of magnitude by increasing the measurement time and applied voltage, or by adjusting the electrostatic potential at the pore entrance.

Electronic Platform for Detection of Specific microRNAs

Electronic detection of small RNAs using a solid-state device may provide an alternative to existing methods for rapid and sensitive miRNA analysis. Microarray-based miRNA profiling, fluorescence, radioactive gel electrophoresis, and other novel techniques can detect sub-femtomole RNA levels, but none of these offer the unique aspects of nanopore detection, such as electronic sensing, single-molecule sensitivity, reusability, use of an unlabeled probe, and avoidance of surface immobilization. To detect a specific miRNA with a nanopore, a sequence-specific enrichment step of a particular miRNA may be useful (but not required), as miRNAs are <1% in concentration relative to other cellular RNAs.

To enrich a specific RNA, the p19 protein from the Carnation Italian ringspot virus was used. P19 binds 21-23 bp dsRNA in a size dependent, sequence independent manner. The p19 protein does not bind ssRNA, tRNA or rRNA.

To enhance isolation of the bound dsRNA C-terminal fusion of p19 with the chitin binding domain (CBD) was created, allowing linkage of the p19 fusion protein to chitin magnetic beads. The magnetic beads simplify the washing steps required to remove unbound RNA. Using p19 beads have achieved over 100,000-fold enrichment of the probe:miRNA duplex from total RNA. The protocol shown in FIG. 61*a* for nanopore-based miRNA detection was used. This begins with isolation of total RNA from tissue and hybridization to a miRNA-specific oligonucleotide RNA probe fully complementary to a target miRNA. In step (I), the probe-hybridized total RNA is incubated with the p19 protein immobilized on magnetic beads, followed by washing to remove the remaining RNA. In step (II), the purified probe:miRNA duplex is eluted from the p19 protein. In step (III), the duplex is detected using a nanopore (see FIG. 71 and associated text). A miRNA enrichment protocol may take several hours starting from isolated cellular RNA.

MiRNAs isolated with p19 may contain agents that interfere with nanopore detection of the probe:miRNA duplex. Along with the eluted duplex, other agents may be present, such as bovine serum albumin (BSA) that coats the beads, SDS used for dsRNA elution from the p19, and trace amounts of other RNAs. To eliminate the possibility of an artifact signal caused by these interfering agents, several controls were performed. The results are summarized in FIG. 61b showing 30 second current traces for different samples, all of which have been treated using p19 beads.

The first trace shown at the top of FIG. 61b is for the probe:miR122a duplex reacted with 1 μg rat liver RNA (RL). The second trace shown is for a positive control (PC), in which 30 ng of synthetic probe:miR122a duplex was bound to and eluted from p19 beads. In addition to the positive control samples, performed four negative controls NC1 to NC4 were performed, as described elsewhere herein. The traces show spikes with current amplitudes typical of dsRNA for samples PC and RL, whereas no spikes of amplitudes greater than 0.3 nA were present in the negative controls. The open pore current was stable to within 5% throughout the experiments.

To quantify the miRNA concentration, a calibration curve of capture rate vs. concentration was constructed using a synthetic probe:miR122a duplex, indicated by the open markers in FIG. 61c. For an unknown miRNA sample, one then counts ~250 current spikes that cross the threshold of $I_o$~0.4 nA (see dashed grey lines in the traces), computes the mean capture rate, and uses the calibration curve to determine the RNA concentration. The PC and RL lines in FIG. 61c show how the capture rates translate to RNA concentration for samples RL and PC, respectively. From the calibration curve, the concentration of the 20-fold diluted miR122a in sample RL is 0.7 fmol/μl, translating to an original abundance of 78±2 pg miR122a/μg liver RNA in rat liver cells, in close agreement with previous findings (58-67 pg miR122a/μg RNA). In addition, sample PC showed a concentration of 5.2 fmol/μl, indicating that the synthetic probe:miR122a duplex efficiently bound to and eluted from the p19 beads. The negative controls did not show any current spikes that cross the threshold over the measurement time (2 min each), indicating a background that is at least two orders of magnitude lower in spike frequency than sample RL (i.e., background noise <7 amol/μl).

FIG. 61d shows the relative error in measured concentration vs. the number of detected molecules. The plot was generated by computing the standard error in the mean capture rates for population subsets of sizes ranging from 100 to 4,000 events. Based on FIGS. 45c and d, one can obtain the time required to analyze a sample with a desired accuracy. For 1 fmol miRNA duplex per μl solution, the capture rate is ~1 molecule/sec, so detection of 250 molecules in ~4 minutes is sufficient to determine miRNA concentration with 93% certainty.

The foregoing demonstrates a process for fabricating uniform, robust and well-defined solid-state membranes that can be manufactured on a full Si wafer, which was used to make solid-state nanopore sensors with the thickness of lipid membranes. Reducing the nanopore thickness improves the signal amplitude from biomolecules, and the use of 3 nm pores in sub-10 nm membranes facilitates electronic discrimination among small nucleic acids. Moreover, nanopores in thin membranes are more easily hydrated than nanopores in thicker membranes, and remain stable over time. Three types of small nucleic acids with different structures were discriminated among with good signal contrast. The systematic study of thin nanopore properties allows development of an electronic detection process for counting individual small RNA molecules, which quantifies miRNA enriched from biological tissue. The inherent ability of these systems to electronically detect single molecules, combined with microfluidic-scale sample volumes (nl) exceeds the detection limits of conventional methods. The systems are capable of simultaneous detection of different molecular species in solution (peptides, miRNA, etc.) by multiplexed read-out of electronic signals from many pores.

Exemplary Methods

The substrates for device fabrication were 5×5 mm² Si chips that have a low-stress silicon nitride (SiN) film deposited on a 5-μm-thick thermally-grown $SiO_2$ layer, used to reduce the electrical noise. Electron beam lithography was used to write square patterns on the membranes, followed by developing the exposed areas and locally thinning the SiN membrane using an $SF_6$ plasma etcher. After lift-off of the resist and hot piranha cleaning, AFM was used to profile the etch depth (Enviroscope, Veeco). Epi-fluorescence was measured using an upright microscope (Nikon Eclipse 80i) with a Nikon Apo 100x 0.95 NA dry objective.

Laser excitation at 488 nm was blocked using a notch filter and detected behind a Chroma 525/50 emission filter using a cooled CCD (Princeton Instruments). Solid-state nanopores were fabricated and analyzed in a JEOL 2010FEG TEM equipped with an annular detector for ADF-STEM. The resulting geometry of nanopores fabricated in solid-state membranes is governed by an interplay between surface tension of the molten SiN and its ablation kinetics. Adjustment of the pore shape by tuning the e-beam fabrication process has been previously reported. In light of a recent report that the TEM beam size influences the nanopore shape, one can use an intense electron beam spot of 1-2 nm diameter to drill the nanopores. All nanopore experiments were carried out using 1M KCl+1 mM EDTA, Tris buffered to pH 8.

An exemplary fluoropolymer cell accommodated volumes of 1-20 μl and features temperature regulation using a thermoelectric device. The nanopore chip was installed between two buffered electrolyte solutions, each equipped with a Ag/AgCl electrode. After piranha cleaning, each chip was installed in a custom fluoropolymer cell that accommodates volumes as small as 1 μl. The fraction of pores that yield a steady ion conductance in good agreement with Eqn. 1 using $h_{eff}$=h/3 was ~100% for h<10 nm, compared to 40-60% for similarly treated pores with h=25 nm. Pores that exhibited fluctuating currents characterized by high 1/f noise and conductance <2 nS were not reported in FIG. 52d and were re-cleaned. When the electrolyte chamber was sealed using a PDMS gasket, or when the cell temperature was reduced to <10° C., the conductance of pores with different thicknesses was stable to within 5% for hours.

For translocation experiments, analyte was added to one of the chambers, and voltage was applied while monitoring current through the pore. Electrical current, measured using an Axopatch 200B amplifier, was digitized at 250 kHz and fed to a computer using custom LabVIEW collection/analysis software. For short nucleic acid analysis one digitally filters the data using a median filter with a rank of 1, in which one finds that events with duration ≥24 μs are undistorted. All DNA samples were purchased from Fermentas (NoLimits®). For the experiments in FIG. 52, 4.0±0.2 nm pores were used, ~1 nM DNA concentrations were placed in one chamber at 21±0.1° C., and 300 mV was applied to the opposite chamber. The miR122a probe was a 22 nucleotide complementary RNA to miR122a, phosphorylated at the 5' terminus (5'-AACACCAUUGUCACACUCCAUA-3'). The probe:miRNA duplex was enriched from RNA using the protocol described herein. For miRNA determination, ~1 sample was added to the negative chamber of a 3 nm nanopore in a 7 nm thick membrane, and current was recorded vs. time at 500 mV and 0° C. See FIG. 61 and associated text. In the first negative control (NC1), 1 μg of liver RNA was hybridized to a non-specific miRNA probe for miR153 (5'-CACUUUUGUGAC- UAUGCAA-3'), which is absent in liver. In the second negative control (NC2), no probe was hybridized to 1 μg of liver RNA. In the third negative control (NC3), miR122a probe was hybridized to yeast RNA, which does not contain miR122a. In the fourth negative control (NC4), single-stranded miR122a was incubated without liver RNA. In Equation 1 in the geometrical model, one neglects the low SiN surface charge density because experiments were performed at high ionic strengths (1M KCl).

Fabricating Different Thickness SiN Membranes

Sub-10 nm thick membranes were fabricated in 5×5 mm$^2$ Si chips that contained a 5-μm-thick thermal $SiO_2$ oxide underneath a 41 nm thick low-stress SiN layer, deposited by low-pressure chemical vapor deposition (Center for Nanoscale Fabrication, Cornell University). For characterization of the etch rate (see FIG. 58c) and for studying DNA transport through 60 nm thick membranes (see FIG. 52), a Si wafer that has a 100 nm thick SiN membrane was used. Prior to processing, the thickness of the SiN membrane was measured at different points on the Si wafer using a Rudolph Research AutoEL III Ellipsometer at a wavelength of 632.8 nm and an incidence angle of 70°.

From the ellipsometric parameters, one can obtain for the SiN film optical parameters of n=2.24, k=0, as well as a film thickness of 41.5±0.3 nm. Standard photolithography followed by anisotropic KOH etch was used to produce a free-standing SiN membrane with approximate dimensions ~50× 50 μm$^2$. A subsequent buffered-oxide etch step was then performed to remove the 5 μm $SiO_2$ layer from the KOH-etched side, in order to obtain freestanding SiN membranes. The SiN membrane was then spun-coated with a PMMA electron beam resist (a 2% solution of 950 kD molecular weight in chlorobenzene, MicroChem Inc.) followed by baking at 180° C. for 10 minutes. Electron beam lithography was then used to write a pattern of squares with sides ranging from 250 nm to 5 μm, using a 50 kV electron beam (Elionix 7500-ELS) and beam dose of 750 μC/cm$^2$. The irradiated device was developed in 1:3 methyl isobutyl ketone:isopropanol volume ratio for 60 seconds followed by rinsing with isopropanol and drying under a stream of compressed nitrogen gas. Thinning of the exposed SiN areas was accomplished using a Technics PEIIA plasma etcher, using a 50 W rf source and 400 mtorr $SF_6$ chamber pressures. The SiN etch rate under these conditions was 1.0±0.1 nm/s. The resist was finally removed by ~1 h incubation in warm acetone at 65° C., drying under a stream of $N_2$, and then heating at 100° C. in hot piranha solution for 10 minutes (made by mixing 1:3 of 30% $H_2O_2$ and conc. $H_2SO_4$); note that piranha is a strong oxidizer that reacts violently with most organic materials and must be handled with caution. The chips were then washed with water, dried, and stored until use.

AFM Characterization of Thinned SiN Membranes

Tapping-mode atomic force microscopy was carried out in order to characterize the process of localized membrane etching. All measurements were performed in ambient air using a Veeco EnviroScope to profile the etch depth and roughness of a given batch of processed chips. TESP Si tips (Veeco) with tip radii of <10 nm were used for all images. In FIG. 62, it is shown in panel (a) an AFM image of the pattern shown in FIG. 58c, following a 17 nm etch process (the membrane curvature has been subtracted using a polynomial in order to improve visibility of the pattern). The dashed yellow line represents the 3×3 array of 250×250 nm squares that is shown in FIG. 58c. In panel (b), three AFM images of 41 nm thick SiN windows in which a 3×3 array of 250 nm squares with a 1 μm pitch were plasma etched for 17, 33, and 40 seconds. Line profiles through a set of 3 squares can be seen below each image, showing step heights of 17±1 nm, 33±1 nm, and for the 40 nm thinning, the image shows a ~100 nm deep triangular profile that resembles the tip shape, indicating that the membrane is completely perforated. The membrane thickness h in the processed region is given by the difference between the initial membrane thickness and the etch depth, i.e., in this case, h=41 nm–etch depth. A membrane robust enough for experiments is a membrane that has been etched for 35 seconds, which yields a membrane thickness of ~6 nm. Membranes with thickness values h≤5 nm did always not survive the piranha cleaning step.

Conductance of Sub 10 nm Thick Nanopores as a Function of Time

FIG. 63 illustrates conductance as a function of time for pores with various diameters d and membrane thicknesses h, denoted as (d, h). The buffer used for all measurements was 1M KCl buffered to pH 8. Conductance values are reported in nS based on the current at 300 mV and an electrolyte temperature of 21° C.

Geometric Model for ΔI of DNA as a Function of Effective Pore Thickness

The values of ΔI upon DNA entry were calculated based on Equation 1 herein, with a modification that takes into account the displaced electrolyte current upon DNA occlusion of the pore. A hydrodynamic diameter for B-form DNA of 2.2 nm was assumed, as it was previously found to explain the observed relative conductance as a function of pore diameter d (see Ref 41 in the manuscript). The current difference between an open pore $I_o$ (see Eqn. 1 in main text) and a DNA-occluded pore $I_{DNA}$ is expressed as:

$$\Delta I = I_o - I_{DNA} = I_o - V([\mu_K + (1-S)\mu_{Cl}]n_{KCl}e)\left(\frac{4h_{\it eff}}{\pi d_{\it eff}^2} + \frac{1}{d_{\it eff}}\right)^{-1} \quad \text{Eqn. 2}$$

where the two added parameters are $d_{\it eff}$, the effective pore diameter of the DNA-occluded pore (calculated from a circle of an equivalent area that is available for KCl transport in the case of the DNA occluded pore case), and S, the fraction of excluded Cl$^-$ ions in the DNA-occluded pore. This exclusion of Cl$^-$ ions was modelled as a coefficient from 0-1 that reduces the mobility of Cl$^-$ ions (this is equivalent to a reduced Cl$^-$ concentration). The rational for chloride exclusion is based on previous results that showed an increase in ΔI with DNA length for a length >1,200 bp, which may be attributable to a decreased effective concentration of anions (e.g., Cl$^-$) near the pore during translocation, due to electrostatic repulsion by the DNA coil. The dashed line in FIG. 52d is a best fit to ΔI for a pore diameter d=4 nm as a function of the effective thickness $h_{\it eff}$, which yields values of $d_{\it eff}$=2.83 nm and S=0.2 (i.e., 20% exclusion of Cl$^-$).

Scatter Plots of ΔI Vs. Transport Time of 3 kbp DNA for Two Pore Thicknesses

FIG. 64 shows a scatter plot of the mean current amplitude of each molecule (I) and the total transport time for 3 kbp dsDNA through 4 nm pores as a function of membrane thickness (h). Thinning the membrane has two observable consequences, one is increased I, which facilitates detection of the DNA, and the second is a minor decrease in transport times. Overall, transport times were ~30% smaller when reducing h from 60 to 6 nm, going from 0.95 ms to 0.72 ms. The plot on the right of FIG. 64 shows transport time distributions for two membrane thicknesses. Mean transport times are determined by fitting the distributions to exponentially decaying distributions.

Figures 66A, 66B:
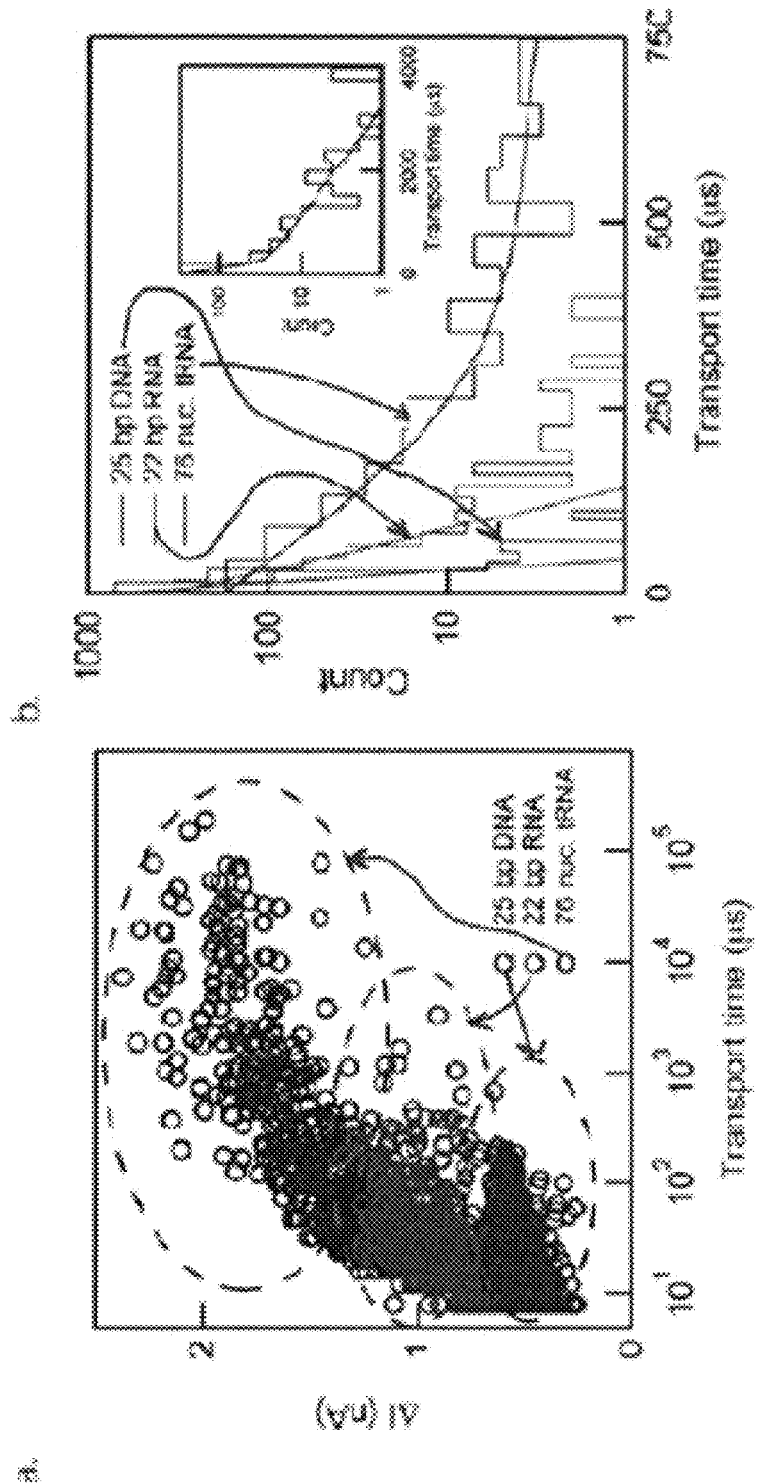
Figure 66C:
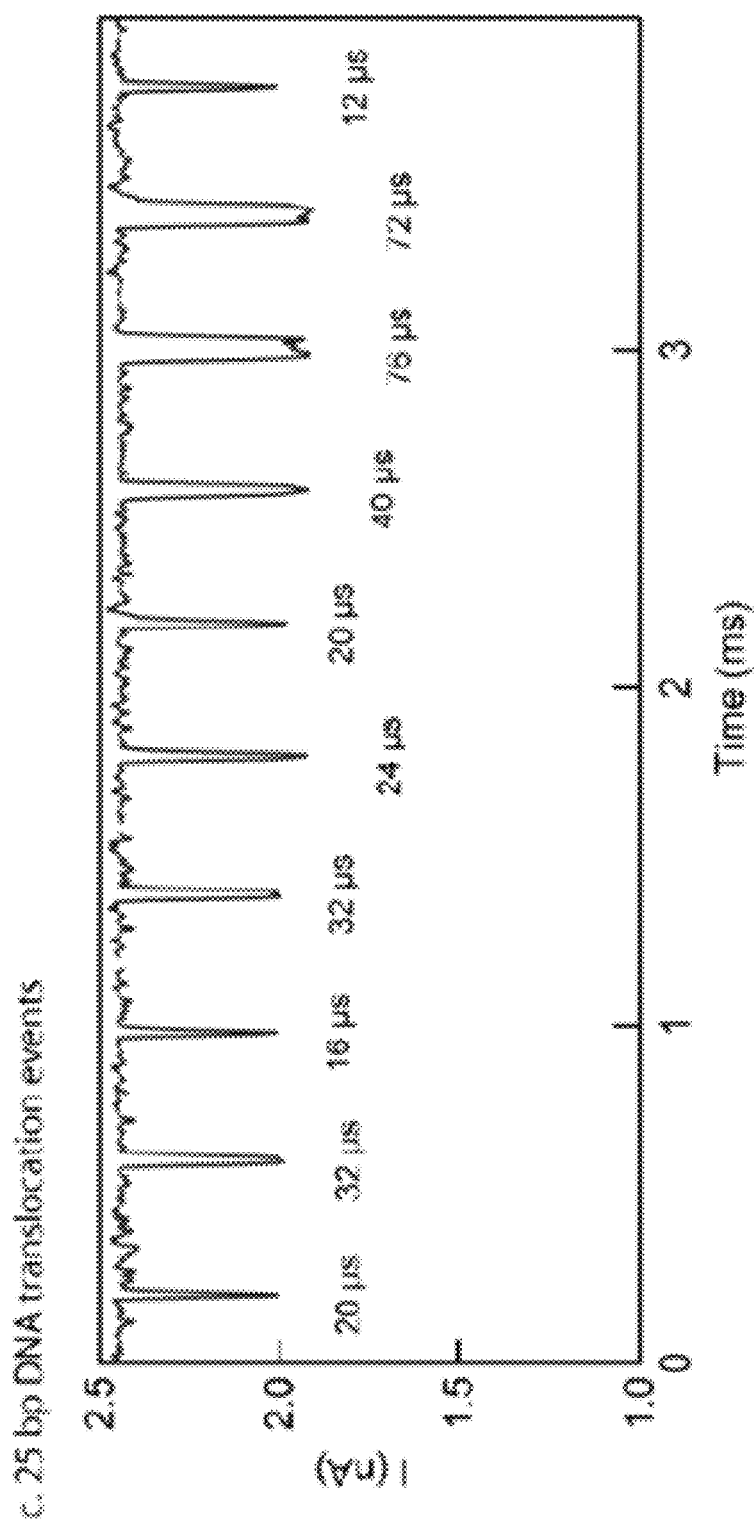

Translocations of 10 bp DNA Through a 3 nm Diameter Pore in a 7 nm Thick Membrane FIG. 65 shows a set of 10 bp translocations through a 3 nm diameter pore in a 7 nm thick membrane under 500 mV applied voltage, at a temperature of 0° C. The events were concatenated by pasting together current spikes that include 2 ms current data before and after each spike. In contrast to events with the 25 bp DNA fragment, one observes many deep and long events for the 10 bp sample, which was observed for many different 3 nm diameter pores. This may be attributed to sideways jamming of the molecule at the pore entrance, which would cause the DNA to stall for a relatively long time (milliseconds). The contour length of the 10 bp DNA is 3.5 nm, slightly higher than the pore diameter. An all-point histogram is shown to the right of the concatenated trace. The difference in amplitude between the first blockade peak and the open pore peak is 0.6 nA, similar to that of the 25 bp DNA sample (see FIG. 60). The second peak (1.1 nA) may be due to entry of two molecules simultaneously or sideways entry of the molecule into the pore. The traces for 25 bp DNA and the 22 bp RNA samples in FIG. 60*a* show that such frequent blocking of the pore does not occur in double-stranded nucleic acids with contour lengths of at least 7 nm. Discrimination Among 25 bp DNA, 22 bp RNA, and 76-Nucleotide tRNA FIG. 66 provides more detail about using a 3 nm diameter pore in a 7 nm thick membrane to discriminate among small nucleic acids of similar size, namely, 25 bp DNA (molecular weight=15 kD), 22 bp RNA (molecular weight=15 kD), and 76-nucleotide tRNA (molecular weight=25 kD). FIG. 66*a* illustrates scatter plots of current amplitude (I) vs. transport time for the three molecules under the same measurement conditions (0° C., 500 mV, 3 nm diameter pore in a 7 nm thick SiN membrane). The dashed ovals represent regions containing >85% of detectable events for each molecule type. FIG. 66*b* illustrates transport-time distributions for >1,000 events of each molecule type. For the 25 bp DNA and 22 bp RNA, >90% of the data fits a single exponential decay, with timescales of 20 µs and 50 µs, respectively.

Figure 66D:
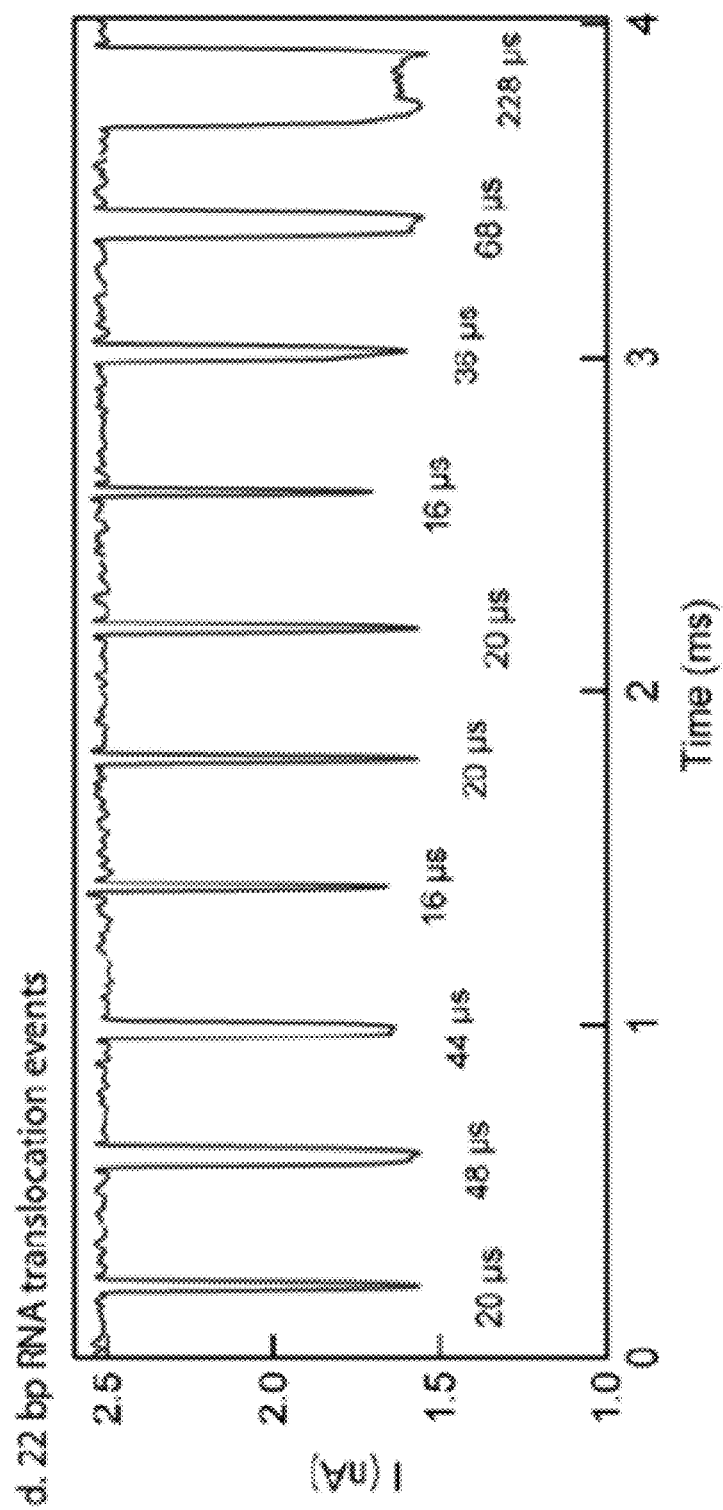

For tRNA, the data fits a two-exponential function, with timescales 80 µs and 1.04 ms (see inset of panel b for expanded view of the transport-time histogram for tRNA). While the short timescale may be due to collisions and fast translocations of the bulky tRNA molecule, the long timescale, in which the majority of events fall in, suggests that the tRNA must deform from its bent equilibrium structure in order to traverse the 3 nm diameter pore, a process that may stall transport, leading to longer dwell times and a broader dwell time distribution. Representative concatenated translocation events (FIG. 66*c*) in the dwell time range of 12-228 µs for 25 bp DNA (c) and 22 bp RNA. In FIG. 66*d*, events for the tRNA molecule are not shown here, because their duration is clearly longer, as seen in FIG. 60*a*. The corresponding transport times are noted below each event. These traces are shown in order to illustrate that the current amplitude for 25 bp DNA and 22 bp RNA are distinctly different, easily seen for events with duration longer than 30 µs. These results suggest that the different amplitude spikes are a result of the different molecular properties between the three nucleic acids, rather than an artifact of fast dwell times close to the detection limit that would distort the current amplitudes.

A more quantitative analysis of the nanopore's ability to discriminate 25-bp DNA from 22-bp RNA based on current amplitudes is shown in FIG. 67. First, in order to test the response of the system to short pulses, a simulation was performed of ideal square current pulses with different durations and current amplitudes in the range 8-48 micro-s. The simulated events indicate that all events with durations <20 micro-s are attenuated in terms of their amplitudes. For example, for pulse widths of 8 micro-s, the mean attenuation factor is 20%. That is, events with 500 pA and 750 pA amplitudes are detected as 400 pA and 600 pA amplitudes, respectively.

Next, is shown the effect of a rank 1 median filter on the real DNA and RNA data collected for the scatter plots shown in FIG. 66. Shown in the figure are ΔI distributions of for all the events in the scatter plots for 25-bp DNA and 22-bp RNA. In this series of histograms, one takes subsets of the dataset that contain events with duration equal to or longer than the indicated value in each plot.

Also indicated in the plots are % certainty values for the discrimination between DNA and RNA, calculated from the fraction of RNA events that lie above the $I_{Thres}$=675 pA threshold (shown as dashed line). The threshold was chosen because <0.1% DNA events were found with larger ΔI values. For example, including only events ≥8 s results in a certainty of 83.3%, because 16.7% of the RNA events have amplitudes that are lower than $I_{Thres}$. In other words, looking at all of the data in the range ≥8 s, one finds that 16.7% of the RNA molecules and mixed with the DNA population, and therefore cannot be distinguished from DNA events. Now, when one looks to data ≥12 microseconds, one finds that 91.3% of the RNA events lie above the threshold, resulting in only 8.7% error in discrimination. This certainty in discrimination improves to >97% when only events ≥16 µs are included. One notes that events with durations ≥16 µs constitute 75% and 73% of the total detected events for DNA and RNA, respectively. Finally, one notes that differences in duration between DNA and RNA cannot explain the differences in current amplitudes, because events longer than 36 µs, which represent about one half of the datapoints, have a clear plateau at the mean current amplitude value, unequivocally showing that DNA and RNA provide distinguishable current amplitude levels.

The bandwidth-limited data acquisition results in asymmetric shapes for the current amplitude distributions, which exhibit "bellies" or "shoulders" at 0.4 nA and 0.6 nA for DNA (left arrow) and RNA (right arrow), respectively. These "bellies", which deviate from Gaussian shapes (see curves), disappear completely for events with durations of ≥16 µs, and the distribution shapes are Gaussian thereafter. Asymmetry may be a result of attenuation by filter.

However, despite the signal attenuation, one still can discriminate among short DNA and RNA, provided that one chooses a suitable threshold amplitude for discrimination that considers the event duration. To illustrate this, shown are ΔI histograms for DNA and RNA events where in each plot are analyzed slices of the data that select all events with an indicated duration, in the range of 8-36 micro-s. In each plot are drawn dashed lines for $\Delta I_{Thres}$=675 pA as a guide to the eye. In FIG. 68, below all the distributions are shown mean ΔI values as a function of event duration (the error bars show one standard deviation in each direction). As seen in these plots, the current amplitude signals for both RNA and DNA are distorted towards lower ΔI values for events in the range 8-16 micro-s, after which there is no apparent shift in the position of the distributions. The magnitude of this distortion for short events is up to 150 pA for the 8 micro-s events (or 22% of the ΔI value), in good agreement with the simulated data. The attenuation factor appears robust as a function of event duration, and therefore one can compensate for attenuated data by adapting the threshold (see lower arched, dashed line in FIG. 68 that connects up to straight dashed line at duration=22 microseconds), in order discriminate DNA from RNA in this regime with >90% confidence.

Continuous Traces for 25 bp DNA Through a 3 nm Pore for Different Voltages

FIG. 69 shows 2-second current traces under different applied voltages of a 25 bp DNA sample analyzed using a 3 nm diameter pore fabricated in a 7 nm thick membrane (data taken at a temperature of 0° C.). Pores are not, of course, limited to 3 nm diameters, as pores can have diameters of 1 nm, 5 nm, 10 nm, 25 nm, 50 nm, 100 nm, and of intermediate values therebetween. The analyte chamber contains 25 bp DNA at a concentration of 81 fmol/μl, and positive voltage is applied to the second chamber in order to drive DNA to the other side. The inset trace in each plot is a zoomed-in 7 ms view, with the same current amplitude scale as the y-axis. On the right-hand side of the figure, all-point current histograms are shown for each trace. Increasing the voltage greatly increases the capture rate, as seen by the increasing amount of deep events. The shallow events for the low voltage traces are presumably collisions of the DNA with the pore. The fraction of these collisions decreases with increasing voltages, in line with a voltage-activated barrier for threading.

Continuous Time Traces for 25 bp DNA at Different Concentrations

FIG. 70 shows current vs. time traces for a 3 nm diameter pore at a measured at a voltage of 500 mV and a temperature of 0° C., when different concentrations of DNA were added to the pore (expressed as fmol/μl solution). While the open pore current remains similar for different concentrations of DNA (~2.5 nA), the number of spikes increases as a function of the concentration. The rate of events shown in FIG. 52d were derived from the time-delay distributions (t) between two successive events (see plot below the traces), which fits a first arrival time distribution function $P_{capture}=A\exp(-Rate*t)$, where the slope of the exponent (i.e., Rate) is the mean capture rate in $s^{-1}$.

Details of p19-Based miRNA Enrichment from Cellular RNA Extracts

The p19 protein binds tightly to double-stranded RNA that is 19 to 22 basepairs in length. There is no binding to single stranded RNA. This tight, selective binding of p19 to dsRNAs allows the enrichment from cellular RNA of probe-hybridized miRNAs that have a very low abundance. For example, miR153, a miRNA with very low abundance compared to other miRNAs, has been enriched by over 100,000-fold from cellular RNA.

The protocol of miRNA enrichment proceeds as follows: A synthetic 22 nucleotide RNA oligo probe of sequence 5'-AA-CACCAUUGUCACAC-UCCAUA-3' (Integrated DNA technologies, Inc.) complementary to miR122a was first phosphorylated at the 5' end using T4 polynucleotide kinase (New England Biolabs, Ipswich, Mass.). The miR122a-specific probe was then added to PCR tubes containing the different RNA samples (rat liver RNA, positive control, and the four negative controls) in 1× p19 binding buffer (20 mM Tris-HCl, pH 7.0, 1 mM EDTA, 1 mM tris(2-carboxyethyl) phosphine, 100 mM NaCl, 0.02% Tween-20) in a total volume of 10 Hybridizations were carried out in a thermal cycler programmed to 75° C. for 5 min, followed by 52° C. for 5 hours. Each 10 μl of hybridization reaction was incubated with 10 μl of p19 beads suspended in 1× p19 binding buffer, 10 units of murine RNase inhibitor (NEB), and 1 mg of BSA in a total volume of 20 μl. The binding reaction was incubated by shaking for 1-2 h at RT in an Orbis shaker (MarketLab, Calcdonia, Mich., USA). Using a magnetic rock (NEB), the unbound RNA was removed by washing 6 times in 600 μl of 1× p19 wash buffer (20 mM Tris-HCl, pH 7.0, 1 mM EDTA, 100 mM NaCl). For each wash, the beads were shaken for 5 min. at 37° C. on a heated shaker. After the third wash, the washing temperature was increased to 42° C. to remove all of the non-specific unbound RNA. The probe:miR122a duplex was eluted from the p19 beads into 20 μl of 1× p19 elution buffer (20 mM Tris-HCl adjusted to pH 7.0, 100 mM NaCl, 1 mM EDTA and 0.5% SDS) by shaking for 20 min at 37° C. SDS was removed by adding 16 μl of 4 M KCl to the 160 μl eluate and cooling to 4° C. After centrifugation for 15 min. at 14,000 rpm in a microfuge, the solution was carefully decanted to a new tube to remove the white SDS pellet. The isolated miRNA were diluted into KCl solutions such that the total KCl concentration was 1M, and the solution was added to a 3 nm diameter nanopore in a 7 nm thick membrane for detection, which was carried out for all samples at 0° C. and 500 mV.

The sequence of experiments that led to the data for FIG. 61 is as follows: A calibration curve for different 22 bp duplex RNA concentrations was first performed using the synthetic probe:miR122a duplex, after which the negative controls NC1-NC4 were tested, and finally, samples RL and PC were tested. Between each sample, the chamber was rinsed 10 times by removing the chamber contents, adding 20 μl of fresh buffer, mixing the chamber contents using a pipette, and repeating the process. After each cleaning procedure, a 20 second trace was collected to verify that the baseline current was within 5% of the open pore current value, and that no detectable events are present. During data acquisition for the negative controls, evidence that the nanopore is active comes from the fact that occasionally shallow events occurred (<0.3 nA), which may be tied to trace amounts of single-stranded RNA (e.g., the hybridization probe) present in the p19-treated samples.

Continuous Time Traces of Different Concentrations of 22 bp RNA

FIG. 71 shows continuous time traces for a 3 nm diameter pore measured at a voltage of 500 mV and a temperature of 0° C., when different concentrations of RNA were added to the pore (expressed as fmol/μl solution). The calibration curve in FIG. 61c was constructed by calculating for each trace the mean capture rate as a function of the RNA concentration.

Response of System to Artificial Short Current Pulses

In order to test the system's response to very fast translocation events, the response of the amplifier tested to synthetic current pulses in the range 8-48 s was tested. The scheme for generating these pulses is shown in FIG. 72: A 2 MHz square wave generator with asymmetric pulse capabilities (TENMA Jupiter 2010) was fed into the compensated RC circuitry shown in FIG. 72. The circuitry converts the voltage signal of the generator into a current pulse train with specified durations and amplitudes, adjusted manually by reading the function generator's output using an oscilloscope. Next, were generated current pulses of durations in the range 8-48 microseconds, fed the signal into the amplifier's headstage, then digitized the output at a sampling rate of 250 kHz using a DAQ card and median filtered the data using a rank of 1. Combined with the 100 kHz bandwidth of the Axopatch 200B patch clamp amplifier, which is set by its internal 4-pole Bessel filter, a rank 1 median filter behaves as a low-pass filter with a corner frequency of $f_c=37.8$ Khz at 250 kHz sampling rate. The roll-off of this median filter is shallower than commercial low-pass filters.

Representative traces are shown for pulses of the indicated durations and two amplitudes, delta I=500 pA (left column of plots) and 750 pA (right column of plots), which model events from the short DNA and RNA molecules, respectively. A plot of the mean delta I values vs. pulse duration shows that events of duration ≤20 microseconds are attenuated. However, the attenuation factor is similar for the 500 pA and the 750 pA pulses: for the 8 microsecond pulses that are detected as a single sample point, the peak amplitude was attenuated by 14% for both pulse amplitudes.

Exemplary Embodiments

One exemplary embodiment of the disclosed devices is shown in FIG. 73. The device will be described here illustrating its use in detecting miRNA, but the device may be used for detecting other analytes, such as DNA and RNA.

In some embodiments, the devices may include a Si-chip. Such chips may have an area of only a few mm². For example, one may use a 5×5 mm² device, with a transparent SiN window that is 100×100 μm². The devices may integrate the disclosed nanopore/electrode devices with fluidics such that analyte isolation (e.g., p19-based miRNA isolation) can be performed in real time.

In some embodiments (illustrated by FIG. 61a), the device accepts an input sample (such as cell contents, including cellular RNA), hybridizes the sample to a probe (e.g., a miRNA probe), immobilizes the probe:analyte duplex (e.g., onto protein p19). The user may then wash, elute, and detect the analyte (miRNA) concentration. These devices thus enable multiplexed delivery and detection of miRNAs using a series of nanopores equipped with electrodes.

The signals (such as changes in electrical current) may be read using independent electrodes that are disposed proximal to each nanopore. The devices are suitably constructed such that nanopores are individually monitored or addressed by electrodes. In this way, the user may assign different analytes to different nanopores, enabling simultaneous, parallel analysis of multiple analytes.

By analyzing the current signal as a function of time, the concentration of each miRNA in each channel is quantified, which may be achieved by comparing the signal (or passage events per time) to a calibration curve. Exemplary electrodes are described in United States Published Applications US 2010/0142259 ("Nanogaps: Methods and Devices Containing Same") and US 2010/0009134 ("Beam Ablation Lithography"), the entireties of which are incorporated herein by reference.

In the exemplary embodiment shown in FIG. 73, a device includes an input chamber. The user may introduce sample material (e.g., the contents of a lysed cell or cells) into this input chamber. The chamber may itself be a lysis chamber, configured to apply or receive lysis reagents, heat, sonication, pressure, and the like to a cell or other sample placed within the chamber. Lysing techniques and reagents are known in the art, and suitable lysing techniques will be known to the user of ordinary skill in the art. The lysing may be accomplished, for example, on a porous membrane under pressure. Alternatively, lysing may be accomplished chemically. In some embodiments, cell contents may be introduced directly into the chamber.

The input chamber may be configured or disposed such that it is in fluid communication with one or more nanopores according to the claimed invention. The fluid communication may be accomplished by having tubes, conduits, channels, or other pathways between the input chamber and the nanopores. The input chamber may have multiple outlets, where each outlet is connected to one or more channels. Alternatively, the input chamber may include or be connected to a manifold, which manifold in turn distributes sample material to the channels. The manifold may be constructed so as to admit material into only a single channel or into multiple channels. The devices suitably include a device that applies a gradient (e.g., fluid pressure, voltage, magnetic) to transport sample or analyte from one location in the device to another.

The exemplary embodiment of FIG. 73 illustrates channels connecting the chamber to the nanopores. The chamber may suitably have an internal volume of 0.1-100 ml, or 1-10 ml, or even about 5 ml, depending on the needs of the user; although larger and smaller volumes are also suitable. The chambers are suitably constructed from polymers, silicon, and from other materials known and used in the fluidics field.

The devices may be constructed such that the capture material, nanopores, channels, or all of the foregoing, are disposed on a chip or other device that is then connected to a sample source or input chamber. In other embodiments, the chamber, nanopores, channels, electrodes and capture materials are all disposed on a single, integrated device, as shown in FIG. 73. The components may be configured as part of a system, where a base or other unit accepts chips having sample containers, capture materials, nanopores, and electrodes in a snap-in or slide-in configuration. The base may include electrode that contact electrical contacts in the chips so as to apply a gradient or to address individual pores. The system may also include pumps, syringes, and/or other means that deliver fluids and samples to the input chambers, channels, pores, or other components.

The devices may be constructed such that each channel has a length of from 0.1 mm to 1 cm or even 10 cm or more. Channels may have internal cross-sectional dimensions of from 0.1 mm to 1 cm, or 1 mm to 100 mm, or even about 5 mm to 10 mm. The channels may be made from a polymer, silicon, an oxide, or other materials used in the fluidics field and known to those of skill in the art.

In some embodiments, one or more channels may include a material that binds to a particular analyte or analytes. For example, in the case of miRNA, the capture material may be p19 (e.g., New England Biolabs, www.neb.com) protein or other material that binds specifically to miRNA. While the p19 protein is considered especially suitable, other proteins that resemble p19 in structure or in function are suitable, as well as mutants derived from the native viral sequence. The material may be cellulose, a Drosha-DGCR8 complex, the PAZ domain on the *C. elegans* genome, and the like. The capture material may be present on a bead, porous support, or other structure, as shown in FIG. 61. Beads are considered especially suitable, but are not necessary to the disclosed devices.

In this way, the user may transport cell contents to the capture materials so as to isolate an analyte (e.g., miRNA), if present, in the sample. Once the target binds to the capture material, the user may flush the channel (and capture material) to remove any unwanted materials.

In certain embodiments, the user may apply an analyte-specific probe to the analyte. Suitable probes include multi-nucleotide probes or even proteins; probes that specifically bind to the analyte of interest are considered especially suitable. The probe may be labeled with a fluorophore or phosphor. A probe may also be labeled magnetically or radioactively. In some embodiments, the analyte (e.g., miRNA) and probe are mixed together, and the capture material binds to the analyte-probe duplexes. In other case, a capture material—such as a bead or a porous support—has bound to it probes that are specific to a particular analyte. For example, a bead (or other support, such as a monolith or a strip) may be decorated with probes that are complementary to a nucleotide sequence on miRNA1. The sample is contacted to the bead, and miRNA1 in the sample—if present—binds to the probes on the bead. Excess sample may be washed away, and the bound miRNA1 may be eluted (in duplex miRNA1:probe form or as miRNA1 alone) and detected at a nanopore. The capture material may also be a microarray, which micro array includes spots or regions that bind specifically to only a particular analyte. For example, such a region on a microarray might include oligonucleotides or even proteins that are specifically complementary to an analyte of interest. Once the analyte binds and excess sample is washed away, the bound analyte is suitably eluted and then detected by a nanopore.

In this way, a device may detect multiple analytes, and may even do so in real time. In one embodiment, the sample chamber is in fluid communication with a first capture material (binding specifically to miRNA1) and a second capture material (binding specifically to miRNA2). Each of these capture materials may be disposed within its own channel, which channel is in turn in fluid communication with its own nanopore. The sample is contacted to the first and second capture materials, which materials bind specifically (respectively) to miRNA1 and miRNA2, if present. The user may then wash away excess sample. The bound miRNA1 and miRNA2 are then eluted into the channels associated with the respective capture materials and are detected by the nanopores associated with those channels, where the user detects the concentration (e.g., in the form of miRNA passages through the nanopore per unit time) of each miRNA.

The probe is suitably designed or selected so as to be complementary to only a particular target. By applying multiple probes to multiple capture materials, the user can simultaneously label multiple analytes. For example, capture material is disposed in channels 1 and 2 of a given device. The user then contacts the bound miRNA in channel 1 with a probe that is complementary only to miRNA1, and contacts the bound miRNA in channel 2 with a probe that is complementary only to miRNA2.

The user elutes any bound miRNA from the capture material (e.g., by application of heat, solvent, reagent, and the like), and the eluted miRNA then travels down the channels to a nanopore or nanopores. Once the eluted miRNA arrives at the nanopores, electrodes monitor the number of miRNA probe-target duplex passage events through the nanopore. In embodiments where the analyte is labeled with a fluorescent, magnetic, or radioactive probe, the nanopores may be used to count the number of visual, magnetic, or radioactive passage events per unit time. The number of passage events may be correlated to the concentration of the analyte; this may be done with the assistance of a calibration curve, as shown in FIG. 61c.

Target material of interest may be bound to a probe for enrichment, or may be in its natural form (i.e., not bound to a probe). The probe may be selected such that the probe binds specifically to the analyte of interest. The probe may also bind to the capture material; in this way, only analyte bound to a probe binds to the capture material, and unbound analyte may be washed away. In some embodiments, the probe is not labeled, and gives rise to a sample:probe duplex than is then isolated and detected by passage through a nanopore. (Nanopores are suitably configured according to any of the nanopore devices and membranes described herein.)

Each channel in a device may be separately addressable; the nanopores are also suitably individually addressable. For example, the first channel in a device may be used to detect the concentration of miRNA1. This may be accomplished by eluting into the nanopore only analyte material that has been exposed to a probe complementary to miRNA1. If duplexes between that material and the probe are present, the user will observe passage events of the duplexes through the nanopore. If no such duplexes are present—e.g., because miRNA1 was not present in the cell sample and the miRNA1 probe consequently had nothing to bind to and was washed away—then the user will observe little to no passage events at the nanopore. The user may create a multiplexed device—as shown in FIG. 73—that includes multiple channels for application of multiple probes, which in turn allows for detection of multiple analytes. A device may be constructed having two, three, or more channels dedicated to a single analyte (e.g., three channels configured to detect miRNA1) so as to perform multiple, simultaneous detections for a single analyte.

The devices may include nanopores and membranes according to any of embodiment disclosed in this application. For example, the devices may include a first capture material that binds specifically to a first molecule; a first membrane having a thickness in the range of from about 5 nm to about 100 nm; and a second membrane disposed adjacent the first membrane, the second membrane having a thickness in the range of sub-nm thickness up to about 20 nm (and all values therebetween), with the second membrane having at least one pore extending therethrough, the pore having a cross-sectional dimension in the range of from about 1 nm to about 100 nm, and the first membrane having a cavity formed thereon, the cavity being in register with at least one pore of the second membrane, the first pore being in fluid communication with the first capture material; a device configured to apply a gradient across the pore; and a detector configured to detect a signal related to passage of a molecule through the first pore.

In another embodiment, the device includes a first capture material configured to bind preferentially to a first molecule; a membrane having a thickness in the range of from about 20 nm to about 100 nm, and the membrane having a thinned region, the thinned region having a thickness in the range of from about 0.1 nm to about 20 nm, and a first pore extending through the thinned region, the first pore being in fluid communication with the capture material; and a detector configured to detect a signal related to passage of the first molecule through the first pore.

While the foregoing examples pertain to miRNAs, the described devices and methods may be used to detect analytes other than miRNA. For example, the devices may be used to detect DNA, RNA, tRNA, mRNA, and the like.

Also provided herein are methods of obtaining sequence or structure information. In these methods, the user may translocate an analyte through a nanopore (described elsewhere herein), and detect a signal related to the structure of the analyte. The signal may be an electrical signal, an optical signal, a magnetic signal, and the like. The signal is suitably related to a structural feature of the analyte. For example, a user may contact a DNA molecule with a labeled probe that bind only to a specific sequence of nucleic acids, e.g., ATTCG. The user may then translocate the sample through a nanopore and detect—if present—a signal (e.g., an optical signal from a fluorescent probe) related to passage of the labeled probe through the nanopore. The signal may, as described elsewhere herein, be correlated to the concentration of the target analyte.

The presence of the signal will indicate that the sequence to which the probe is complementary is present on the analyte. The user may perform sequencing by contacting segments of a target analyte (e.g., segments that are generated by restriction enzyme or enzymes) with labeled, sequence specific probes, and then detecting the presence—or absence—of signals when the segments are translocated through the nanopore.

Alternatively, the user may apply restriction enzymes with known binding sequences to an analyte and detect the presence—or absence—of segments cleaved from the analyte by the restriction enzyme. In this way, if a segment is detected, the user will know that the analyte from which that segment was removed included the sequence of nucleic acids to which the restriction enzyme bound.

This description and attached figures are illustrative only, and do not limit the scope of the present disclosure or claims. Variations on the foregoing description are also within the scope of the present disclosure. Any documents cited herein are incorporated by reference in their entireties for any and all purposes.

DISCRIMINATION BETWEEN DNA BASES

Here, it is shown that solid-state nanopores (such as those nanopores described elsewhere herein) are uniquely capable of detecting modified cytosines and that these changes are a result of altered DNA mechanical properties. Molecular dynamics (MD) simulations, previously used to describe the physics of DNA translocation through a nanopore, and used to understand the mechanisms that alter the physical properties of the modified DNA.

In one aspect, the present disclosure presents methods. These methods suitably include applying a voltage gradient across a nanopore such that at least a portion of an oligonucleotide from a first sample translocates through the nanopore; collecting a first signal related to the translocation of the at least a portion of an oligonucleotide through the nanopore; and correlating the at least one signal to the presence of a structural characteristic of the oligonucleotide. The first signal may be a current amplitude related to the passage of the at least a portion of an oligonucleotide through the nanopore. The first signal may also be a duration signal that corresponds to the duration of the passage of a portion of an oligonucleotide (e.g., a base) through the nanopore. The user may also collect a second signal related to the translocation of the at least a portion of the oligonucleotide through the nanopore. Such a second signal may be a duration of a translocation event, which event may be the passage of a nucleotide through the nanopore.

As explained elsewhere herein, structural characteristics may include, for example, the presence of a methyl group, a hydroxylmethyl group, or both on the oligonucleotide. An oligonucleotide may comprise a methyl-modified cytosine base, a hydroxymethyl-modified cytosine base, or both. The structural characteristic of the oligonucleotide may also be a methyl-modified adenosine base.

In some embodiments, the user may also collect a second signal related to the translocation of the at least a portion of a second oligonucleotide through a nanopore; correlate the second signal to a structural characteristic of the second oligonucleotide; and correlate a difference between the first and second signals to a structural difference between the first and second oligonucleotides. For example, the user may correlate a difference in current amplitudes related to the passages of the first and second nucleotides to the presence (or absence) of methylated cytosines or hydroxymethylated cytosines on one or both of the oligonucleotides.

The present disclosure provides additional analysis methods. These methods suitably include translocating a population of oligonucleotides through a nanopore having a cross-sectional dimension in the range of from about 1 nm to about 1000 nm formed in a membrane having a thickness in the range of from about 20 nm to about 1000 nm, collecting a plurality of signals related to the translocation of the population of oligonucleotides through the nanopore; and correlating the plurality of signals to the presence of methylated bases, hydroxymethylated bases, or both, present in the population of oligonucleotides.

Nanopore devices suitable for the disclosed methods are described in detail elsewhere herein; solid-state nanopores are considered especially suitable. The nanopores described in patent application PCT/US2011/025434 (filed on Feb. 19, 2011 and incorporated herein by reference in its entirety) are considered especially suitable. A signal may be a signal that corresponds to the duration of the translocation of a base of an oligonucleotide through the nanopore. A signal may also be a current associated with the translocation of a base of an oligonucleotide through a nanopore, or even a voltage associated with translocation of a base of an oligonucleotide through a nanopore, or any combination thereof.

The user may suitably correlate the plurality of signals to the presence or even the level of methylated bases, hydroxymethylated bases, or both, present in the population of oligonucleotides. A user may also correlate the plurality of signals to the proportion of methylated bases, hydroxymethylated bases, or both, present in the population of oligonucleotides. In this way, a user may determine whether a sample contains methylated or hydroxymethylated bases (or both) and may also determine the proportion of the foregoing within the sample.

Translocation of the oligonucleotides is suitably effected by application of a voltage across the nanopore. The nanopore may be disposed so as to place two reservoir into fluid communication with one another. An electrolyte fluid may be used in such an embodiment, with the oligonucleotide being disposed within the electrolyte.

Results

FIG. 81$a$ shows a thin silicon nitride membrane separating two electrolyte chambers, with a nanopore being the only junction between the two chambers. Application of voltage $\Delta V$ across the membrane drives ions through the pore, resulting in a steady-state ion current that is measured using a low-noise current amplifier. When biomolecules pass through the pore, the magnitude of residual ion current is used to report on the structure of the biomolecule. FIG. 81$b$ shows continuous time traces of the current through a 4 nm diameter pore in a 20 nm thick membrane before and after the addition of 3 kbp doublestranded DNA to the chamber with the negative electrode. Addition of DNA results in a sequence of current blockade spikes, each corresponding to the transport of a single DNA molecule. The magnitude of each spike is related to the excluded volume of biopolymer that occupies the pore. One may define here two quantities (see FIG. 81$b$): $\Delta I$ corresponds to the mean current amplitude of an event, and tT corresponds to the transport time, or total duration of the event. The all-point current histogram in FIG. 81$b$ shows that DNA occlusion of the pore produces characteristic current amplitude. Characterization of a sample is performed by statistical analysis of the two parameters $\Delta I$ and tT.

Differentiation of Cytosine and 5-Methylcytosine from 5-Hydroxymethylcytosine.

One may show that nanopores can discriminate among identical DNA sequences with different cytosine modifications. Toward this goal, PCR conditions that utilize Phusion DNA polymerase (Finnzymes/NEB) were optimized to yield approximately equal incorporation of native and modified cytosine nucleotides into the replicated strands. Using these conditions, DNA fragments were prepared that exclusively contain cytosine, 5-methylcytosine, or 5-hydroxymethylcytosine, hereafter called C-DNA, mC-DNA, or hmC-DNA, respectively. Sequencing the amplified DNA fragments verified that no specific mutations were introduced during PCR amplification.

Ion current traces for a 3 kbp fragment with different cytosine modifications reveal larger ΔI and tT values for hmC-DNA than for C-DNA or mC-DNA (FIG. 81c). This result may be considered striking, given the small chemical differences between the different cytosines. We consistently observed similar results for at least 10 pores of diameters in the range 4.0 (0.3 nm, as well as for a set of 400 bp DNA fragments (see FIG. 88). These results were also reproduced by measurements of mC-DNA and hmC-DNA in a blind experiment using an alternative nanopore measurement setup.

To explore the mechanism that accounts for deeper blockade amplitudes for hmC-DNA, the dependence of ΔI on bath temperature was studied (see FIG. 82). To generate the plots, one may fit the ΔI distributions to Gaussian functions in order to find the most-likely current amplitudes, $\Delta I_{max}$. Full ΔI distributions for all three DNA molecules at 10 and 21° C. are shown in the inset to the plot. One finds find that $\Delta I_{max}$ values for mC-DNA and C-DNA are similar at all temperatures. For clarity, one may focus on comparing $\Delta I_{max}$ values for mC-DNA to hmC-DNA, both of which increase with temperature. However, while the increase in $\Delta I_{max}$ is expected with temperature because of the increased ion mobility, $\Delta I_{hmC}$ increases more sharply than $\Delta I_{mC}$ in the range 10-30° C. The ratio $\Delta I_{hmC}/\Delta I_{mC}$, shown above the plot in FIG. 82, systematically shows that hmC-DNA blocks more current amplitude than mC-DNA, by as much as 40% at 30° C. At 21° C., this difference in $\Delta I_{max}$ between mC-DNA and hmC-DNA is ~300 pA.

As shown, one may distinguish between DNA that exclusively contains either mC-DNA or hmC-DNA, but mammalian DNA contains relatively small amounts of hmC, up to a few percent of total cytosines. To test the sensitivity of nanopores to sparsely modified DNA, identical sequences were prepared that contain different fractions of hmC compared to either C or mC and confirmed the cytosine ratio using mass spectrometry (see FIG. 89). FIG. 83 shows normalized ΔImax values for 3 kbp DNA samples with different hmC:C ratios. The position of ΔInorm increases with the fraction of hmC for samples that have mixed hmC:C and hmC:mC nucleotides. A linear regression fit to the data yields a slope of 8 (0.5 pA per percent of hmC. Statistical analysis is shown in FIG. 92. From the fits to the Gaussian distributions, the certainty in the mean in ΔInorm for a population of >1000 molecules is 3 pA.

Effect of Cytosine Modifications on DNA Structure.

The different ΔImax values for mC-DNA and hmC-DNA show that transport through the pore is influenced by differences in DNA structure. In FIG. 84a is shown mean transport times tT for the three DNAs as a function of temperature. In the range of 10-30° C., one may note two main observations: First, tT values follow the trend hmC-DNA>C-DNA>mC-DNA. Second, while tT values decrease for C-DNA and mC-DNA with increasing temperatures, tT values increase for hmC-DNA, which may suggest a thermally activated process that stalls DNA transport for hmC-DNA. One may also note that transport times for C-DNA are significantly slower than for mC-DNA, although the difference is not as pronounced as the difference between mC-DNA and hmC-DNA. The reduced-ψ2 values for all of the transport time fits were between 0.8 and 1.7.

The anomalous behavior of hmC-DNA suggests a change of the structure, as the three modifications have identical visible mobilities in agarose gel electrophoresis. Thermal annealing experiments were applied to the three duplexes in order to shed light on structural differences, as shown in FIG. 84b. Thermal annealing curves were obtained by monitoring the fluorescence of SYBR Green I while reducing the temperature of the solution from 98° C. in decrements of 0.2° C. Annealing is indicated by an inflection point in the raw fluorescence data (see FIG. 90), which appears as a peak in the differential −dF/dT. The temperature at which a peak in the differential curve is reached is referred to as the annealing or melting temperature $T_m$. The three molecules have a significant difference in $T_m$ values, with hmcDNA<C-DNA<mC-DNA (see FIG. 84a). Also, complete annealing of the duplex occurs over a wider temperature range for hmC-DNA, as shown in the inset of FIG. 84b. Similar results were obtained in the six replicates that were performed.

Without being bound to any single theory, the nanopore transport time data suggest that hmC-DNA stalls for longer times in the nanopore as temperature is increased, as opposed to smoother transport for mC-DNA or C-DNA. Similarly, the lower annealing temperature and lower annealing rate for hmC-DNA suggest that the duplex structure is less energetically stable, as compared to the other two molecules. Despite the temperature gap between the nanopore experiments and the annealing curves, both pieces of evidence suggest hmC-DNA has a more easily perturbed duplex structure, which can promote slower translocation through the pore.

Molecular dynamics (MD) simulations were performed on model DNA duplexes in 1M KCl solution at neutral pH under ambient temperature and pressure (see FIG. 91). 0.12-μs-long trajectories were computed for a series of 27 bp d(A*CT)$_9$•d(AGT)$_9$ duplexes, where *C is either C, mC, or hmC. This sequence was chosen to study the dynamics of isolated cytosines (i.e., G-*C bps spaced by two A-T bps).

Throughout the simulations, all duplexes maintained a B-form double helix of nearly identical diameter and axial orientation. While steric effects from the modifications produced very minor changes in the duplex's average local structure, the most prominent effects of the modifications occur locally within G-*C bps. The polarity of the modification governs the strength of cytosine-water interactions. Average interaction energies, i.e., electrostatic and van der Waals energies, between cytosine major groove atoms and water molecules within the first solvation shell were −1.5, −1.0, and −1.8 kcal/mol for C-DNA, mC-DNA, and hmC-DNA, respectively.

These energetic differences, along with the structure and volume of the chemical modifications, may affect solvation dynamics in the major groove. FIG. 85a displays differential water densities for hmC-DNA and mC-DNA relative to C-DNA. The excluded volume of the methyl and hydroxymethyl groups pushes solvent around the cytosine farther away from the duplex, as seen by the magenta bubbles in the figure. Alternatively, van der Waals attraction between water molecules and the modifications increases solvent density around nearby phosphates and N4 atoms in mC and hmC. Significant changes in solvation are observed for hmC, because its hydroxymethyl group extends into the major groove toward the DNA 5' end, creating polar cavities that increase solvation in the major groove (see cyan bubbles in FIG. 85a). These cavities can capture water molecules within the first solvation shell, thereby increasing the probability of water binding to hmC for long (~100 ps) time scales.

The MD simulations also show that the polarity of cytosine modifications dictates local structural fluctuations in G-*C bps. The local geometry of DNA can be described by parameters that specify intra-bp, inter-bp, and local helical axis conformations. FIG. 85b displays plots of intra-bp fluctuation amplitudes for G-mC and G-hmC bps relative to G-C bps.

Fluctuations in shear, stretch, stagger, and buckle are 3-7% smaller in G-mC, while they are 1-5% larger in G-hmC. Due to steric constraints, rotary motion about the helical axis is impeded in G-mC and G-hmC bps, which results in reduced fluctuations in propeller twist and opening. Nevertheless, the overall trend for intra-base-pair fluctuations is G-hmC>G-C>G-mC. This result is consistent with the polarity of the chemical modification and can be understood as a solvent-mediated effect; fluctuations enable greater opportunities for contact between DNA and water molecules. Because water has the highest affinity for hmC, G-hmC bps experience the largest fluctuations. In contrast, water is less favorable to solvate the hydrophobic methyl group of mC, which increases the rigidity of G-mC bps. Solvent effects are also responsible for an interesting conformational change in the amine attached to the cytosine 4 position. Water molecules can collide with this group and cause it to rotate by 180° (FIG. 85c). This rotation is accompanied by a temporary disruption of hydrogen bonding in G-*C bps. Over the simulation time scales, 31 amine rotations are observed throughout the hmC-DNA duplex, compared to only 12 and 7 rotations in mC- and C-DNA duplexes, respectively.

Without being bound to any single theory, DNA fluctuations are governed by interplay of the steric effects and polarity of the modification. However, for intra-base-pair fluctuations, the trend is clear: increasing the size of the modification tends to increase the local rigidity within base pairs, while increasing the polarity of the modification decreases rigidity. A novel aspect of these findings is that the steric constraints of the modification, which increase local rigidity, can be mitigated by introducing a more polar modification. Thus, the hydrophilic hydroxymethyl group destabilizes G-hmC bps, while the hydrophobic methyl group stabilizes G-mC bps.

To determine how these microscopic fluctuations of modified cytosine bases affect global DNA structure, atomic force microscopy (AFM) was used to image surface-immobilized DNA molecules. Measurements of the contour length (L) and end-to-end distance (R) of DNA molecules deposited on a flat 2D mica substrate yield the mean persistence length (P) of the DNA:

$$\langle R^2 \rangle_{2D} = 4PL\left(1 - \frac{2P}{L}(1 - e^{-L/2P})\right) \quad (1)$$

where the relationship between P and R was derived from a mathematical analysis of worm-like chain bending along its contour.

To minimize excluded volume effects from two interacting DNA segments in a long molecule, two short DNA fragments were synthesized that were 410 and 1100 bp long and made the different cytosine variants for each length. For each DNA length, samples were deposited onto freshly cleaved mica under conditions that were optimized to achieve a uniform density of DNA molecules adsorbed on the surface. A comparatively low concentration of $Mg_{2+}$ ions was used to adsorb the DNA, resulting in diffusion and equilibration of the DNA onto the mica surface.

Following the acquisition of a set of AFM images, Gwyddion software was used to measure R for a set of molecules of each type. In addition, we have measured L for a representative set of molecules in each sample by drawing polyline segments along DNA contours using ImageJ software. For the 410 bp samples, measurement of L values for 30-40 molecules of each kind yielded 137 (2, 138 (3, and 135 (3 nm for C-DNA, mcDNA, and hmC-DNA, respectively. These mean L values are in close agreement with the expected contour length based on a helical B-form DNA pitch of 0.34 nm/bp. In contrast, R values were statistically different for each DNA type. By constructing histograms of R and fitting them to Gaussian distributions (see FIG. 46), one finds a difference between the mean R values that follows the trend hmC<C<mC, suggesting differences in DNA flexibility. Using eq 1 to compute P for each sample, we find that the range of P values for each modification are (based on) R* values (uncertainties for both DNA lengths): $(P_{hmC-DNA}*)$ 29-38 nm, $(P_{C-DNA}*)$ 41-49 nm, and $(P_{mC-DNA}*)$ 50-65 nm (see FIG. 53 for further statistical details).

The mean of the calculated P values for C-DNA was somewhat smaller than those found by others (52 nm). Smaller P values have been ascribed to DNA that adsorbs onto the mica in a partially trapped configuration and are known to be sensitive to the sample preparation conditions. Other sources of deviation may be the presence of sequences that inherently contain more unstable base-pairing interactions than ordinary DNA sequences, sequences that contain bends (e.g., A-tracts), or metrology errors due to tip-mediated artifacts. Therefore, using the same DNA sequence, deposition condition, and AFM tip for each set of molecules ensured that the differences in values of P between samples are trustworthy.

These data, computational and experimental, suggest that increasing the polarity of cytosine modifications reduces the rigidity of a DNA fragment. Without being bound to any single theory these findings may be important in explaining epigenetic effects of modified DNAs on transcription factor binding or chromatin assembly, as well as revealing information on the packaging efficiency of certain viruses. This may at least partially support the disclosed ability to discriminate among hmC-DNA and mC-DNA using nanopores: in the temperature range of 10-30° C., hmC-DNA undergoes significant local duplex destabilization, which increases both the mean transport time and current amplitude of hmC-DNA. MD simulations reveal that the dynamics of DNA translocation through a confined nanopore involves a complex interplay of DNA interactions with solvent, nanopore walls, ions as well as intra-DNA interactions.

Structurally, the 5' position of cytosine faces outward toward the grooves, leaving them accessible for interactions with the nanopore. In addition, the presented findings suggest that the relative stability of modified duplexes is an important factor. The combination of hydrophilic pore walls, high electric field inside the pore, and duplex stability, contribute to structural perturbations of hmC-DNA in the nanopore. More simply stated, pulling hmC-DNA through the nanopore may stall transport by deforming or locally denaturing the duplex. Interactions with the hydrophilic nanopore interface may be augmented by contact with deformed DNA structures at the pore. Also, local denaturation of hmC-DNA may promote the presence of multiple DNA strands occupying the pore simultaneously (e.g., three denatured single strands). This may explain the deep current blockades, longer transport times, and more complex current signatures that are observed with hmC-DNA.

Thus, it was shown that physical properties of DNA molecules with identical sequences may be dependent on the cytosine modification polarity. These properties give rise to different ion current signatures for DNA molecules threaded through nanopores, and nanopore measurements of as little as a few hundred molecules are sufficient to distinguish mC-DNA from hmC-DNA. Further, different proportions of hmC in fragments containing C-DNA or mC-DNA can be quantified based on the ion current signatures. MD simulations were used to probe the molecular basis of our findings, revealing that polar cytosine modifications increase the flexibility of DNA by promoting solvent-mediated fluctuations in G-C bps. In addition, AFM revealed that the mean end-to-end distance for the more polar hmC-DNA was significantly shorter than for C-DNA and mCDNA, indicating an increased flexibility for hmC-DNA. Nanopore-based discrimination among hmC-DNA and mC-DNA is nondestructive, high-throughput, and sensitive. Provided a better understanding of DNA transport through nanopores, this approach may enable the mapping of cytosine modification patterns directly in unamplified DNA fragments from living cells.

Materials and Methods

DNA molecules studied were prepared by PCR using Phusion DNA polymerase (Finnzymes/NEB). The 3 kb sequence was amplified from T4 genomic DNA. The 400 bp and 1100 bp samples were amplified from pBR322 plasmid (NEB). To verify that modified cytosines do not introduce mismatches, all types of products were sequenced following PCR amplification. To make DNA samples with mixed cytosine proportions, different cytosine mononucleotide ratios were added in the PCR mix. Following PCR amplification, the percentage of hmC was qualitatively determined by digestion with a methylation dependent restriction enzyme (MspJI) (see FIG. 87). The 3 kbp DNA products were subjected to a 1% agarose gel electrophoresis as shown in Figure S1A. The PCR products were then incubated with MspJI modification-dependent restriction endonuclease. As demonstrated in FIG. 87B, DNA with modified cytosines was digested, and the extent of digestion qualitatively correlates with the fraction of C with respect to hmC in the PCR mix.

Substrates for nanopore fabrication were 5×5 mm2 Si chips that have a 20-nm-thick low-stress silicon nitride (SiN) film deposited on a 5-µm-thick, thermally grown SiO2 layer, used to reduce the electrical noise. Following removal of the underlying oxide layer, solid-state nanopores in the range 3.5-4.5 nm were fabricated and imaged in a JEOL 2010FEG TEM. The nanopore devices were cleaned using piranha solution, followed by copious water wash, assembly in the fluoropolymer cell using a homemade quick cure PDMS gasket, and immersion with 1M KCl+1 mM EDTA buffered to pH 8 using 10 mM Tris-HCl. The fluoropolymer cell used accommodates volumes of 1-20 µL and features temperature regulation using a thermoelectric device connected to a copper block that houses the cell. Each chamber was equipped with a Ag/AgCl electrode. An Axopatch 200B patch clamp amplifier was used to apply voltage and measure current through the pore. The analog signal output was sampled at 250 kHz sampling rate using a 16-bit DAQ card (NI PCI-6230). Data were collected and analyzed using custom LabVIEW and Igor Pro software.

FIG. 87 presents PCR amplification of DNA with different cytosine compositions (C, mC, and hmC). As mentioned, the DNA molecules used herein were prepared by PCR using Phusion DNA polymerase (Finnzymes/NEB). The 3 kb sequence was amplified from T4 genomic DNA. The 400 bp and 1100 bp samples were amplified from pBR322 plasmid (NEB). To verify that modified cytosines do not introduce mismatches, all types of products were sequenced following PCR amplification. To make DNA samples with mixed cytosine proportions, different cytosine mononucleotide ratios were added in the PCR mix. Following PCR amplification, the percentage of hmC was qualitatively determined by digestion with a methylation dependent restriction enzyme (MspJI) (see FIG. 87). The 3 kbp DNA products were subjected to a 1% agarose gel electrophoresis as shown in FIG. 87A below. The PCR products were then incubated with MspJI modification-dependent restriction endonuclease. As shown in FIG. 87B, DNA with modified cytosines was digested, and the extent of digestion qualitatively correlates with the fraction of C with respect to hmC in the PCR mix.

FIG. 88 presents current amplitude histograms for 410 bp C-DNA, mC-DNA, and hmC-DNA. FIG. 89 presents a mass spectrometry analysis of DNA products with mixed cytosines.

In order to quantify the different cytosine contents in DNA produced using PCR, liquid chromatography/mass spectrometry (LC/MS) experiments were performed on the digested PCR product samples. Purified PCR fragments were digested using Antarctic Phosphatase (NEB) and Phosphodiesterase I from Crotalus Adamanteus venom (Sigma). Digested nucleoside samples were analyzed by reverse phase liquid chromatography (LC) and electrospray ionization/time-of-flight mass spectrometry (ESI-TOF MS). A reverse phase column, 1×150 mm, Develosil RP-Aqueous C30, 3 µm particles, 140 Å pore size (Phenomenex), was developed at a flow rate of 20 µl/min at 30.0 using an Agilent 1100 capillary LC connected directly to an Agilent 6210 series ESI-TOF MS. The column was equilibrated with 50 mM ammonium acetate, pH 6 in water. A nucleoside sample of up to 8 µl volume was injected, initial conditions were maintained for two-minutes and then the column was developed with a 15-minute linear gradient from 0% to 22.5% acetonitrile, and was held at 22.5% acetonitrile for an additional five minutes. Nucleosides eluted approximately 16-23 minutes following injection. Mass spectra were acquired over a range of 100 to 400 m/z at one cycle/sec and 10,000 transients per scan. The following ionization conditions were used: a VCap of 4000 V, 300 C with a drying gas 7.0 l/min; a nebulizer pressure of 15 psi and a fragmentor voltage of 215 V. The acquired spectra were extracted with Agilent MassHunter Qualitative Analysis Software (with Bioconfirm B 2.0.2) software using mass ranges of 136.0-136.1, 112.0-112.1, 152.0-152.1, 127.0-127.1, 126.0-126.2, 142.0-142.2, 305.1-305.2 for the liberated base fragments of dA, dC, dG, dT, d(5m)C, d(5hm)C and d(5Glucose,hm)C, respectively.

A standard calibration curve of solutions of A, G, T, C, and hmC at different proportions of hmC and C were prepared, maintaining the condition [A]=[G]=[T]=[C]+[hmC]. Extracted ion chromatograms for different bases in different samples and standards are shown in FIG. 89. The 0.3 and 0.6 hmC/C ratios are presented for both the 3 kb product and the standard dNTP mix samples. The C (red) and hmC (black) peaks differ in their ratios between the two sample sets.

The intensity of the peaks corresponds to the amount, as detected by MS. In FIG. 90a, we show the relative area for each type of mononucleoside as a function of the hmC/C ratio in the nucleotide mix. The relative areas of A, G, and T are not identical, despite their being of equal concentrations due to variation in the ionization from one chemical species to another. To account for this, we normalized the peak areas based on the standards. As expected, increasing the relative concentration of hmC relative to C results in a decrease in the relative area of C (red), and simultaneously, an increase in the relative area of hmC (purple). Finally, based on the normalized curves, in FIG. 90b we display the ratios of hmC with respect to C in DNA samples generated with different relative concentrations of hmC to C. Linearity in the curves suggests the incorporation of different cytosines into growing DNA strands in PCR is non-selective.

FIG. 90 illustrates raw fluorescence annealing curves for 3 kbp C-DNA, mC-DNA, and hmC-DNA. This figure shows raw fluorescence of SYBR Green I® in the presence of 3 kbp DNA with different cytosine types. To collect the data, samples were prepared in a 96-well plates in triplicates, sealed using a plastic adhesive sticker, and inserted into a RT-PCR instrument programmed to heat to 95° C. and held for one minute, heat to 98° C. and hold for one minute, then repeat a cycle in which the temperature is decreased by 0.2° C. for 30 sec, followed by exciting the samples at 488 nm and measuring the fluorescence emission at 530 nm. SYBR Green I is a dye that intercalates between the bases of dsDNA, and when doing so, its quantum yield increases dramatically. The presence of dsDNA in the sample is associated with as increase in fluorescence of SYBR Green I in the solution. Raw fluorescence intensities are shown as the temperature of the solution is cooled from 98° C. to 40° C. in decrements of 0.2° C. After complete annealing, the linear increase in fluorescence is typical for SYBR Green I. Thus, the data shown in FIG. 84b are the inverse of the differential of the curves shown in FIG. 90 here, i.e., −df/dT.

FIG. 91 presents computational details. Electronic structure calculations were performed with Gaussian 03 using the B3LYP functional and the 6-311G* basis set. Methyl and hydroxymethyl modifications can rotate about the C—C bond that connects these groups to the pyrimidine ring. Thus, to ensure that the optimized structures represented the global energy minimum, our procedure included a scan of the potential energy surface associated with rotations about this bond.

Molecular dynamics simulations were performed on d(A*CT)9•(AGT)9 duplexes using NAMD. Here, *C represents either C, mC or hmC. The duplexes were simulated in aqueous solution containing 1M KCl at neutral pH. Each system was simulated for approximately 0.12 μs under ambient temperature and pressure using a 1.5 fs time step. The DNA and counter ions were modeled with the CHARMM force field. The force field for the cytosine modifications was developed following the standard CHARMM protocol and is given in SI. The TIP3P water model was employed for the solvent. Electrostatic interactions were computed using the particle mesh Ewald method and a grid point density of about 1/Å. Analyses of the trajectories was performed in VMD. X3DNA was used to calculate the local helical parameters of the duplexes.

Table S1 shown below presents parameters for modified cytosines. Only the parameters for the modified atoms are listed; all other values are taken from the CHARMM cytosine parameters.

5-Methylcytosine

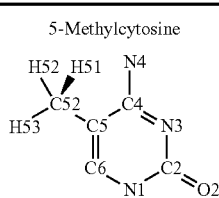

| Atom name | Type | Charge |
|---|---|---|
| C5 | CN3 | −0.06 |
| C52 |  | −0.27 |
| H51 |  | 0.09 |
| H52 |  | 0.09 |
| H53 |  | 0.09 |

| Bond | Force Constant | Equilibrium Distance |
|---|---|---|
| CN3—CT3 | 230 | 1.478 |

| Angle | Force Constant | Equilibrium Angle |
|---|---|---|
| CN3—CT3—HA | 33.43 | 110.1 |
| CN3—CN3—CT3 | 38.0 | 124.6 |

| | | |
|---|---|---|
| CN2—CN3—CT3 | 38.0 | 118.7 |

| Dihedral | Force Constant | Multiplicity | Phase |
|---|---|---|---|
| CN2—CN3—CT3—HA | 0.46 | 3 | 0 |
| CN3—CN3—CT3—HA | 0.46 | 3 | 0 |

5-Hydroxymethylcytosine

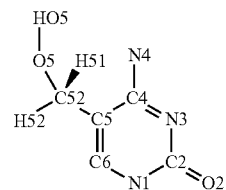

| Atom Name | Type | Charge |
|---|---|---|
| C5 | CN3 | −0.06 |
| C52 | CT2 | 0.05 |
| H51 | HA | 0.09 |
| H52 | HA | 0.09 |
| O5 | OH1 | −0.66 |
| HO5 | H | 0.43 |

| Bond | Force Constant | Equilibrium Distance |
|---|---|---|
| CN3—CT3 | 230 | 1.49 |

| Angle | Force Constant | Equilibrium Angle |
|---|---|---|
| CN3—CT2—HA | 33.43 | 110.1 |
| CN3—CN3—CT2 | 38.0 | 124.6 |
| CN2—CN3—CT2 | 38.0 | 118.7 |
| CN3—CT2—OH1 | 75.7 | 110.1 |

| Dihedral | Force Constant | Multiplicity | Phase |
|---|---|---|---|
| CN3—CN3—CT2—HA | 0.46 | 3 | 0 |
| CN2—CN3—CT2—HA | 0.46 | 3 | 0 |
| CN3—CN3—CT2—OH1 | 0.46 | 3 | 0 |
| CN2—CN3—CT2—OH1 | 0.46 | 3 | 0 |

Analysis of Current Amplitude Data for C-DNA, mC-DNA, and hmC-DNA.

Presented here is statistical analysis exemplary current amplitude data, which analysis establishes that the discrimination among hmC-DNA and mC-DNA or C-DNA, as well as the detection of % hmC-DNA, is statistically significant.

1) Top of FIG. 95: Histograms of ΔI values for the three molecules at 21° C. and 10° C.

2). Bottom of FIG. 95: Receiver operating characteristic (ROC) curves for the three different 3 kbp cytosine variants at these two temperatures.

Considering hmC-DNA as a positive result, and either C-DNA or mC-DNA is a negative result, the positive rate was calculated as a function of the false positive rate for different threshold ΔI values. The ΔI range of data used in the calculation was 1000-2600 pA with 200 pA intervals for 21° C., whereas a range of 400-2200 pA with 200 pA intervals were used for the data at 10° C. This curve is useful to learn about sensitivity (ordinate) vs. specificity (abscissa) in our signals: At 21° C., one can observe all of the hmC-DNA signals by detecting all events with amplitudes above a threshold of 1000 pA (sensitivity of 1, or TPR=1), although the rate of false positives (mC-DNA or C-DNA events) would also be 1 (i.e., our system would also detect all of mC-DNA events). In contrast, selecting a threshold of 1800 pA reduces sensitivity to 0.52 (i.e., 50% of hmC-DNA events are undetected), but specificity increases to 99.7% because the false positive rate is 0.003.

The following table presents a statistical analysis of current amplitude data for different % hmcDNA samples. Specifically, to test the significance of the differences in the mean between the sample populations, unpaired Student's T-tests were performed for each neighboring population. That is, 3% hmC was compared to 0% hmC, 10% hmC compared to to 3% hmC, and 30% hmC was compared to 10% hmC. The null hypothesis of this t-test is that the two means are the same. Therefore, based on the t-value, the corresponding p-value represents the probability that the null hypothesis is correct. In order to analyze all samples, hypotheses were formulated that every neighboring pair of samples is similar. This was done for both the hmC-DNA with C-DNA background and the hmC-DNA with mC-DNA background. T-values and p-values

| Sample | $\Delta I_{norm}$ (pA) | St. Dev. (pA) | N (events) | t | p (two-tailed) |
|---|---|---|---|---|---|
| 30% hmC/C | 249 | 129 | 1,419 | 32.9 | <0.0001 |
| 10% hmC/C | 82 | 100 | 1,392 | 9.13 | <0.0001 |
| 3% hmC/C | 27 | 99 | 1,427 | 1.69 | 0.09 |
| 0% hmC/C | 0 | 111 | 1,419 | — | — |
| 0% hmC/mC | 0 | 120 | 1,200 | — | — |
| 3% hmC/mC | 56 | 105 | 1,502 | 3.90 | 0.001 |
| 10% hmC/mC | 105 | 93 | 1,299 | 7.91 | <0.0001 |
| 30% hmC/mC | 225 | 130 | 1,401 | 16.0 | <0.0001 |

The p-values on the right column of the above Table show that the discrimination is robust.

Statistical Analysis of Persistence Length from AFM Data

The raw data collected from the AFM images are the mean end-to-end distance <R> (nm). Using Eqn. 1 and contour lengths of 0.34 (nm/bp)*N(bp), the mean values of <R> for the two DNA lengths have been converted to the persistence length P (nm). The uncertainty of the mean μerr was determined from the following general formula:

$$\mu_{err} = \frac{s}{\sqrt{n}},$$

where s is the standard deviation of the Gaussian fit and n is the number of measurements FIG. 96 right shows curves of P as a function of R based on Eqn 1. Superimposed on the curves are the experimental values of <R> determined from AFM, where error bars of ±μerr are shown. The boxes around each point are drawn in order to translate the error magnitude in <R> to the respective error in P. From these data one may estimate the range of P values as quoted elsewhere herein, taking into account the largest error from each measurement. Additionally, to test the significance of the differences in the mean between the sample populations, we performed unpaired Student's T-tests for each population with respect to C-DNA. For example, in the 1100 bp DNA case, assuming the null hypothesis that <R>mC-DNA=<R>C-DNA, we obtain t=2.90 for the 428 measurements (190 for mC-DNA and 223 for C-DNA, degrees of freedom are n−2=411). This yields a p-value of 0.0040, which means that the probability of the null hypothesis to be correct is 0.4%. So we are 99.6% confident that <R>mC-DNA≠<R>C-DNA. From the table below, one may conclude that the <R> values are significantly different for all three cytosine variants with at least 99.6% certainty.

The following table presents the means, t-values, and p-values for our measurements (NOTE: cDNA data do not have t-values and p-values because the other measurements are being compared to it).

| Sample | <R> (nm) | St. Dev. (nm) | n | t | p (two-tailed) |
|---|---|---|---|---|---|
| mC-DNA, 1100 bp | 270 | 54 | 190 | 2.90 | 0.004 |
| C-DNA, 1100 bp | 255 | 47 | 223 | — | — |
| hmC-DNA, 1100 bp | 231 | 58 | 205 | 4.78 | <0.0001 |
| mC-DNA, 410 bp | 129 | 33 | 155 | 5.04 | <0.0001 |
| C-DNA, 410 bp | 112 | 19 | 127 | — | — |
| hmC-DNA, 410 bp | 102 | 24 | 117 | 3.45 | 0.001 |

The foregoing description and attached figures are illustrative only, and do not limit the scope of the present disclosure or claims. Variations on the foregoing description are also within the scope of the present disclosure. A number of references are provided below; these references are incorporated herein in their entireties.

What is claimed:

1. A method of detecting an analyte, comprising:
    contacting a sample to a first capture material that preferentially binds to a first analyte;
    eluting the first analyte from the capture material;
    translocating the first analyte through a first pore of a detection device, the detection device comprising:
    a membrane having a top surface and a bottom surface,
    the membrane having a cavity formed thereon, the cavity extending from the top surface of the membrane to an intermediate surface of the membrane,
    the top surface and the bottom surface of the membrane defining a thickness therebetween in the range of from about 20 nm to about 100 nm,
    the intermediate surface and the bottom surface of the membrane defining a thickness therebetween in the range of from about 0.1 nm to about 20 nm,
    the membrane having the first pore formed thereon, the first pore being in register with the cavity, and the first pore extending through the intermediate and bottom surfaces of the membrane, the first pore having an effective height in the range of from about 0.1 nm to about 10 nm; and
    detecting a signal related to the translocation of the molecule through the first pore.

2. A method, comprising:
    translocating a population of oligonucleotides through a first pore of a detection device, the detection device comprising:
    a membrane having a top surface and a bottom surface;
    the membrane having a cavity formed thereon, the cavity extending from the top surface of the membrane to an intermediate surface of the membrane,
    the top surface and the bottom surface of the membrane defining a thickness therebetween in the ranger of from about 20 nm to about 100 nm,
    the intermediate surface and the bottom surface of the membrane defining a thickness therebetween in the range of from about 0.1 nm to about 20 nm,
    the membrane having the first pore formed thereon, the first pore being in register with the cavity, and the first pore extending through the intermediate and bottom surfaces of the membrane, the first pore having an effective height in the range of from about 0.1 nm to about 10 nm;
    collecting a plurality of signals related to the translocation of the population of oligonucleotides through the nanopore; and
    correlating the plurality of signals to the presence of methylated bases, hydroxymethylated bases, or both, present in the population of oligonucleotides.

3. The method of claim 2, wherein a signal comprises a passage duration signal associated with translocation of a base of an oligonucleotide through a nanopore, a current associated with translocation of a base of an oligonucleotide through a nanopore, a voltage associated with translocation of a base of an oligonucleotide through a nanopore, or any combination thereof.

4. The method of claim 2, further comprising correlating the plurality of signals to the level methylated bases, hydroxymethylated bases, or both, present in the population of oligonucleotides.

5. The method of claim 2, further comprising correlating the correlating the plurality of signals to the proportion of methylated bases, hydroxymethylated bases, or both, present in the population of oligonucleotides.

6. A detection device, comprising:
a first capture material that binds specifically to a first molecule;
a first membrane having a top surface and a bottom surface,
the first membrane having a cavity formed thereon, the cavity extending from the top surface of the membrane to an intermediate surface of the membrane,
the top surface and the bottom surface of the first membrane defining a thickness therebetween in the range of from about 20 nm to about 100 nm,
the intermediate surface and the bottom surface of the membrane defining a thickness therebetween in the range of from about 0.1 nm to about 20 nm,
the membrane having the first pore formed thereon, the first pore being in register with the cavity, and the first pore extending through the intermediate and bottom surfaces of the membrane, the first pore having an effective height in the range of from about 0.1 nm to out 10 nm; and
a second membrane disposed adjacent the first membrane,
the second membrane having a thickness in the range of from about 2 nm to about 20 nm, the second membrane having at least one pore extending therethrough,
the pore having a cross-sectional dimension in the range of from about 1 nm to about 100 nm, and
the cavity of the first membrane being in register with the at least one pore of the second membrane,
the first pore being in fluid communication with the first capture material;
a device configured to apply a gradient across the first pore; and
a detector configured to detect a signal related to passage of a molecule through the first pore.

7. The detection device of claim 6, wherein the first membrane has a thickness in the range of from about 2 nm to about 20 nm.

8. The detection device of claim 6, further comprising a second capture material that binds preferentially to a second miRNA molecule that differs in at least one aspect from the first miRNA molecule.

9. A detection device, comprising:
a membrane having a top surface and a bottom surface,
the membrane having a cavity formed thereon, the cavity extending from the top surface of the membrane to an intermediate surface of the membrane,
the top surface and the bottom surface of the membrane defining a thickness therebetween in the range of from about 20 nm to about 100 nm,
the intermediate surface and the bottom surface of the membrane defining a thickness therebetween in the range of from about 0.1 nm to about 20 nm,
the membrane having a first pore formed thereon, the first pore being in register with the cavity, and the first pore extending through the intermediate and bottom surfaces of the membrane, and the first pore having an effective height in the range of from about 0.1 nm to about 10 nm.

10. The detection device of claim 9, further comprising a detector configured to detect a signal related to passage of a molecule through the first pore.

11. The detection device of claim 9, wherein the first pore has an effective height in the range of from about 0.5 nm to about 5 nm.

12. The detection device of claim 11, wherein the first pore has an effective height in the range of from about 1 nm to about 2 nm.

13. The detection device of claim 9, further comprising a capture material configure to bind preferentially to a first molecule.

14. The detection device of claim 13, wherein the first capture material is selected to as to bind preferentially to miRNA.

15. The detection device of claim 14, wherein the first capture material binds preferentially to a preselected miRNA.

16. The detection device of claim 13, further comprising a second capture material that binds preferentially to a second miRNA molecule that differs in at least one aspect from the first miRNA molecule.

17. The detection device of claim 9, wherein the first pore comprises a cross-sectional dimension in the range of from about 1 nm to about 100 nm.

* * * * *